(12) United States Patent
Konno

(10) Patent No.: US 8,136,974 B2
(45) Date of Patent: Mar. 20, 2012

(54) METAL COORDINATION COMPOUND AND LIGHT-EMITTING MATERIAL CONTAINING THE SAME

(75) Inventor: Hideo Konno, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 291 days.

(21) Appl. No.: 12/517,954

(22) PCT Filed: Dec. 7, 2007

(86) PCT No.: PCT/JP2007/073720
§ 371 (c)(1),
(2), (4) Date: Jun. 5, 2009

(87) PCT Pub. No.: WO2008/069322
PCT Pub. Date: Jun. 12, 2008

(65) Prior Publication Data
US 2010/0317858 A1    Dec. 16, 2010

(30) Foreign Application Priority Data

Dec. 8, 2006  (JP) ................................ 2006-332649
Feb. 14, 2007 (JP) ................................ 2007-034124

(51) Int. Cl.
*F21V 7/04* (2006.01)
*C07F 17/02* (2006.01)
*C07D 221/02* (2006.01)

(52) U.S. Cl. .............................. 362/555; 546/4; 546/74

(58) Field of Classification Search .................. 362/555; 546/4, 74
See application file for complete search history.

(56) References Cited

U.S. PATENT DOCUMENTS

| 2004/0127710 A1 | 7/2004 | Park et al. |
| 2004/0142208 A1 | 7/2004 | Hamada et al. |

FOREIGN PATENT DOCUMENTS

| JP | 2003-253145 A | 9/2003 |
| JP | 2004-210779 A | 7/2004 |
| JP | 2005-298483 A | 10/2005 |
| JP | 2006-151888 A | 6/2006 |
| JP | 2007-262134 A | 10/2007 |
| WO | WO-00/70655 A2 | 11/2000 |
| WO | WO-02/064700 A1 | 8/2002 |
| WO | WO-2006/059758 A1 | 6/2006 |

*Primary Examiner* — Rebecca Anderson
*Assistant Examiner* — Samantha Shterengarts
(74) *Attorney, Agent, or Firm* — Birch, Stewart, Kolasch & Birch, LLP

(57) ABSTRACT

To provide a light-emitting device that is capable of red-light-emitting with high luminance and high efficiency and that is excellent in endurance; and a metal coordination compound metal coordination compound having a partial structure represented by formula (1) that can be used in the light-emitting device, and that can also be used in applications, such as organic electroluminescent device materials, electrochemiluminescence (ECL) device materials, emission sensors, photosensitizers, displays, photographic materials, laser dyes, color filter dyes, optical communications, color conversion filters, backlights, illuminations, photosensitizing dyes, various light sources, and the like.

[Chemical formula 1]

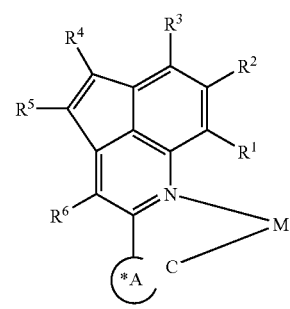

Formula (1)

*A means Ring A

29 Claims, 6 Drawing Sheets

[Fig. 1]
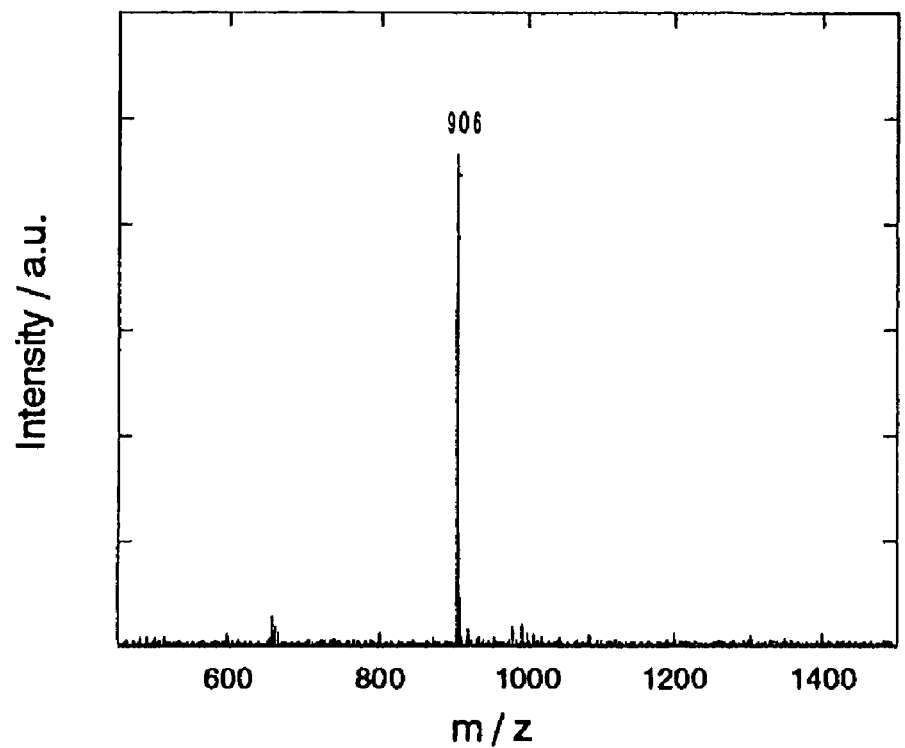
[Fig. 2]
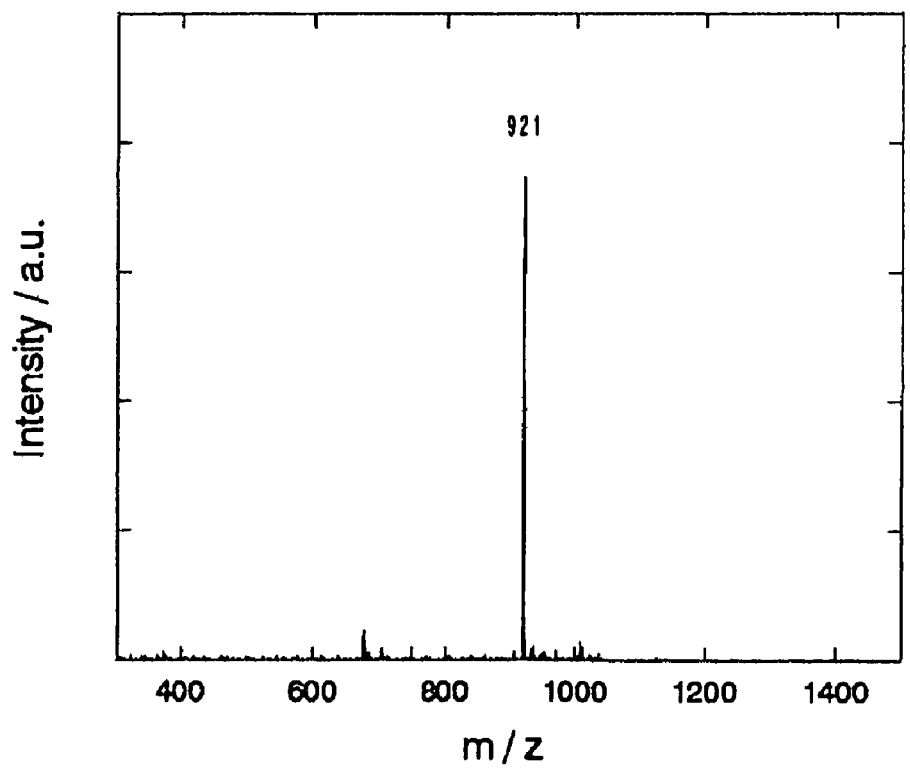

[Fig. 3]
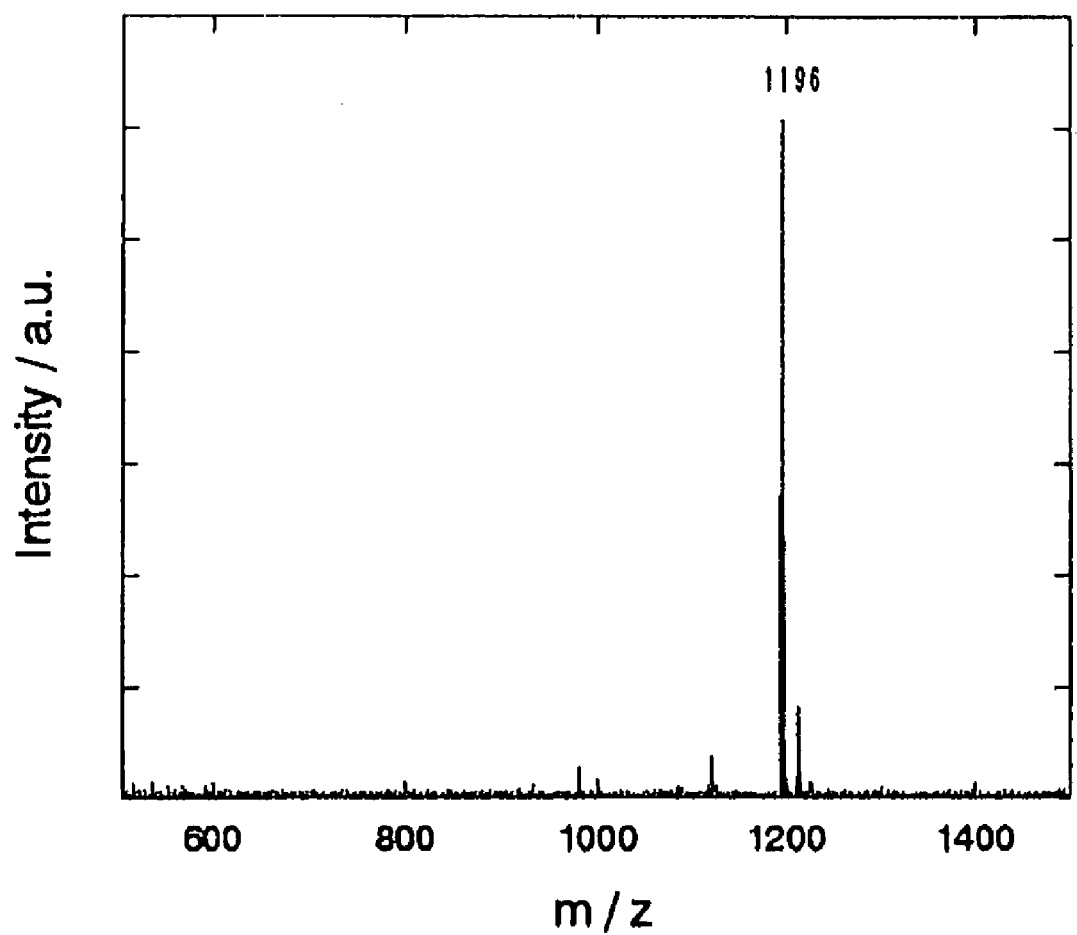

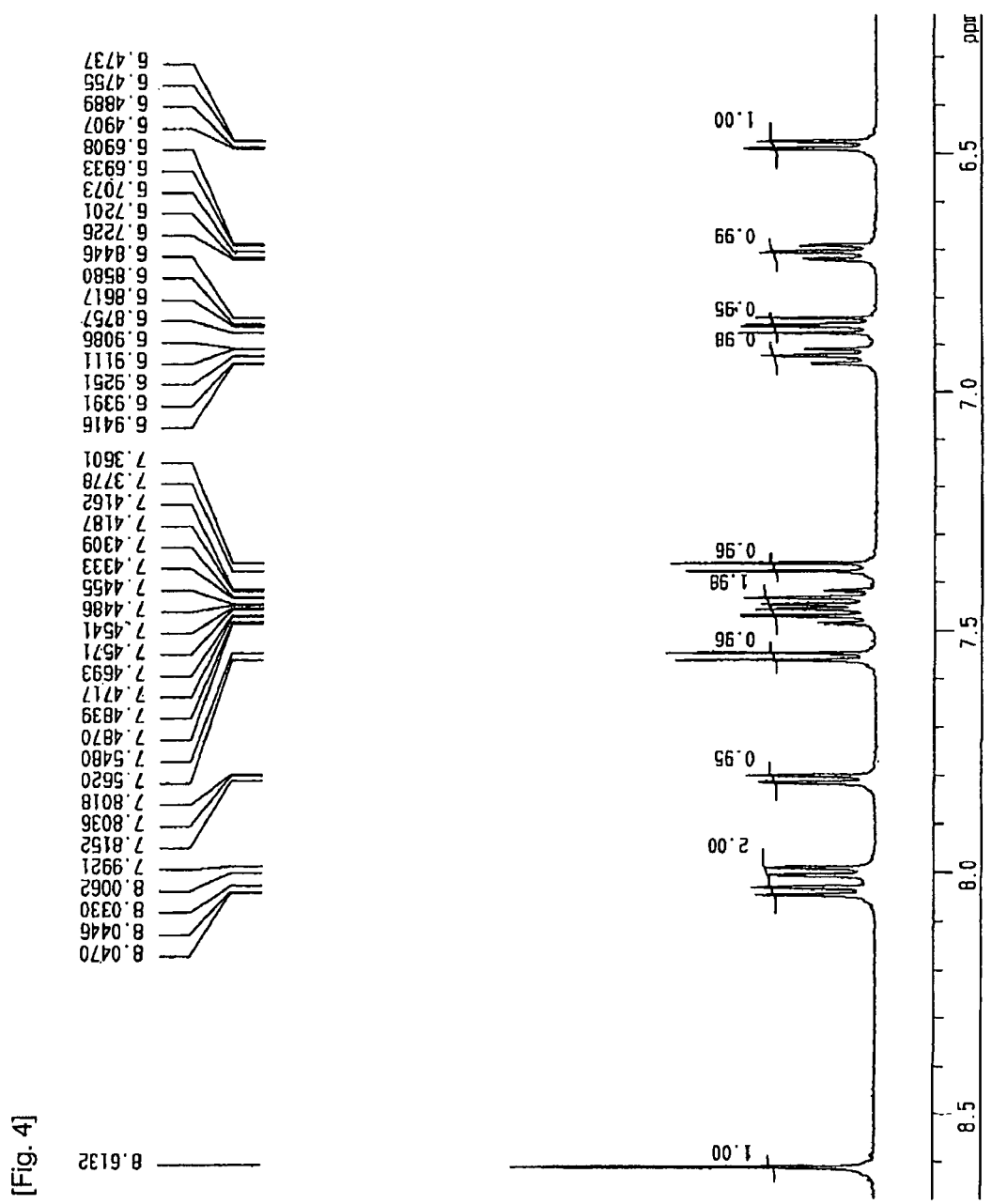
[Fig. 4]

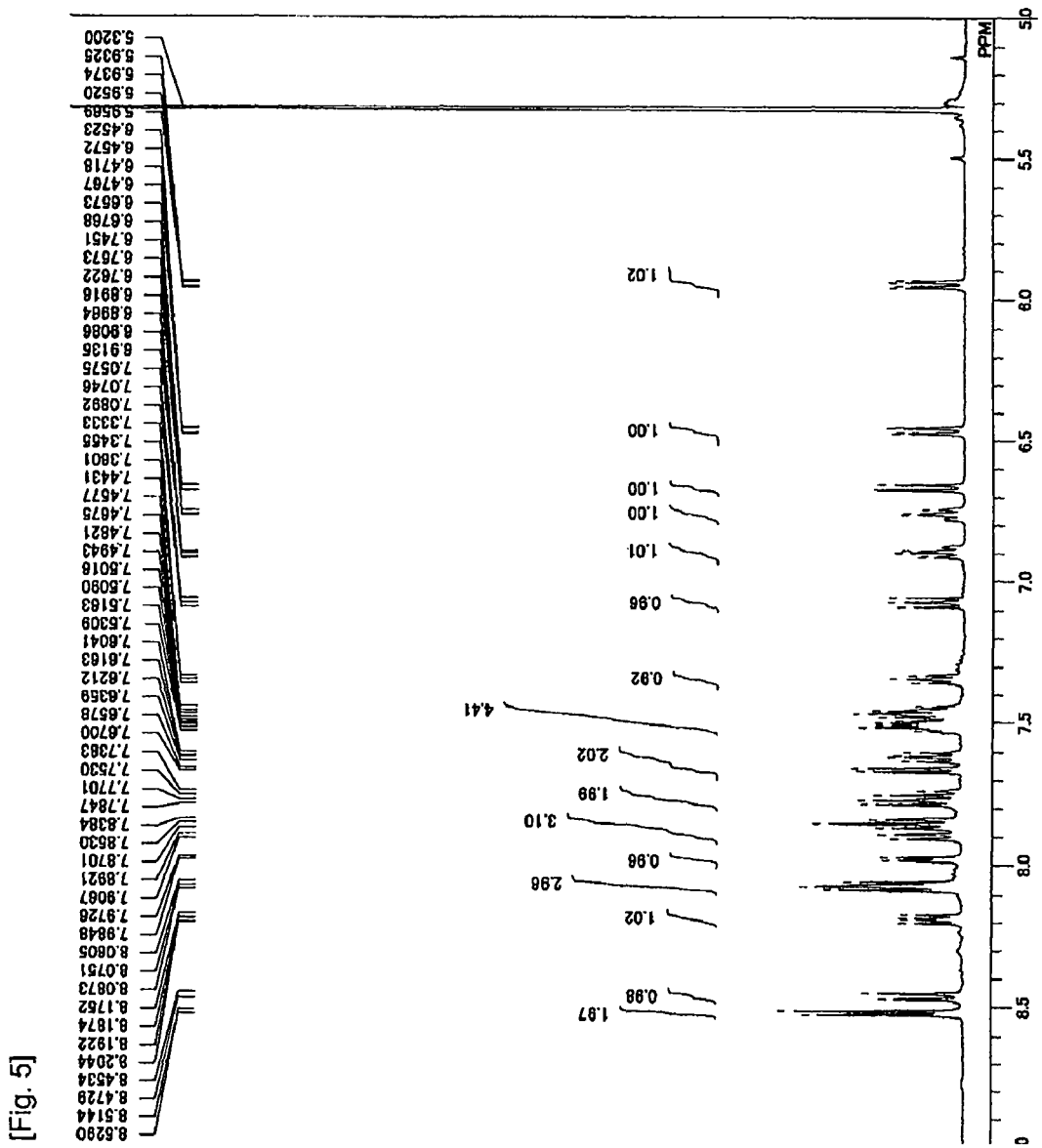
[Fig. 5]

[Fig. 6]
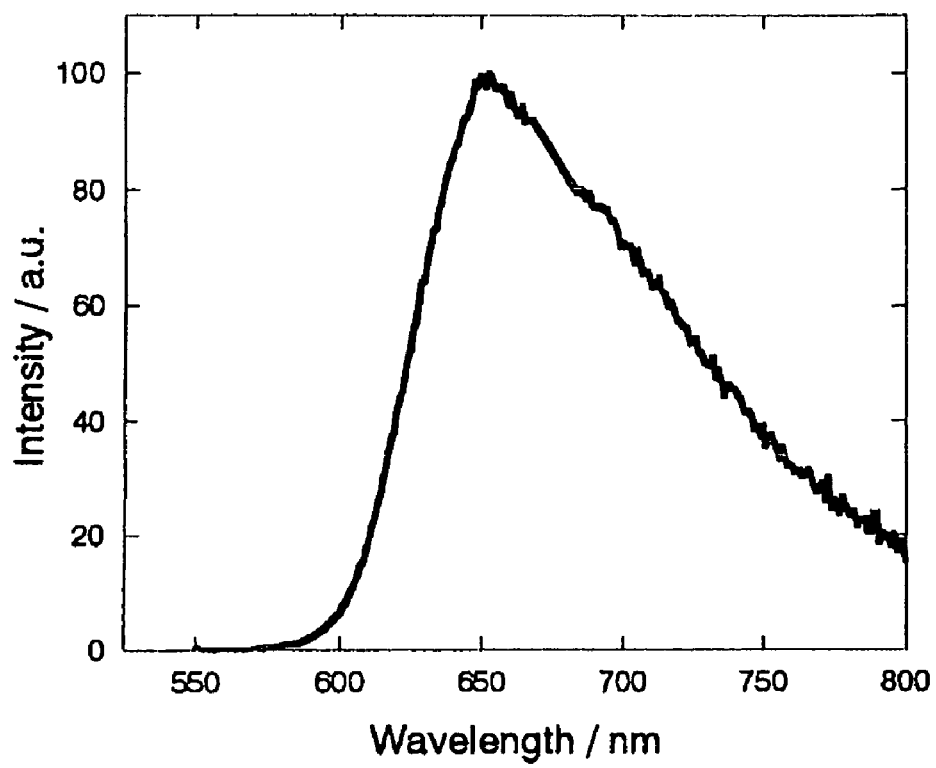
[Fig. 7]
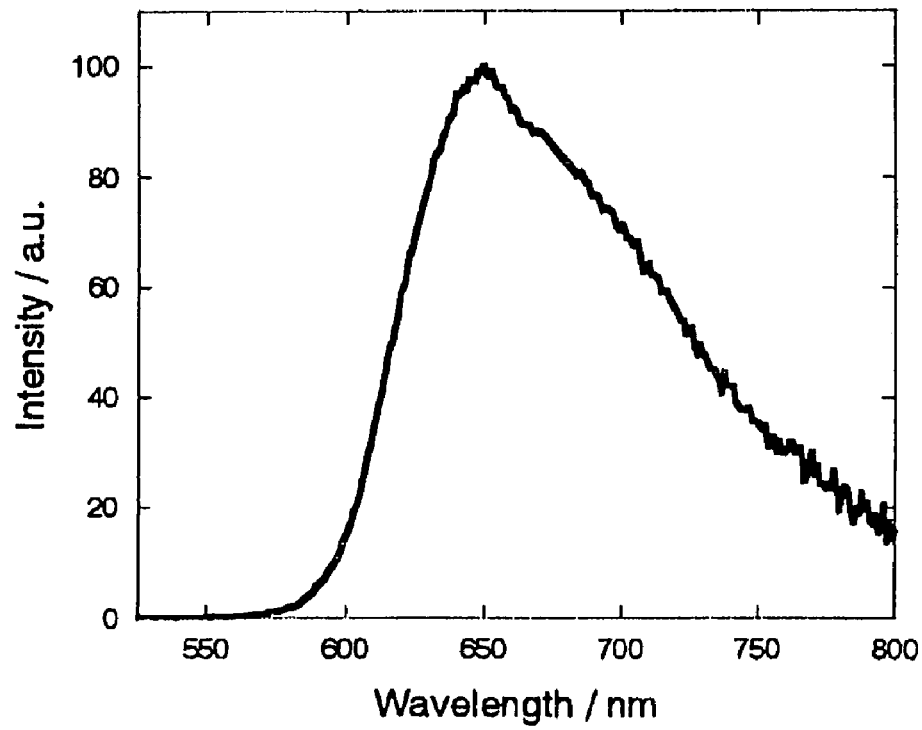

[Fig. 8]
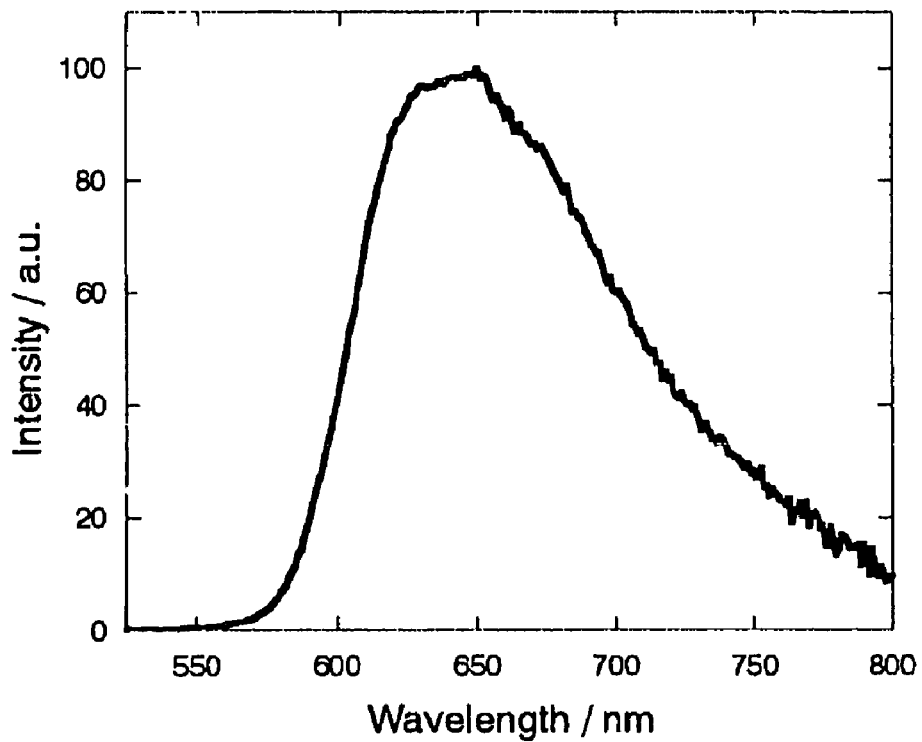
[Fig. 9]
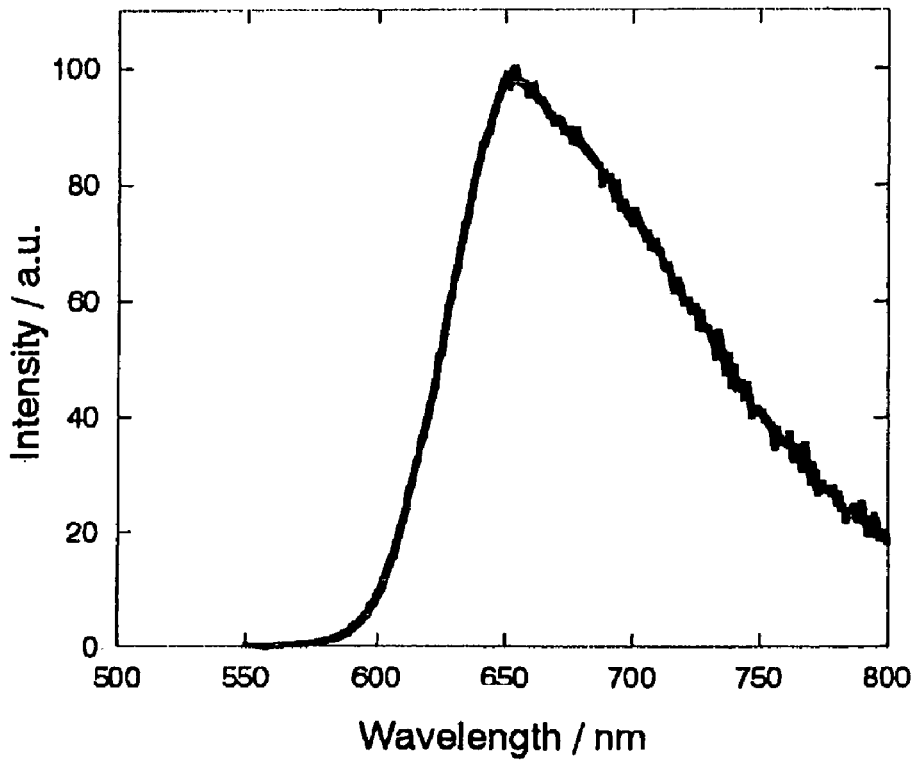

METAL COORDINATION COMPOUND AND LIGHT-EMITTING MATERIAL CONTAINING THE SAME

TECHNICAL FIELD

The present invention relates to a metal coordination compound that is useful in application, such as organic electroluminescent device materials, electrochemiluminescence (ECL) device materials, emission sensors, photosensitizers, displays, photographic materials, laser dyes, color filter dyes, optical communications, color conversion filters, backlights, illuminations, photosensitizing dyes and various light sources, and also to a light-emitting material containing the compound.

BACKGROUND ART

Organic electroluminescent devices are attracting attention as next-generation display devices, and recently, there are increasing intensively studies for development of various organic materials for use in such light-emitting devices. In particular, as the light-emitting materials, phosphorescent materials that use emission from excited triplet state are attracting attention.

When emission from excited singlet state is used, the probability of generation of the light-emitting excited species is only 25% since the singlet excitons and triplet excitons are generated at a ratio of 1:3 and the emission extraction efficiency is approximately 20%, and thus the external extraction quantum efficiency is at most 5%. On the other hand, if emission from the excited triplet state is also used, the maximum internal quantum efficiency is 100%, and the emission efficiency becomes in principle 4 times larger than that in the case of emission from the excited singlet state. For that reason, intensive studies for development of organic electroluminescent devices using a phosphorescent material are under progress. In particular, as the phosphorescent materials, orthometalated iridium complexes, including as a typical example tris(2-phenylpyridine)iridium complexes, are compounds which particularly attracting attention (Patent Document 1). However, this type phosphorescent material shows only green emission, and there is a need for development of another novel phosphorescent material.

Patent Document 1: WO 00/70655 Pamphlet

SUMMARY OF THE INVENTION

Problems that the Invention is to Solve

The present invention is contemplated for providing a light-emitting device that is capable of emitting with high luminance and high efficiency and that is excellent in endurance, and for providing a novel metal coordination compound that can be used in the light-emitting device, and that can also be used in applications, such as organic electroluminescent device materials, electrochemiluminescence (ECL) device materials, emission sensors, emission probes, photosensitizers, displays, photographic materials, laser dyes, color filter dyes, optical communications, color conversion filters, backlights, illuminations, photosensitizing dyes, various light sources, and the like.

Means to Solve the Problems

After intensive studies under the circumstances above, the inventors of the present invention have found that a novel metal coordination compound represented by formula (1), (2) or (11) having a platinum group element as the central metal, has excellent emission characteristics in the visible light region (in particular, in the red region) and is useful as a light-emitting material in various applications, thereby to attain the present invention.

That is, according to this application, the following inventions are provided.

<1> A metal coordination compound, having a partial structure represented by formula (1):

[Chemical formula 1]

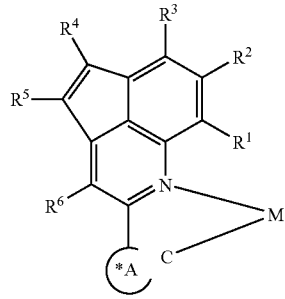

Formula (1)

*A means Ring A wherein, in formula (1), M represents a platinum group element; N represents a nitrogen atom; C represents a carbon atom; $R^1$ to $R^6$ each independently represent a hydrogen atom or a substituent, and the adjacent substituents may bond to each other, to form a ring structure; and the ring A represents an aromatic hydrocarbon ring or an aromatic hetero ring, each of which ring may have a substituent.

<2> A metal coordination compound, represented by formula (2):

[Chemical formula 2]

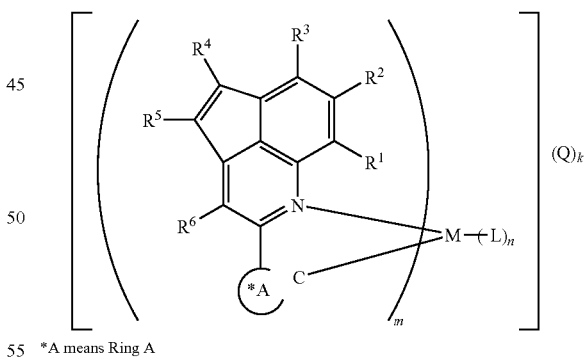

Formula (2)

*A means Ring A wherein, in formula (2), M represents a platinum group element; N represents a nitrogen atom; C represents a carbon atom; m is an integer of 1 to 3; n is an integer of 0 to 2; m+n is 2 or 3; $R^1$ to $R^6$ each independently represent a hydrogen atom or a substituent, and the adjacent substituents may bond to each other, to form a ring structure; the ring A represents an aromatic hydrocarbon ring or an aromatic hetero ring, each of which ring may have a substituent; L represents a bidentate ligand; Q represents a counter anion; and k is an integer of 0 to 2.

<3> The metal coordination compound described in the above item <2>, wherein L is an anionic bidentate ligand.
<4> The metal coordination compound described in the above item <2> or <3>, wherein L is a bidentate ligand forming M-nitrogen and M-carbon bonds, a bidentate ligand forming M-nitrogen and M-oxygen bonds, a bidentate ligand forming two M-oxygen bonds, a bidentate ligand forming two M-nitrogen bonds, a bidentate ligand forming two M-sulfur bonds, a bidentate ligand forming two M-phosphorus bonds, or a bidentate ligand forming two M-carbon bonds.
<5> The metal coordination compound described in any one of the above items <2> to <4>, wherein L is represented by any one of formulae (3) to (10):

[Chemical formula 3]

(3)
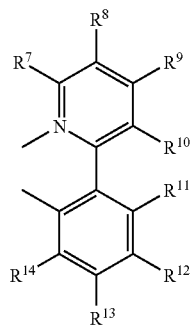

(4)
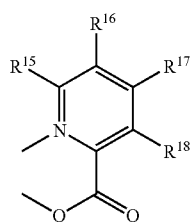

(5)
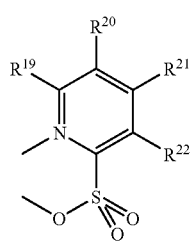

(6)
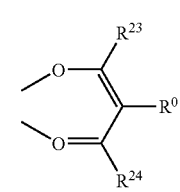

(7)
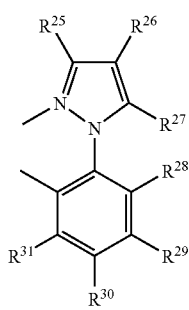

(8)
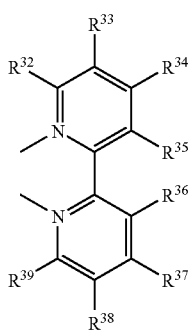

(9)
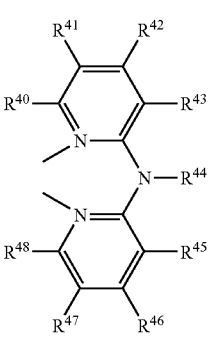

(10)
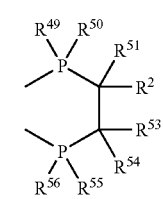

wherein, in formulae (3) to (10), $R^7$ to $R^{56}$, and $R^0$ each independently represent a hydrogen atom or a substituent, and the adjacent substituents may bond to each other, to form a ring structure.

<6> The metal coordination compound described in any one of the above items <2> to <5>, wherein L is represented by any one of formulae (3) to (6):

<7> The metal coordination compound described in any one of the above items <1> to <6>, wherein the ring A is a benzene ring, a substituted benzene ring, a naphthalene ring, a substituted naphthalene ring, a thiophene ring, a substituted thiophene ring, a furan ring, a substituted furan ring, a fluorene ring, or a substituted fluorene ring.

<8> The metal coordination compound described in any one of the above items <1> to <7>, wherein the substituent on the ring A is selected from a cyano group, a trifluoromethyl group, a halogen atom, a hydroxy group, a substituted or unsubstituted alkyl group having 1 to 30 carbon atoms, a substituted or unsubstituted aryl group having 6 to 30 carbon atoms, a substituted or unsubstituted alkenyl group having 1 to 30 carbon atoms, a substituted or unsubstituted alkoxy group having 1 to 30 carbon atoms, a substituted or unsubstituted heterocyclic group having 1 to 30 carbon atoms, or a substituted or unsubstituted amino group having 0 to 30 carbon atoms, in which a hydrogen atom in any of the substituent may be replaced with a fluorine atom.

<9> The metal coordination compound described in any one of the above items <1> to <8>, wherein $R^1$ to $R^6$ is selected from a hydrogen atom, a cyano group, a trifluoromethyl group, a halogen atom, a hydroxy group, a substituted or unsubstituted alkyl group having 1 to 30 carbon atoms, a substituted or unsubstituted aryl group having 6 to 30 carbon atoms, a substituted or unsubstituted alkenyl group having 1 to 30 carbon atoms, a substituted or unsubstituted alkoxy group having 1 to 30 carbon atoms, a substituted or unsubstituted heterocyclic group having 1 to 30 carbon atoms, or a substituted or unsubstituted amino group having 0 to 30 carbon atoms, in which a hydrogen atom in any of the substituent may be replaced with a fluorine atom.

<10> The metal coordination compound described in any one of the above items <1> to <8>, wherein $R^1$ to $R^6$ each are a hydrogen atom.

<11> The metal coordination compound described in any one of the above items <1> to <9>, wherein $R^4$ and $R^5$ bond to each other, to form a benzene ring.

<12> The metal coordination compound described in any one of the above items <2>, and <7> to <11>, wherein m=3 and n=0.

<13> The metal coordination compound described in any one of the above items <2> to <11>, wherein m=2 and n=1.

<14> The metal coordination compound described in any one of the above items <1> to <13>, wherein M is iridium.

<15> A metal coordination compound, represented by formula (11):

[Chemical formula 4]

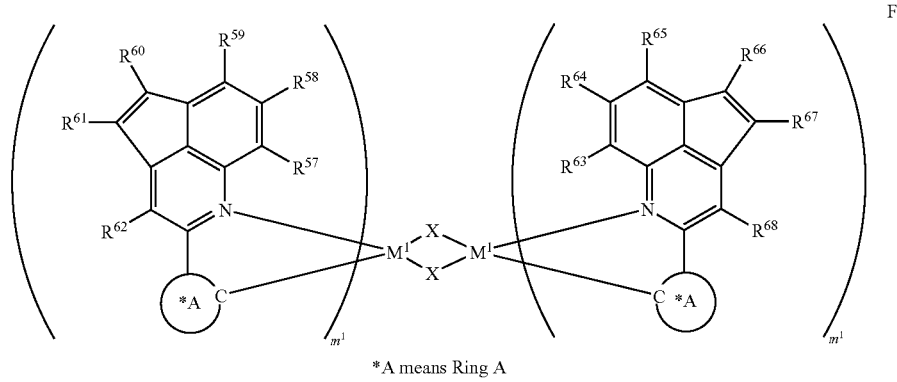

Formula (11)

wherein, in formula (11), $M^1$ represents iridium, platinum, rhodium, or palladium; N represents a nitrogen atom; C represents a carbon atom; $m^1$ is an integer of 1 or 2; $R^{57}$ to $R^{68}$ each independently represent a hydrogen atom or a substituent; the rings A each represent an aromatic hydrocarbon ring or an aromatic hetero ring, each of which ring may have a substituent; and the adjacent substituents may bond to each other, to form a ring structure; and X represents a halogen atom.

<16> A light-emitting material, comprising the metal coordination compound described in any one of the above items <1> to <15>.

<17> A light-emitting device, comprising the light-emitting material described in the above item <16>.

<18> An aromatic compound, represented by formula (12):

[Chemical formula 5]

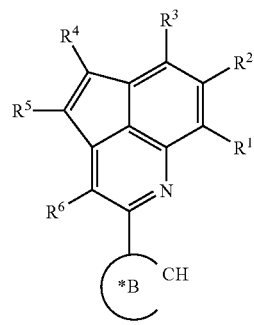

Formula (12)

*B means Ring B wherein, in formula (12), N represents a nitrogen atom; C represents a carbon atom; $R^1$ to $R^6$ each independently represent a hydrogen atom or a substituent, and the adjacent substituents may bond to each other, to form a ring structure, but $R^6$ and the ring B do not bond to each other, to form any ring structure; the ring B is a benzene ring, a substituted benzene ring, a naphthalene ring, a substituted naphthalene ring, a thiophene ring, a substituted thiophene ring, a furan ring, a substituted furan ring, a fluorene ring, or a substituted fluorene ring, each of which ring may have a substituent.

Advantageous Effects of the Invention

The novel metal coordination compound of the present invention shows high-luminance emission in the visible light region (in particular, in the red region) efficiently at low power consumption, and thus the light-emitting device containing the compound is used favorably in the fields of display device, display, backlight, analyzer detector unit, electrophotography, lighting source, recording light-source, exposing source, reading light-source, signs and marks, signboards, interior products, and others. Further, the compound of the present invention is also applicable to the fields of medical product, photographic material, UV-absorbing material, laser dye, color filter dye, color conversion filter, emission sensor, emission probe, optical communication, and others.

BRIEF DESCRIPTION OF THE DRAWINGS

FIG. 1 is a mass spectrum of a compound (2-410) of the present invention.

FIG. 2 is a mass spectrum of a compound (2-411) of the present invention.

FIG. 3 is a mass spectrum of a compound (2-413) of the present invention.

FIG. 4 is a proton NMR spectrum of a compound (2-43) of the present invention in deuterated dichloromethane.

FIG. 5 is a proton NMR spectrum of a compound (2-476) of the present invention in deuterated dichloromethane.

FIG. 6 is an emission spectrum of a compound (2-295) of the present invention in THF at room temperature.

FIG. 7 is an emission spectrum of a compound (2-411) of the present invention in THF at room temperature.

FIG. 8 is an emission spectrum of a compound (2-410) of the present invention in THF at room temperature.

FIG. 9 is an emission spectrum of a compound (2-476) of the present invention in THF at room temperature.

BEST MODE FOR CARRYING OUT THE INVENTION

The metal coordination compound according to the present invention is represented by the formula (1), (2) or (11) above, and it is possible to obtain a light-emitting device showing excellent emission color in the visible light region (in particular, in the red region), by adding such a metal coordination compound to a light-emitting layer or a plurality of organic compound layers including the light-emitting layer in the light-emitting device. It is also possible to produce a high-efficiency white-light-emitting device, utilizing, as a base device, the red-light-emitting device containing the compound of the present invention, in combination with a blue- to green-light-emitting device.

Hereinafter, the present invention will be described more in detail.

The metal coordination compound of the present invention, characteristically has a bidentate organic ligand carrying a ring A bonded to the 2-position of the cyclopenta[de]quinoline skeleton represented by formula (13):

[Chemical formula 6]

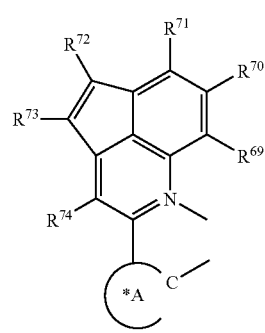

Formula (13)

*A means Ring A wherein, in formula (13), N represents a nitrogen atom; C represents a carbon atom; $R^{69}$ to $R^{74}$ each independently represent a hydrogen atom or a substituent, and the adjacent substituents may bond to each other, to form a ring structure; and the ring A represents an aromatic hydrocarbon ring or an aromatic hetero ring, each of which ring may have a substituent.

That is, when the bidentate ligand represented by formula (13) is bonded to a platinum group element that is the central metal, thereby to form a bond, intersystem crossing from the excited singlet state to excited triplet state is accelerated by heavy-atom effect of the platinum group element (iridium, platinum, rhodium, palladium, ruthenium, or osmium), and the metal coordination compound of the present invention exhibits highly-efficient phosphorescence emission therefrom.

Further, the metal coordination compound of the present invention having a cyclopenta[de]quinoline skeleton (e.g., 2-phenylcyclopenta[de]quinoline-containing metal coordination compound) has an expanded ligand conjugation system, and thus shows excellent emission characteristics in the visible light region particularly in the red region, as compared to a known metal coordination compound having a pyridine skeleton (e.g., 2-phenylpyridine-containing metal coordination compounds) and a known metal coordination compounds having a quinoline skeleton (e.g., 2-phenylquinoline-containing metal coordination compounds).

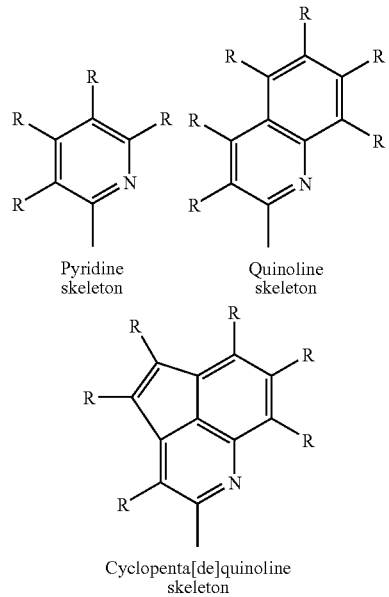

Pyridine skeleton

Quinoline skeleton

Cyclopenta[de]quinoline skeleton (R=a hydrogen atom or a substituent)

It is sufficient for the metal coordination compound of the present invention to be represented by any one of formulae (1), (2) or (11), and the compound may include any isomers thereof (e.g., facial isomers, meridional isomers, the isomers described in JP-A-2006-278781 ("JP-A" means unexamined published Japanese patent application), and others).

When the metal coordination compound of the present invention is represented by formula (2), and m=3 and n=0, there are geometrical isomers (a facial or meridional isomer), but the facial isomer is more preferable. The content of meridional isomer is preferably less than 3%, more preferably less than 1%, and particularly preferably less than 0.1%. The content of meridional isomer can be determined by liquid chromatography or proton NMR.

The metal coordination compound of the present invention is preferably a neutral or cationic metal complex, more preferably a neutral metal complex.

Among the metal coordination compounds of the present invention, those having an emission quantum yield in solution of 0.01 or more are preferable; those of 0.1 or more are more preferable; those of 0.2 or more are particularly preferable; and those of 0.4 or more are most preferable. The emission quantum yield in solution is favorably determined, after the solution in which the light-emitting material has been dissolved is purged with an argon or nitrogen gas, or after the solution in which the light-emitting material has been dissolved is deaerated as it is frozen, for removal of dissolved oxygen. Either an absolute or relative method may be used for determination of the emission quantum yield. In the relative method, the emission quantum yield can be determined, in comparison with the emission spectrum of a standard substance (e.g., quinine sulfate salt). In the absolute method, the emission quantum yield can be determined by using a commercially available instrument (Absolute PL Quantum Yield Analyzer (C9920-02), manufactured by Hamamatsu Photonics K.K.). The emission quantum yield in solution can be determined in any of various solvents, but the metal coordination compound of the present invention preferably satisfies the above emission quantum yield in any one solvent.

Among the metal coordination compounds of the present invention, those having a maximum emission wavelength in emission spectrum in the range of 400 nm to 900 nm are preferable; those in the range of 500 nm to 800 nm are more preferable; those in the range of 550 nm to 750 nm are particularly preferable; and those in the range of 600 nm to 700 nm are most preferable.

The metal coordination compound of the present invention preferably emits red light.

The symbols used in formulae (1) to (13) above (M, $M^1$, m, $m^1$, n, Q, k, X, L, Ring A, Ring B, $R^1$ to $R^{74}$, and $R^0$) will be described below.

M represents a platinum group element. Specifically, it is iridium, platinum, rhodium, palladium, ruthenium, or osmium; among them, iridium, platinum, ruthenium, or osmium is preferable; iridium or platinum is particularly preferable; and iridium is most preferable.

As for the valency of M, it is preferably trivalent when M is iridium or rhodium. It is preferably divalent when M is platinum, palladium, osmium or ruthenium.

$M^1$ represents iridium, platinum, rhodium or palladium, preferably iridium or platinum, and more preferably iridium. As for the valency of $M^1$, it is preferably trivalent when $M^1$ is iridium or rhodium. It is preferably divalent when $M^1$ is platinum or palladium.

m represents an integer of 1 to 3; n represents an integer of 0 to 2; and m+n is 2 or 3. When M is iridium or rhodium, m+n is 3; m is preferably 2 or 3; and n is preferably 0 or 1. When M is platinum, palladium or copper, m+n is 2; m is preferably 1 or 2; and n is preferably 0 or 1. When M is ruthenium or osmium, m+n is 3; m is 1 to 3; and n is 0 to 2.

$m^1$ is 1 or 2. When $M^1$ is iridium or rhodium, $m^1$ is 2, and when $M^1$ is platinum or palladium, $m^1$ is 1.

Q represents a counter anion. The counter anion is not particularly limited, but preferably an alkali metal ion, an alkali-earth metal ion, a halogen ion, a perchlorate ion, a $PF_6$ ion, an ammonium ion, a $CF_3CF_2CF_2COO$ ion, a $SbF_6$ ion, a dicyan amide ion, a bis(trifluoromethanesulfonyl)amide ion, a borate ion or a phosphonium ion.

k is an integer of 0 to 2. k is preferably 0 or 1, more preferably 0.

X represents a halogen atom, preferably chlorine, bromine or iodine, more preferably chlorine or bromine, and particularly preferably chlorine.

L represents a bidentate ligand. It is preferably a neutral or anionic bidentate ligand, more preferably an anionic bidentate ligand, and particularly preferably a monoanionic bidentate ligand.

Further, L is preferably a bidentate ligand forming M-nitrogen and M-carbon bonds, a bidentate ligand forming M-nitrogen and M-oxygen bonds, a bidentate ligand forming two M-oxygen bonds, a bidentate ligand forming two M-nitrogen bonds, a bidentate ligand forming two M-sulfur bonds, a bidentate ligand forming two M-phosphorus bonds, or a bidentate ligand forming two M-carbon bonds; more preferably a bidentate ligand forming M-nitrogen and M-carbon bonds, a bidentate ligand forming M-nitrogen and M-oxygen bonds, a bidentate ligand forming two M-oxygen bonds, or a bidentate ligand forming two M-nitrogen bonds; particularly preferably an anionic bidentate ligand forming M-nitrogen and M-carbon bonds, an anionic bidentate ligand forming M-nitrogen and M-oxygen bonds, an anionic bidentate ligand forming two M-oxygen bonds, an anionic bidentate ligand forming two M-nitrogen bonds, or a neutral bidentate ligand forming two M-nitrogen bonds; and most preferably, an anionic bidentate ligand forming M-nitrogen and M-carbon bonds, an anionic bidentate ligand forming M-nitrogen and M-oxygen bonds, or an anionic bidentate ligand forming two M-oxygen bonds.

Examples of the bidentate ligands forming M-nitrogen and M-carbon bonds include 2-phenylpyridine derivatives, 2-phenylquinoline derivatives, 1-phenylisoquinoline derivatives, 3-phenylisoquinoline derivatives, 2-(2-benzothiophenyl)pyridine derivatives, 2-thienyl pyridine derivatives, 1-phenylpyrazole derivatives, 1-phenyl-1H-indazole derivatives, 2-phenylbenzothiazole derivatives, 2-phenylthiazole derivatives, 2-phenylbenzoxazole derivatives, 2-phenyloxazole derivatives, 2-furanylpyridine derivatives, 2-(2-benzofuranyl)pyridine derivatives, 7,8-benzoquinoline derivatives, 7,8-benzoquinoxaline derivatives, dibenzo[f,h]quinoline derivatives, dibenzo[f,h]quinoxaline derivatives, benzo[h]-5,6-dihydroquinoline derivatives, 9-(2-pyridyl)carbazole derivatives, 1-(2-pyridyl)indole derivatives, 1-(1-naphthyl)isoquinoline derivatives, 1-(2-naphthyl)isoquinoline derivatives, 2-(2-naphthyl)quinoline derivatives, 2-(1-naphthyl) quinoline derivatives, 3-(1-naphthyl)isoquinoline derivatives, 3-(2-naphthyl)isoquinoline derivatives, 2-(1-naphthyl)pyridine derivatives, 2-(2-naphthyl)pyridine derivatives, 6-phenylphenanthridine derivatives, 6-(1-naphthyl)phenanthridine derivatives, 6-(2-naphthyl)phenanthridine derivatives, benzo[c]acridine derivative, benzo[c]phenazine derivatives, dibenzo[a,c]acridine derivatives, dibenzo[a,c]phenazine derivatives, 2-phenylquinoxaline derivatives, 2,3-diphenylquinoxaline derivatives, 2-benzylpyridine derivatives, 2-phenylbenzimidazole derivatives, 3-phenyl pyrazole derivatives, 4-phenyl imidazole derivatives, 1-phenylimidazole derivatives, 4-phenyltriazole derivatives, 5-phenyltetrazole derivatives, 2-alkenylpyridine derivatives, and 2-phenylcyclopenta[de]quinoline derivatives.

Preferable examples thereof include 2-phenylpyridine derivatives, 2-phenylquinoline derivatives, 1-phenylisoquinoline derivatives, 3-phenylisoquinoline derivatives, 2-(2-benzothiophenyl)pyridine derivatives, 2-thienylpyridine derivatives, 1-phenylpyrazole derivatives, 7,8-benzoquinoline derivatives, 7,8-benzoquinoxaline derivatives, dibenzo[f,h]quinoline derivatives, dibenzo[f,h]quinoxaline derivatives, benzo[h]-5,6-dihydroquinoline derivatives, 1-(1-naphthyl)isoquinoline derivatives, 1-(2-naphthyl)isoquinoline derivatives, 2-(2-naphthyl)quinoline derivatives, 2-(1-naphthyl) quinoline derivatives, 3-(1-naphthyl)isoquinoline derivatives, 3-(2-naphthyl)isoquinoline derivatives, 2-(1-naphthyl)pyridine derivatives, 2-(2-naphthyl)pyridine derivatives, 6-phenylphenanthridine derivatives, 6-(1-naphthyl)phenanthridine derivatives, 6-(2-naphthyl)phenanthridine derivatives, benzo[c]acridine derivative, benzo[c]phenazine derivatives, dibenzo[a,c]acridine derivatives, dibenzo[a,c]phenazine derivatives, 2-phenylquinoxaline derivatives, 2,3-diphenylquinoxaline derivatives, 2-benzylpyridine derivatives, 2-phenylbenzimidazole derivatives, 1-phenylimidazole derivatives, and 2-phenylcyclopenta[de]quinoline derivatives.

More preferable examples thereof include 2-phenylpyridine derivatives, 2-phenylquinoline derivatives, 1-phenylisoquinoline derivatives, 3-phenylisoquinoline derivatives, 2-(2-benzothiophenyl)pyridine derivatives, 2-thienylpyridine derivatives, 1-phenylpyrazole derivatives, 7,8-benzoquinoline derivatives, 7,8-benzoquinoxaline derivatives, dibenzo[f,h]quinoline derivatives, dibenzo[f,h]quinoxaline derivatives, 2-(2-naphthyl)quinoline derivatives, 2-(1-naphthyl)quinoline derivatives, 3-(1-naphthyl)isoquinoline derivatives, 3-(2-naphthyl)isoquinoline derivatives, 2-(1-naphthyl)pyridine derivatives, 2-(2-naphthyl)pyridine derivatives, benzo[c]acridine derivative, benzo[c]phenazine derivatives, dibenzo[a,c]acridine derivatives, dibenzo[a,c]phenazine derivatives, 2-phenylquinoxaline derivatives, 2,3-diphenylquinoxaline derivatives, 2-phenylbenzimidazole derivatives, 1-phenylimidazole derivatives, and 2-phenylcyclopenta[de]quinoline derivatives.

Particularly preferable examples thereof include 2-phenylpyridine derivatives, 2-phenylquinoline derivatives, 1-phenylisoquinoline derivatives, 3-phenylisoquinoline derivatives, 7,8-benzoquinoline derivatives, 7,8-benzoquinoxaline derivatives, dibenzo[f,h]quinoline derivatives, dibenzo[f,h]quinoxaline derivatives, 2-(2-naphthyl)quinoline derivatives, 2-(1-naphthyl)quinoline derivatives, benzo[c]acridine derivative, benzo[c]phenazine derivatives, 2-phenylquinoxaline derivatives, 2,3-diphenylquinoxaline derivatives, 2-phenylbenzimidazole derivatives, 1-phenylimidazole derivatives, and 2-phenylcyclopenta[de]quinoline derivatives.

Most preferable examples thereof include 2-phenylpyridine derivatives, 2-phenylquinoline derivatives, 1-phenylisoquinoline derivatives, and 2-phenylcyclopenta[de]quinoline derivatives.

Specific examples thereof are described in, for example, WO 2004/085450, WO 2006/075905, WO 2002/44189, WO 2002-/45466, WO 2006/046980, WO 2006-059758, JP-A-2006-182772, JP-A-2006-151888, JP-A-2006-151887, JP-A-2006-93665, JP-A-2006-100393, WO 2004/101707, WO 2005/073339, WO 2005/056719, WO 2005/056716, WO 2005/056715, WO 2005/048315, WO 2005/033244, WO 2004/081019, WO 2004/045000, WO 2004/044089, WO 2004/026886, JP-A-2002-234894, JP-A-2002-226495, JP-A-2003-59667, JP-A-2001-345183, JP-A-2001-247859, JP-A-2003-7469, JP-A-2003-73388, JP-A-2003-109758, JP-A-2003-123982, JP-A-2003-133074, JP-A-2003-131464, JP-A-2003-131463, JP-A-2004-107441, JP-A-2004-67658, JP-A-2003-342284, JP-A-2005-29784, JP-A-2005-29783, JP-A-2005-29782, JP-A-2005-23072, JP-A-2005-23071, JP-A-2005-23070, JP-A-2005-2101, JP-A-2005-2053, JP-A-2005-78996, JP-A-2005-68110, JP-A-2005-60374, JP-A-2005-44802, JP-A-2005-29785, JP-A-2005-104843, JP-A-2005-97549, JP-A-2005-220136, JP-A-2005-213348, JP-A-2005-170851, JP-A-2005-163036, JP-A-2005-154396, JP-A-2005-272411, JP-A-2005-327526, JP-A-2005-325048, JP-A-2005-314663, JP-A-2006-13222, JP-A-2006-8688, JP-A-2006-80419, JP-A-2006-76969, WO 2002/15645, WO 2002/02714, WO 2002/064700, WO 2003/033617, WO 2003/000661, WO 2002/081488, and US 2006/0251923.

Examples of the bidentate ligands forming M-nitrogen and M-oxygen bonds include picolinic acid derivatives, pyridinesulfonic acid derivatives, quinolinesulfonic acid derivatives, and quinolinecarboxylic acid derivatives, preferably, picolinic acid derivatives and pyridinesulfonic acid derivatives. Specific examples thereof are described in, for example, JP-A-2006-16394, JP-A-2006-307210, JP-A-2006-298900, WO 2006/028224, WO 2006/097717, JP-A-2004-111379, and JP-A-2005-29785.

Examples of the bidentate ligands forming two M-oxygen bonds include β-diketone derivatives, carboxylic acid derivatives, and tropolone derivatives. β-diketone derivatives and carboxylic acid derivatives are preferable, and β-diketone derivatives are more preferable. Specific examples thereof are described in, for example, JP-A-2005-35902, JP-A-2004-349224, JP-A-2006-28101, and JP-A-2005-29785.

Examples of the bidentate ligands forming two M-sulfur bonds include dithiocarboxylic acid derivatives. Specific examples thereof are described in, for example, JP-A-2004-349224, and JP-A-2003-264086.

Examples of the bidentate ligands forming two M-nitrogen bonds include 2,2'-bipyridine derivatives, 1,10-phenanthroline derivatives, 2,2'-biquinoline derivatives, 2,2'-dipyridylamine derivatives, imidazole derivatives, pyrazolylborate derivatives, and pyrazole derivatives. 2,2'-bipyridine derivatives, 1,10-phenanthroline derivatives, and 2,2'-dipyridylamine derivatives are preferable. Specific examples thereof are described in, for example, JP-A-2005-298483, JP-A-2006-213720, and JP-A-2003-133074.

The bidentate ligand forming two M-phosphorus bonds is a phosphine or phosphite derivative. Specific examples thereof are described in, for example, JP-A-2002-170684, JP-A-2005-247791, JP-A-2005-239648, and JP-A-2006-286749.

The bidentate ligand forming M-carbon bond is a carbene derivative. Specific examples thereof are described in, for example, WO 2005/113704, and WO 2006/115301.

The ring A represents an aromatic hydrocarbon ring or an aromatic hetero ring, each of which ring may have one or more substituents. An aromatic hydrocarbon or hetero ring having 4 to 50 carbon atoms is preferable, an aromatic hydrocarbon or hetero ring having 4 to 30 carbon atoms is more preferable, and an aromatic hydrocarbon or hetero ring having 4 to 15 carbon atoms is particularly preferable. Examples of the ring A satisfying such conditions include a benzene ring, a naphthalene ring, a pyridine ring, a pyridazine ring, a pyrimidine ring, a pyrazine ring, a pyrazole ring, a furan ring, a thiophene ring, a fluorene ring, a substituted benzene ring, a substituted naphthalene ring, a substituted pyridine ring, a substituted pyridazine ring, a substituted pyrimidine ring, a substituted pyrazine ring, a substituted pyrazole ring, a substituted furan ring, a substituted thiophene ring, and a substituted fluorene ring, and the like; a benzene ring, a substituted benzene ring, a naphthalene ring, a substituted naphthalene ring, a thiophene ring, a substituted thiophene ring, a furan ring, a substituted furan ring, a fluorene ring, or a substituted fluorene ring is preferable; a benzene ring, a substituted benzene ring, a naphthalene ring, a substituted naphthalene ring, a fluorene ring, or a substituted fluorene ring is more preferable; and a benzene ring or a substituted benzene ring is particularly preferable. The kinds and favorable range of the substituent(s) on the ring A are the same as those for the $R^1$ to $R^{74}$ described below. The hydrogen atoms in the substituents may be replaced with fluorine atoms.

Examples of the rings B include a benzene ring, a substituted benzene ring, a naphthalene ring, a substituted naphthalene ring, a thiophene ring, a substituted thiophene ring, a furan ring, a substituted furan ring, a fluorene ring, and a substituted fluorene ring; a benzene ring, a substituted benzene ring, a naphthalene ring, a substituted naphthalene ring, a fluorene ring, or a substituted fluorene rings is preferable; and a benzene ring or a substituted benzene ring is more preferable. The kind and favorable range of the substituent(s) on the ring B are the same as those for $R^1$ to $R^{74}$ described below. The hydrogen atoms in the substituents may be replaced with fluorine atoms.

$R^1$ to $R^{74}$ and $R^0$ each independently represent a hydrogen atom or a substituent. Examples of the substituent include an alkyl group (preferably an alkyl group having 1 to 30 carbon atoms, more preferably 1 to 20 carbon atoms, particularly preferably 1 to 10 carbon atoms, e.g. methyl, ethyl, isopropyl, t-butyl, n-octyl, n-decyl, n-hexadecyl, cyclopropyl, cyclopentyl, and cyclohexyl), an alkenyl group (preferably an alkenyl group having 2 to 30 carbon atoms, more preferably 2 to 20 carbon atoms, particularly preferably 2 to 10 carbon atoms, e.g. vinyl, allyl, 2-butenyl, and 3-pentenyl), an alkynyl group (preferably an alkynyl group having 2 to 30 carbon atoms, more preferably 2 to 20 carbon atoms, particularly preferably 2 to 10 carbon atoms, e.g. propargyl, and 3-pentynyl), an aryl group (preferably an aryl group having 6 to 30 carbon atoms, more preferably 6 to 20 carbon atoms, particularly preferably 6 to 12 carbon atoms, e.g. phenyl, p-methylphenyl, naphthyl, and anthranyl), an amino group (preferably an amino group having 0 to 30 carbon atoms, more preferably 0 to 20 carbon atoms, particularly preferably 0 to 10 carbon atoms, e.g. amino, methylamino, dimethylamino, diethylamino, dibenzylamino, diphenylamino, and ditolylamino), an alkoxy group (preferably an alkoxy group having 1 to 30 carbon atoms, more preferably 1 to 20 carbon atoms, particularly preferably 1 to 10 carbon atoms, e.g. methoxy, ethoxy, butoxy, and 2-ethylhexyloxy), an aryloxy group (preferably an aryloxy group having 6 to 30 carbon atoms, more preferably 6 to 20 carbon atoms, particularly preferably 6 to 12 carbon atoms, e.g. phenyloxy, 1-naphtyloxy, and 2-naphtyloxy), a heterocyclic oxy group (preferably a heterocyclic oxy group having 1 to 30 carbon atoms, more preferably 1 to 20 carbon atoms, particularly preferably 1 to 12 carbon atoms, e.g. pyridyloxy, pyrazyloxy, pyrimidyloxy, and quinolyloxy), an acyl group (preferably an acyl group having 1 to 30 carbon atoms, more preferably 1 to 20 carbon atoms, particularly preferably 1 to 12 carbon atoms, e.g. acetyl, benzoyl, formyl, and pivaloyl group), an alkoxycarbonyl group (preferably an alkoxycarbonyl group having 2 to 30 carbon atoms, more preferably 2 to 20 carbon atoms, particularly preferably 2 to 12 carbon atoms, e.g. methoxycarbonyl, and ethoxycarbonyl), an aryloxycarbonyl group (preferably an aryloxycarbonyl group having 7 to 30 carbon atoms, more preferably 7 to 20 carbon atoms, particularly preferably 7 to 12 carbon atoms, e.g. phenyloxycarbonyl), an acyloxy group (preferably an acyloxy group having 2 to 30 carbon atoms, more preferably 2 to 20 carbon atoms, particularly preferably 2 to 10 carbon atoms, e.g. acetyloxy, and benzoyloxy), an acylamino group (preferably an acylamino group having 2 to 30 carbon atoms, more preferably 2 to 20 carbon atoms, particularly preferably 2 to 10 carbon atoms, e.g. acetylamino, and benzoylamino), an alkoxycarbonylamino group (preferably an alkoxycarbonylamino group having 2 to 30 carbon atoms, more preferably 2 to 20 carbon atoms, particularly preferably 2 to 12 carbon atoms, e.g. methoxycarbonylamino), an aryloxycarbonylamino group (preferably an aryloxycarbonylamino group having 7 to 30 carbon atoms, more preferably 7 to 20 carbon atoms, particularly preferably 7 to 12 carbon atoms, e.g. phenyloxycarbonylamino), a sulfamoylamino group (preferably a sulfamoylamino group having 1 to 30 carbon atoms, more preferably 1 to 20 carbon atoms, particularly preferably 1 to 12 carbon atoms, e.g. methanesulfonylamino, and benzenesulfonylamino), a sulfamoyl group (preferably a sulfamoyl group having 0 to 30 carbon atoms, more preferably 0 to 20 carbon atoms, particularly preferably 0 to 12 carbon atoms, e.g. sulfamoyl, methylsulfamoyl, dimethylsulfamoyl, and phenylsulfamoyl), a carbamoyl group (preferably a carbamoyl group having 1 to 30 carbon atoms, more preferably 1 to 20 carbon atoms, particularly preferably 1 to 12 carbon atoms, e.g. carbamoyl, methylcarbamoyl, diethylcarbamoyl, and phenylcarbamoyl), an alkylthio group (preferably an alkylthio group having 1 to 30 carbon atoms, more preferably 1 to 20 carbon atoms, particularly preferably 1 to 12 carbon atoms, e.g. methylthio, and ethylthio), an arylthio group (preferably an arylthio group having 6 to 30 carbon atoms, more preferably 6 to 20 carbon atoms, particularly preferably 6 to 12 carbon atoms, e.g. phenylthio group), a heterocyclic thio group (preferably a heterocyclic thio group having 1 to 30 carbon atoms, more preferably 1 to 20 carbon atoms, particularly preferably 1 to 12 carbon atoms, e.g. pyridylthio, 2-benzimidazorylthio, 2-benzoxazolylthio, and 2-benzothiazolylthio), a sulfonyl group (preferably a sulfonyl group having 1 to 30 carbon atoms, more preferably 1 to 20 carbon atoms, particularly preferably 1 to 12 carbon atoms, e.g. mesyl, and tosyl), a sulfinyl group (preferably a sulfinyl group having 1 to 30 carbon atoms, more preferably 1 to 20 carbon atoms, particularly preferably 1 to 12 carbon atoms, e.g. methanesulfinyl, and benzenesulfinyl), a ureido group (preferably a ureido group having 1 to 30 carbon atoms, more preferably 1 to 20 carbon atoms, particularly preferably 1 to 12 carbon atoms, e.g. ureido, methylureido, and phenylureido), a phosphoric acid amido group (preferably a phosphoric acid amido group having 1 to 30, more preferably 1 to 20, and particularly preferably 1 to 12 carbon atoms, e.g. diethylphosphoric acid amido, and phenylphosphoric acid amido), a hydroxy group, a mercapto group, a halogen atom (e.g. a fluorine atom, a chlorine atom, a bromine atom, or an iodine atom), a cyano group, a sulfo group, a carboxyl group, a nitro group, a trifluoromethyl group, a hydroxamic acid group, a sulfino group, a hydrazino group, an imino group, a heterocyclic group (preferably a heterocyclic group having 1 to 30, and more preferably 1 to 12 carbon atoms; containing, as a hetero atom(s), for example, a nitrogen atom, an oxygen atom, or a sulfur atom, and specifically, e.g. imidazolyl, pyridyl, quinolyl, furyl, thienyl, piperidyl, morpholino, benzoxazolyl, benzimidazolyl, benzthiazolyl, carbazolyl, and azepinyl group can be exemplified), a silyl group (preferably a silyl group having 3 to 40 carbon atoms, more preferably 3 to 30 carbon atoms, particularly preferably 3 to 24 carbon atoms, e.g. trimethylsilyl, and triphenylsilyl), and a silyloxy group (preferably a silyloxy group having 3 to 40 carbon atoms, more preferably 3 to 30 carbon atoms, particularly preferably 3 to 24 carbon atoms, e.g. trimethylsilyloxy, and triphenylsilyloxy).

Among those, preferable examples of the substituent include a cyano group, a hydroxy group, a nitro group, a trifluoromethyl group, a halogen atom, a substituted or unsubstituted alkenyl group having 2 to 10 carbon atoms, a substituted or unsubstituted alkyl group having 1 to 10 carbon atoms, a substituted or unsubstituted alkoxy group having 1 to 10 carbon atoms, a substituted or unsubstituted aryl group having 6 to 12 carbon atoms, a substituted or unsubstituted amino group having 0 to 10 carbon atoms, and a substituted or unsubstituted heterocyclic group having 1 to 12 carbon atoms. Any of the hydrogen atoms in the substituents may be replaced with a fluorine atom.

It is also preferable that adjacent two or more groups $R^1$ to $R^{74}$ bond to each other, to form a saturated or unsaturated carbon ring or hetero ring. Groups $R^4$ and $R^5$, $R^{60}$ and $R^{61}$, $R^{66}$ and $R^{67}$, and $R^{72}$ and $R^{73}$ each preferably bonds to each other; groups $R^4$ and $R^5$, $R^{60}$ and $R^{61}$, $R^{66}$ and $R^{67}$, and $R^{72}$ and $R^{73}$ more preferably each bond to each other, to form a unsaturated carbon ring; groups $R^4$ and $R^5$, $R6^0$ and $R^{61}$, $R^{66}$ and $R^{67}$, and $R^{72}$ and $R^{73}$ each particularly preferably bond to each other, to form a benzene ring. Thus, particularly preferably, an indeno[1,2,3-de]quinoline skeleton (see formula (14)) is formed.

[Chemical formula 7]

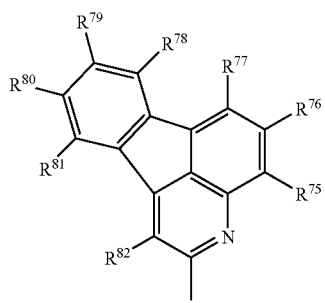

Formula 14

Indeno[1,2,3-de]quinoline skeleton

In formula (14), N represents a nitrogen atom, $R^{75}$ to $R^{82}$ each independently represent a hydrogen atom or a substituent, and the adjacent substituents may bond to each other, to form a ring structure.

Among the bidentate ligands represented by formula (13), the bidentate ligands represented by formula (15) are preferable; the bidentate ligands represented by any one of formulae (16) to (21) are more preferable; the bidentate ligands represented by any one of formulae (16) to (19) are particularly preferable; and the bidentate ligands represented by formula (16) are most preferable.

[Chemical formula 8]

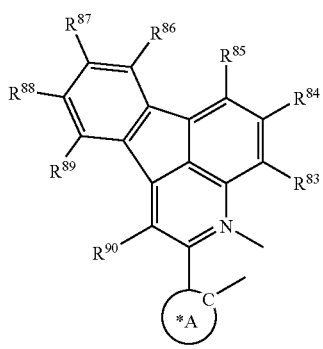

Formula (15)

*A means Ring A

[Chemical formula 9]

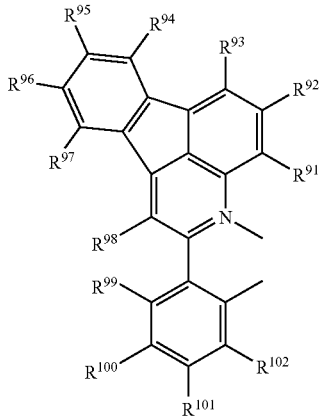

Formula (16)

[Chemical formula 10]

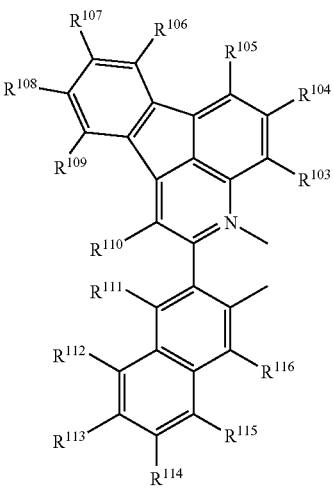

Formula (17)

[Chemical formula 11]

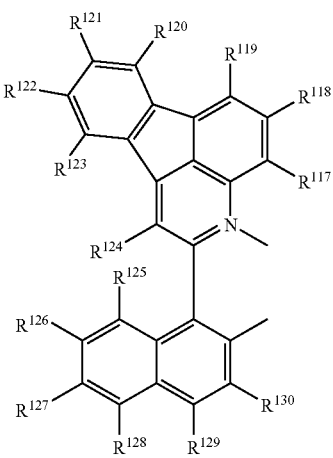

Formula (18)

[Chemical formula 12]

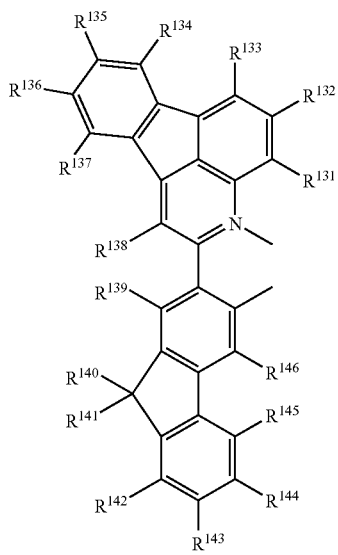

Formula (19)

[Chemical formula 13]

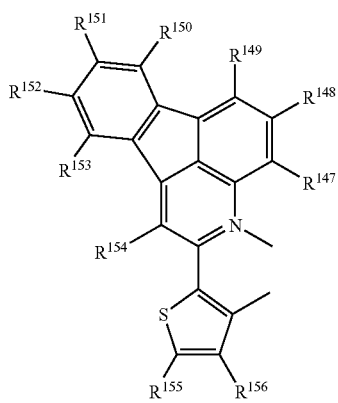

Formula (20)

[Chemical formula 14]

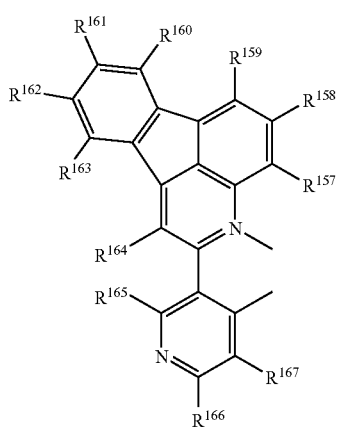

Formula (21)

In formulae (15) to (21), N represents a nitrogen atom, $R^{83}$ to $R^{167}$ each independently represent a hydrogen atom or a substituent, and the adjacent substituents may bond to each other, to form a ring structure.

As the bidentate ligand represented by formula (13), the bidentate ligand represented by any one of formulae (22) to (25) can be used preferably, and the bidentate ligand represented by formula (22) can be used more preferably.

[Chemical formula 15]

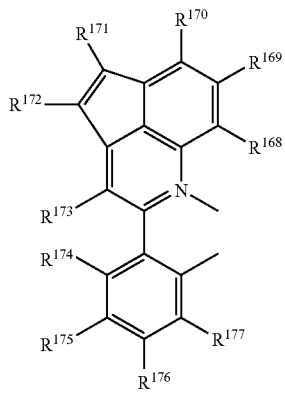

Formula (22)

[Chemical formula 16]

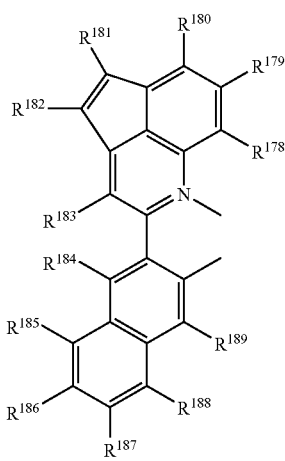

Formula (23)

[Chemical formula 17]

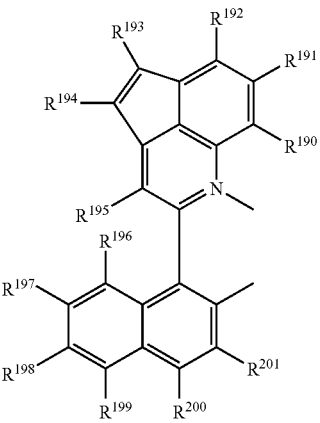

Formula (24)

-continued

[Chemical formula 18]

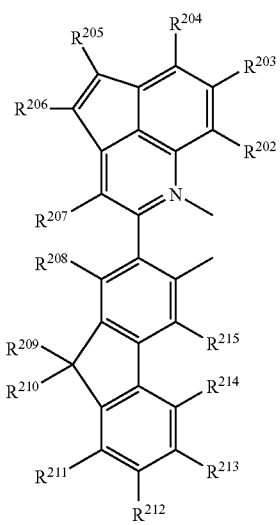

Formula (25)

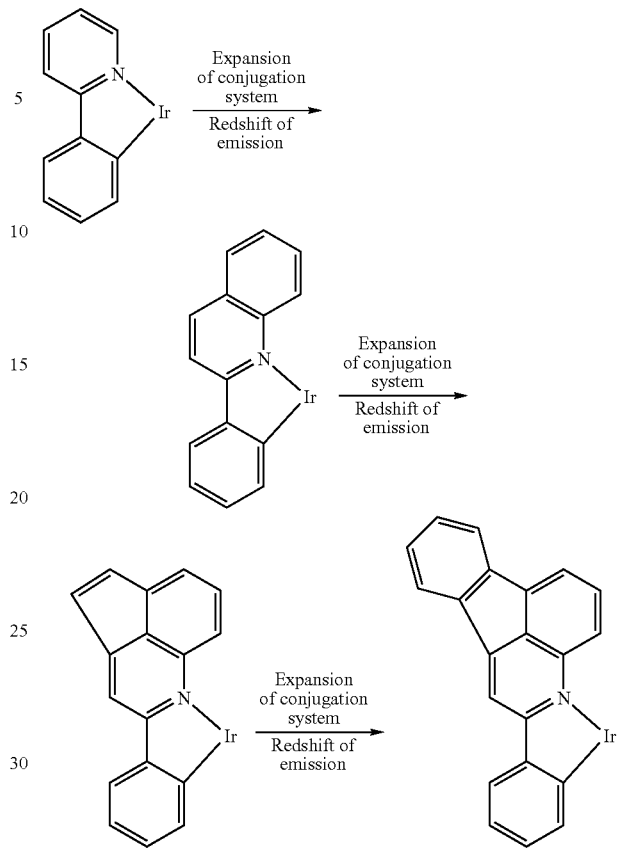

In formulae (22) to (25), N represents a nitrogen atom, $R^{168}$ to $R^{215}$ each independently represent a hydrogen atom or a substituent, and the adjacent substituents may bond to each other, to form a ring structure.

$R^{75}$ to $R^{215}$ in formulae (14) to (25) have the same meanings as defined for $R^1$ to $R^{74}$, and the favorable ranges thereof are also the same.

$R^{23}$ and $R^{24}$ are particularly preferably an alkyl group or an aryl group, most preferably an alkyl group. $R^0$ is particularly preferably a hydrogen atom or an alkyl group, most preferably a hydrogen atom. $R^{44}$ is particularly preferably a hydrogen atom, an alkyl group, an aryl group or a heterocyclic group; most preferably an alkyl group or an aryl group. $R^{49}$, $R^{50}$, $R^{55}$ and $R^{56}$ are particularly preferably an alkyl group, an aryl group or an alkoxy group; most preferably an aryl group. $R^{140}$, $R^{141}$, $R^{209}$ and $R^{210}$ are particularly preferably an alkyl group.

Further, the cyclopenta[de]quinoline skeleton-containing metal coordination compounds of the present invention (e.g., 2-phenylcyclopenta[de]quinoline-containing iridium complexes) have an expanded ligand conjugation system, and thus shows red-emission characteristics excellent in color purity, compared to pyridine skeleton-containing metal coordination compounds (e.g., 2-phenylpyridine-containing iridium complexes) and quinoline skeleton-containing metal coordination compounds (e.g., 2-phenylquinoline-containing iridium complexes). Further, indeno[1,2,3-de]quinoline skeleton-containing metal coordination compounds (e.g., 2-phenylindeno[1,2,3-de]quinoline-containing iridium complexes), which have a ligand conjugation system much more expanded than that of cyclopenta[de]quinoline, show deeper red emission, and thus they are particularly useful as red-light-emitting materials higher in color purity.

Further, it is possible to adjust the emission wavelength of the cyclopenta[de]quinoline skeleton-containing metal coordination compound of the present invention, by modifying the ligand L above. In the field of the art, the ligand L is considered not directly contributed to the emission characteristics of metal coordination compound, but considered to be capable of changing the emission characteristics slightly, and thus, called as an auxiliary ligand (see e.g., JP-T-2006-513278 ("JP-T" means published searched patent publication)).

On the other hand, the cyclopenta[de]quinoline skeleton-containing bidentate ligand is considered to contribute mainly in expression of the emission characteristics (red-emission characteristics) by the metal coordination compound of the present invention, as described above. Thus, use of a cyclopenta[de]quinoline skeleton-containing bidentate organic ligand in combination with a known auxiliary ligand (e.g., a picolinic acid derivative, pyridinesulfonic acid derivative, quinolinesulfonic acid derivative, quinolinecarboxylic acid derivative, β-diketone derivative, carboxylic acid derivative, tropolone derivative, 2,2'-bipyridine derivative, 1,10-phenanthroline derivative, 2,2'-biquinoline derivative, 2,2'-dipyridylamine derivative, imidazole derivative, pyrazole derivative, phosphine derivative, phosphite derivative, 2-phenylpyridine derivative, 2-phenylquinoline derivative, 1-phenylisoquinoline derivative, 3-phenylisoquinoline derivative, or the like), allows modification of the emission wavelength mainly in the red region, according to application intended.

Further, introduction of a substituent into the bidentate ligand having a cyclopenta[de]quinoline skeleton, also allows control of the emission wavelength of the metal coordination compound of the present invention. For example, introduction of an electron-withdrawing group (e.g., fluorine atom, cyano group, or trifluoromethyl group) or an electron-donating group (e.g., methyl or methoxy group) into the ring A, can lead to redshift or blueshift of the emission wavelength. In addition, introduction of an alkyl group (e.g., methyl, ethyl, iso-propyl, tert-butyl, n-octyl, n-decyl, n-hexadecyl, cyclopropyl, cyclopentyl, or cyclohexyl) into the bidentate ligand having a cyclopenta[de]quinoline skeleton, can improve the solubility of the metal coordination compound of the present invention in a solvent. Improvement in solubility in a solvent is advantageous in production of light-emitting devices by coating process, and the resultant-improved metal complex can be used favorably in such a production. Further, introduction of a trifluoromethyl group or fluorine substituent into the bidentate ligand having a cyclopenta[de]quinoline skeleton leads to decrease in intermolecular interaction, thereby to make it possible to improve the sublimation property of the compound of the present invention. In this case, it is advantageous in production of light-emitting devices in the film-making process by vacuum deposition.

Further, the metal coordination compound represented by formula (1), (2) or (11) may be a low-molecular weight compound, and also may be used as a so-called oligomer or polymer compound having recurring units containing the partial structure represented by formula (1), (2) or (11) (its mass-average molecular weight (based on polystyrene standard) is preferably 1,000 to 5,000,000, more preferably 2,000 to 1,000,000, and more preferably 3,000 to 100,000). Examples of the polymerization method include those described in JP-A-2003-119179, JP-A-2003-171391 and JP-A-2003-113246, Japanese Patent No. 2003-206320, and JP-A-2003-147021.

Further, the metal coordination compound represented by formula (1) or (2) can be used as a so-called dendrimer having an orderly branched structure from the center. Examples of the metal complex-containing light-emitting dendrimers include those described in JP-T-2004-530254, JP-T-2005-521210, JP-T-2005-537321, JP-A-2006-188673, and WO 2005/026144.

It is thus possible, by the method described above, to produce a light-emitting polymer and a light-emitting dendrimer, by using the metal coordination compound represented by formula (1) or (2) as a light-emitting material.

Preferable examples of the bidentate ligands represented by formula (12) or (13) are shown in Tables 1 and 2.

TABLE 1

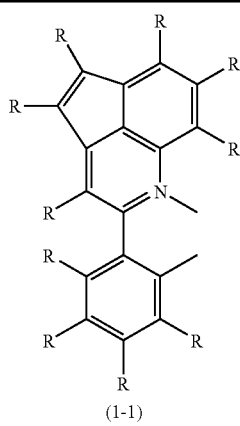

(1-1)

TABLE 1-continued

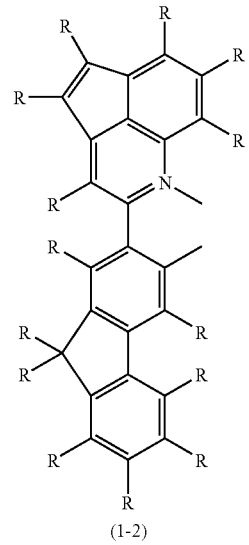

(1-2)

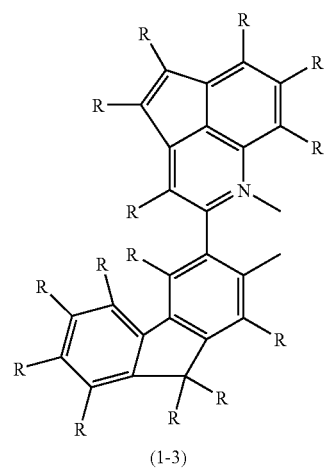

(1-3)

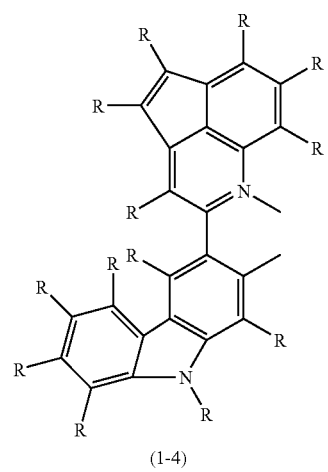

(1-4)

TABLE 1-continued
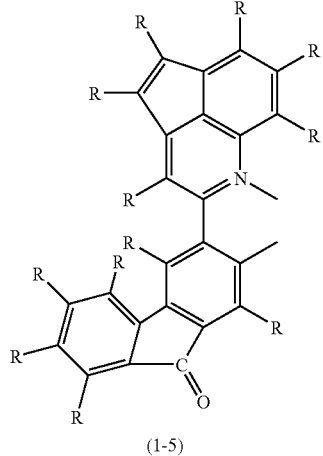
(1-5)
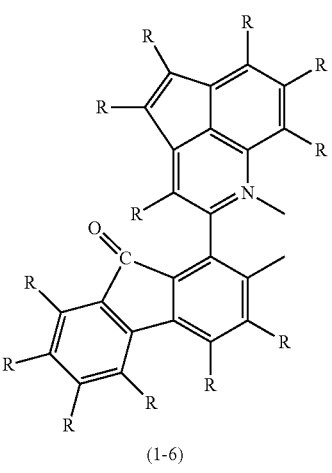
(1-6)
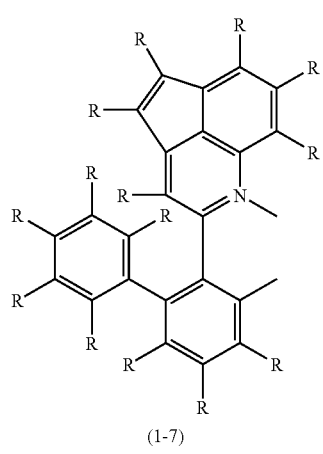
(1-7)
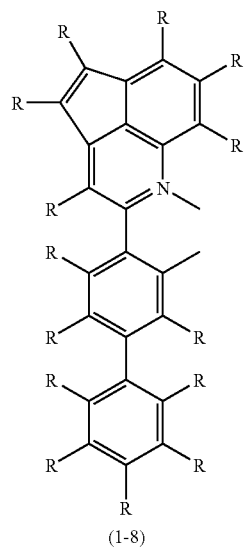
(1-8)
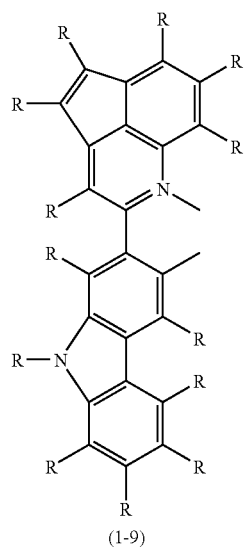
(1-9)
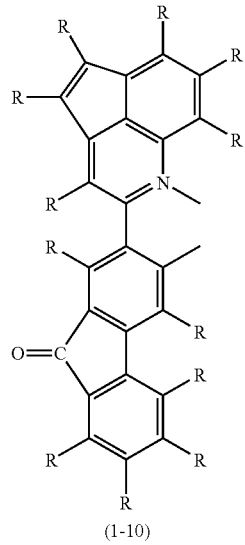
(1-10)

TABLE 1-continued
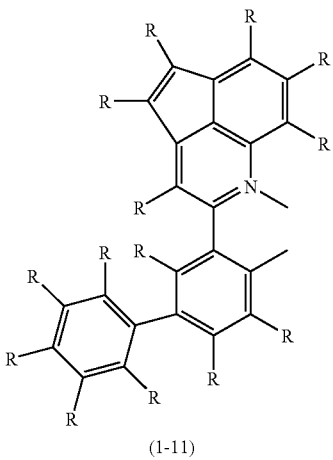
(1-11)
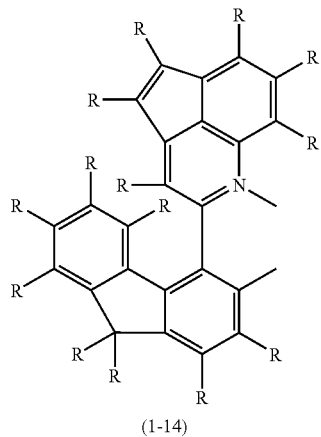
(1-14)
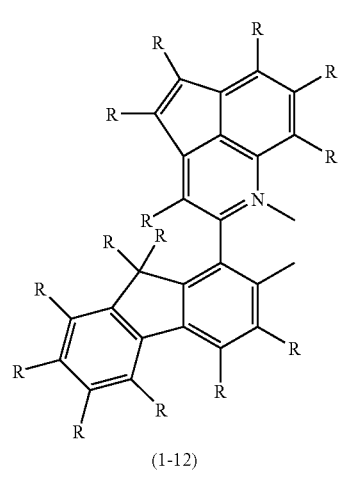
(1-12)
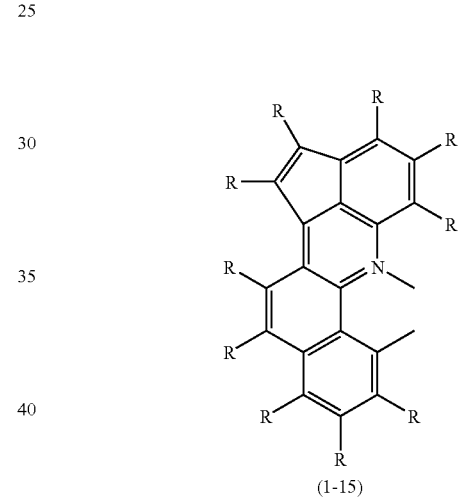
(1-15)
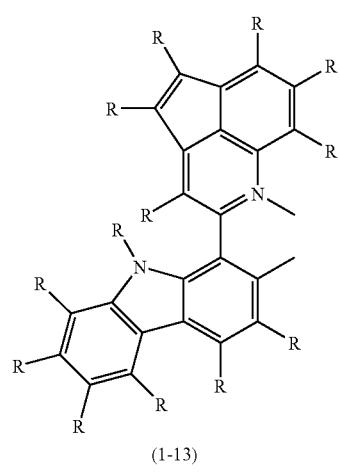
(1-13)
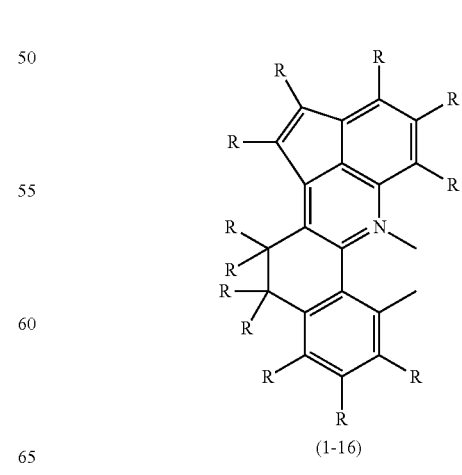
(1-16)

TABLE 1-continued
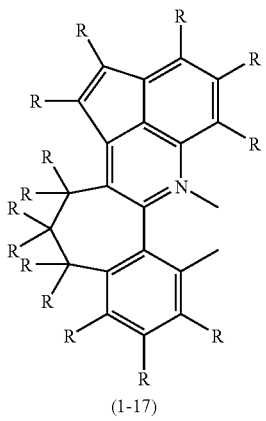
(1-17)
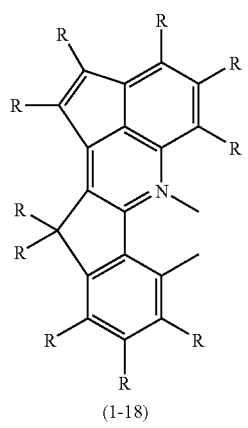
(1-18)
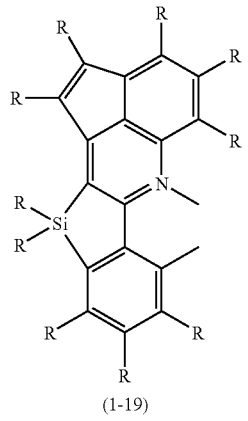
(1-19)
TABLE 1-continued
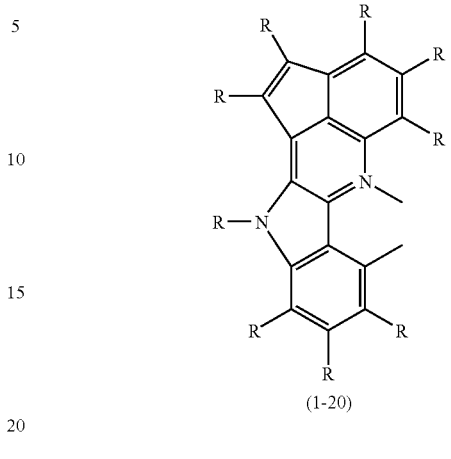
(1-20)
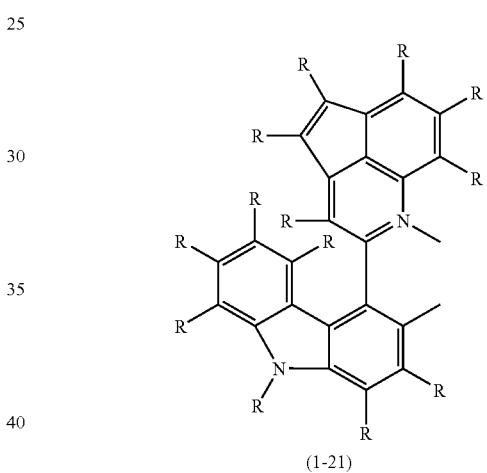
(1-21)
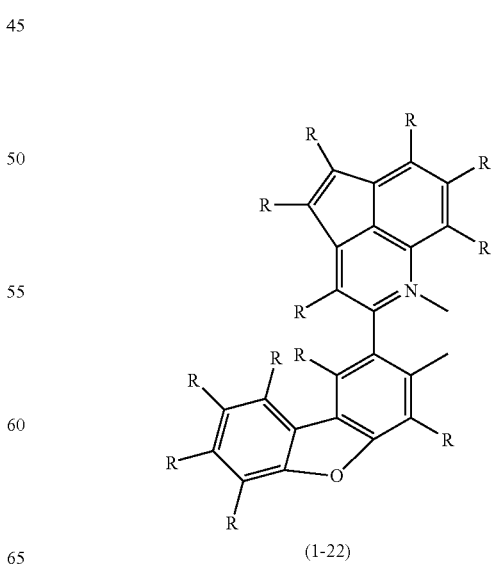
(1-22)

TABLE 1-continued
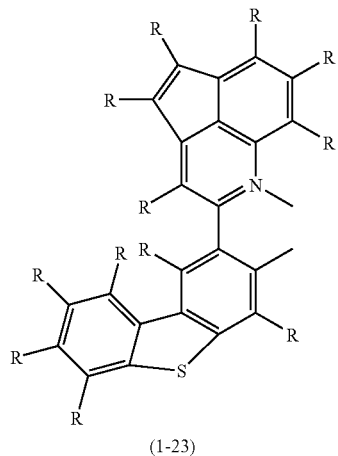
(1-23)
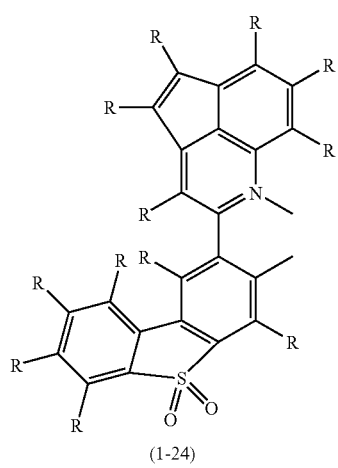
(1-24)
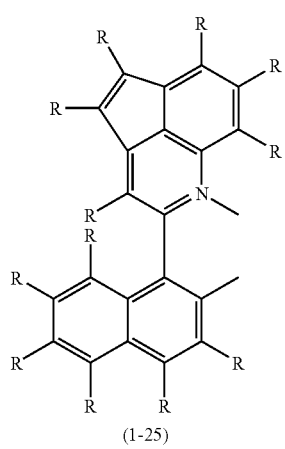
(1-25)
TABLE 1-continued
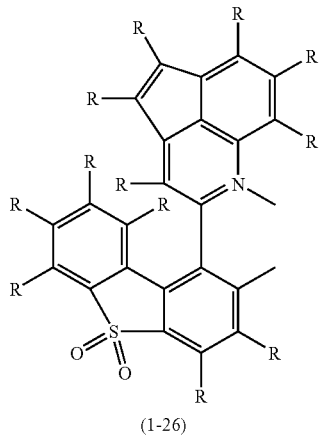
(1-26)
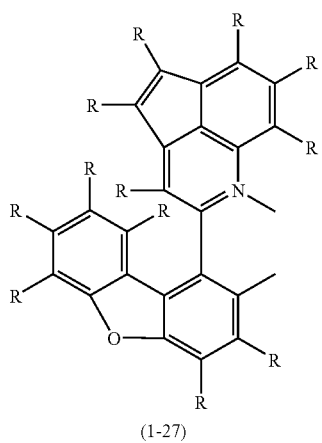
(1-27)
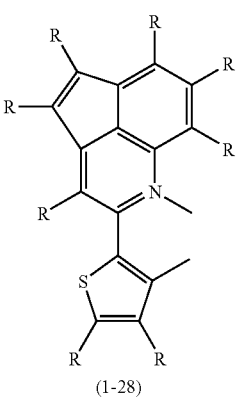
(1-28)

TABLE 1-continued
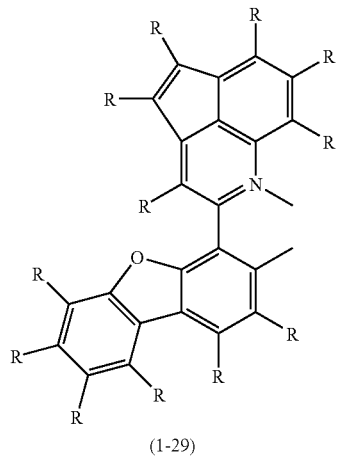
(1-29)
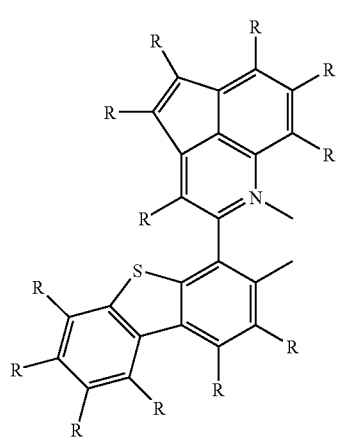
(1-30)
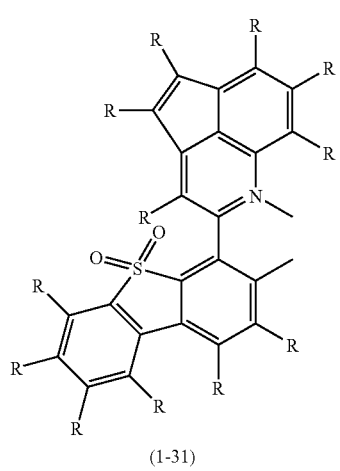
(1-31)
TABLE 1-continued
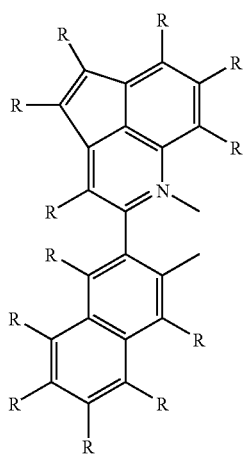
(1-32)
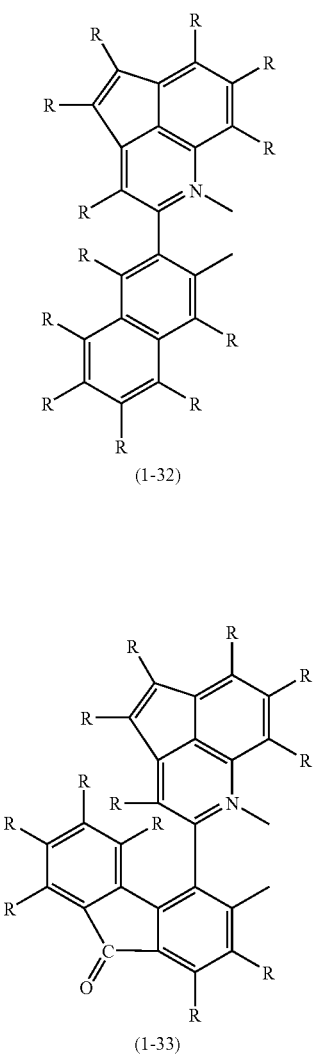
(1-33)
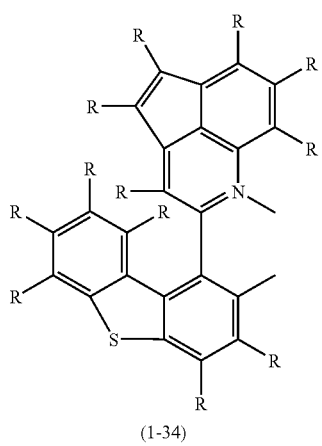
(1-34)

TABLE 1-continued
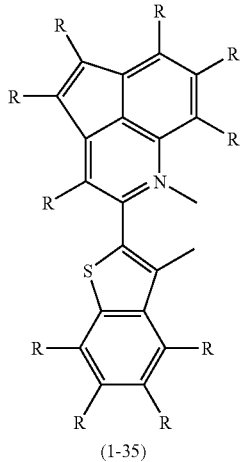
(1-35)
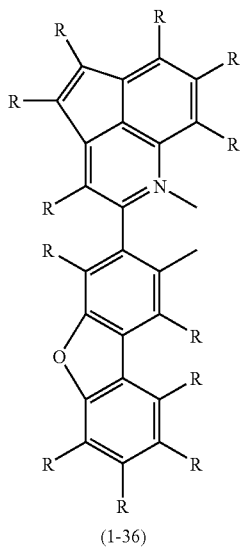
(1-36)
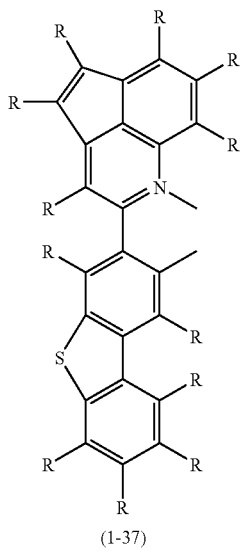
(1-37)
TABLE 1-continued
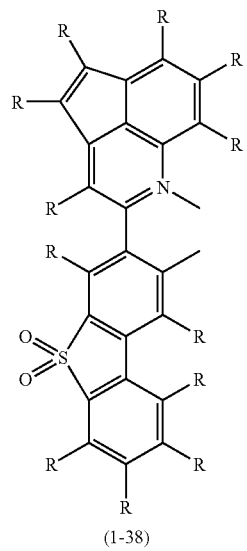
(1-38)
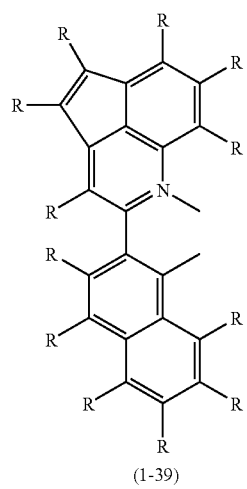
(1-39)
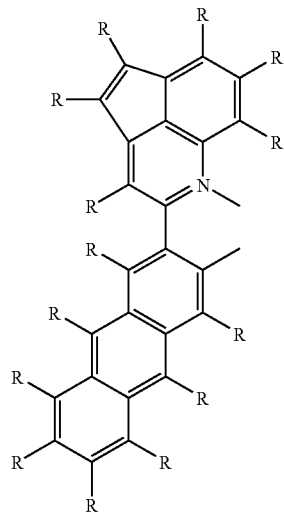
(1-40)

TABLE 1-continued
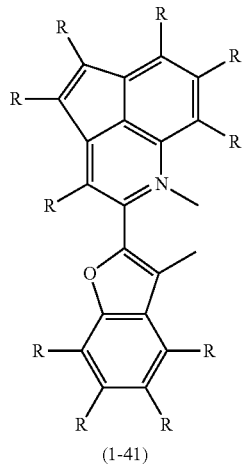
(1-41)
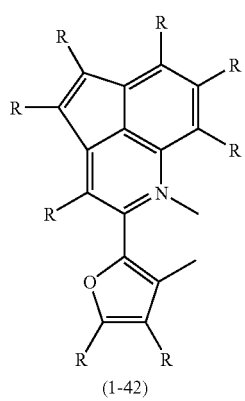
(1-42)
TABLE 2
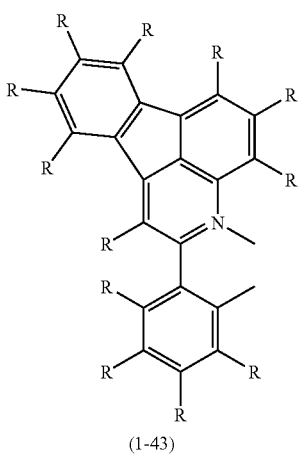
(1-43)
TABLE 2-continued
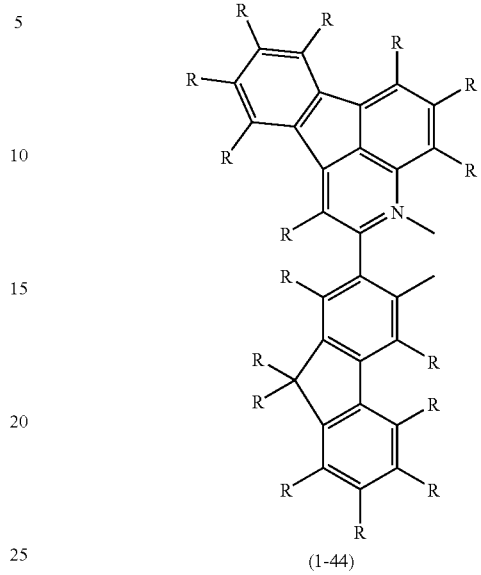
(1-44)
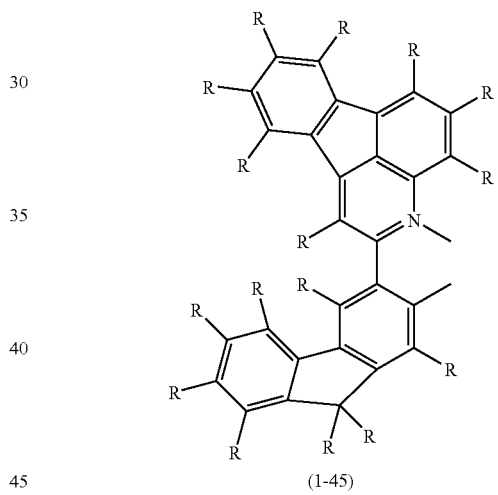
(1-45)
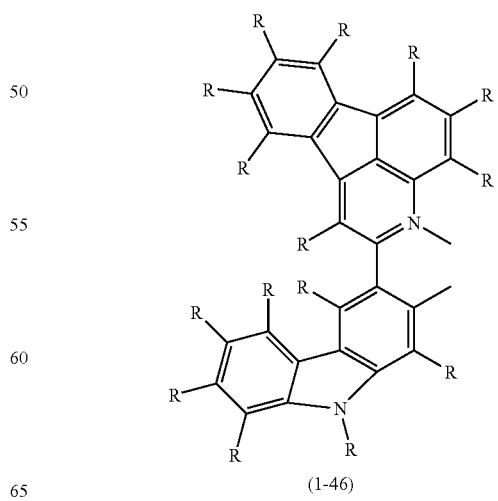
(1-46)

TABLE 2-continued
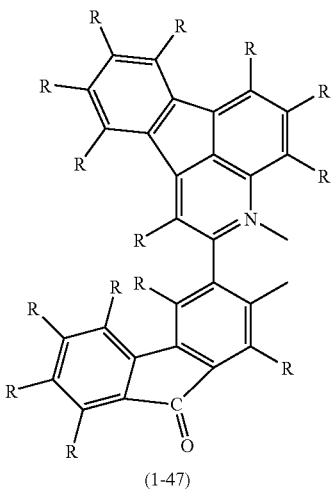
(1-47)
(1-48)
(1-49)
TABLE 2-continued
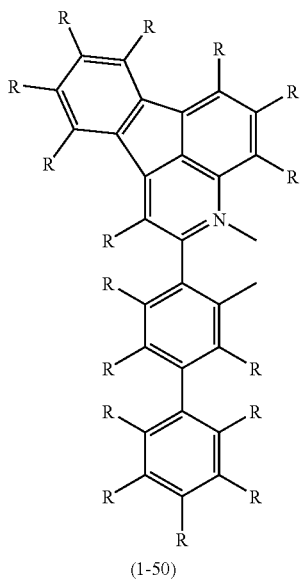
(1-50)
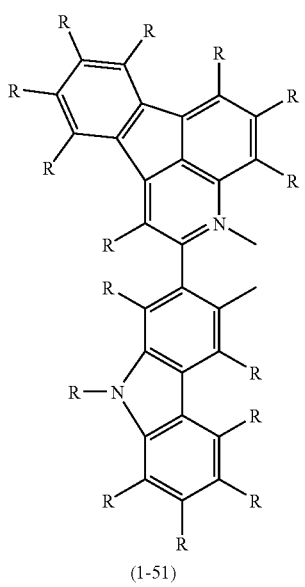
(1-51)

TABLE 2-continued
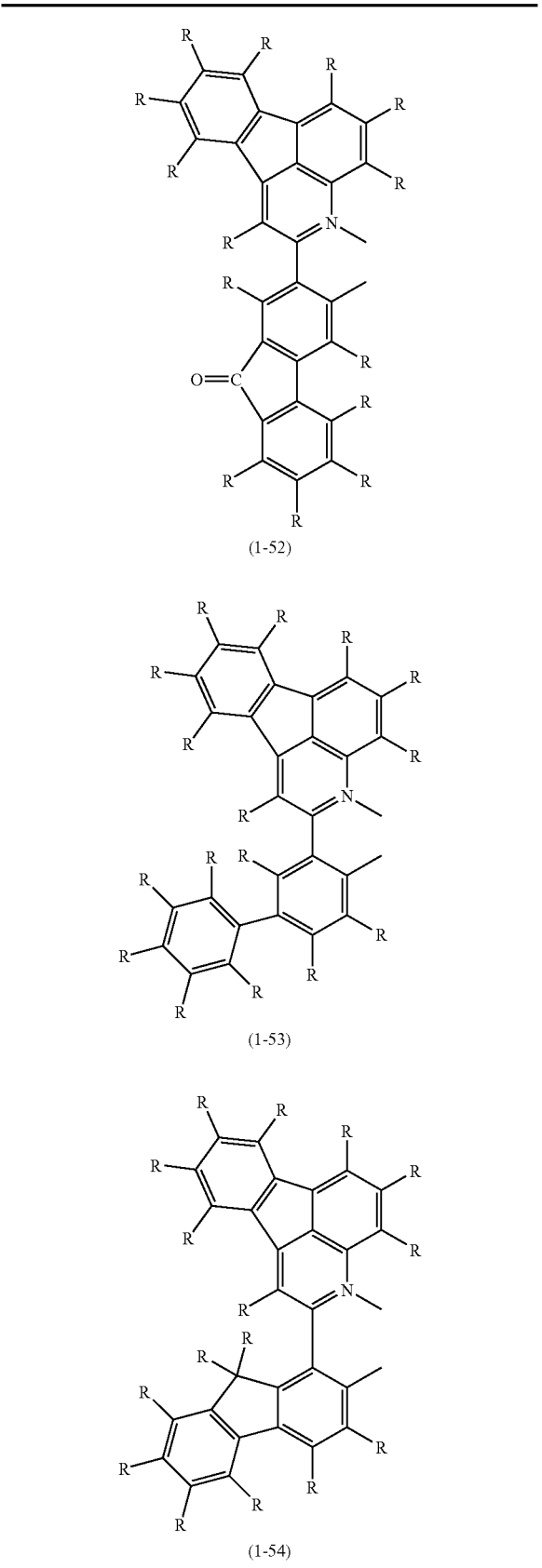
(1-52)
(1-53)
(1-54)
TABLE 2-continued
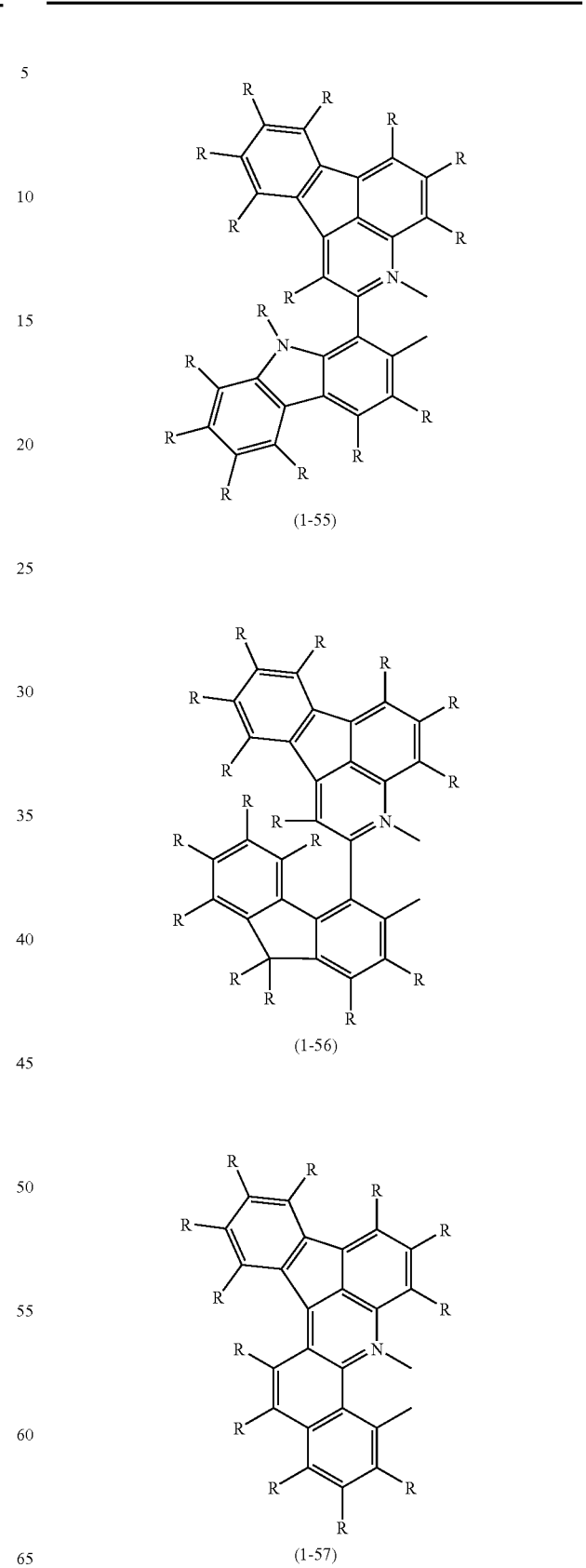
(1-55)
(1-56)
(1-57)

TABLE 2-continued
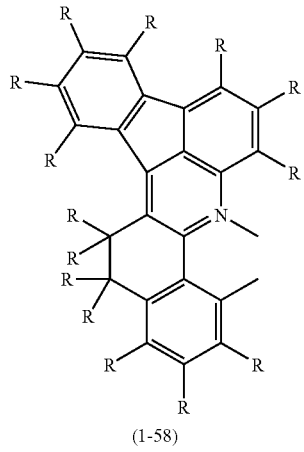
(1-58)
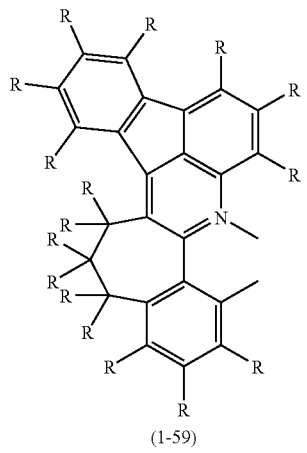
(1-59)
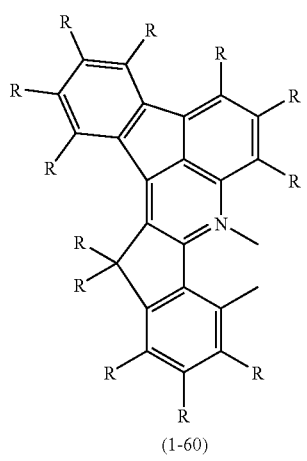
(1-60)
TABLE 2-continued
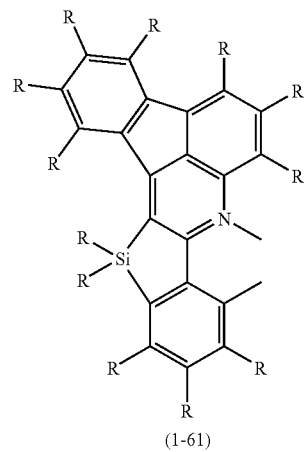
(1-61)
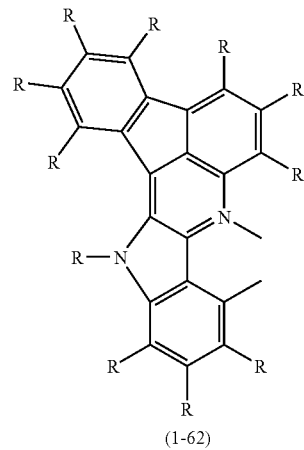
(1-62)
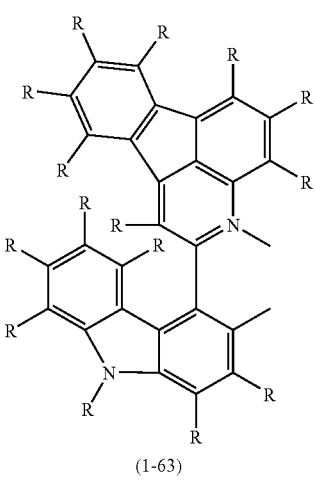
(1-63)

TABLE 2-continued
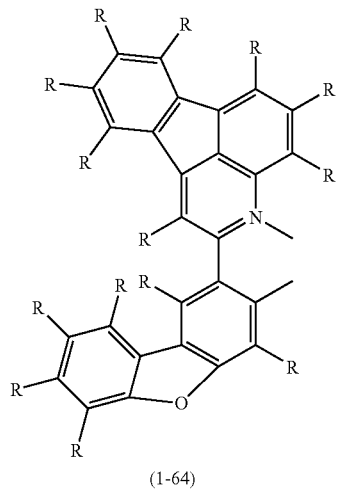
(1-64)
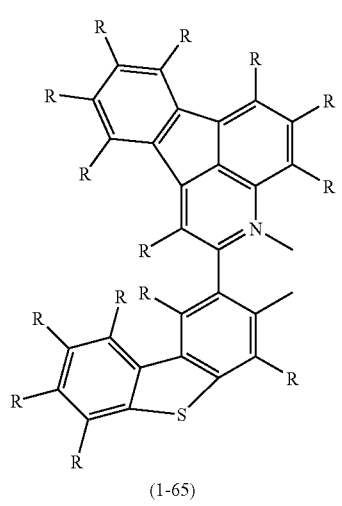
(1-65)
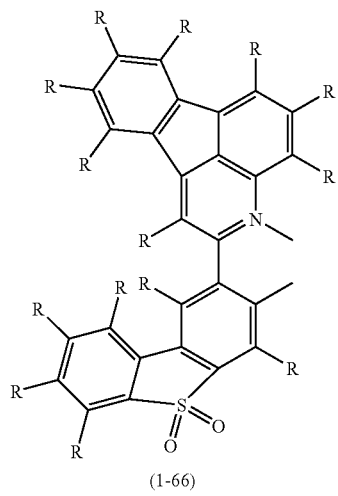
(1-66)
TABLE 2-continued
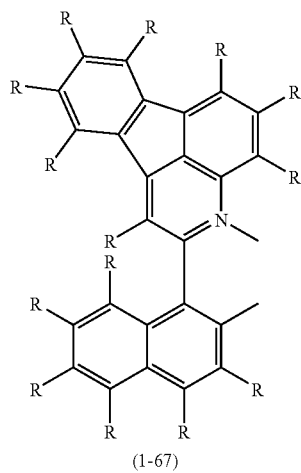
(1-67)
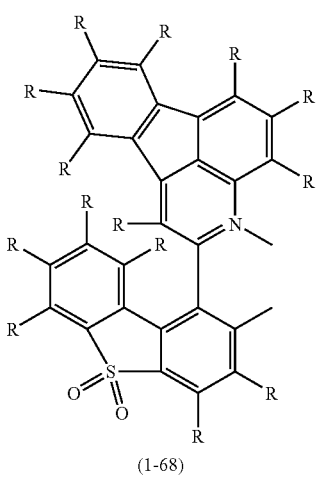
(1-68)
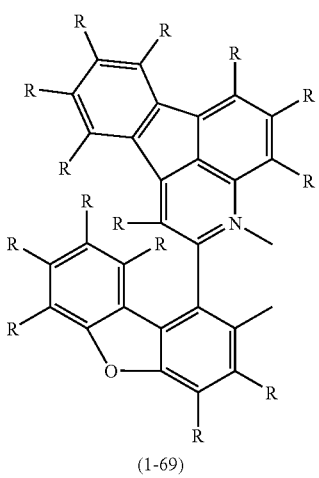
(1-69)

TABLE 2-continued
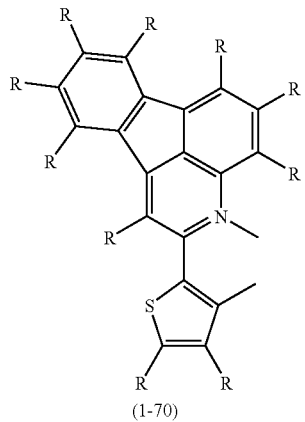
(1-70)
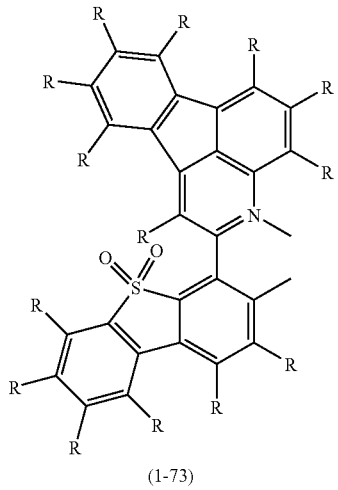
(1-73)
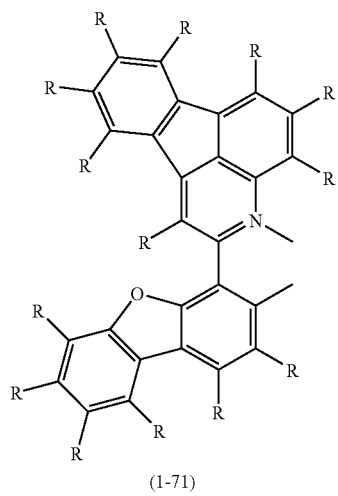
(1-71)
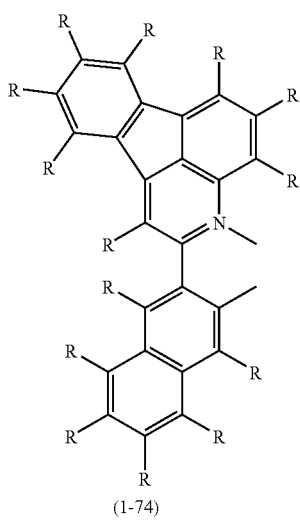
(1-74)
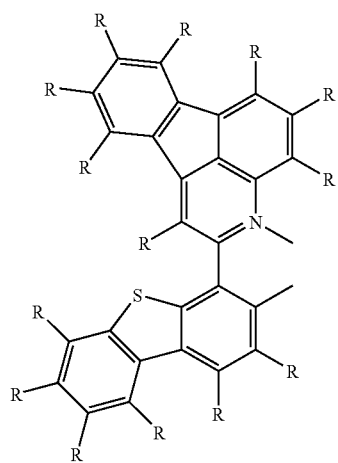
(1-72)
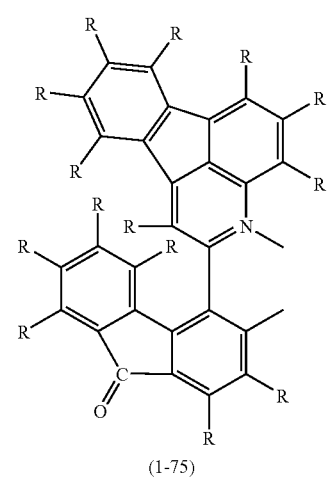
(1-75)

TABLE 2-continued
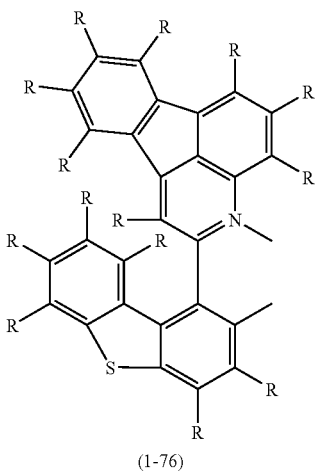
(1-76)
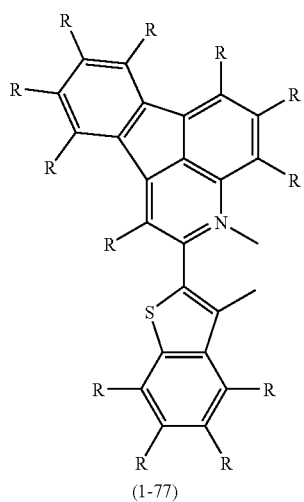
(1-77)
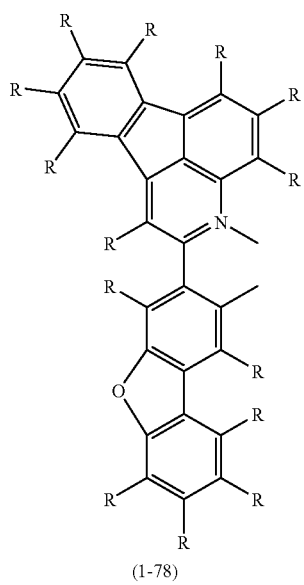
(1-78)
TABLE 2-continued
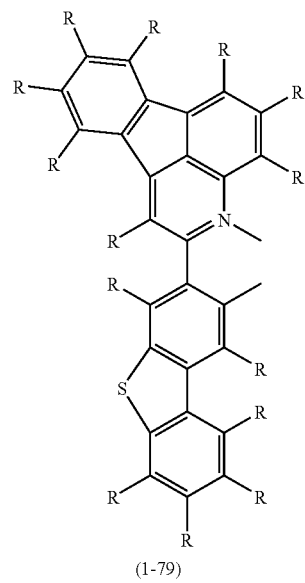
(1-79)
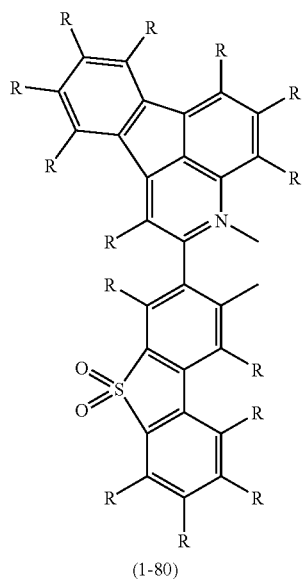
(1-80)

TABLE 2-continued

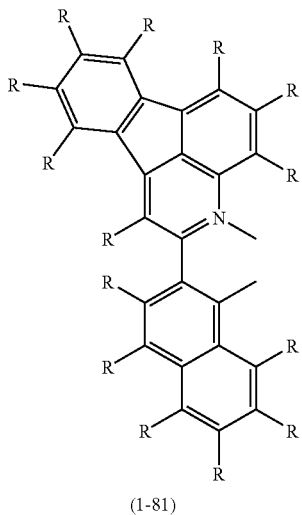

(1-81)

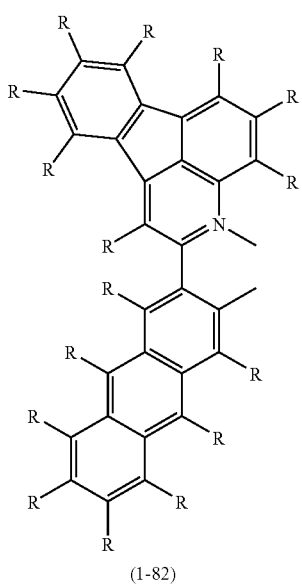

(1-82)

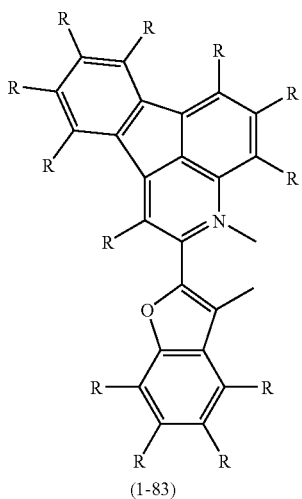

(1-83)

TABLE 2-continued

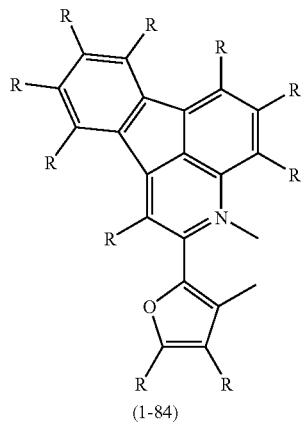

(1-84)

In formulae (1-1) to (1-84), N represents a nitrogen atom, a plurality of R each independently represent a hydrogen atom or a substituent, and the adjacent substituents may bond to each other, to form a ring structure.

Among the bidentate ligands shown in Tables 1 and 2, preferable basic skeletons are (1-1) to (1-14), (1-21) to (1-56), and (1-63) to (1-84); more preferable basic skeletons are (1-1), (1-2), (1-7), (1-8), (1-11), (1-25), (1-32), (1-43), (1-44), (1-49), (1-50), (1-53), (1-67), and (1-74); and particularly preferable basic skeletons are (1-1), (1-11), (1-43), and (1-53).

The bidentate organic ligands represented by formula (12) or (13) can be prepared by various methods, and for example, those can be prepared readily by the method shown in formula (A), with reference to J. Org. Chem., 2003, 68, p. 883, and Synlett, 1999, 1, p. 45.

[Chemical formula 19]

Formula (A)

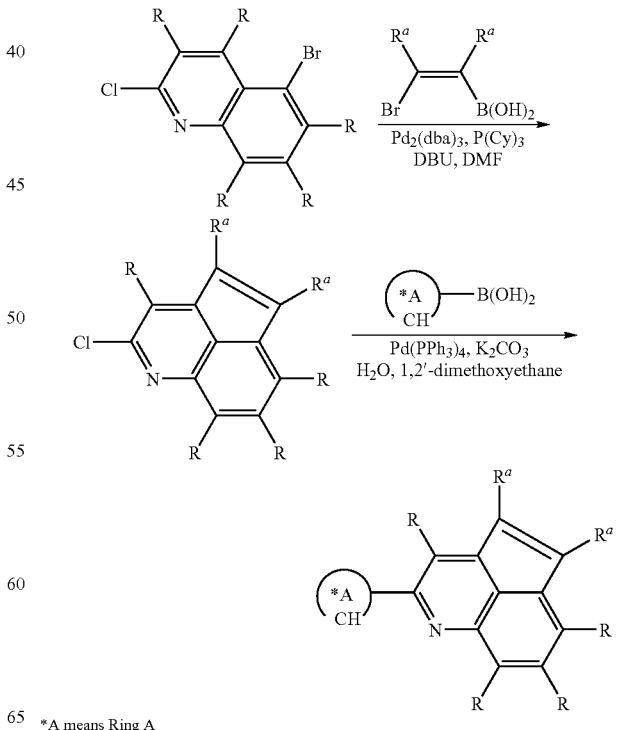

*A means Ring A

Further, via another method other than the above, those can also be prepared readily by the method shown in formula (B), with reference to Tetrahedron Letters, 2003, 44, p. 255.

[Chemical formula 20]

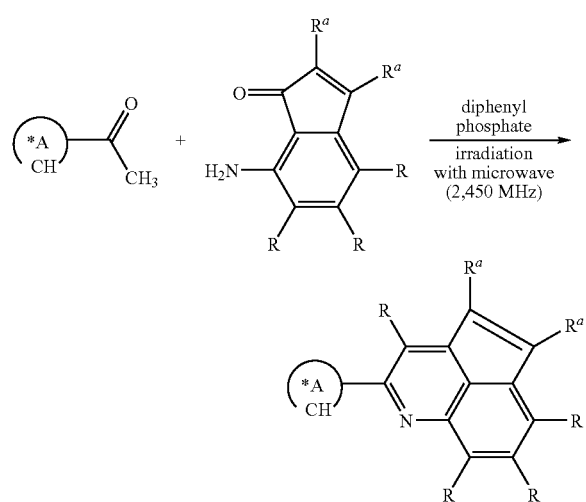

Formula (B)

*A means Ring A

In formula (A) or (B), N represents a nitrogen atom; R and $R^a$ each independently represent a hydrogen atom or a substituent, and the adjacent substituents may bond to each other, to form a ring structure.

Among the bidentate ligands shown in Tables 1 and 2, basic skeletons preferable from the viewpoint of manufacturing processes shown by formulae (A) and (B), are (1-1) to (1-14), (1-21) to (1-56), and (1-63) to (1-84).

In the case of an iridium or platinum complex, the compound of the present invention represented by formula (2) can be produced, for example, according to the method of any of formulae (C) to (E), via a reaction by a usual method (in the presence or absence of a solvent, in the presence or absence of a base, in the presence or absence of a silver compound as a dehalogenating agent, at normal temperature or under heating). The reaction is also carried out preferably under a nitrogen or argon atmosphere. Further, the heating means is not particularly limited, but microwave irradiation is also preferable for smoother progress of the reaction. The wavelength of the microwave is not particularly limited, but generally 2,000 to 3,000 MHz, preferably 2,400 to 2,500 MHz. Any commercially available known microwave oscillator may be used as the microwave oscillator. The heating means for use may be an oil bath, a mantle heater, or the like.

[Chemical formula 21]

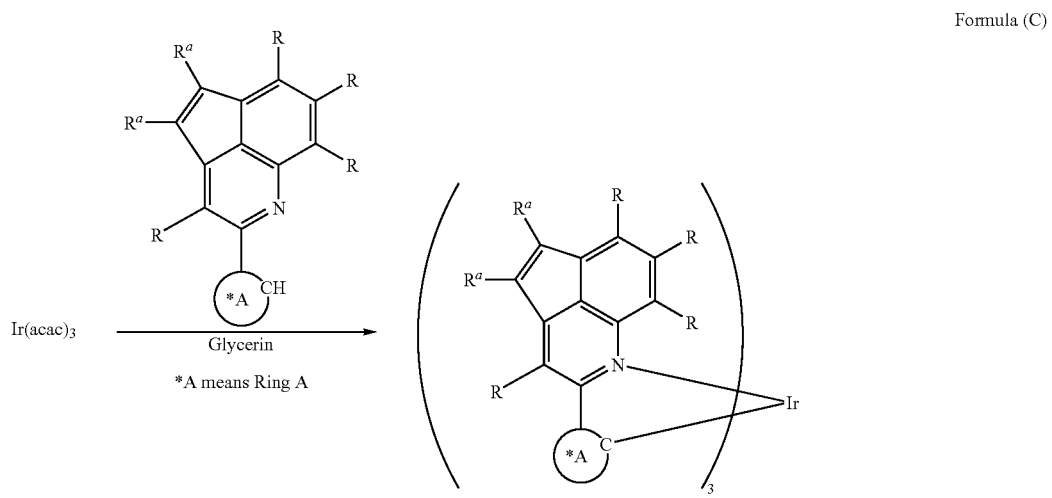

Formula (C)

*A means Ring A acac = acetylacetonato

[Chemical formula 22]
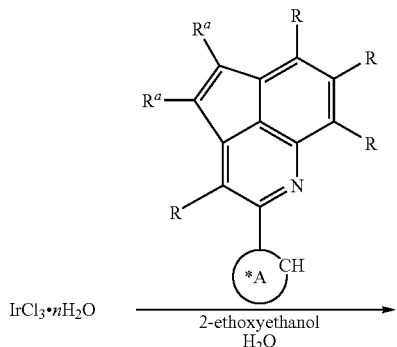
IrCl$_3$·nH$_2$O $\xrightarrow{\text{2-ethoxyethanol} \atop \text{H}_2\text{O}}$
*A means Ring A
Formula (D)
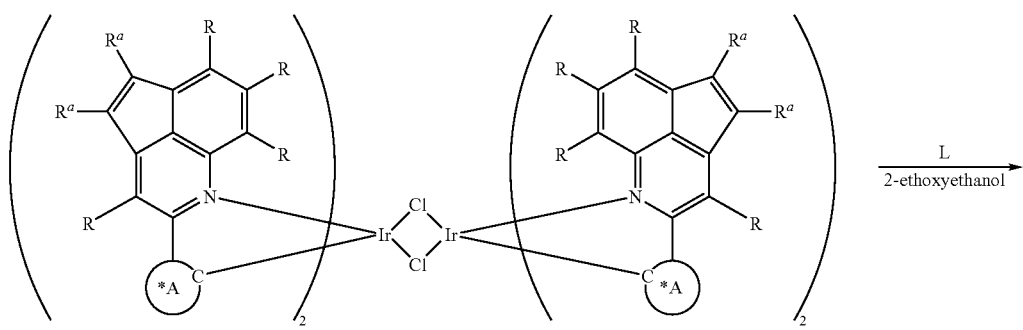
$\xrightarrow{\text{L} \atop \text{2-ethoxyethanol}}$
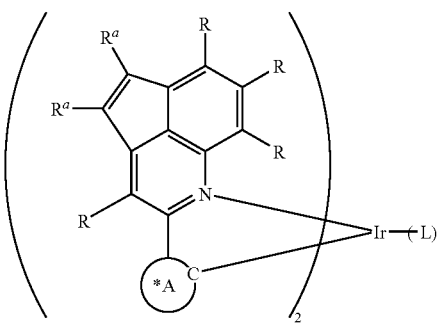
[Chemical formula 23]
Formula (E)
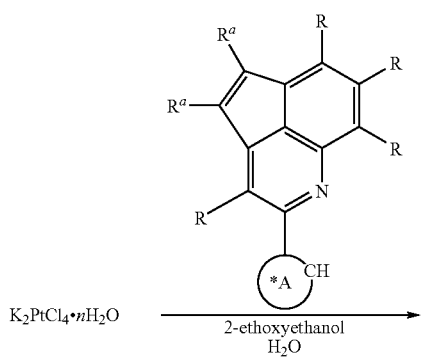
K$_2$PtCl$_4$·nH$_2$O $\xrightarrow{\text{2-ethoxyethanol} \atop \text{H}_2\text{O}}$
*A means Ring A

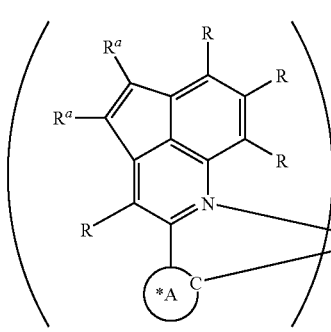 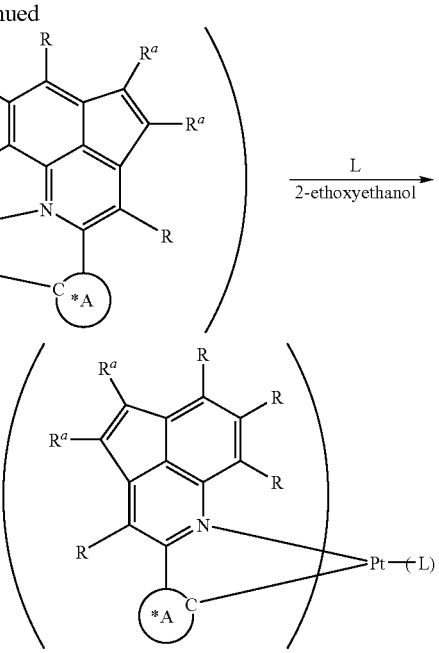

In formulae (C) to (E), N represents a nitrogen atom; C represents a carbon atom; R and $R^a$ each independently represent a hydrogen atom or a substituent, and the adjacent substituents may bond to each other, to form a ring structure; the ring A represents an aromatic hydrocarbon ring or an aromatic hetero ring, each of which ring may have a substituent; and L represents a bidentate ligand.

The compound of the present invention represented by formula (11) is produced, for example, via a reaction of a metal raw material, such as iridium trichloride, iridium hexachloride, potassium tetrachloropiatinate, platinous chloride, rhodium trichloride, or palladium acetate, with a bidentate ligand represented by formula (12) or (13), in a solvent, for example, with reference to the method described in Inorganic Chemistry, 2001, 40, p. 1704, Inorganic Chemistry, 2002, 41, p. 3055, JP-A-2004-319438, or JP-A-2001-181616.

R and $R^a$ in Tables 1 to 2 and formulae (A) to (E) have the same meanings as defined for $R^1$ to $R^{74}$ above, and the favorable ranges thereof are also the same.

Use of a reaction solvent is preferable for further smooth progress of the reaction in production of the metal coordination compound according to the present invention. Such a solvent is not particularly limited, and alcoholic solvents, protic solvents, aprotic solvents, nitrile-based solvents, and the like are used preferably. The reaction temperature, the reaction pressure, and the reaction time may vary, according to the raw materials, solvents, and others to be used, but generally, the reaction temperature is 40 to 250° C., preferably 50 to 230° C., and more preferably 60 to 220° C., and the reaction pressure is 1 to 30 atm, preferably 1 to 5 atm.

The metal coordination compound according to the present invention is processed by a usual post-treatment of synthetic reaction, and can be used as it is or after it is purified if required. Examples of the post-treatment operation include extraction, cooling, crystallization by addition of water or an organic solvent, evaporation of the solvent from the reaction mixture, and the like, and these operations may be carried out singly or in combination of two or more of those. The purification methods include recrystallization, distillation, sublimation, column chromatography, and others, and these operations may be carried out singly or in combination.

Tables 3 to 5 show typical examples of the metal coordination compound, according to the present invention, as represented by formula (11), but the present invention is not limited to these compounds. The following formula (26) is the same and has the same meaning, as those described above, except that the bidentate ligand of formula (11) is indicated by "A".

[Chemical formula 24]

Formula (26)

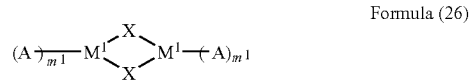

(In Table 3, "No." represents a compound number; $M^1$, A, $m^1$, R, and X are the symbols as described in formula (11) or (26) above; and A represents the number of the bidentate ligand shown in Tables 1 to 2 above).

TABLE 3

| Compound No. | $M^1$ | A | $m^1$ | R | X |
|---|---|---|---|---|---|
| 3-1 | Ir | 1-1 | 2 | H | Cl |
| 3-2 | Ir | 1-2 | 2 | H | Cl |
| 3-3 | Ir | 1-3 | 2 | H | Cl |
| 3-4 | Ir | 1-4 | 2 | H | Cl |
| 3-5 | Ir | 1-5 | 2 | H | Cl |
| 3-6 | Ir | 1-6 | 2 | H | Cl |
| 3-7 | Ir | 1-7 | 2 | H | Cl |
| 3-8 | Ir | 1-8 | 2 | H | Cl |
| 3-9 | Ir | 1-9 | 2 | H | Cl |
| 3-10 | Ir | 1-10 | 2 | H | Cl |
| 3-11 | Ir | 1-11 | 2 | H | Cl |
| 3-12 | Ir | 1-12 | 2 | H | Cl |
| 3-13 | Ir | 1-13 | 2 | H | Cl |
| 3-14 | Ir | 1-14 | 2 | H | Cl |
| 3-15 | Ir | 1-15 | 2 | H | Cl |

TABLE 3-continued

| Compound No. | $M^1$ | A | $m^1$ | R | X |
|---|---|---|---|---|---|
| 3-16 | Ir | 1-16 | 2 | H | Cl |
| 3-17 | Ir | 1-17 | 2 | H | Cl |
| 3-18 | Ir | 1-18 | 2 | H | Cl |
| 3-19 | Ir | 1-19 | 2 | H | Cl |
| 3-20 | Ir | 1-20 | 2 | H | Cl |
| 3-21 | Ir | 1-21 | 2 | H | Cl |
| 3-22 | Ir | 1-22 | 2 | H | Cl |
| 3-23 | Ir | 1-23 | 2 | H | Cl |
| 3-24 | Ir | 1-24 | 2 | H | Cl |
| 3-25 | Ir | 1-25 | 2 | H | Cl |
| 3-26 | Ir | 1-26 | 2 | H | Cl |
| 3-27 | Ir | 1-27 | 2 | H | Cl |
| 3-28 | Ir | 1-28 | 2 | H | Cl |
| 3-29 | Ir | 1-29 | 2 | H | Cl |
| 3-30 | Ir | 1-30 | 2 | H | Cl |
| 3-31 | Ir | 1-31 | 2 | H | Cl |
| 3-32 | Ir | 1-32 | 2 | H | Cl |
| 3-33 | Ir | 1-33 | 2 | H | Cl |
| 3-34 | Ir | 1-34 | 2 | H | Cl |
| 3-35 | Ir | 1-35 | 2 | H | Cl |
| 3-36 | Ir | 1-36 | 2 | H | Cl |
| 3-37 | Ir | 1-37 | 2 | H | Cl |
| 3-38 | Ir | 1-38 | 2 | H | Cl |
| 3-39 | Ir | 1-39 | 2 | H | Cl |
| 3-40 | Ir | 1-40 | 2 | H | Cl |
| 3-41 | Ir | 1-41 | 2 | H | Cl |
| 3-42 | Ir | 1-42 | 2 | H | Cl |
| 3-43 | Ir | 1-43 | 2 | H | Cl |
| 3-44 | Ir | 1-44 | 2 | H | Cl |
| 3-45 | Ir | 1-45 | 2 | H | Cl |
| 3-46 | Ir | 1-46 | 2 | H | Cl |
| 3-47 | Ir | 1-47 | 2 | H | Cl |
| 3-48 | Ir | 1-48 | 2 | H | Cl |
| 3-49 | Ir | 1-49 | 2 | H | Cl |
| 3-50 | Ir | 1-50 | 2 | H | Cl |
| 3-51 | Ir | 1-51 | 2 | H | Cl |
| 3-52 | Ir | 1-52 | 2 | H | Cl |
| 3-53 | Ir | 1-53 | 2 | H | Cl |
| 3-54 | Ir | 1-54 | 2 | H | Cl |
| 3-55 | Ir | 1-55 | 2 | H | Cl |
| 3-56 | Ir | 1-56 | 2 | H | Cl |
| 3-57 | Ir | 1-57 | 2 | H | Cl |
| 3-58 | Ir | 1-58 | 2 | H | Cl |
| 3-59 | Ir | 1-59 | 2 | H | Cl |
| 3-60 | Ir | 1-60 | 2 | H | Cl |
| 3-61 | Ir | 1-61 | 2 | H | Cl |
| 3-62 | Ir | 1-62 | 2 | H | Cl |
| 3-63 | Ir | 1-63 | 2 | H | Cl |
| 3-64 | Ir | 1-64 | 2 | H | Cl |
| 3-65 | Ir | 1-65 | 2 | H | Cl |
| 3-66 | Ir | 1-66 | 2 | H | Cl |
| 3-67 | Ir | 1-67 | 2 | H | Cl |
| 3-68 | Ir | 1-68 | 2 | H | Cl |
| 3-69 | Ir | 1-69 | 2 | H | Cl |
| 3-70 | Ir | 1-70 | 2 | H | Cl |
| 3-71 | Ir | 1-71 | 2 | H | Cl |
| 3-72 | Ir | 1-72 | 2 | H | Cl |
| 3-73 | Ir | 1-73 | 2 | H | Cl |
| 3-74 | Ir | 1-74 | 2 | H | Cl |
| 3-75 | Ir | 1-75 | 2 | H | Cl |
| 3-76 | Ir | 1-76 | 2 | H | Cl |
| 3-77 | Ir | 1-77 | 2 | H | Cl |
| 3-78 | Ir | 1-78 | 2 | H | Cl |
| 3-79 | Ir | 1-79 | 2 | H | Cl |
| 3-80 | Ir | 1-80 | 2 | H | Cl |
| 3-81 | Ir | 1-81 | 2 | H | Cl |
| 3-82 | Ir | 1-82 | 2 | H | Cl |
| 3-83 | Ir | 1-83 | 2 | H | Cl |
| 3-84 | Ir | 1-84 | 2 | H | Cl |
| 3-85 | Ir | 1-1 | 2 | H | Br |
| 3-86 | Ir | 1-1 | 2 | H | I |
| 3-87 | Ir | 1-43 | 2 | H | Br |
| 3-88 | Ir | 1-43 | 2 | H | I |
| 3-89 | Pt | 1-1 | 1 | H | Cl |
| 3-90 | Pt | 1-2 | 1 | H | Cl |
| 3-91 | Pt | 1-8 | 1 | H | Cl |
| 3-92 | Pt | 1-11 | 1 | H | Cl |
| 3-93 | Pt | 1-25 | 1 | H | Cl |
| 3-94 | Pt | 1-32 | 1 | H | Cl |
| 3-95 | Pt | 1-43 | 1 | H | Cl |
| 3-96 | Pt | 1-44 | 1 | H | Cl |
| 3-97 | Pt | 1-50 | 1 | H | Cl |
| 3-98 | Pt | 1-53 | 1 | H | Cl |
| 3-99 | Pt | 1-67 | 1 | H | Cl |
| 3-100 | Pt | 1-74 | 1 | H | Cl |

TABLE 4

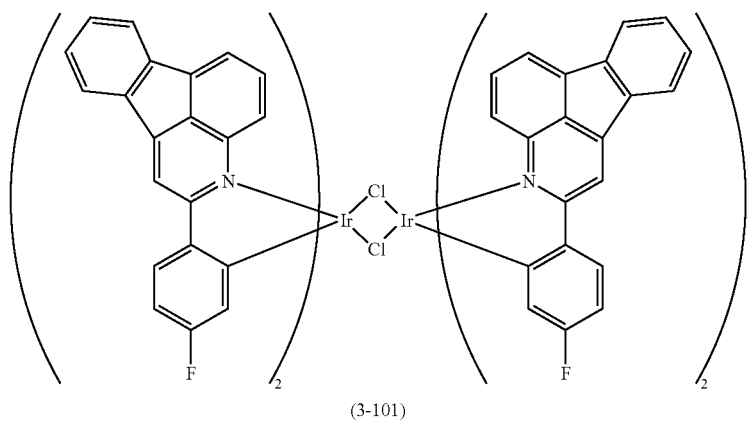

(3-101)

TABLE 4-continued
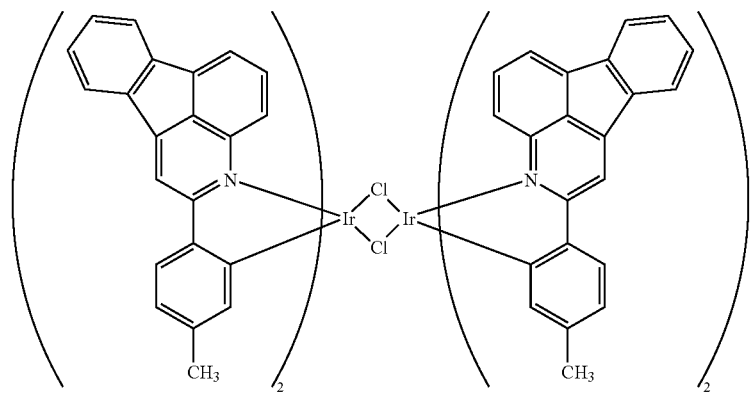
(3-102)
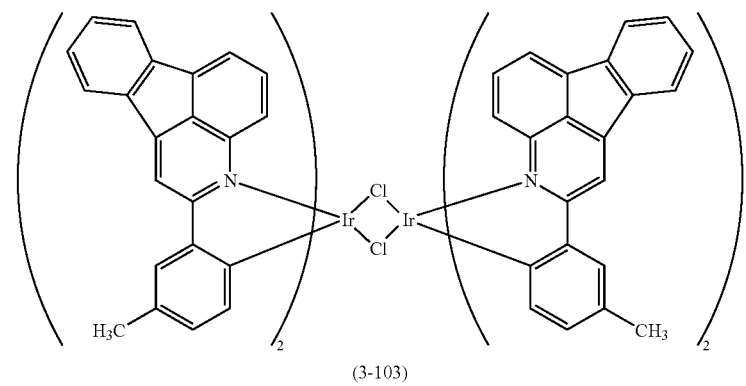
(3-103)
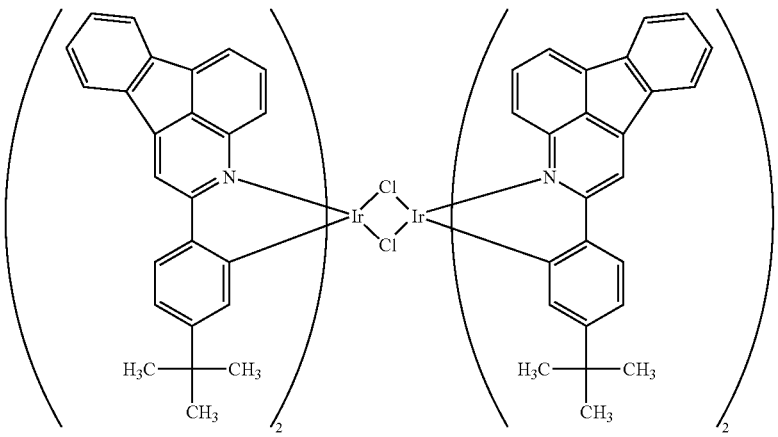
(3-104)
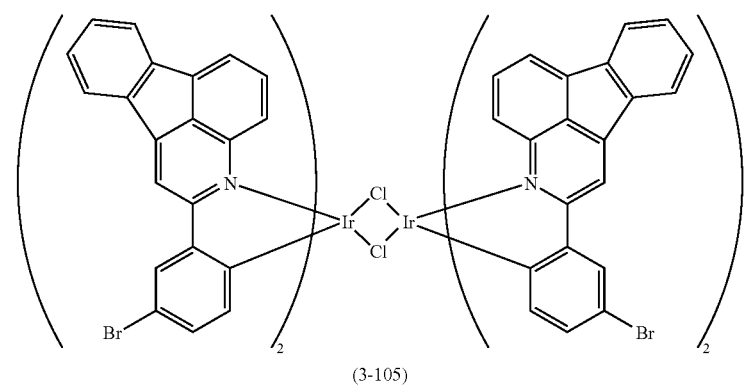
(3-105)

TABLE 4-continued
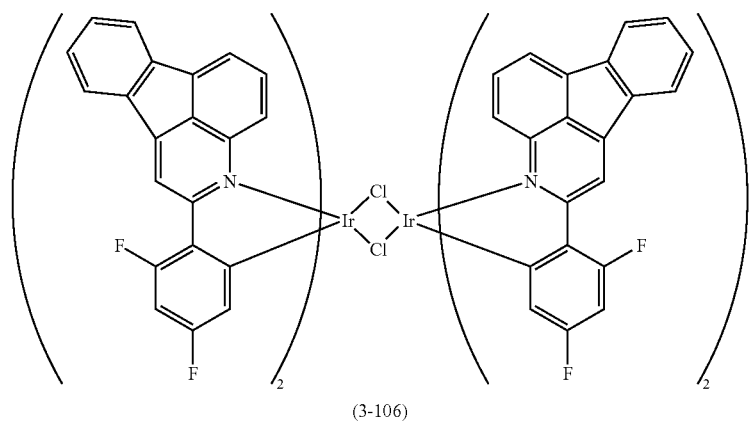
(3-106)
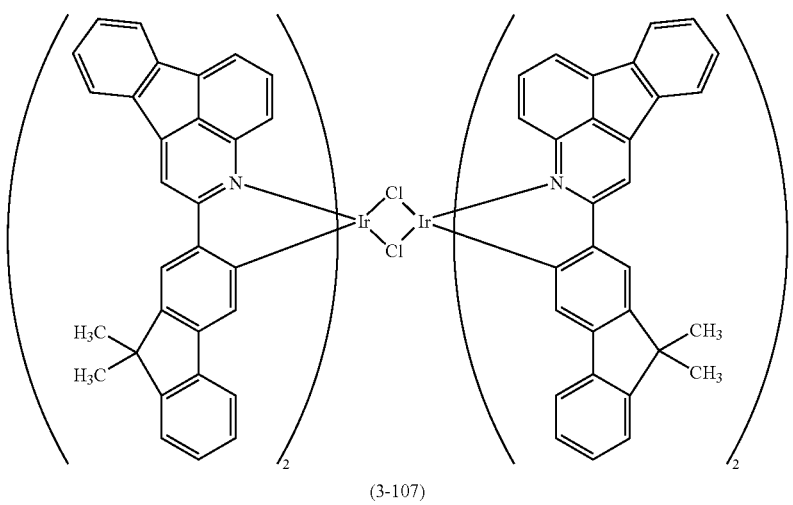
(3-107)
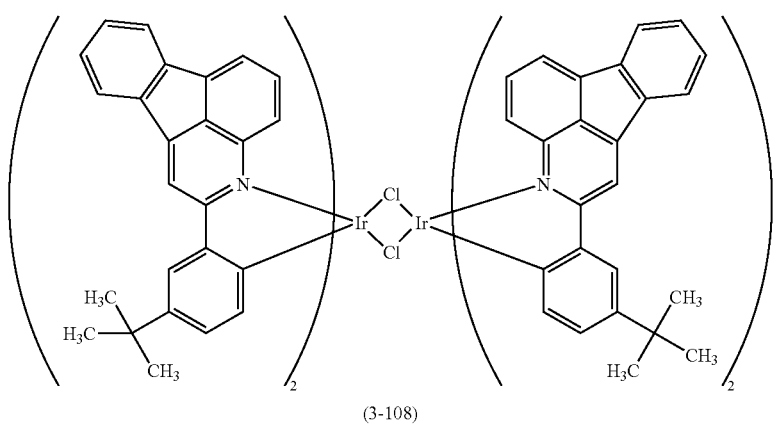
(3-108)

TABLE 4-continued
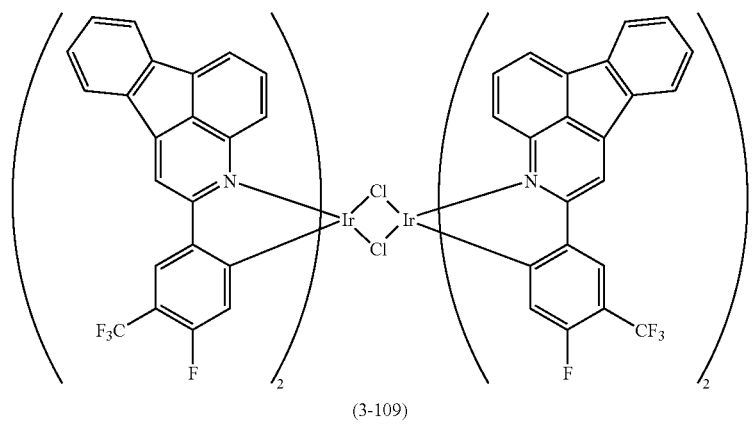
(3-109)
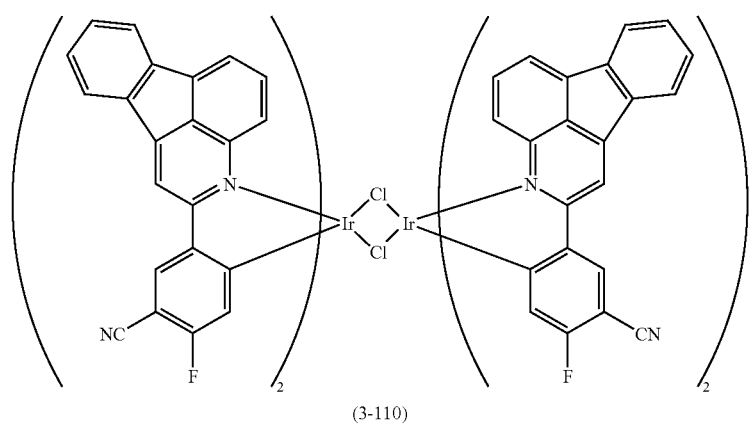
(3-110)
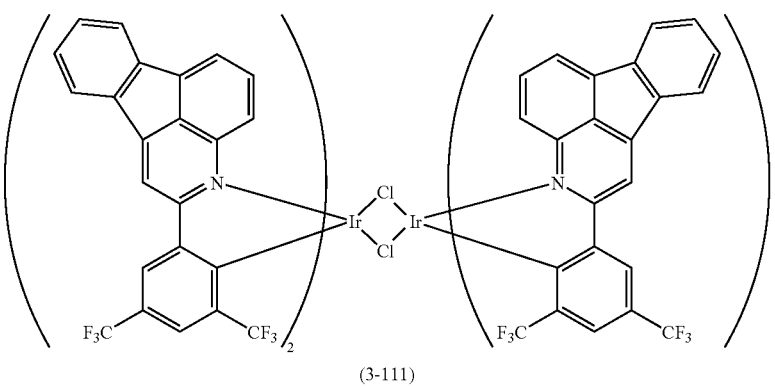
(3-111)
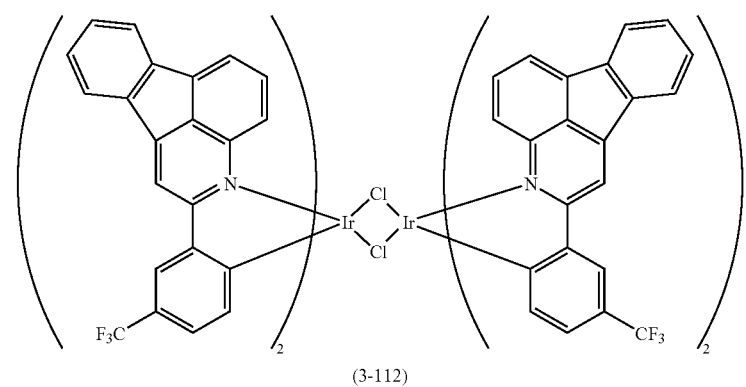
(3-112)

TABLE 4-continued
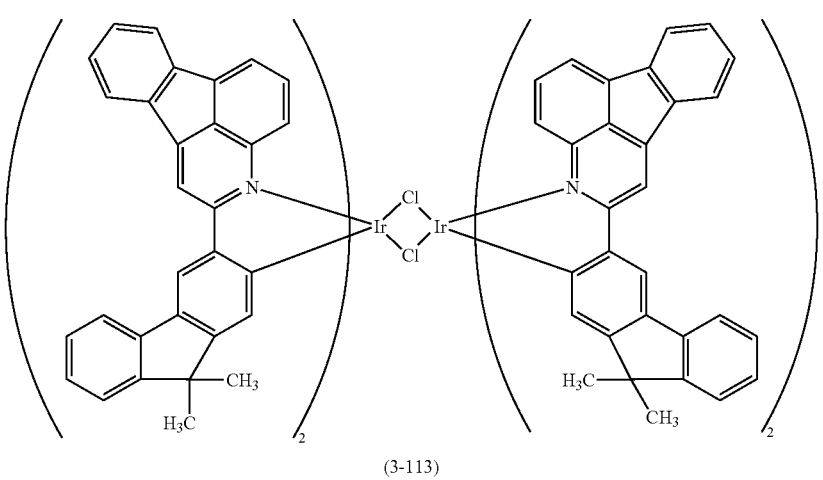
(3-113)
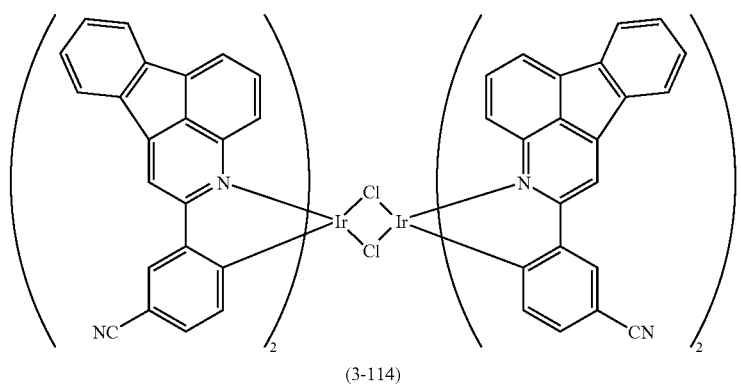
(3-114)
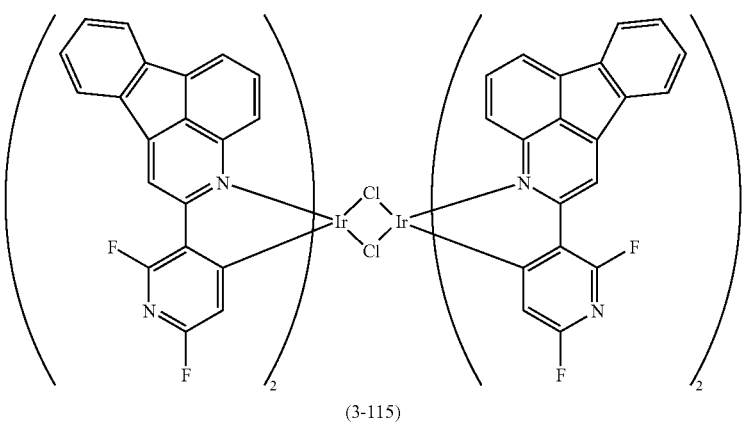
(3-115)

TABLE 4-continued
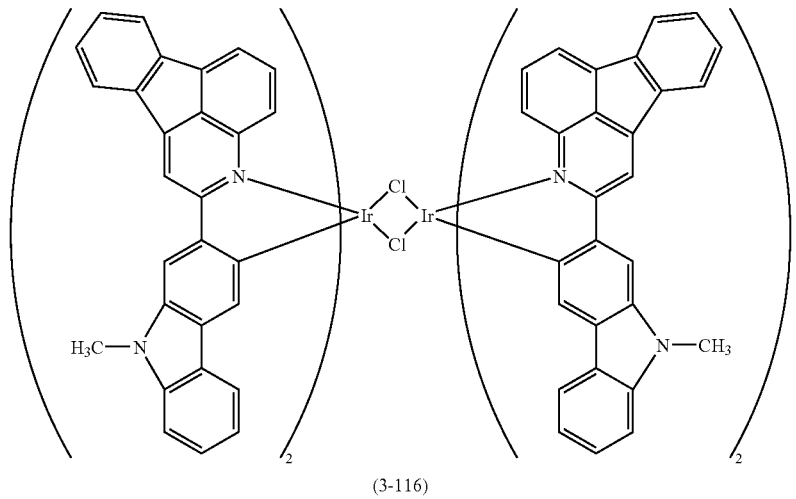
(3-116)
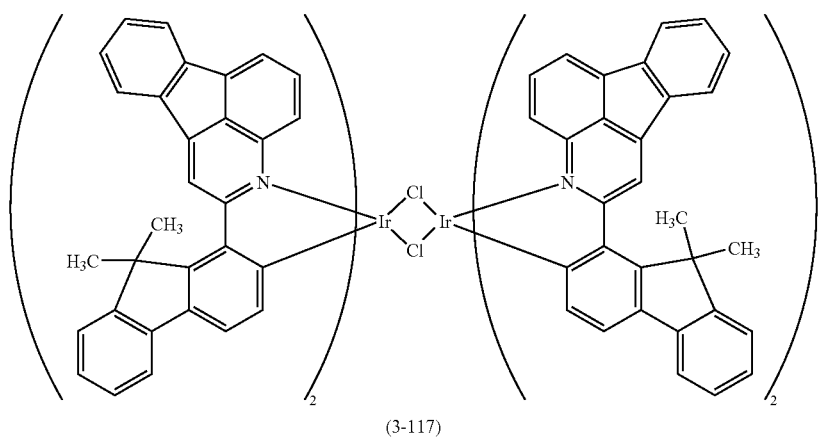
(3-117)
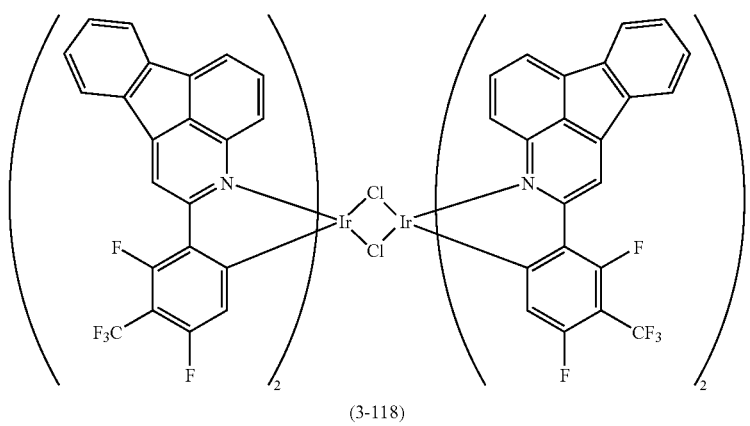
(3-118)

TABLE 5
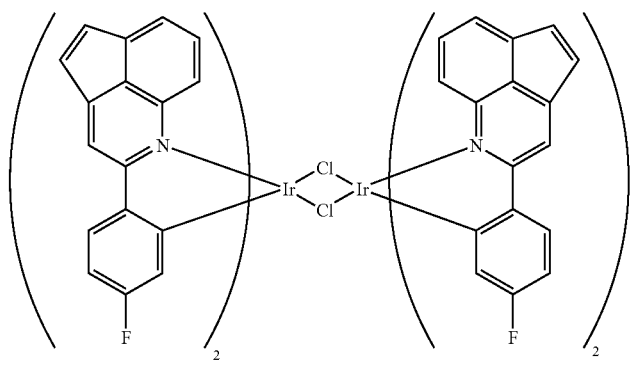
(3-119)
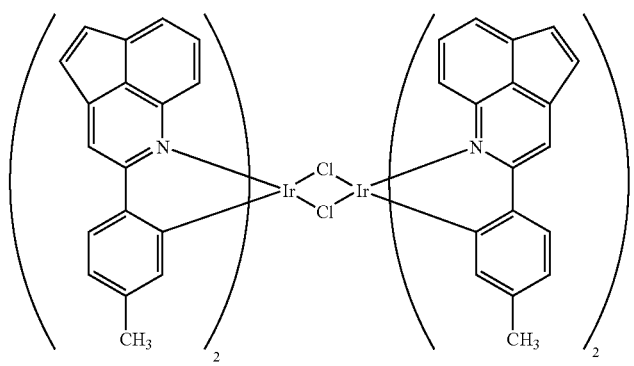
(3-120)
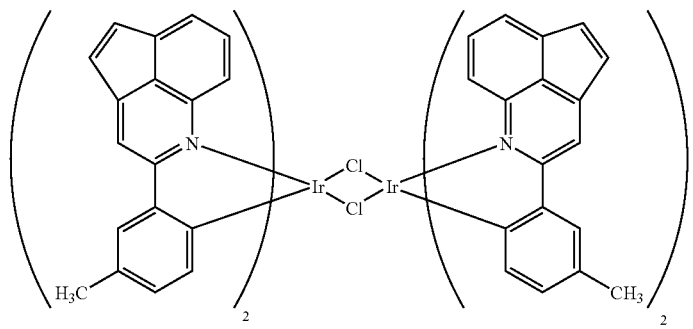
(3-121)
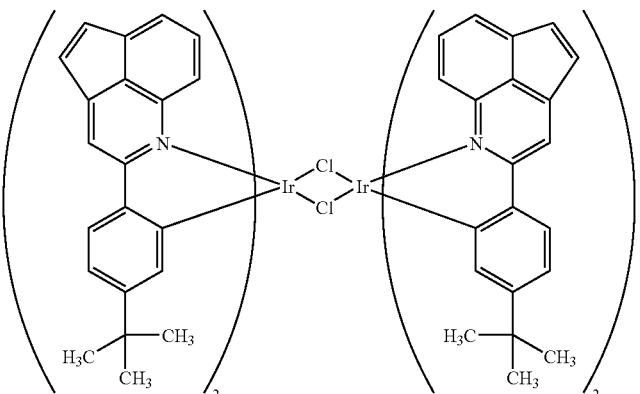
(3-122)

TABLE 5-continued
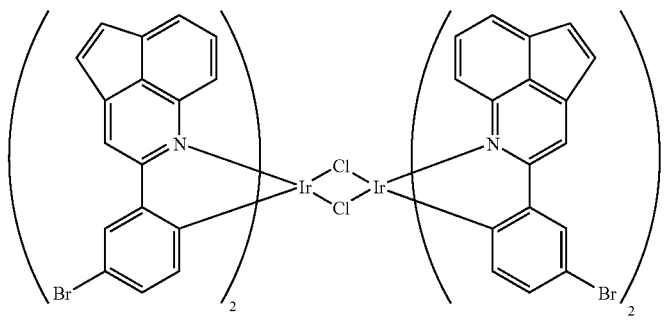
(3-123)
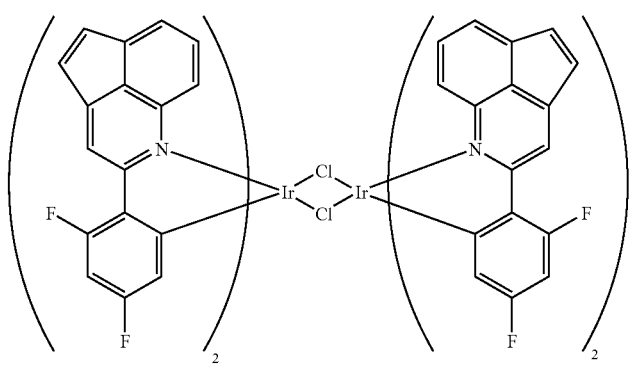
(3-124)
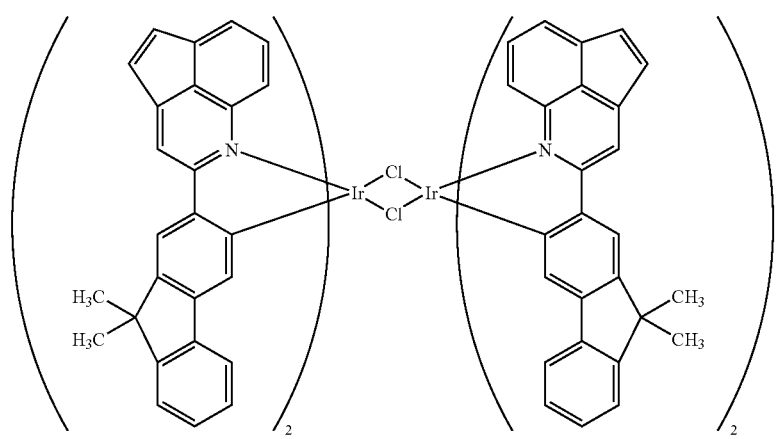
(3-125)

TABLE 5-continued
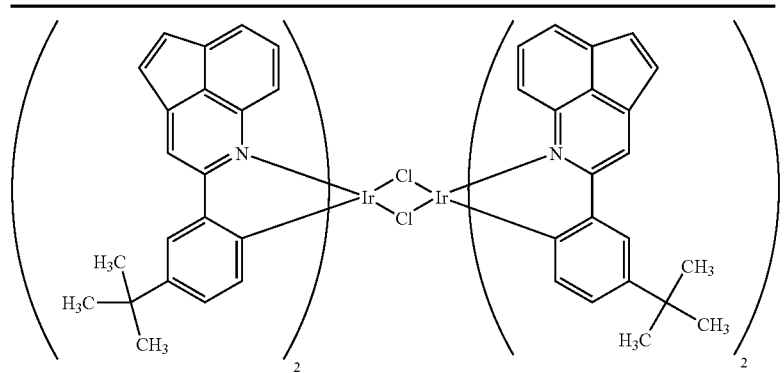
(3-126)
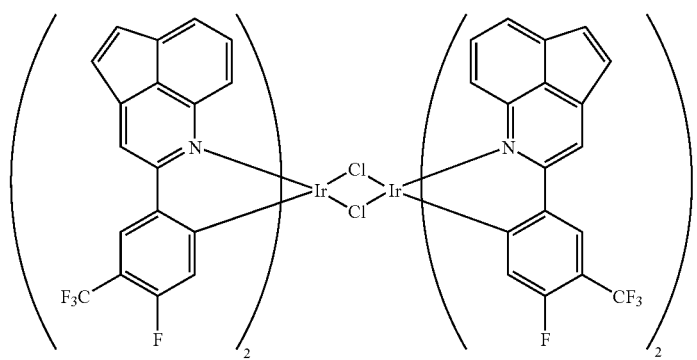
(3-127)
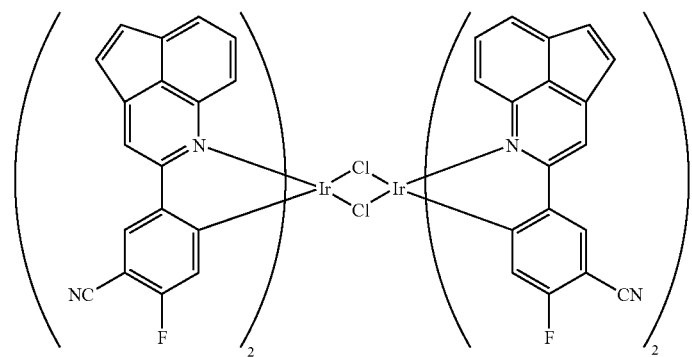
(3-128)
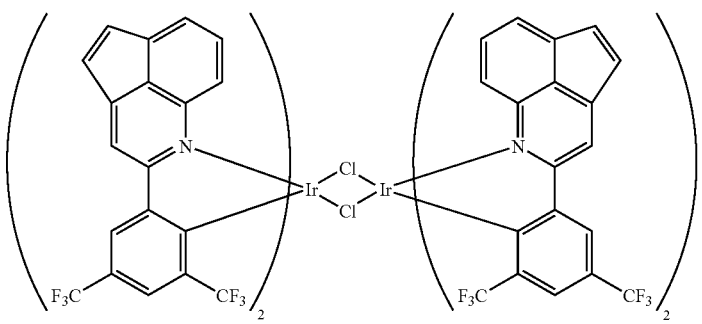
(3-129)

TABLE 5-continued
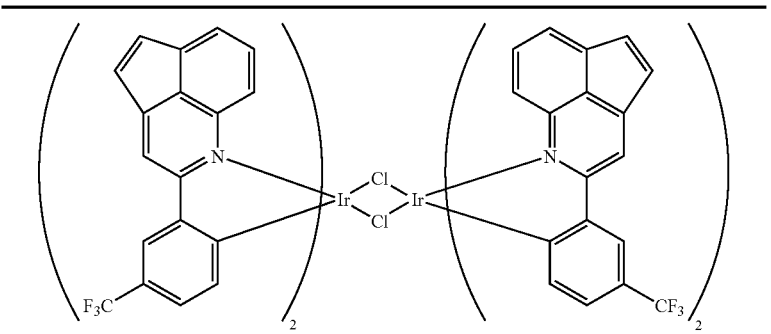
(3-130)
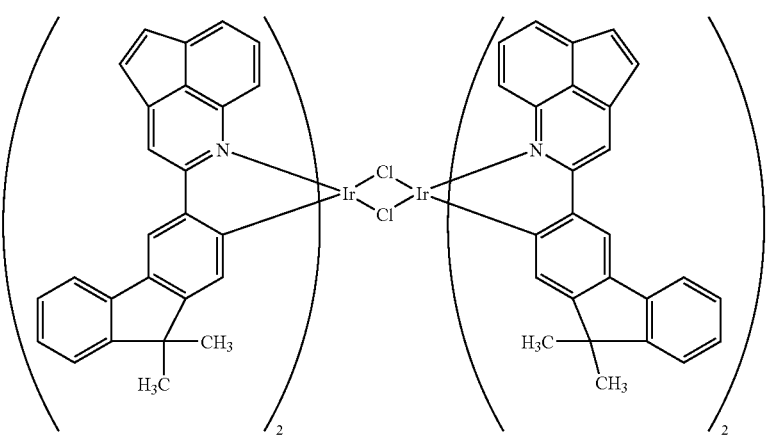
(3-131)
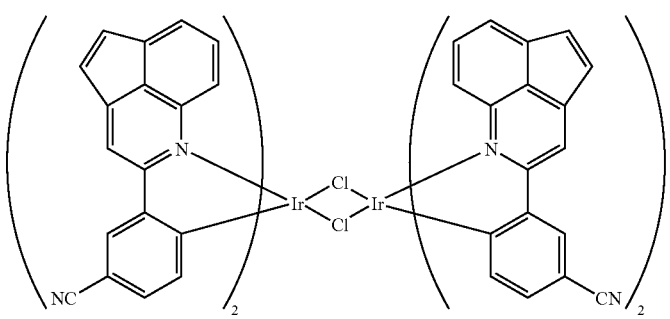
(3-132)
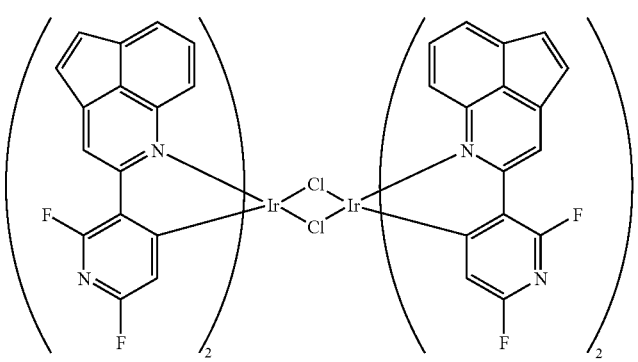
(3-133)

TABLE 5-continued
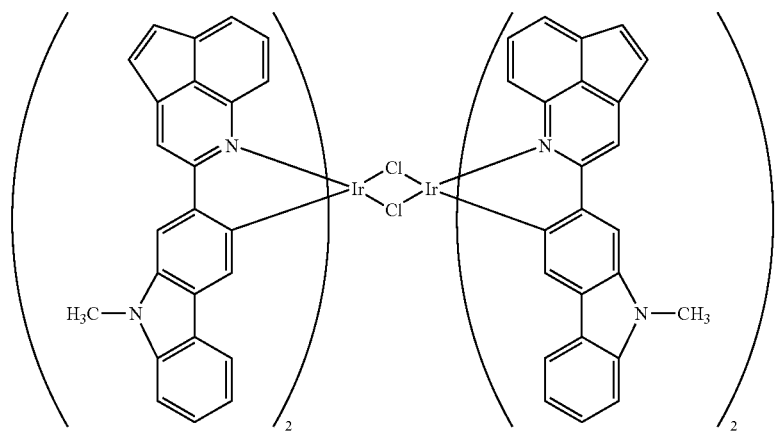
(3-134)
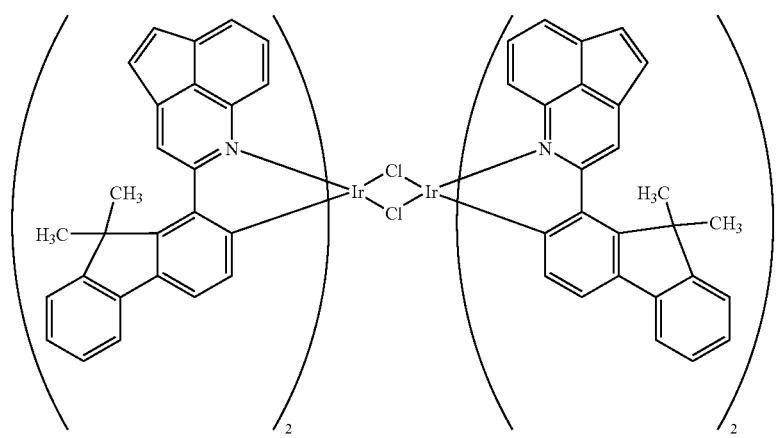
(3-135)
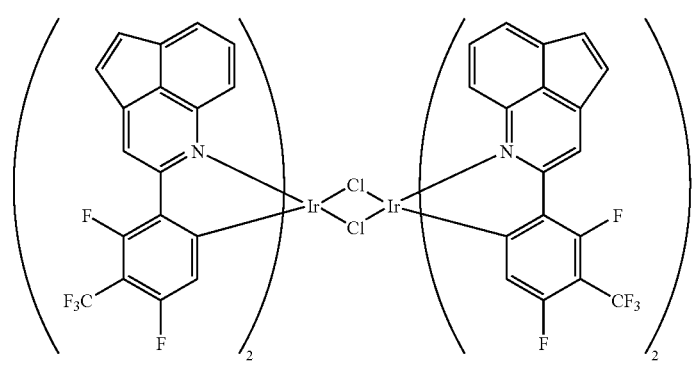
(3-136)
Hereinafter, typical examples of the metal coordination compounds, according to the present invention, as represented by formula (1) or (2) will be shown, but the present invention is not limited thereto.

TABLE 6
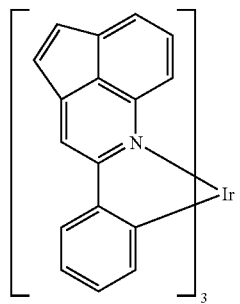
(2-1)
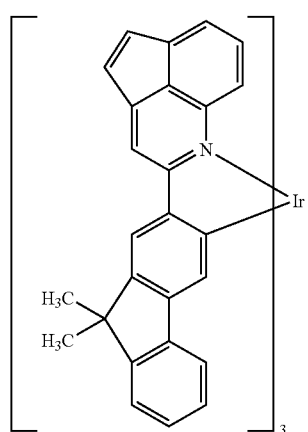
(2-2)
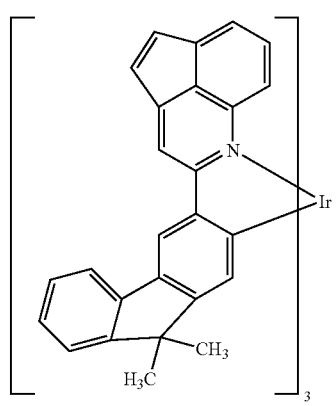
(2-3)
TABLE 6-continued
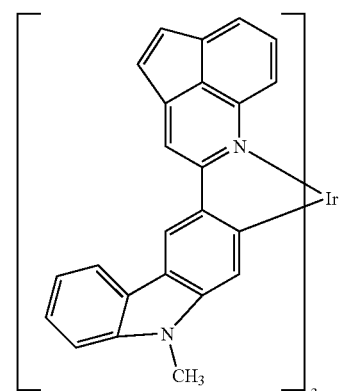
(2-4)
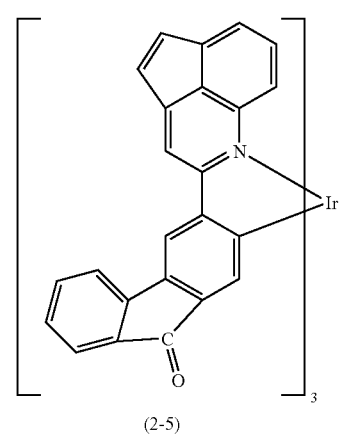
(2-5)
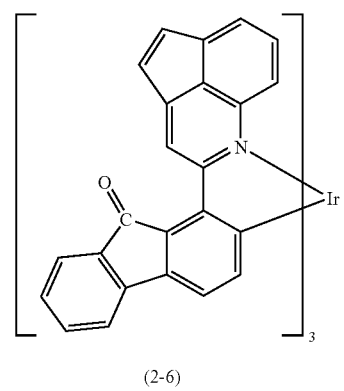
(2-6)
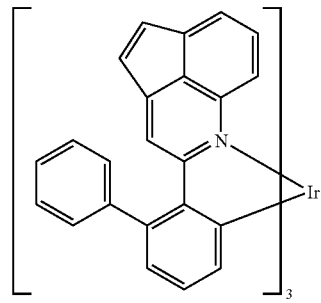
(2-7)

TABLE 6-continued
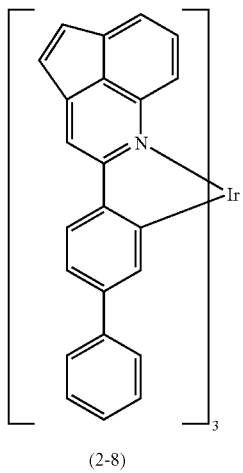
(2-8)
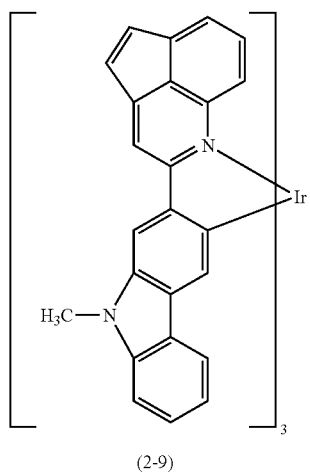
(2-9)
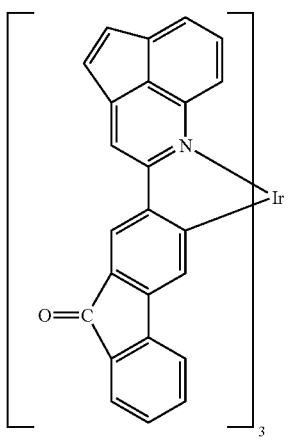
(2-10)
TABLE 6-continued
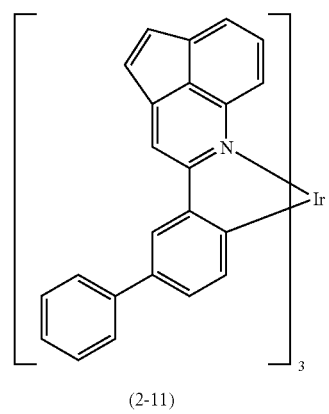
(2-11)
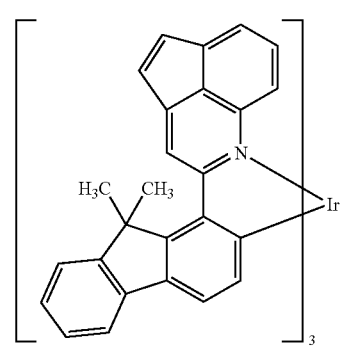
(2-12)
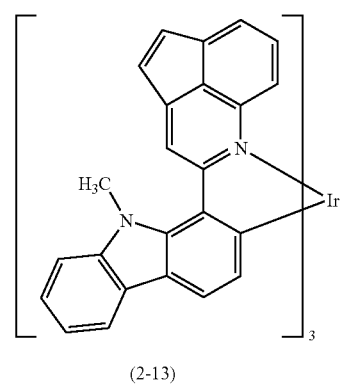
(2-13)
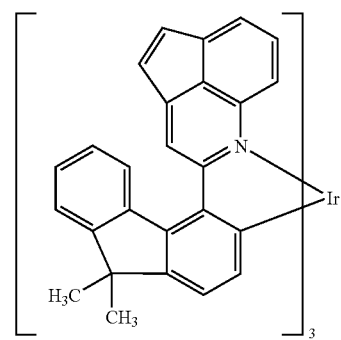
(2-14)

TABLE 6-continued
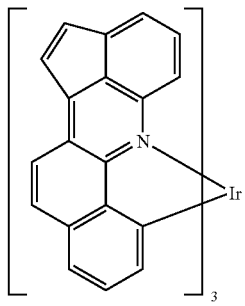
(2-15)

(2-16)
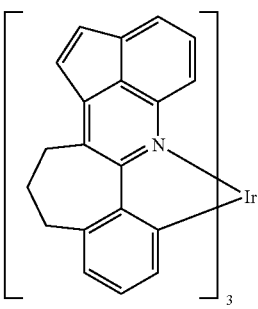
(2-17)
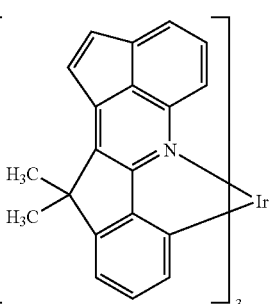
(2-18)
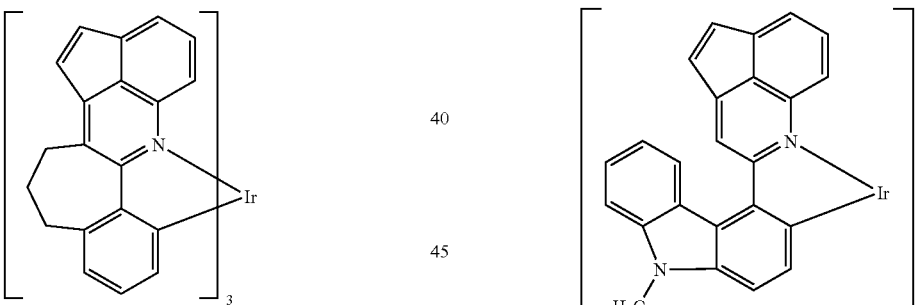
(2-19)
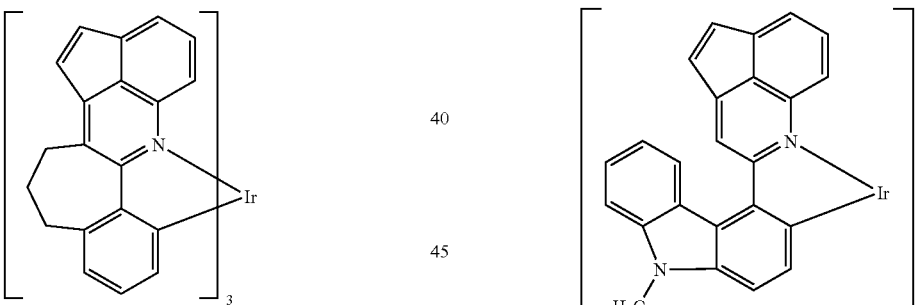
(2-20)
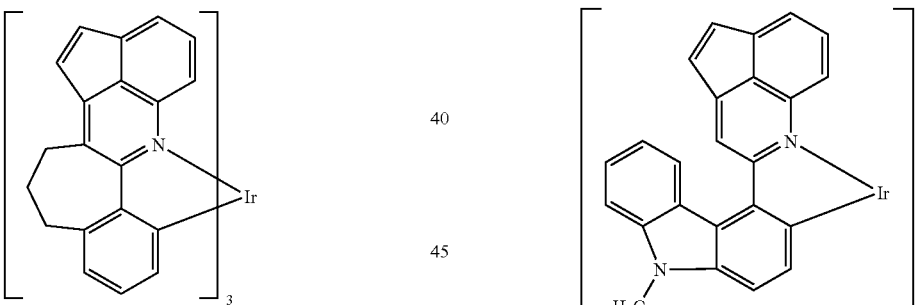
(2-21)
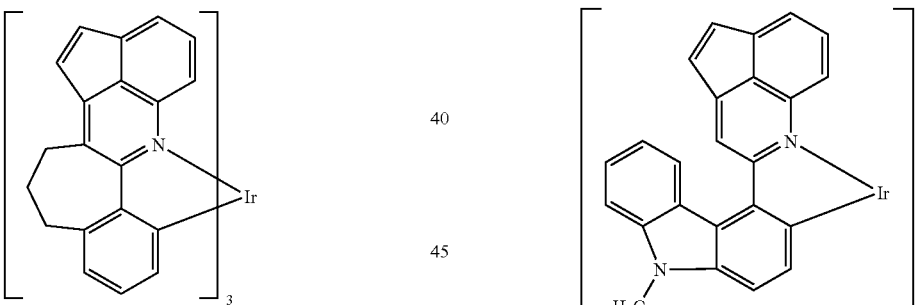
(2-22)

TABLE 6-continued
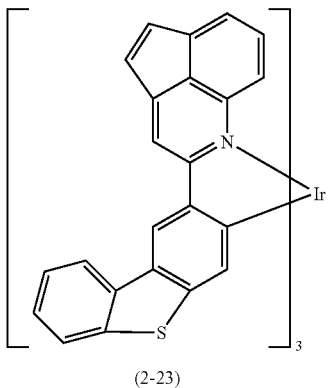
(2-23)
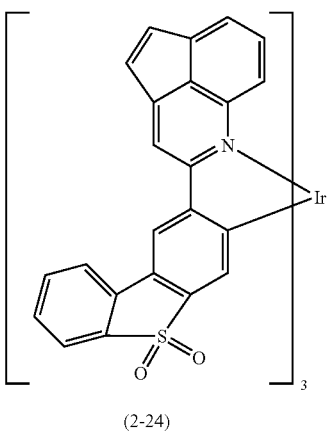
(2-24)
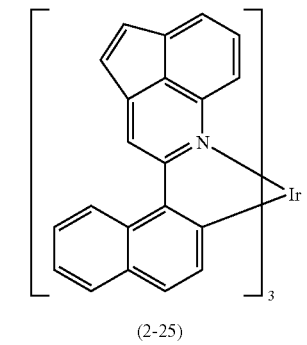
(2-25)
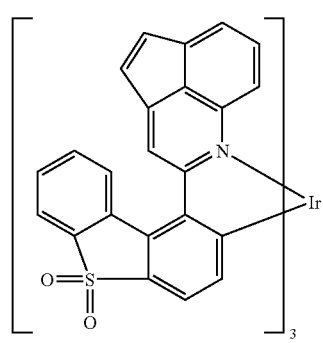
(2-26)
TABLE 6-continued
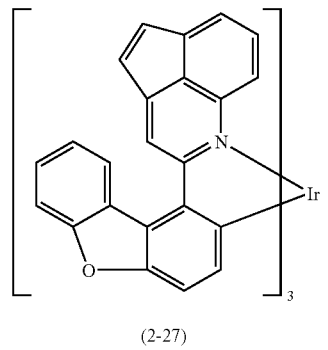
(2-27)
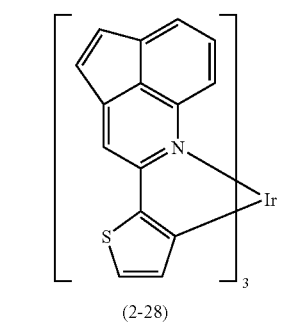
(2-28)
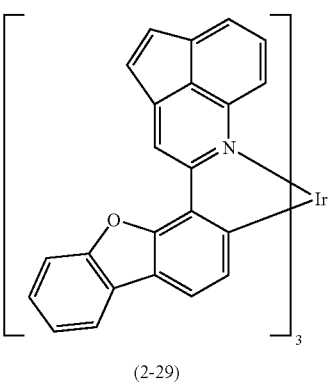
(2-29)
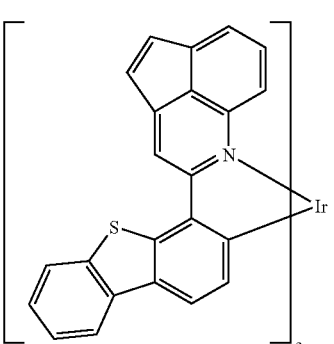
(2-30)

TABLE 6-continued
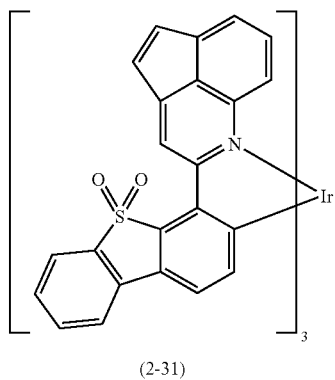
(2-31)
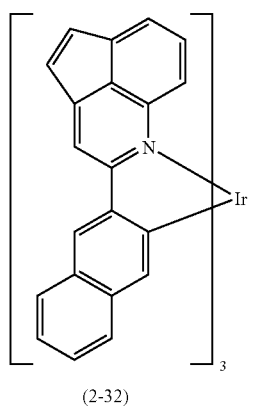
(2-32)
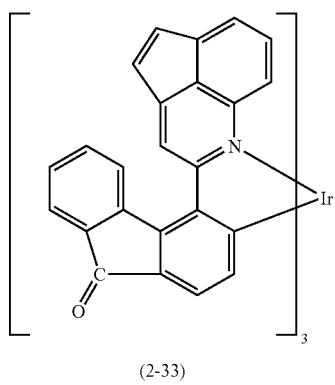
(2-33)
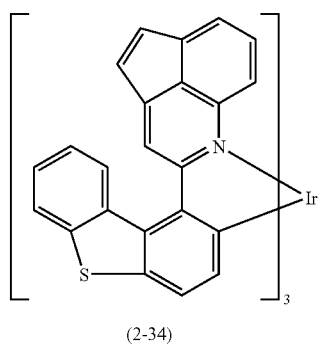
(2-34)
TABLE 6-continued
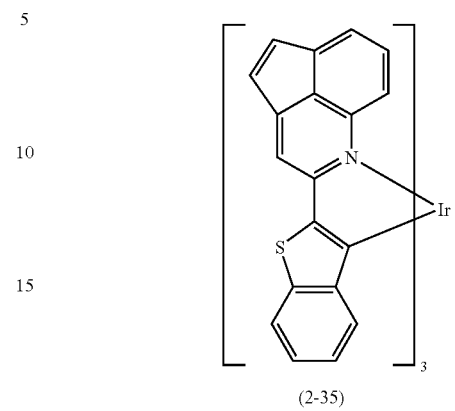
(2-35)
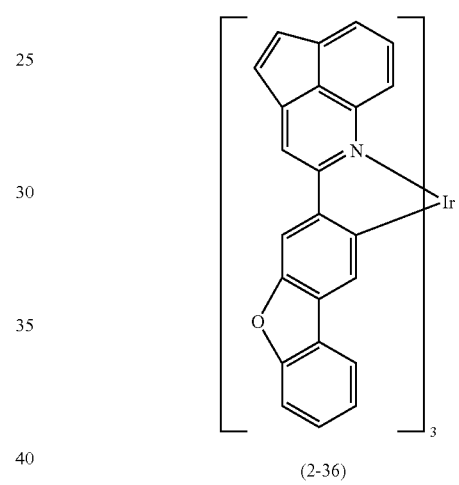
(2-36)
TABLE 7
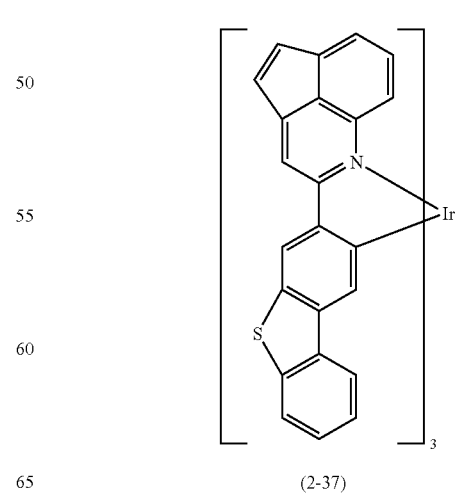
(2-37)

TABLE 7-continued
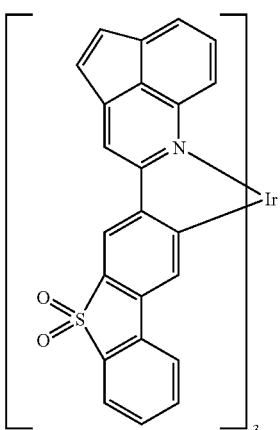
(2-38)
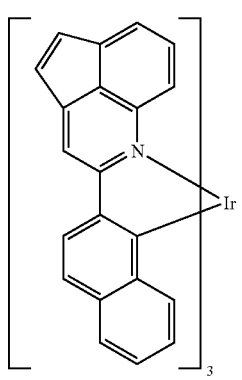
(2-39)
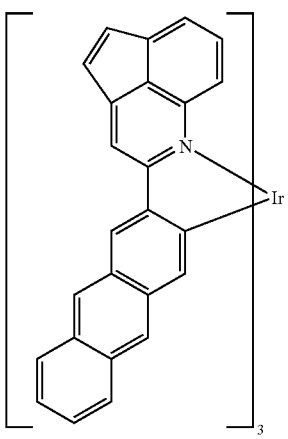
(2-40)
TABLE 7-continued
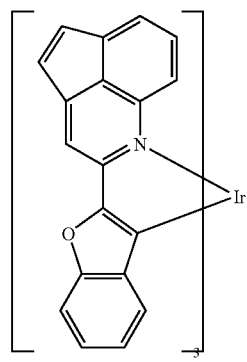
(2-41)
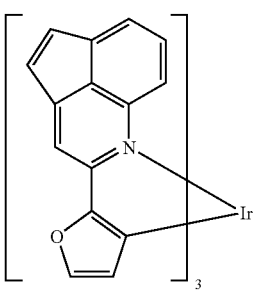
(2-42)
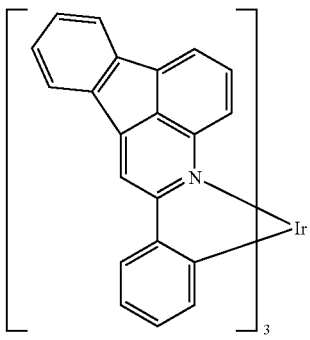
(2-43)
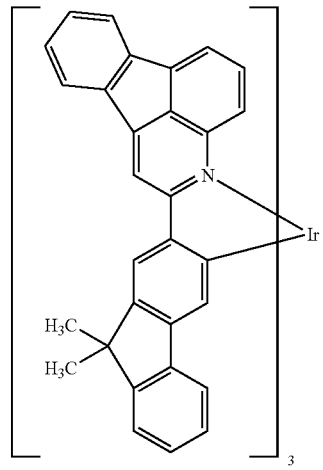
(2-44)

TABLE 7-continued
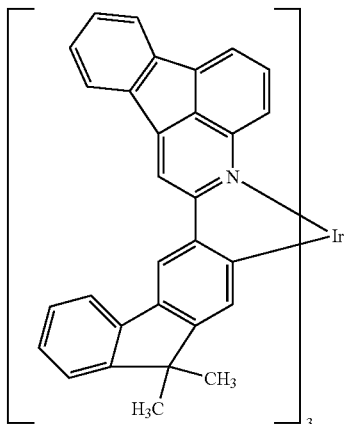
(2-45)
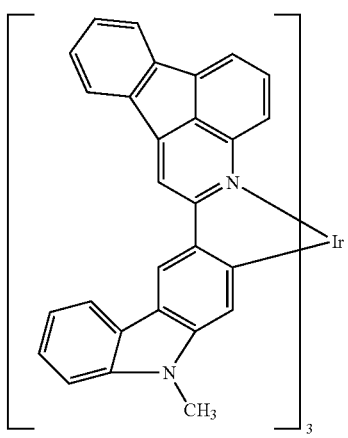
(2-46)
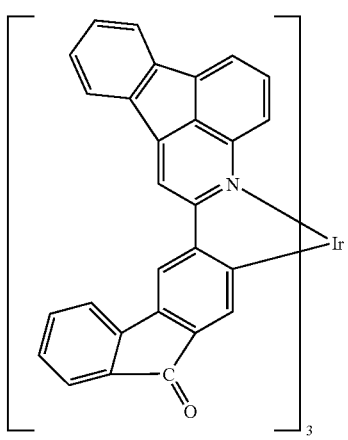
(2-47)
TABLE 7-continued
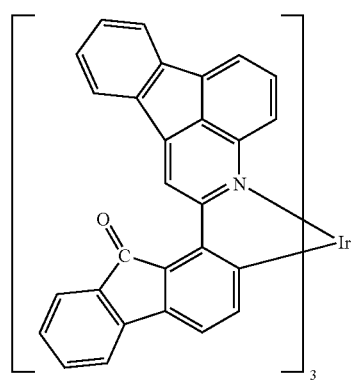
(2-48)
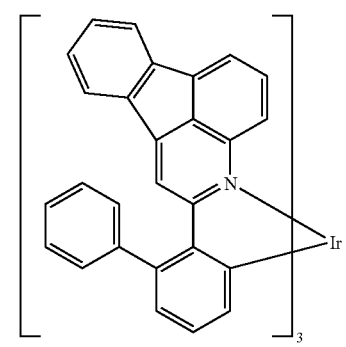
(2-49)
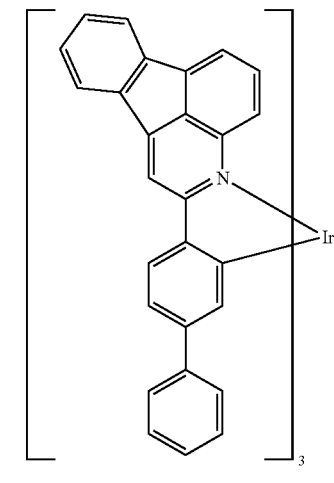
(2-50)

TABLE 7-continued
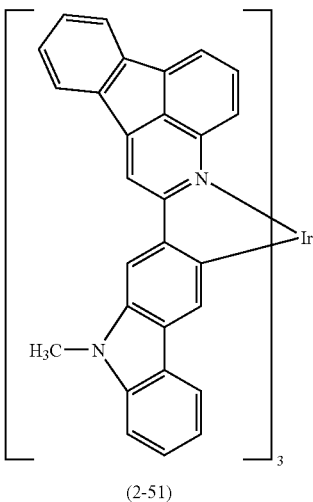
(2-51)
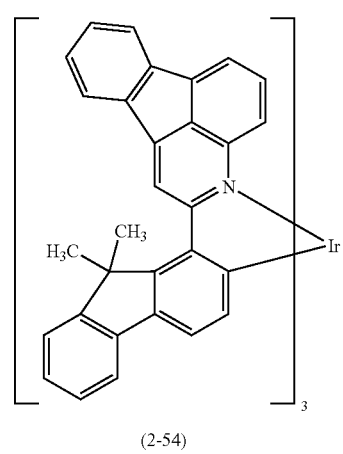
(2-54)
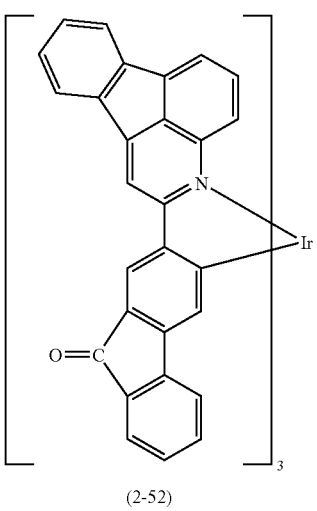
(2-52)
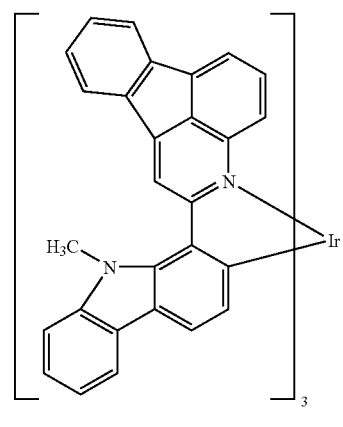
(2-55)
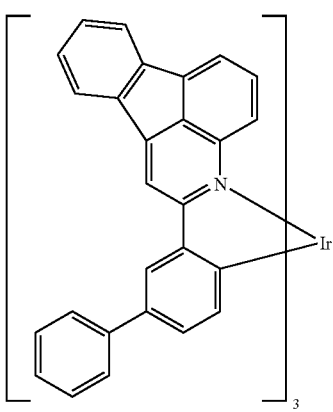
(2-53)
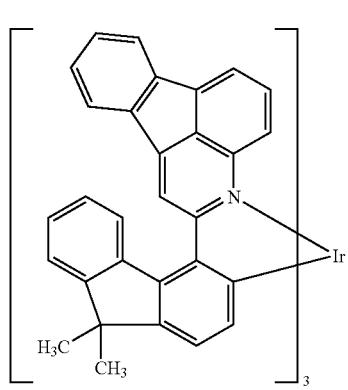
(2-56)

TABLE 7-continued
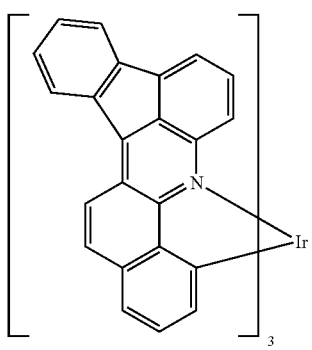
(2-57)
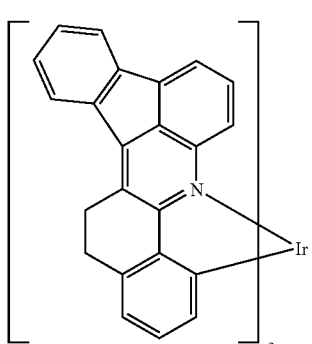
(2-58)
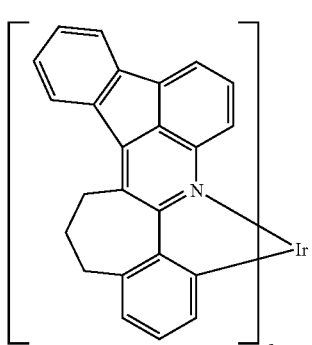
(2-59)
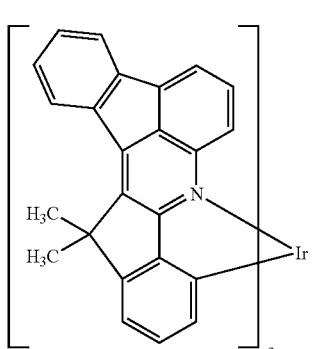
(2-60)
TABLE 7-continued
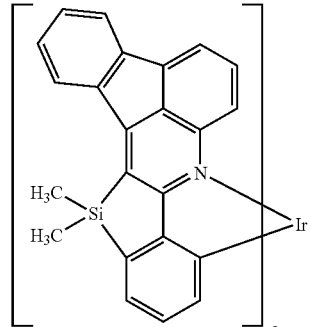
(2-61)
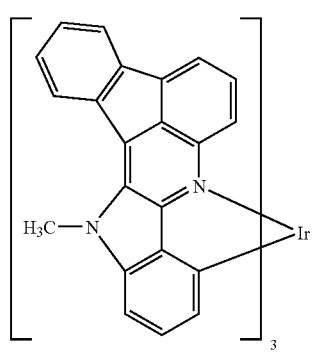
(2-62)
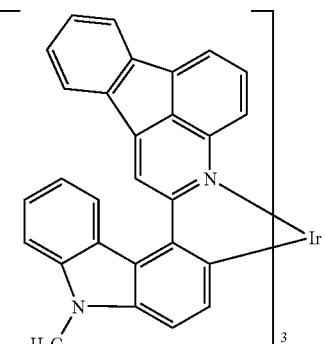
(2-63)
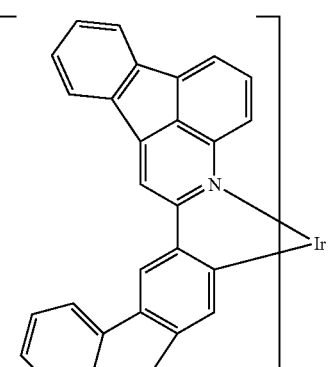
(2-64)

TABLE 7-continued
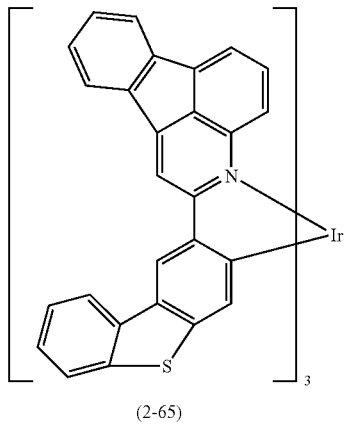
(2-65)
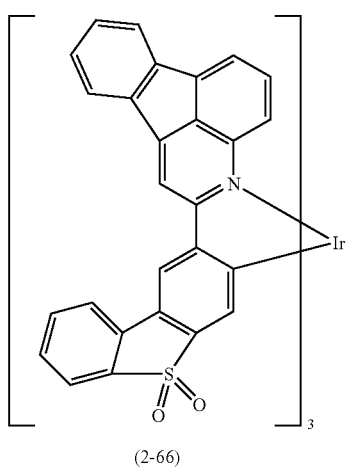
(2-66)
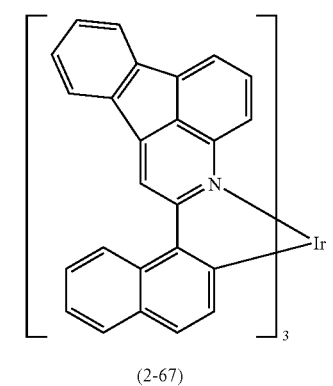
(2-67)
TABLE 7-continued
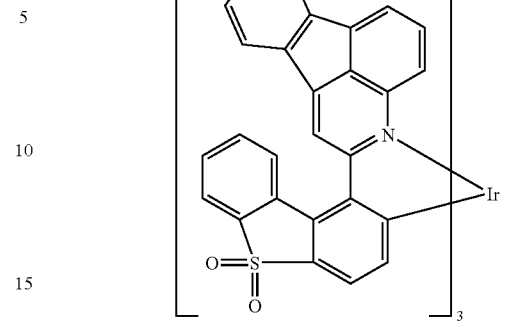
(2-68)
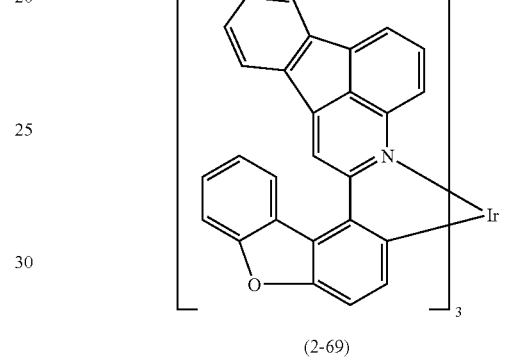
(2-69)
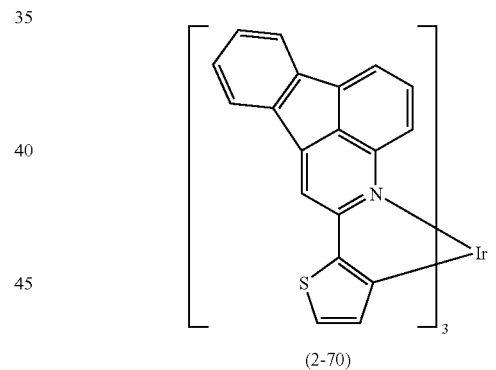
(2-70)
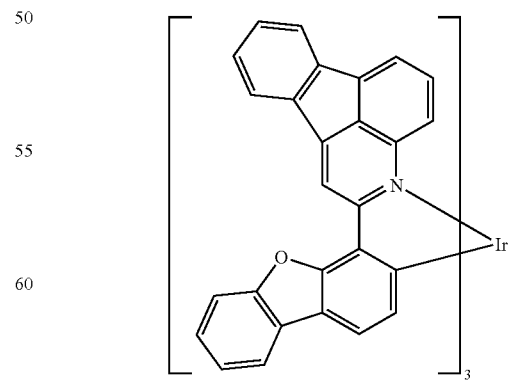
(2-71)

TABLE 7-continued
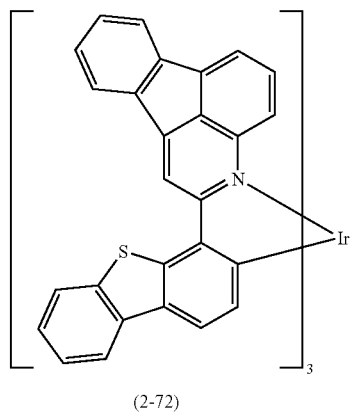
(2-72)
TABLE 8
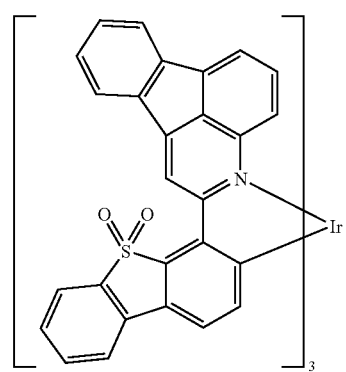
(2-73)
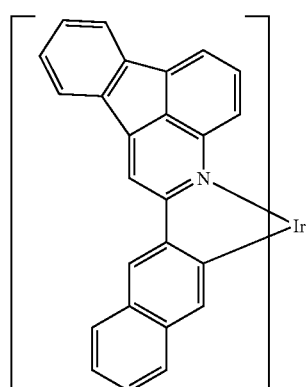
(2-74)
TABLE 8-continued
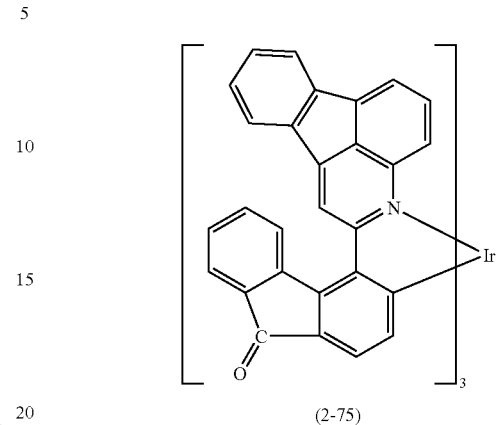
(2-75)
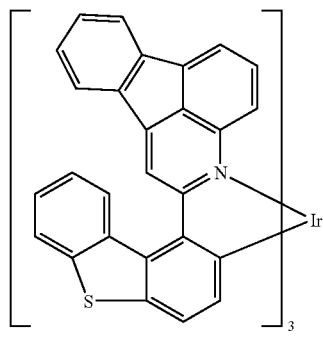
(2-76)
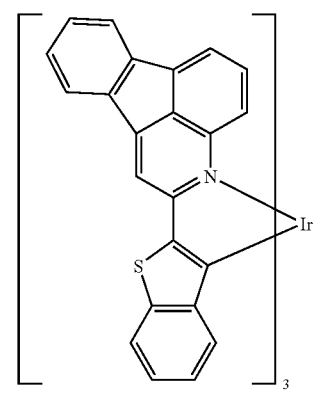
(2-77)

TABLE 8-continued
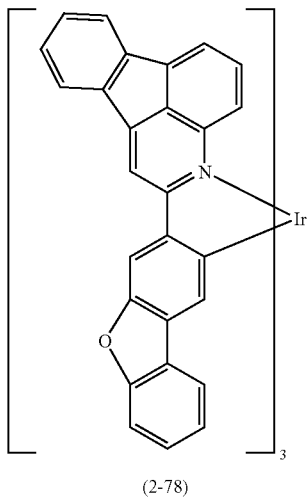
(2-78)
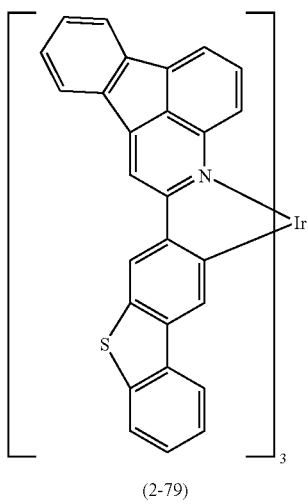
(2-79)
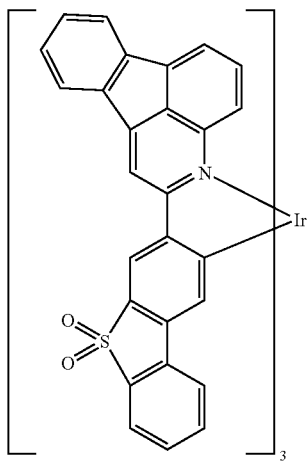
(2-80)
TABLE 8-continued
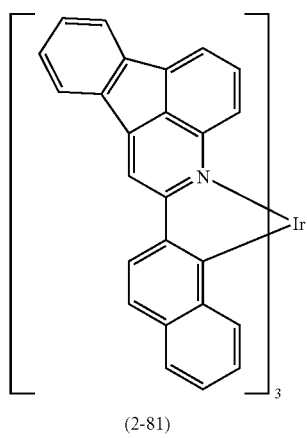
(2-81)
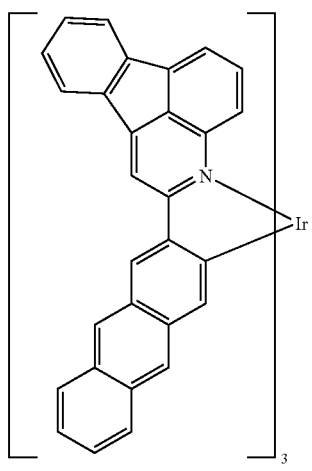
(2-82)
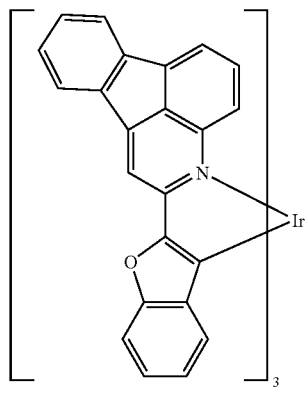
(2-83)

TABLE 8-continued
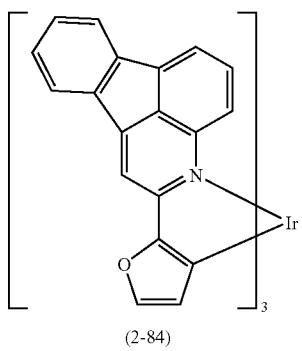
(2-84)
TABLE 9
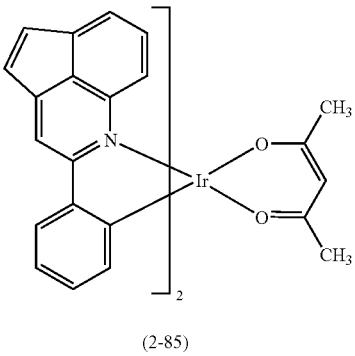
(2-85)
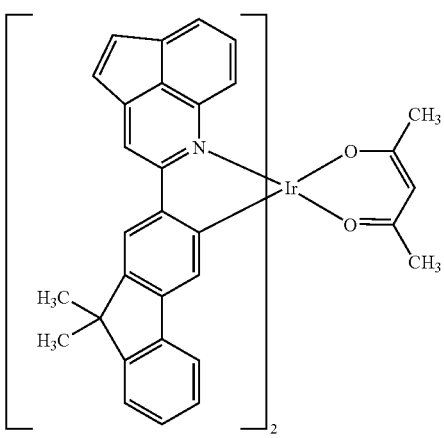
(2-86)
TABLE 9-continued
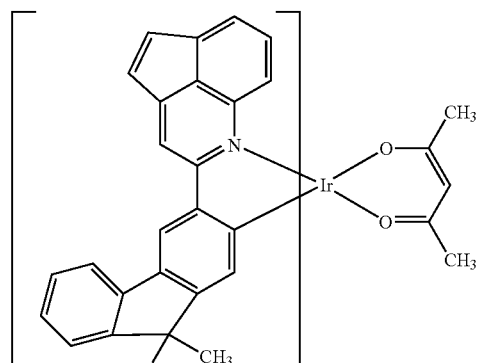
(2-87)
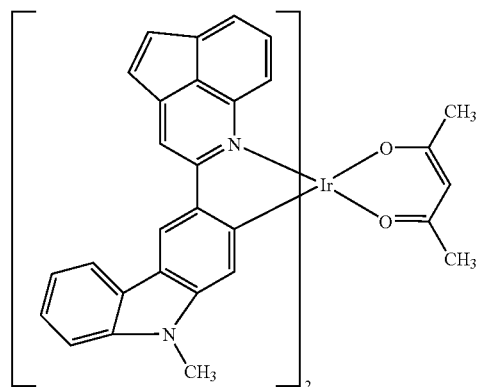
(2-88)
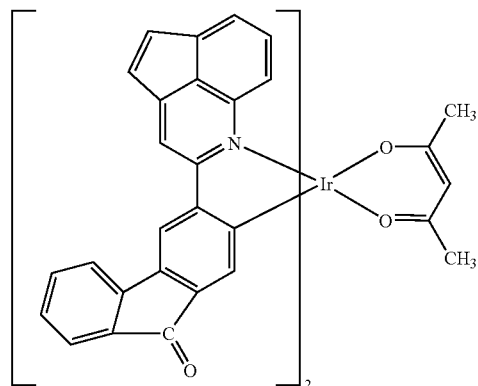
(2-89)

TABLE 9-continued
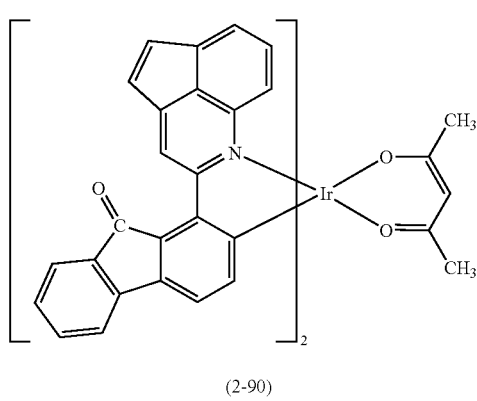
(2-90)
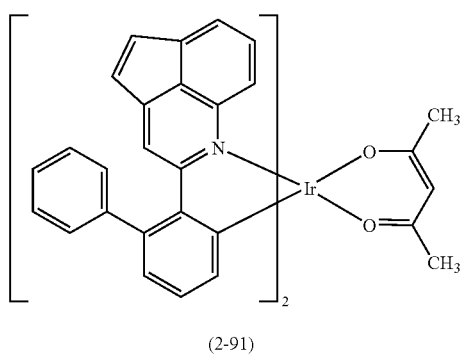
(2-91)
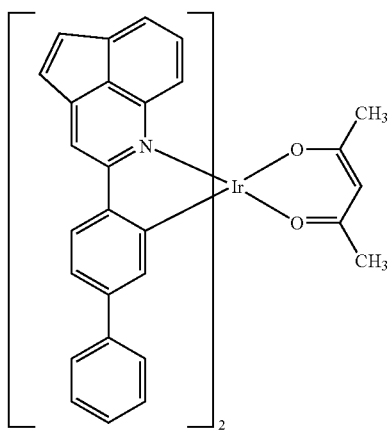
(2-92)
TABLE 9-continued
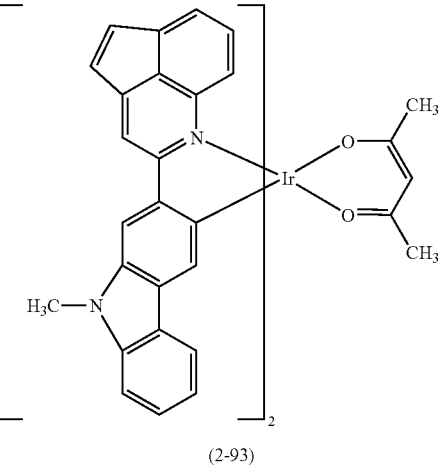
(2-93)
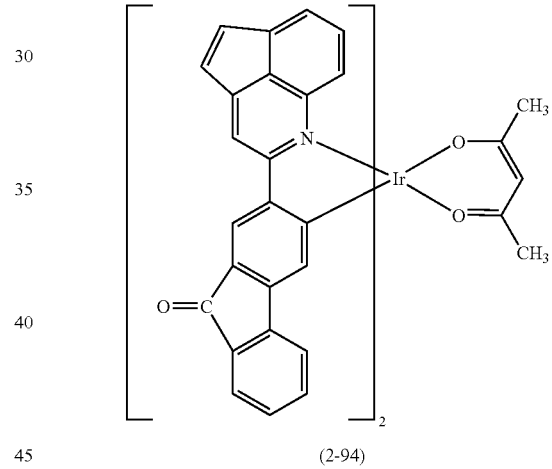
(2-94)
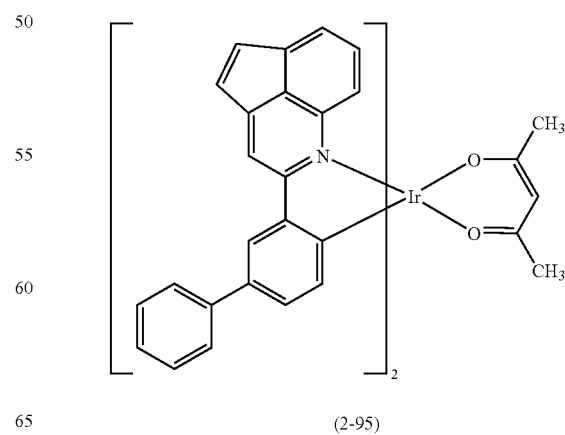
(2-95)

TABLE 9-continued
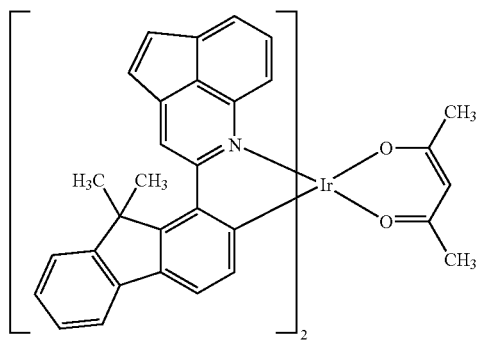
(2-96)
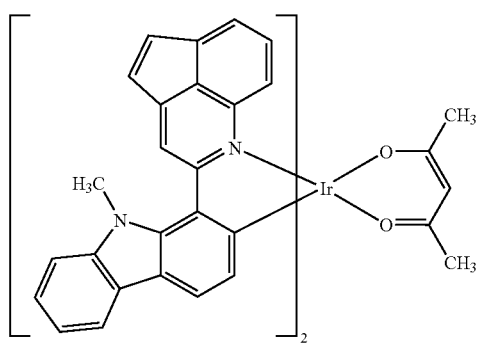
(2-97)
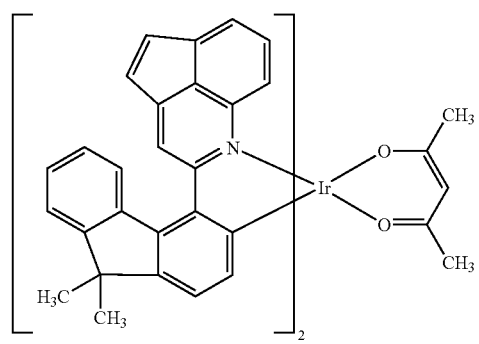
(2-98)
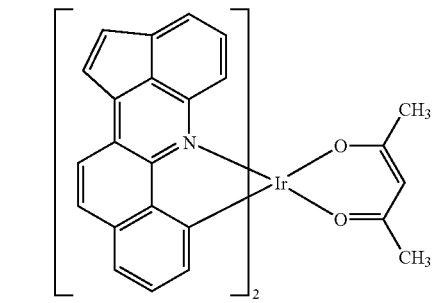
(2-99)
TABLE 9-continued
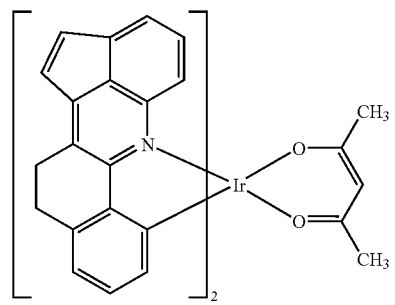
(2-100)
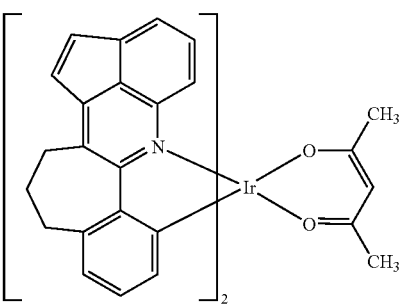
(2-101)
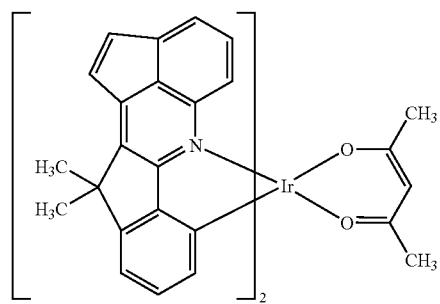
(2-102)
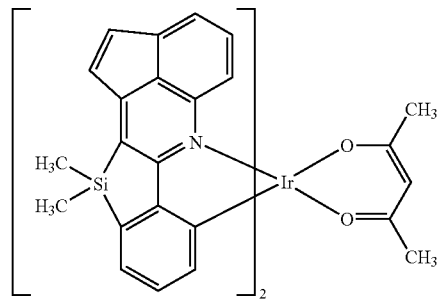
(2-103)

TABLE 9-continued
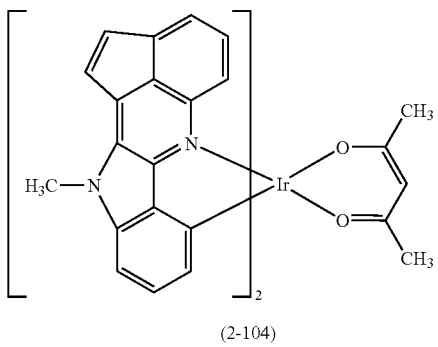
(2-104)
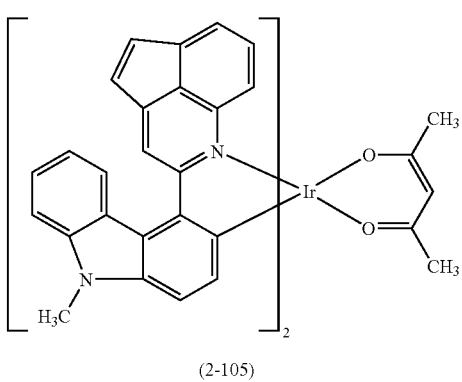
(2-105)
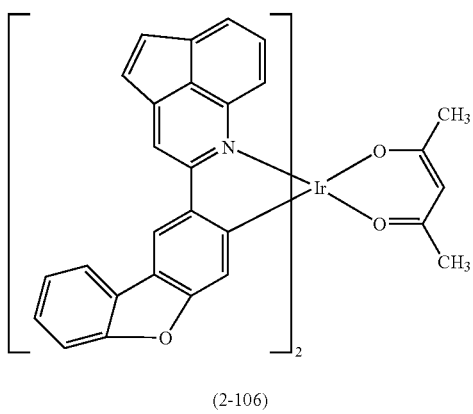
(2-106)
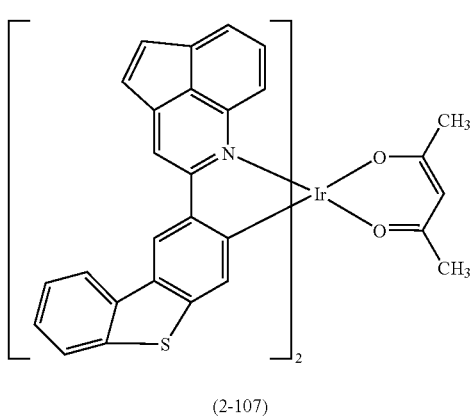
(2-107)
TABLE 9-continued
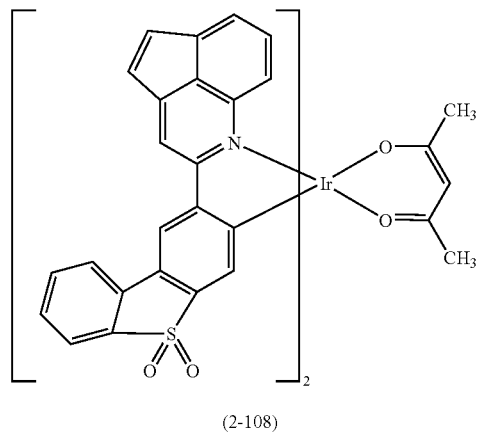
(2-108)
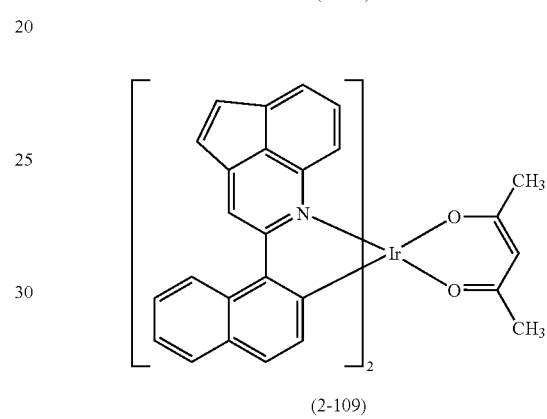
(2-109)
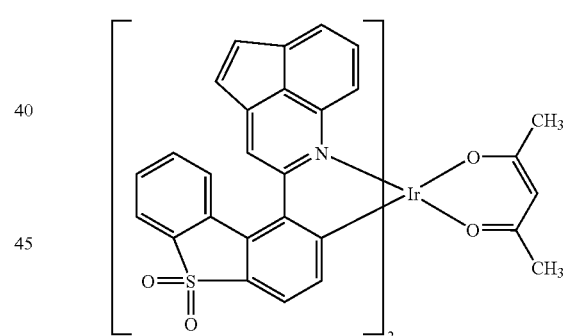
(2-110)
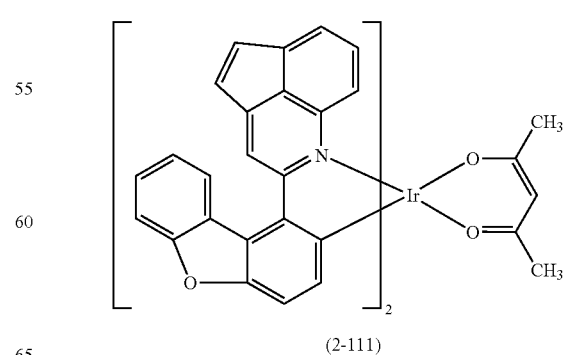
(2-111)

TABLE 9-continued
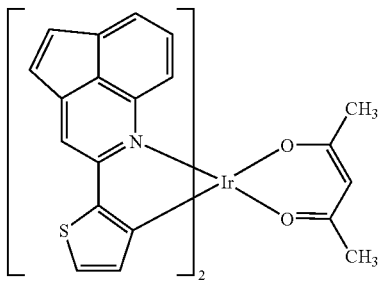
(2-112)
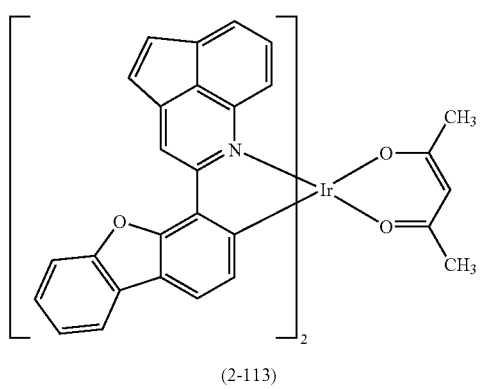
(2-113)
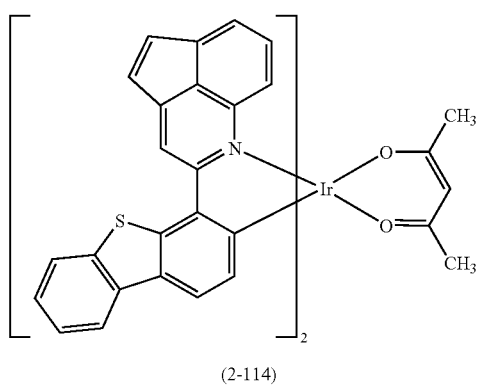
(2-114)
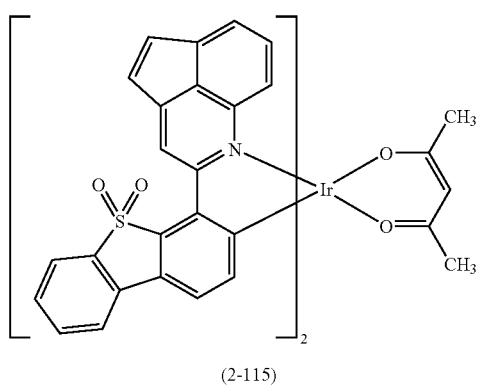
(2-115)
TABLE 9-continued
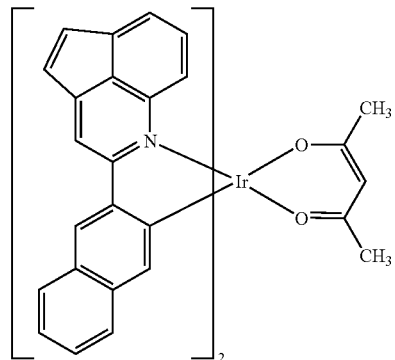
(2-116)
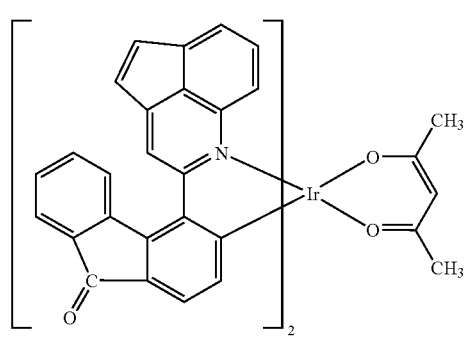
(2-117)
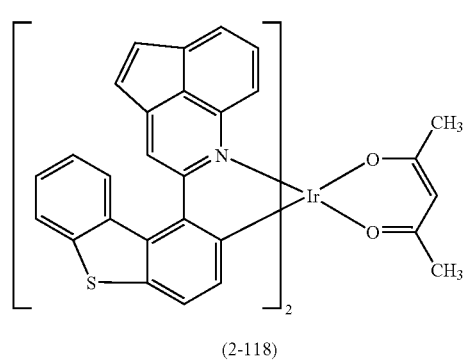
(2-118)
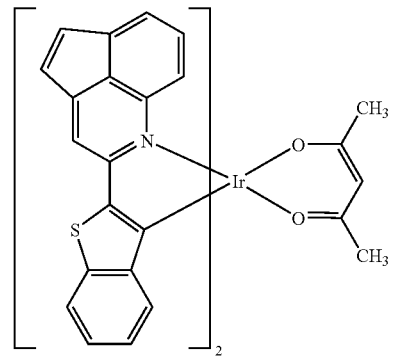
(2-119)

TABLE 9-continued
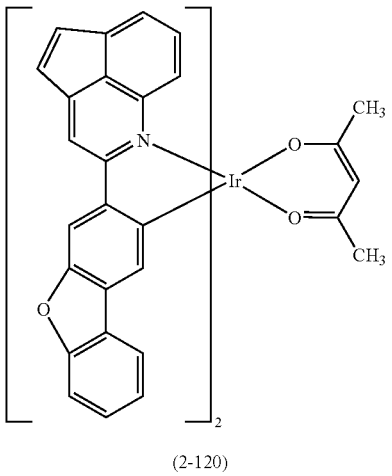
(2-120)
TABLE 10
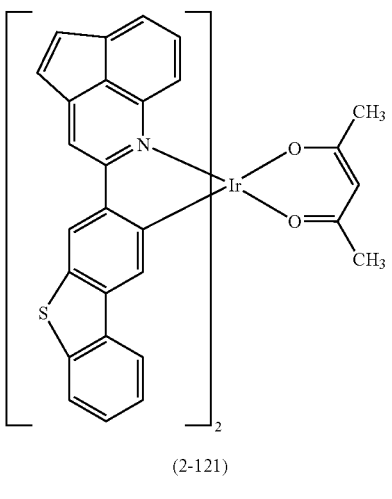
(2-121)
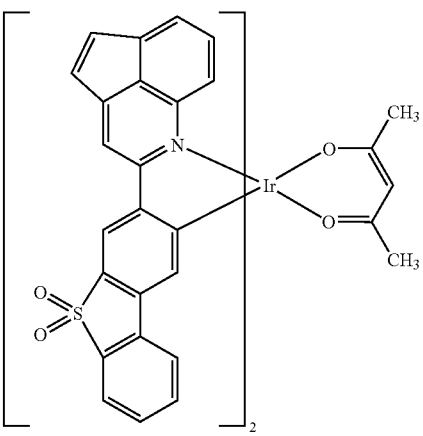
(2-122)
TABLE 10-continued
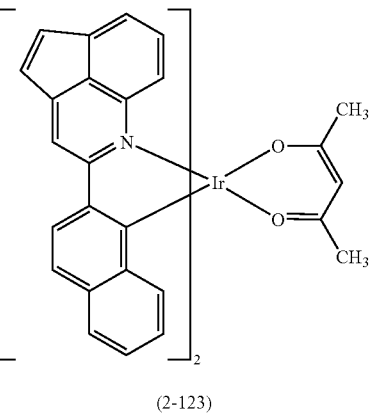
(2-123)
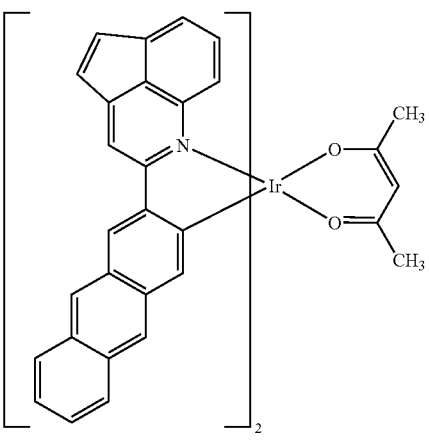
(2-124)
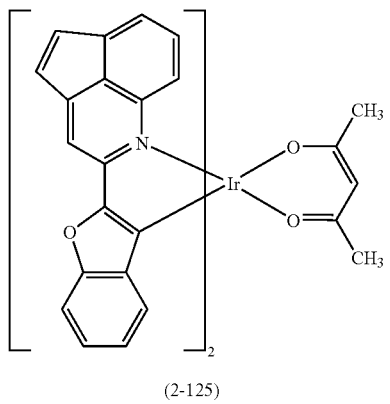
(2-125)
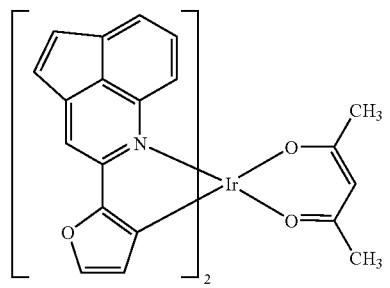
(2-126)

TABLE 10-continued
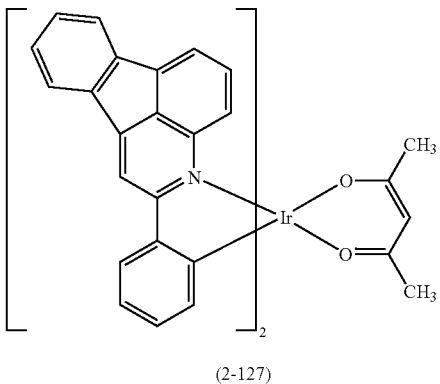
(2-127)
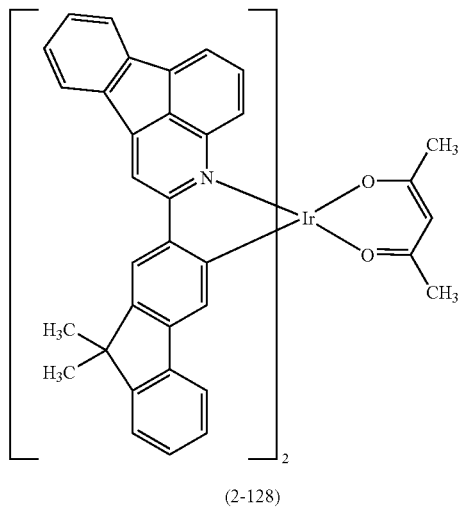
(2-128)
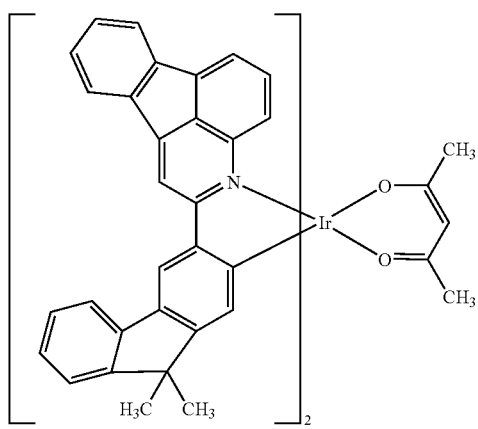
(2-129)
TABLE 10-continued
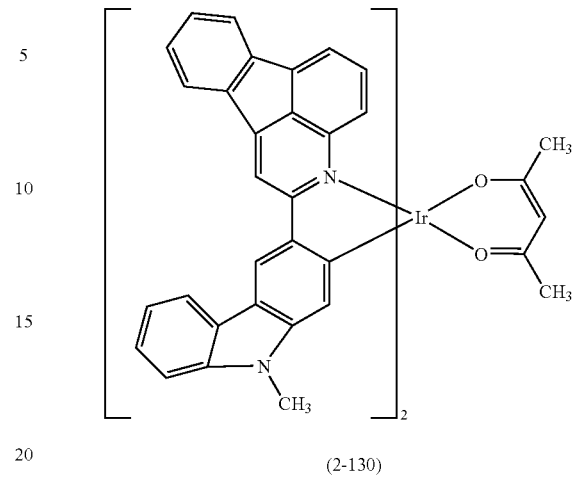
(2-130)
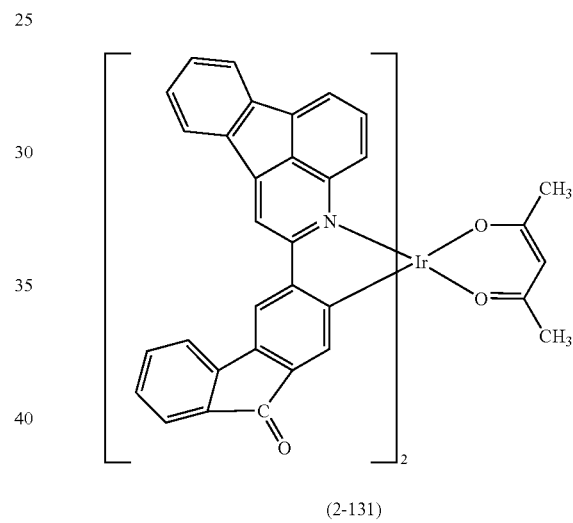
(2-131)
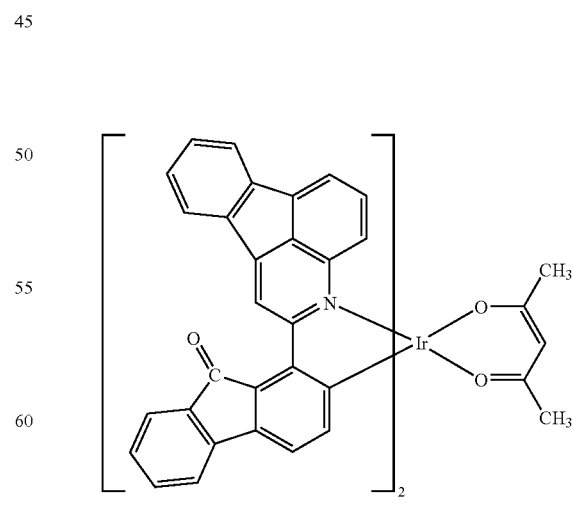
(2-132)

TABLE 10-continued
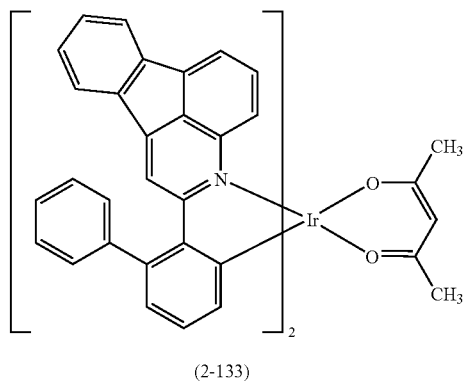
(2-133)
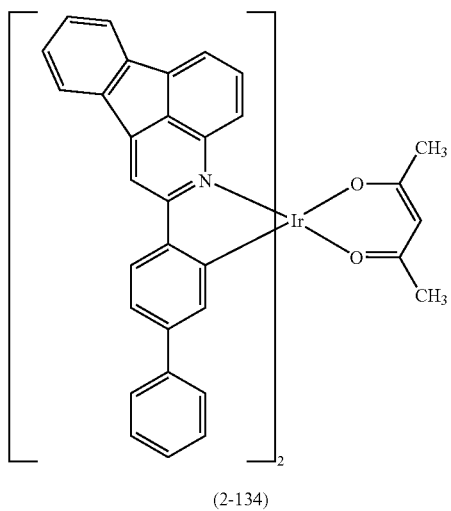
(2-134)
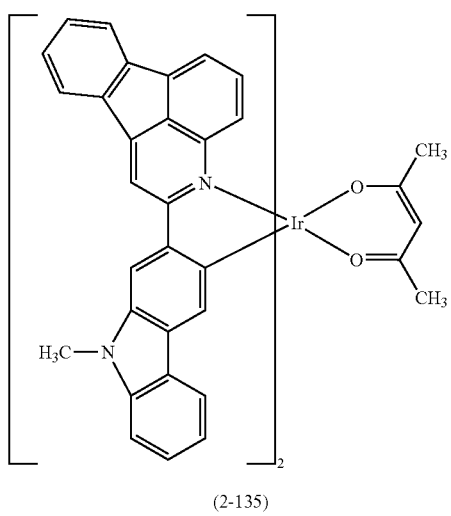
(2-135)
TABLE 10-continued
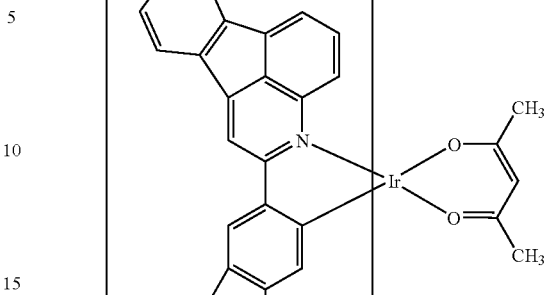
(2-136)
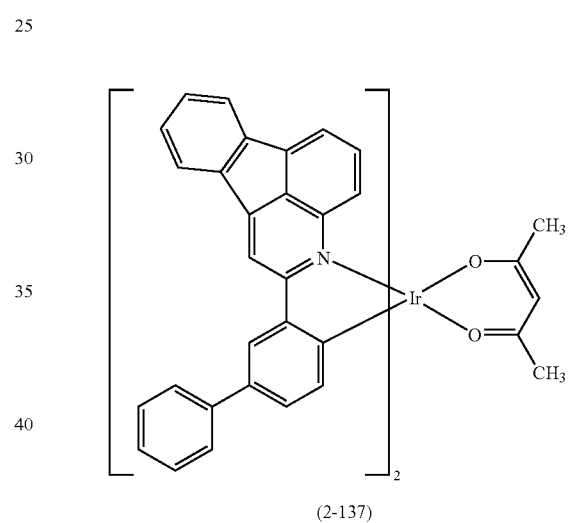
(2-137)
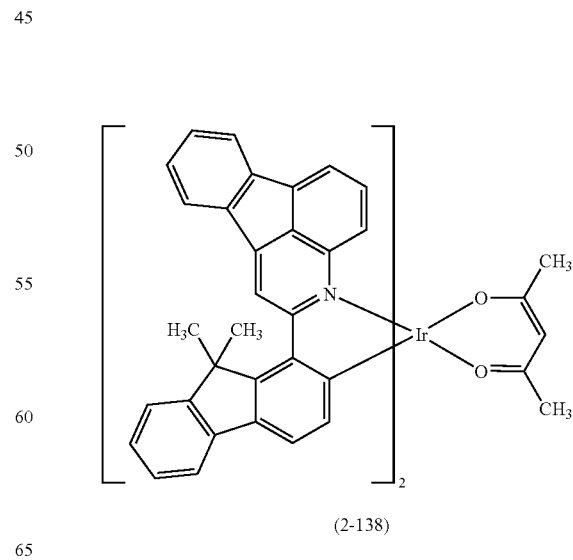
(2-138)

TABLE 10-continued
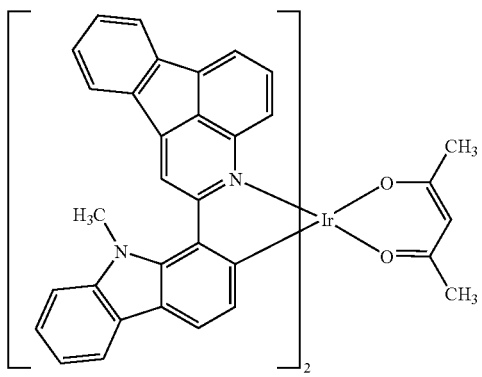
(2-139)
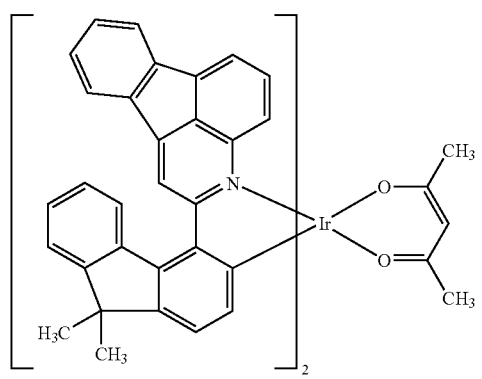
(2-140)
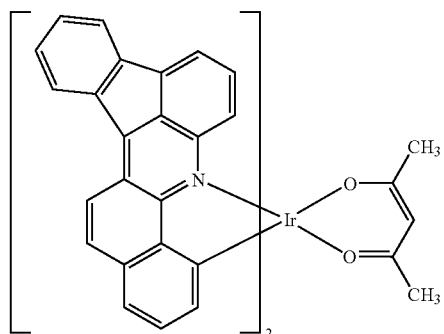
(2-141)
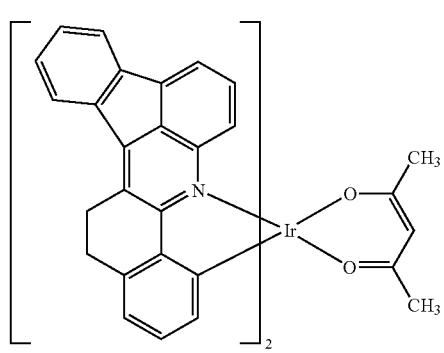
(2-142)
TABLE 10-continued
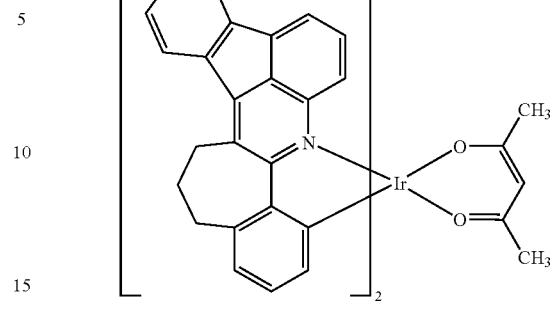
(2-143)
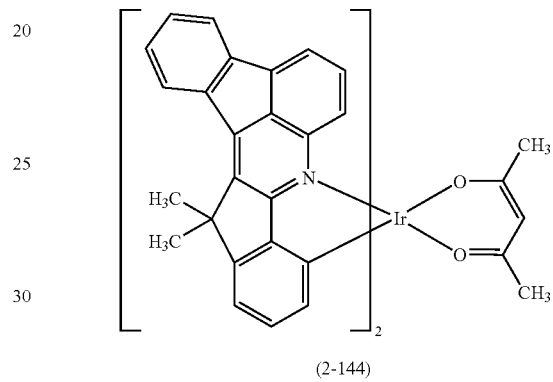
(2-144)
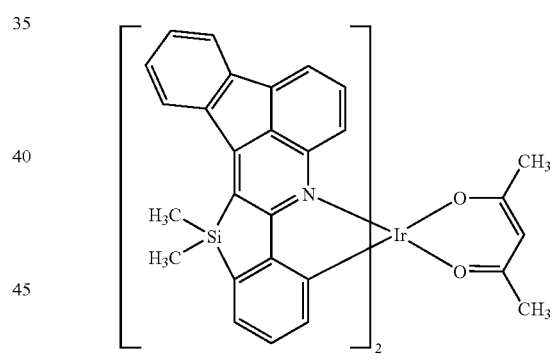
(2-145)
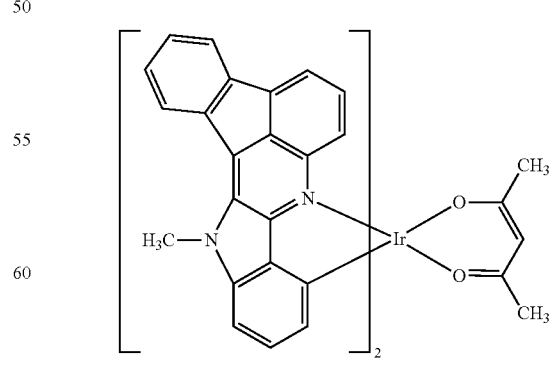
(2-146)

TABLE 10-continued
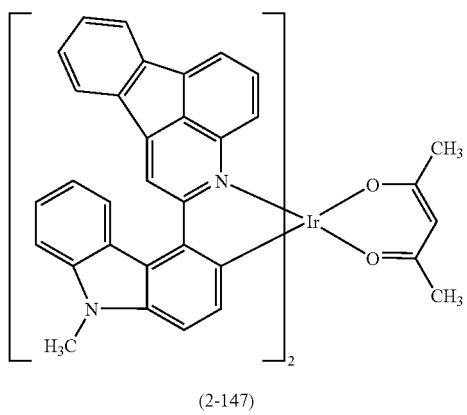
(2-147)
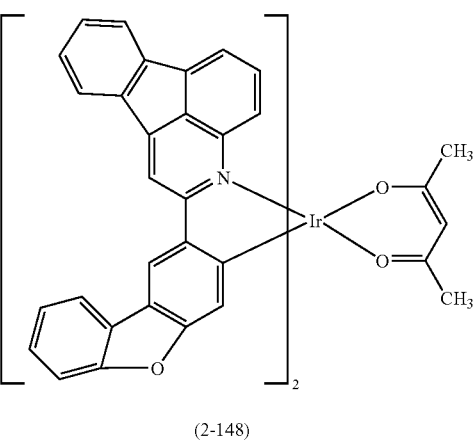
(2-148)
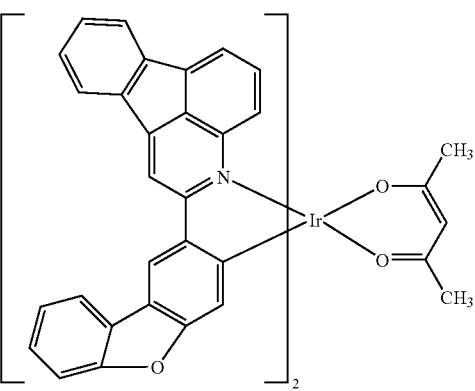
(2-149)
TABLE 10-continued
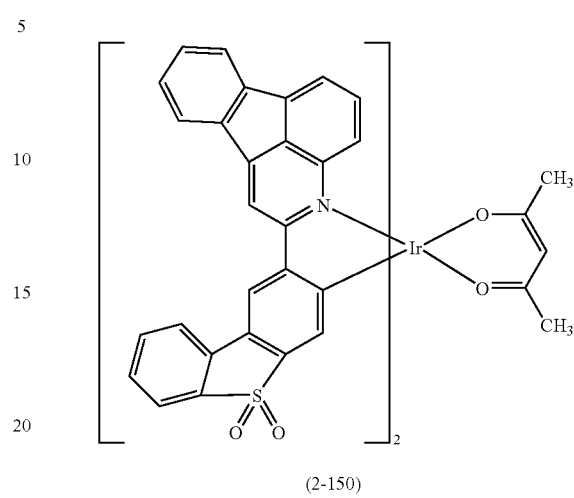
(2-150)
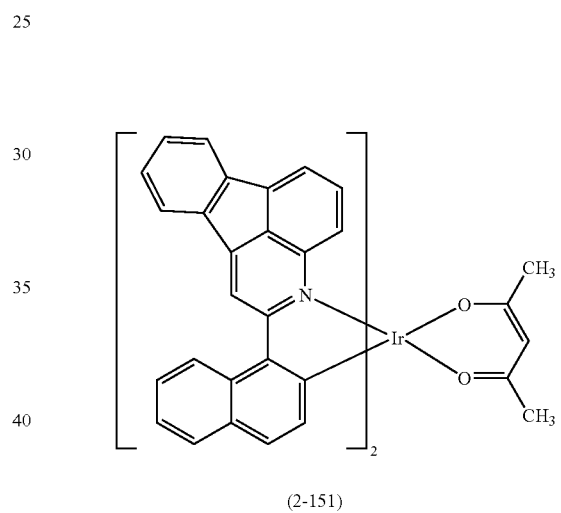
(2-151)
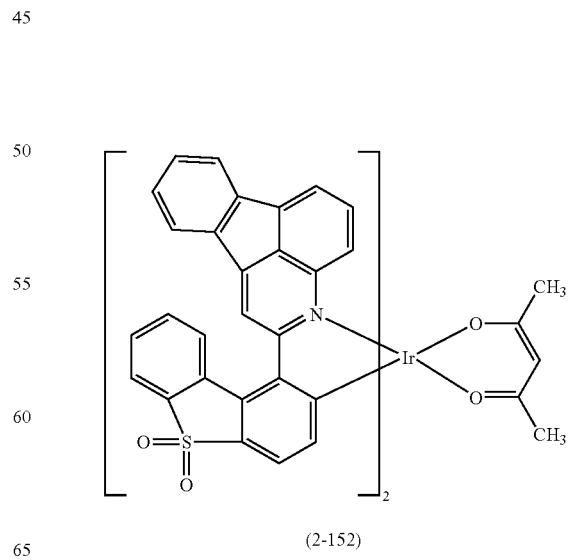
(2-152)

TABLE 10-continued
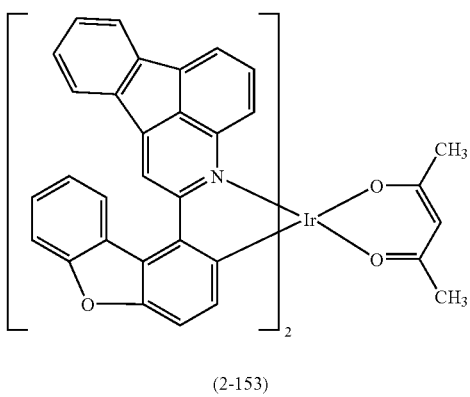
(2-153)
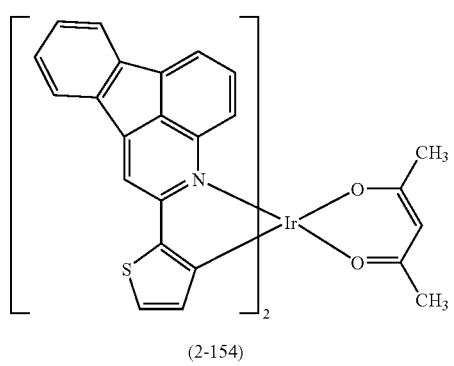
(2-154)
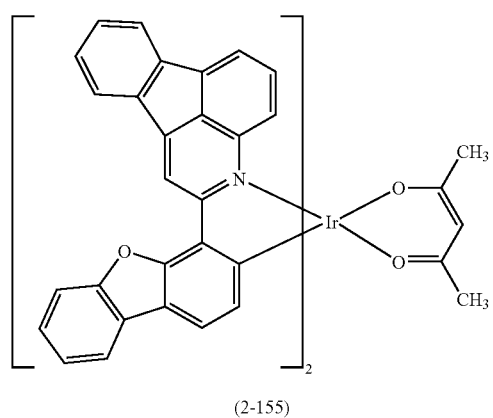
(2-155)
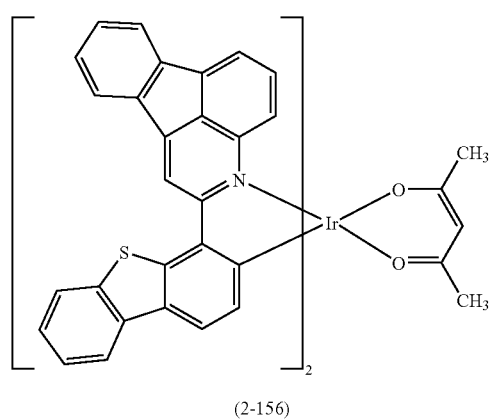
(2-156)
TABLE 11
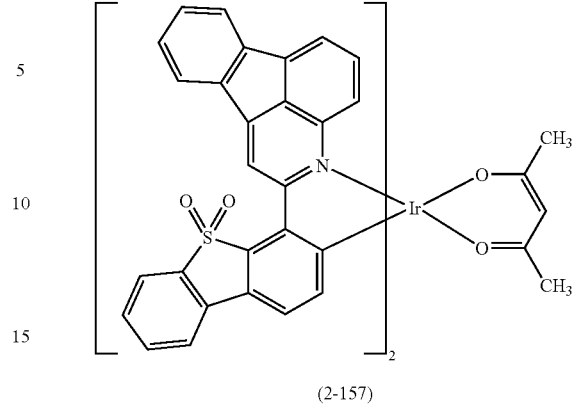
(2-157)
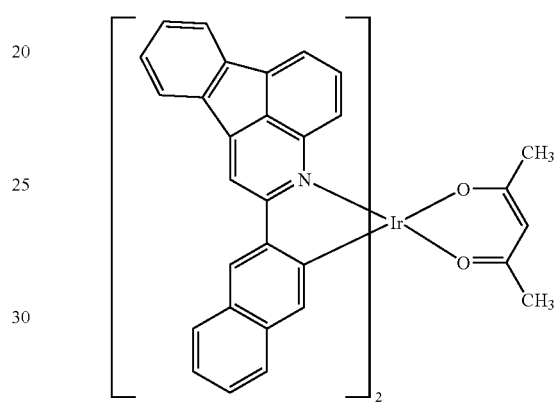
(2-158)
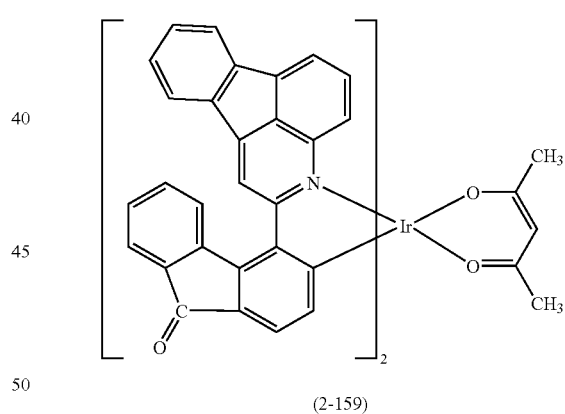
(2-159)
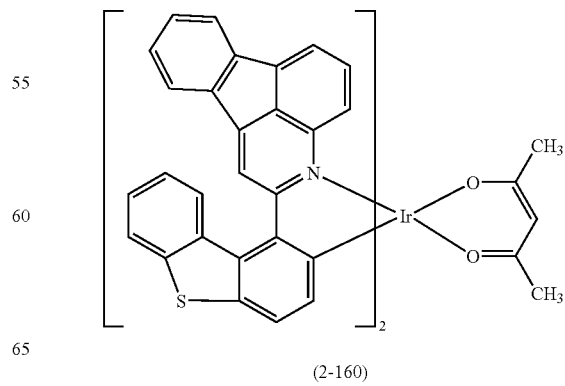
(2-160)

TABLE 11-continued
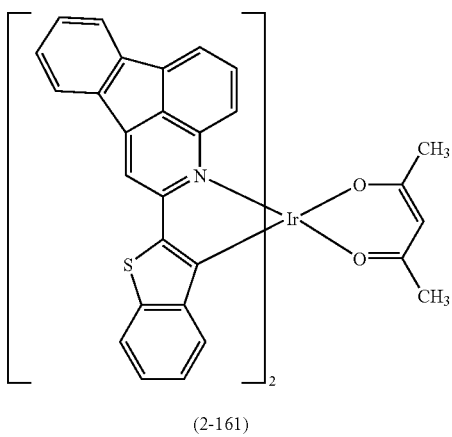
(2-161)
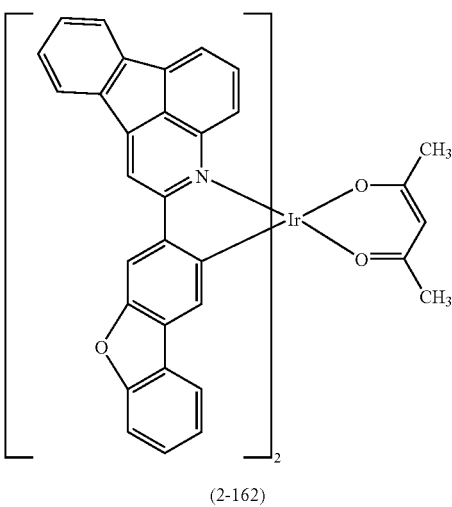
(2-162)
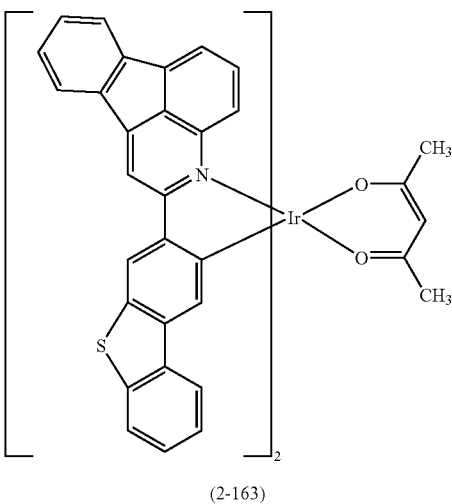
(2-163)
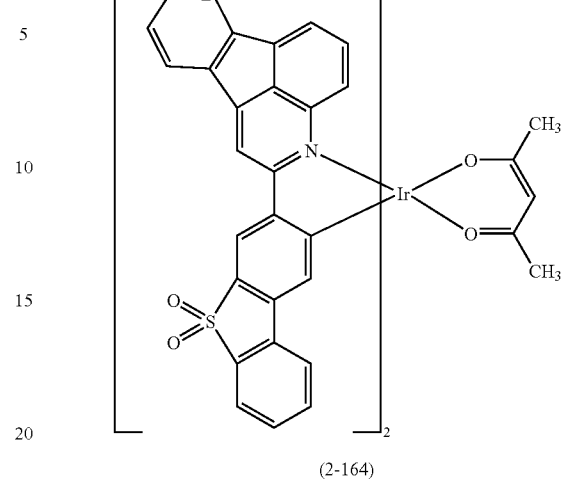
(2-164)
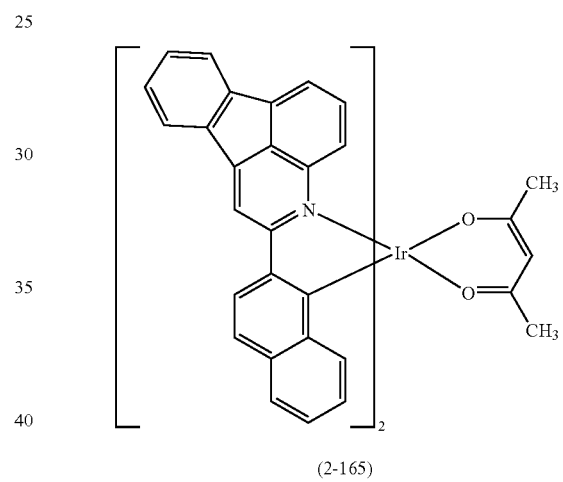
(2-165)
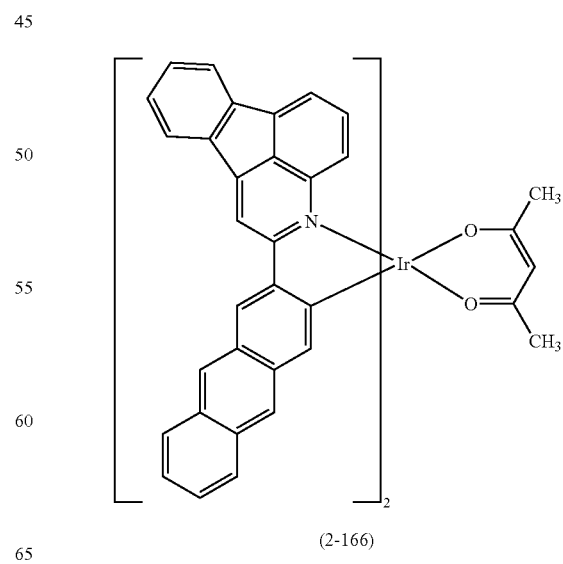
(2-166)

TABLE 11-continued
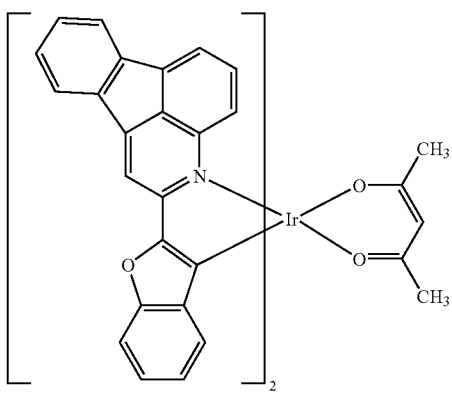
(2-167)
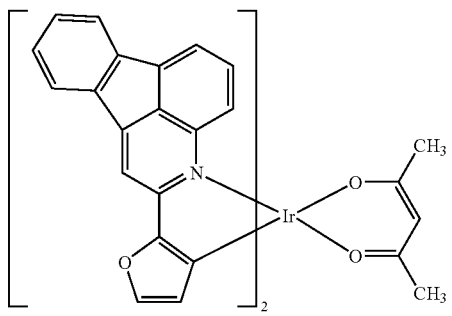
(2-168)
TABLE 12
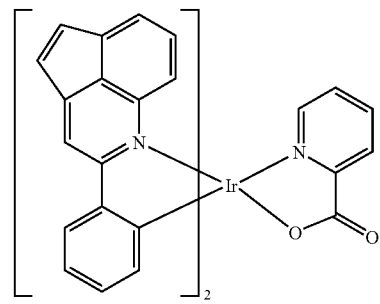
(2-169)
TABLE 12-continued
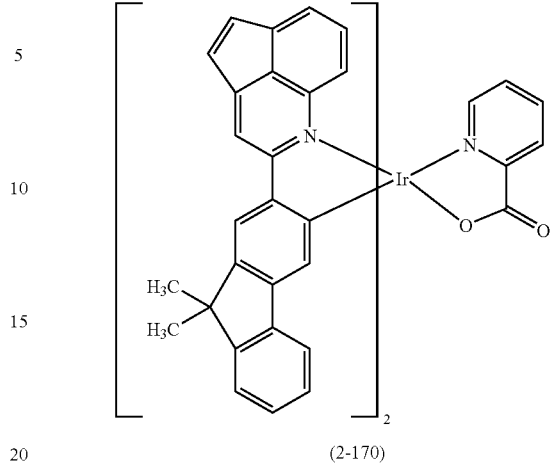
(2-170)
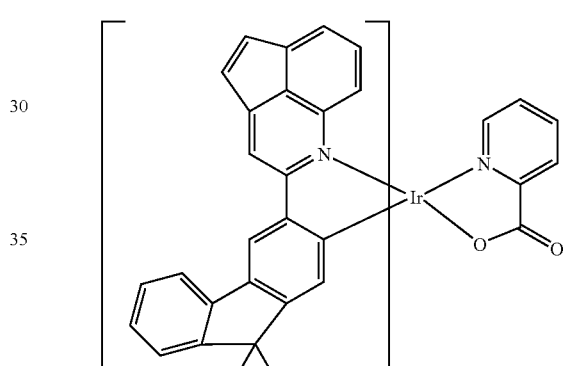
(2-171)
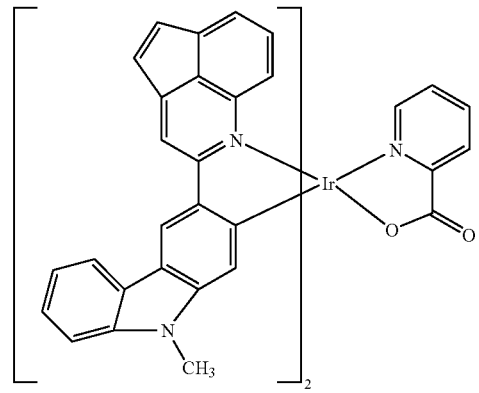
(2-172)

TABLE 12-continued
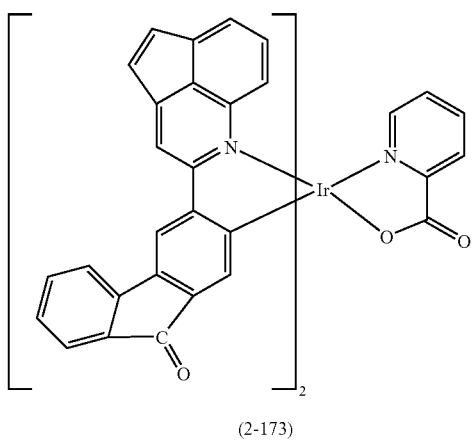
(2-173)
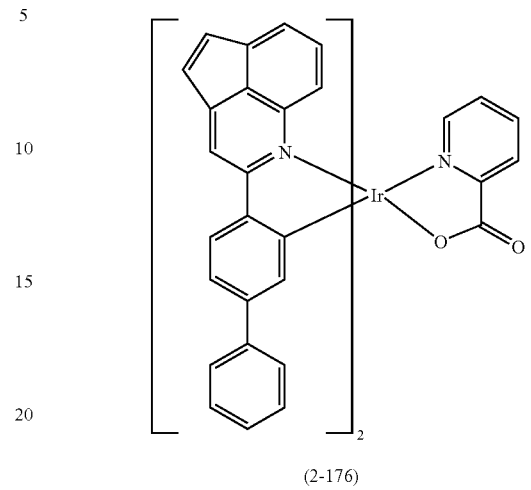
(2-176)
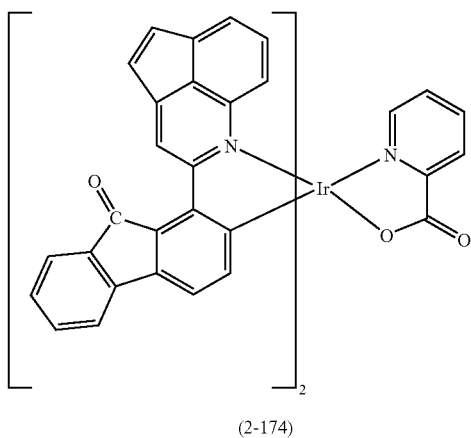
(2-174)
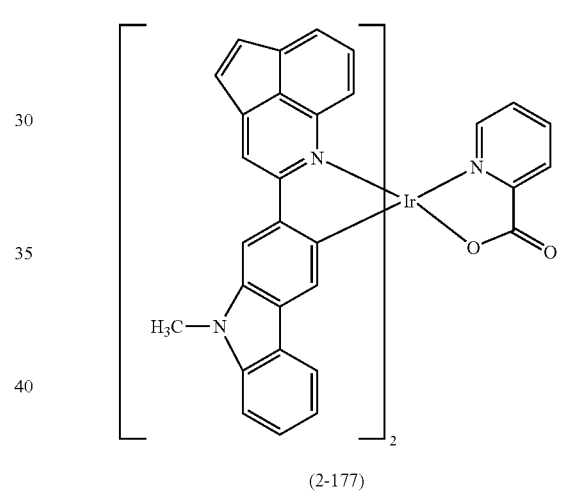
(2-177)
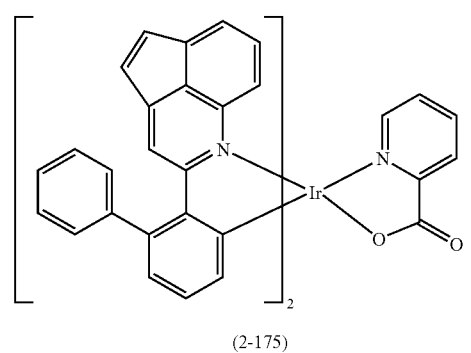
(2-175)
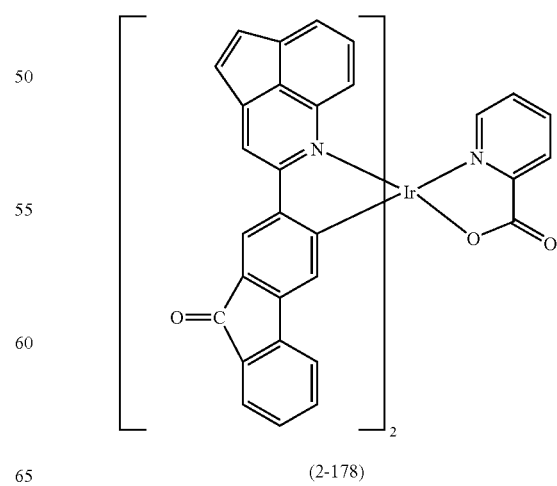
(2-178)

TABLE 12-continued
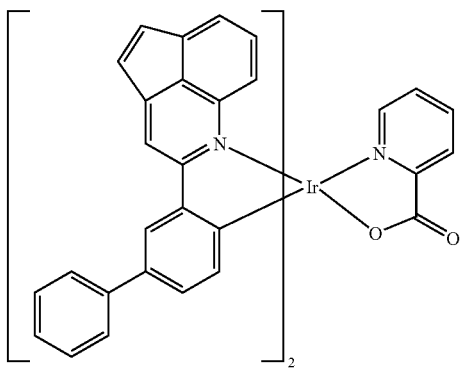
(2-179)
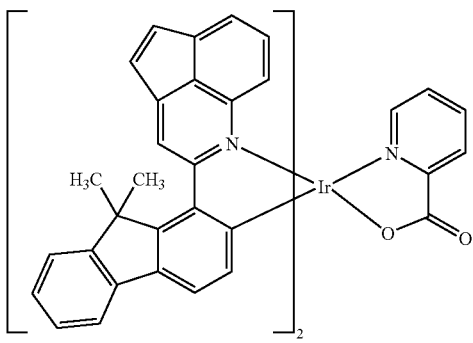
(2-180)
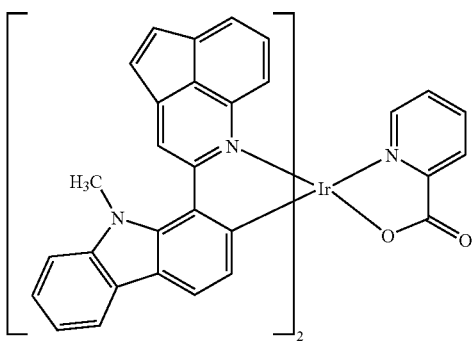
(2-181)
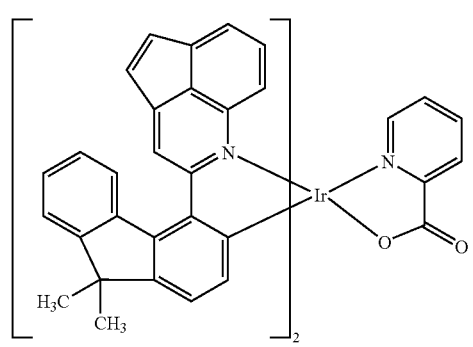
(2-182)
TABLE 12-continued
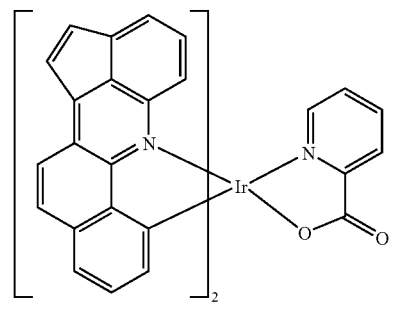
(2-183)
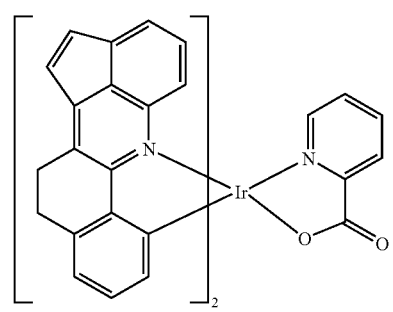
(2-184)
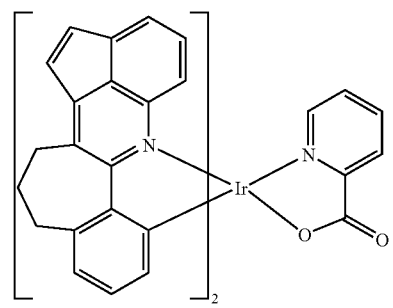
(2-185)
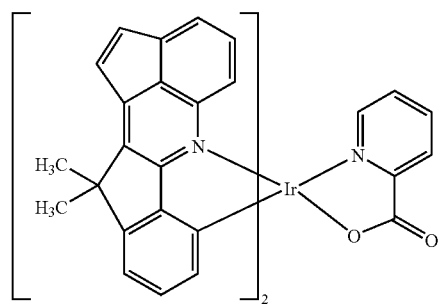
(2-186)

TABLE 12-continued
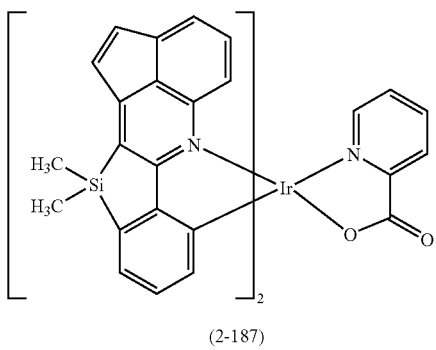
(2-187)
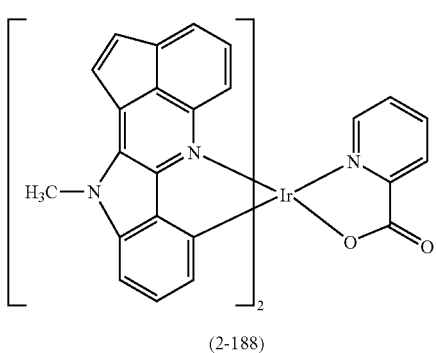
(2-188)
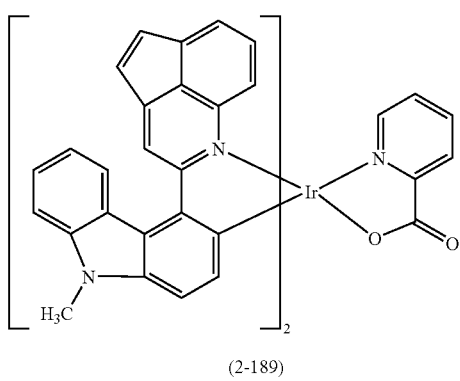
(2-189)
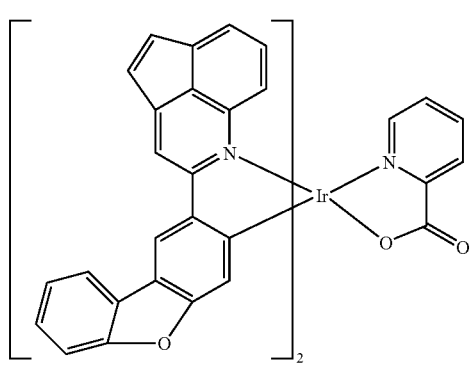
(2-190)
TABLE 12-continued
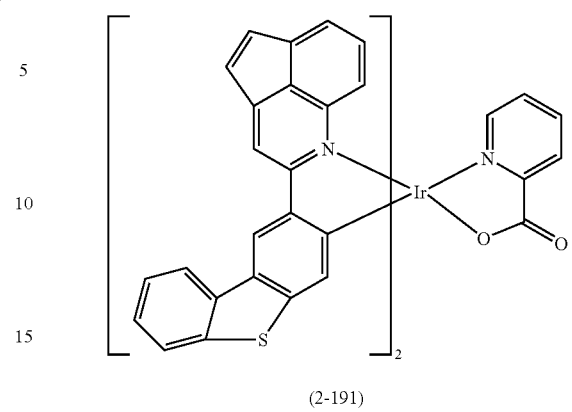
(2-191)
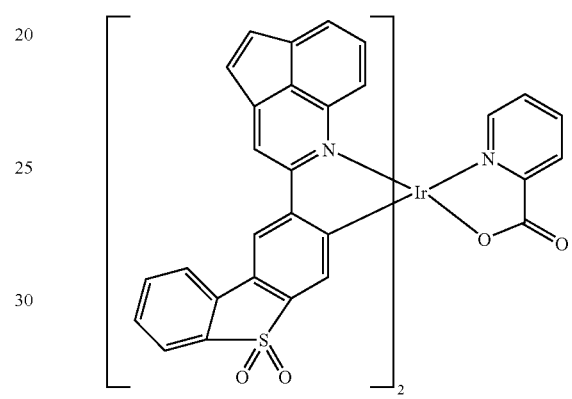
(2-192)
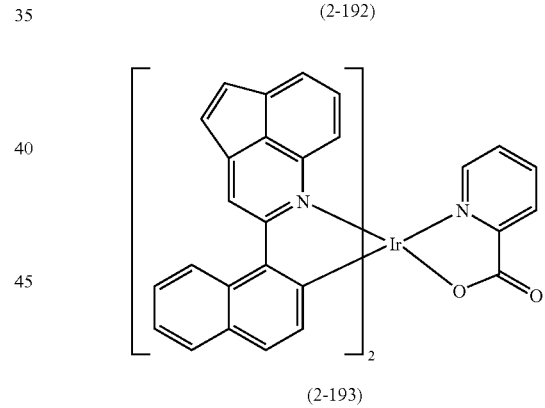
(2-193)
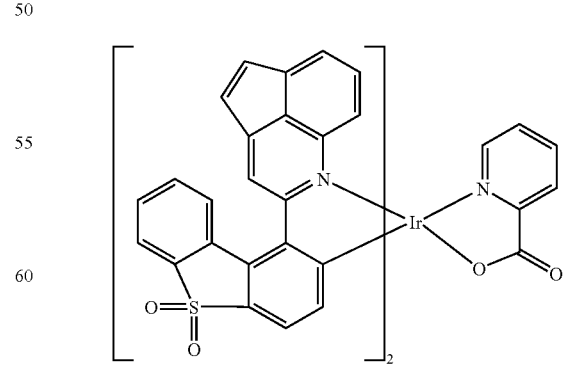
(2-194)

TABLE 12-continued
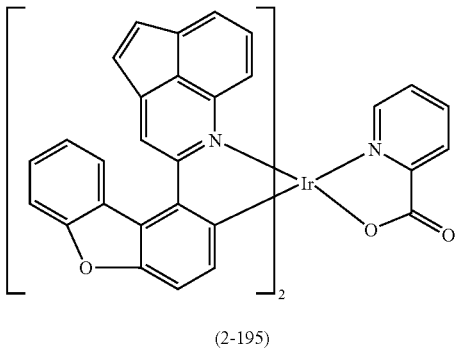
(2-195)
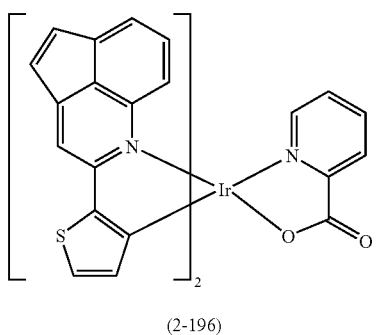
(2-196)
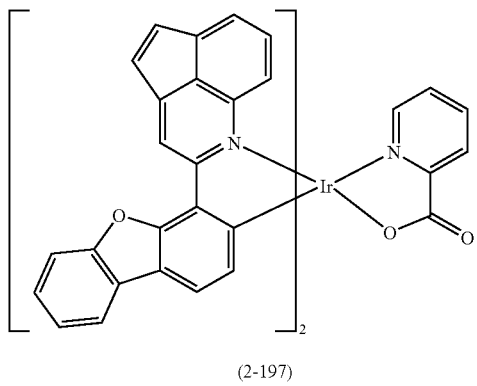
(2-197)
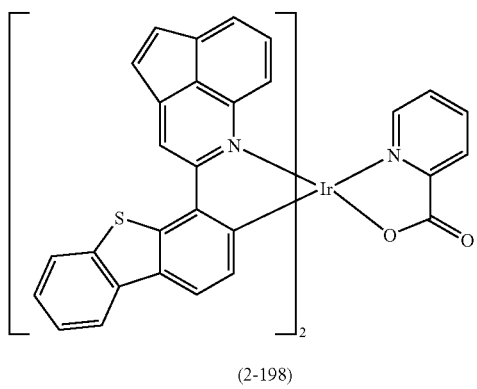
(2-198)
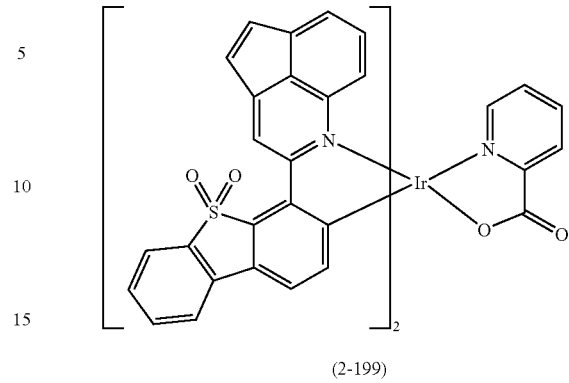
(2-199)
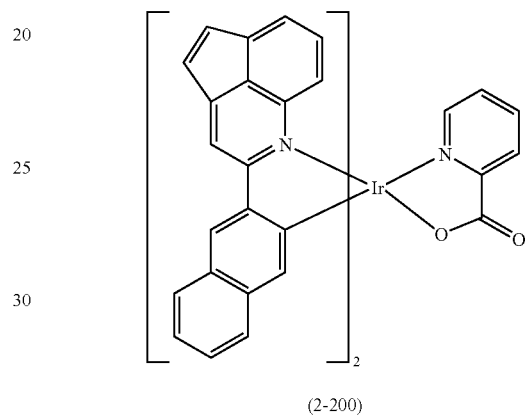
(2-200)
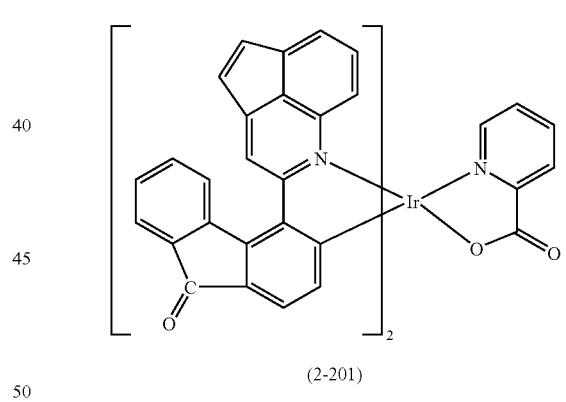
(2-201)
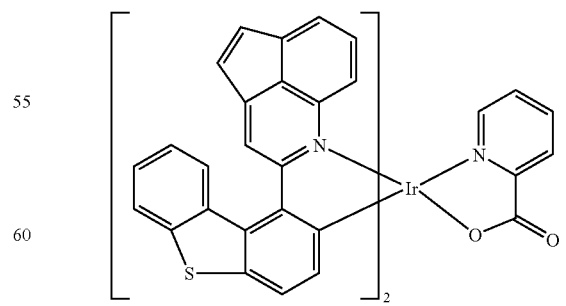
(2-202)

TABLE 12-continued
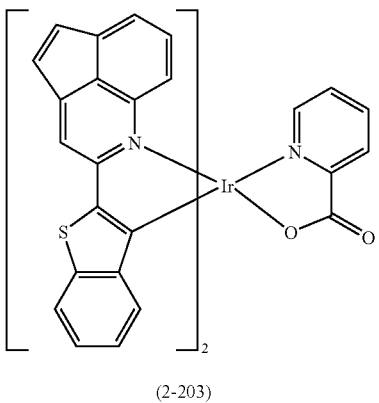
(2-203)
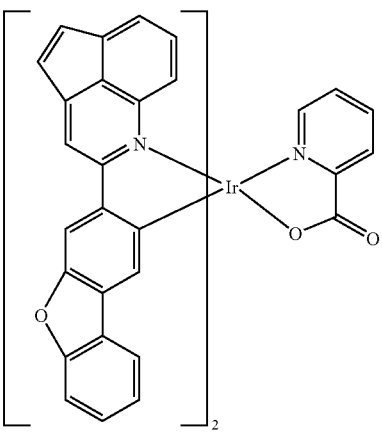
(2-204)
TABLE 13
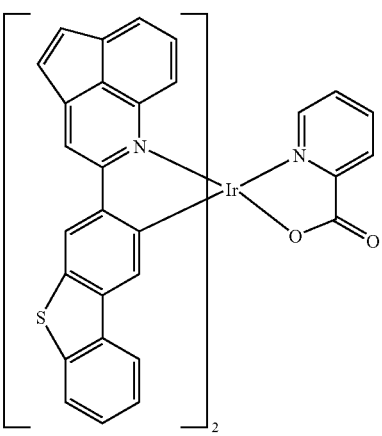
(2-205)
TABLE 13-continued
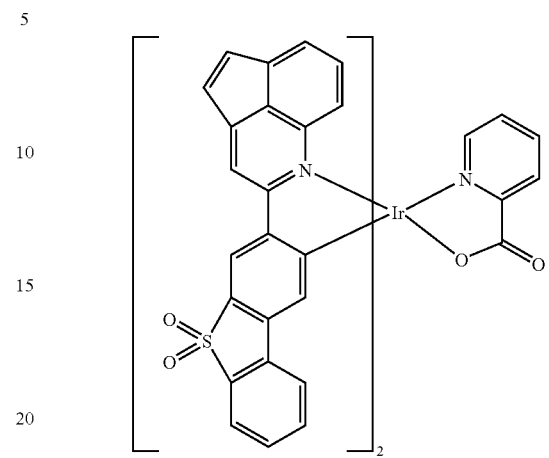
(2-206)
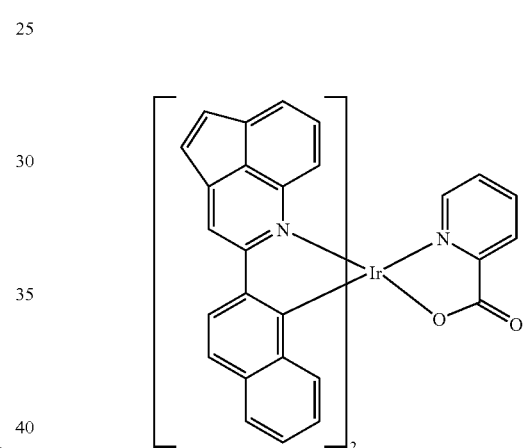
(2-207)
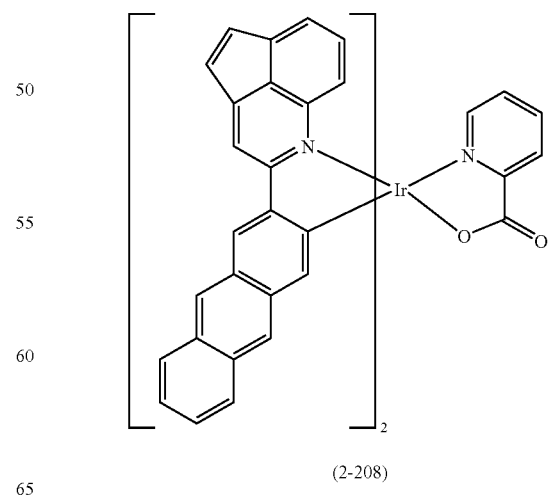
(2-208)

TABLE 13-continued
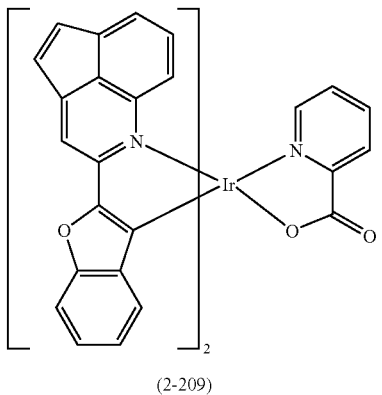
(2-209)
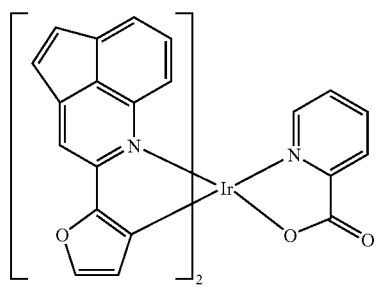
(2-210)
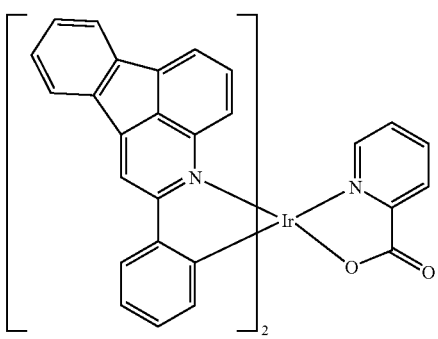
(2-211)
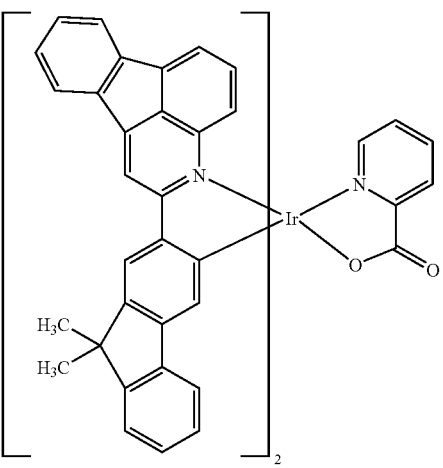
(2-212)
TABLE 13-continued
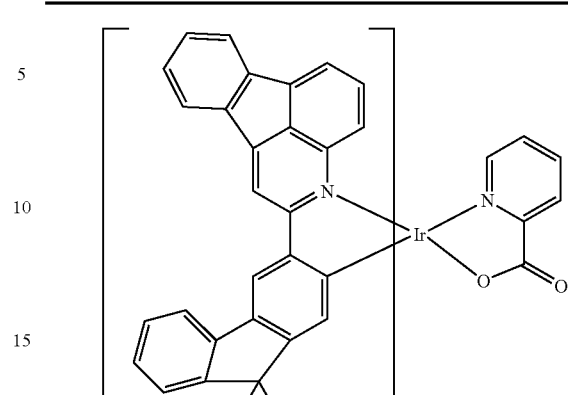
(2-213)
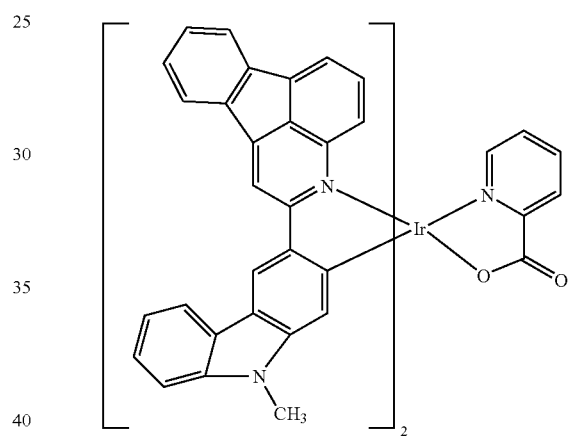
(2-214)
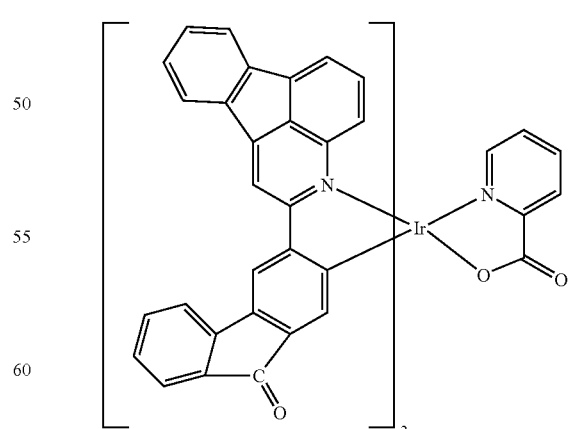
(2-215)

TABLE 13-continued
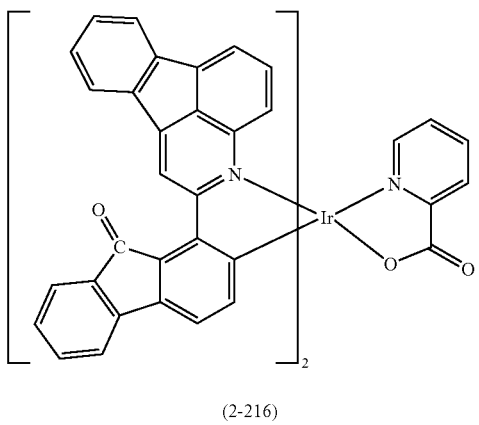
(2-216)
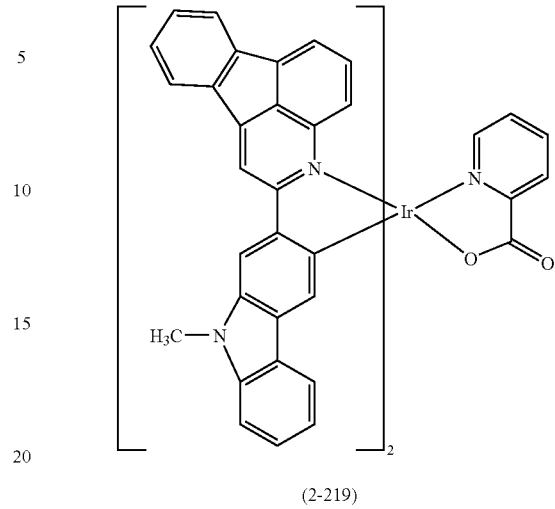
(2-219)
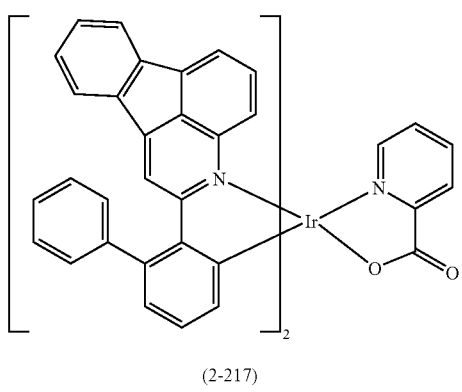
(2-217)
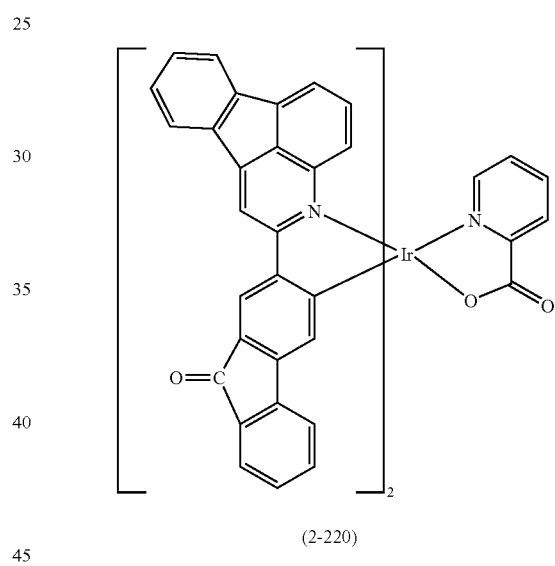
(2-220)
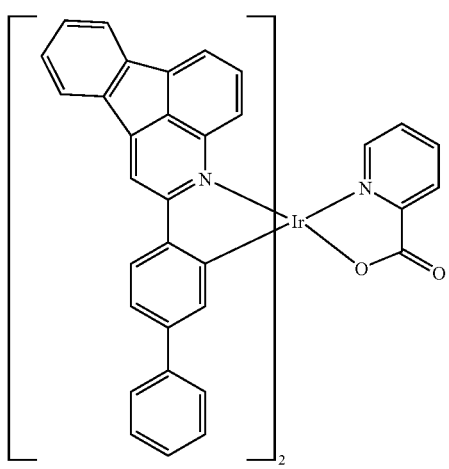
(2-218)
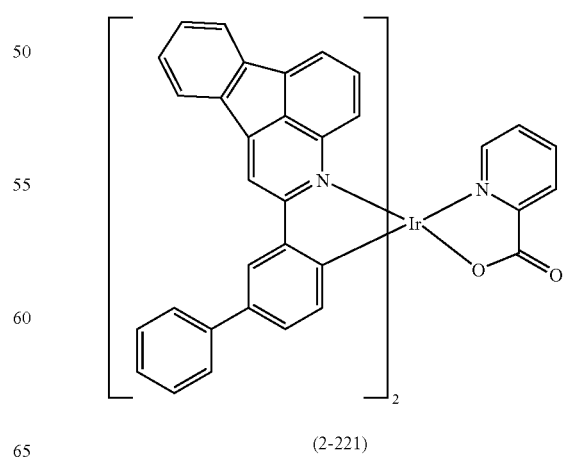
(2-221)

TABLE 13-continued
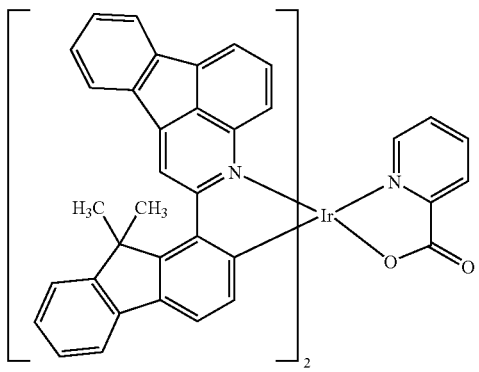
(2-222)
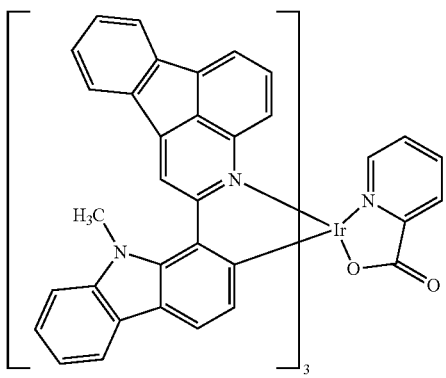
(2-223)
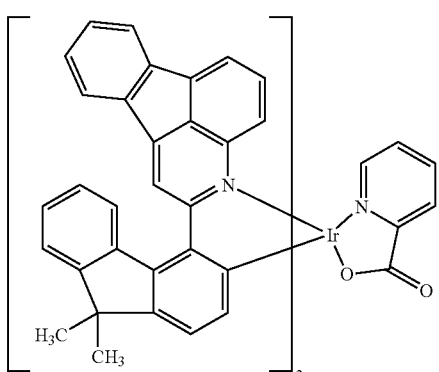
(2-224)
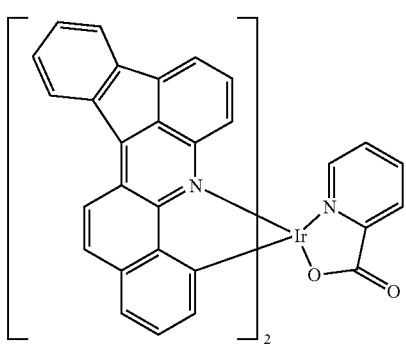
(2-225)
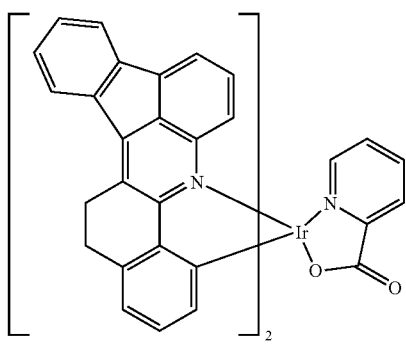
(2-226)
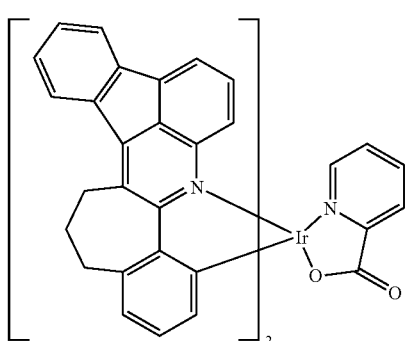
(2-227)
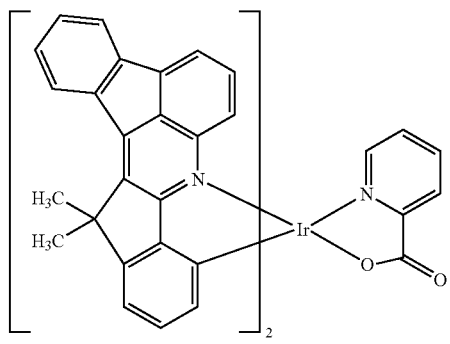
(2-228)
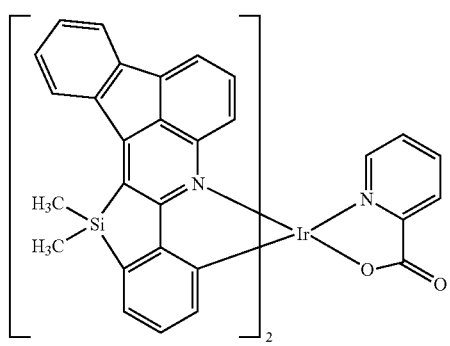
(2-229)

TABLE 13-continued
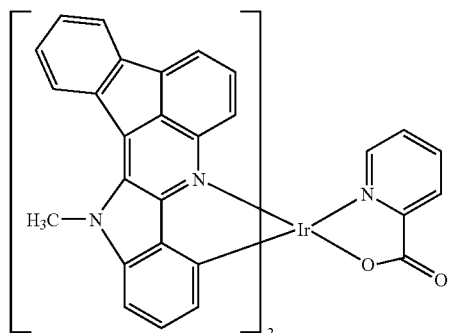
(2-230)
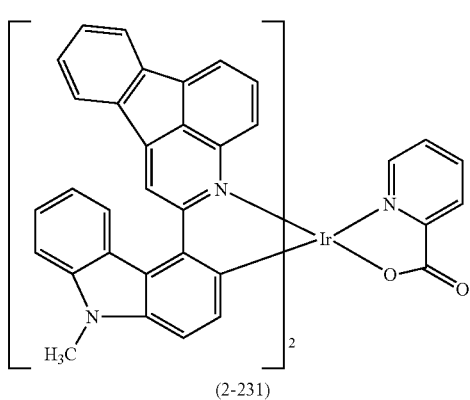
(2-231)
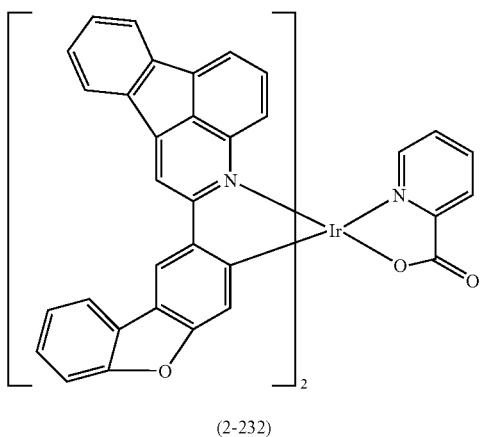
(2-232)
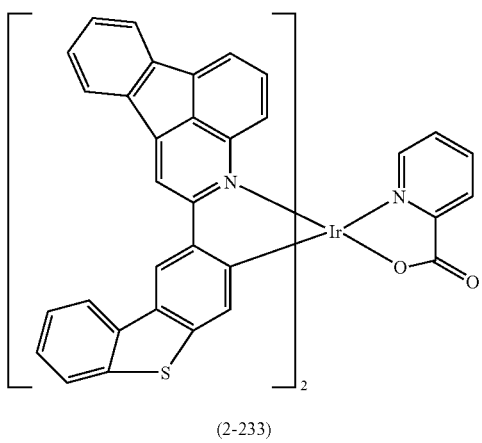
(2-233)
TABLE 13-continued
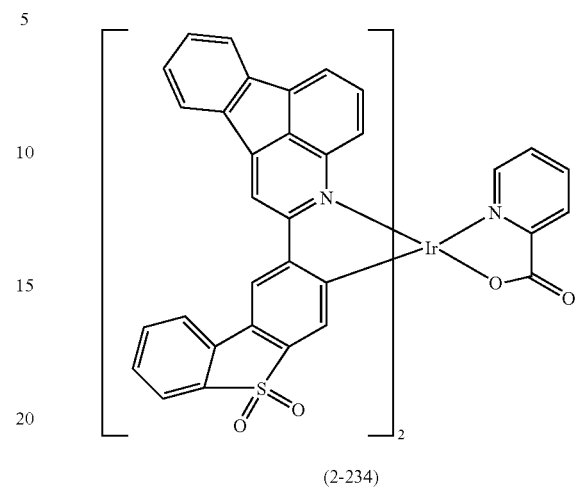
(2-234)
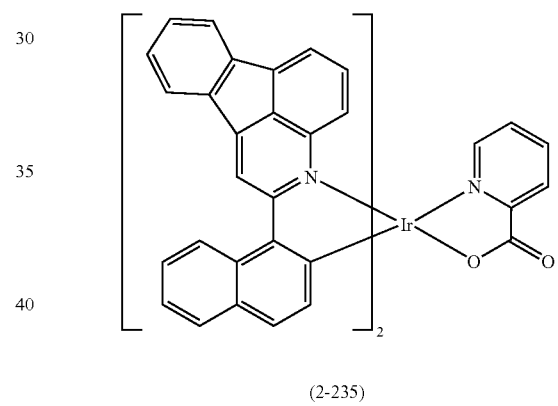
(2-235)
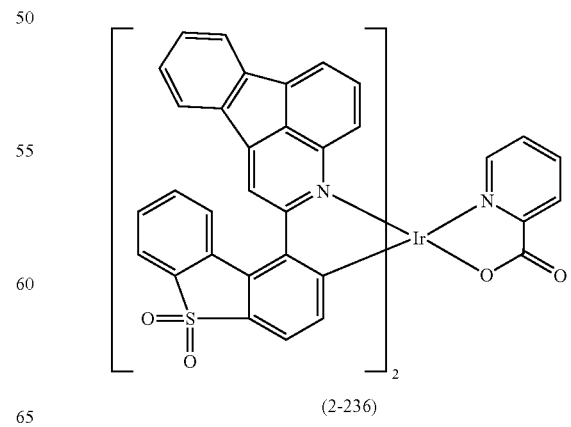
(2-236)

TABLE 13-continued
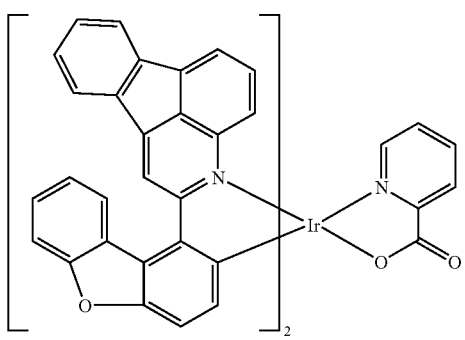
(2-237)
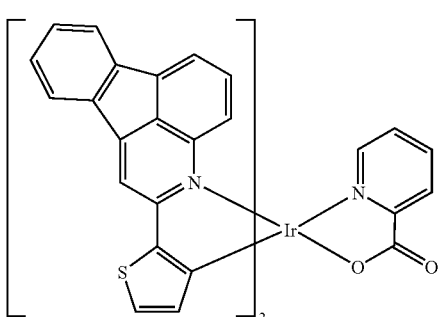
(2-238)
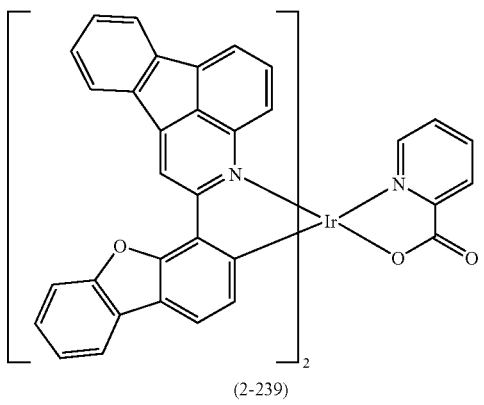
(2-239)
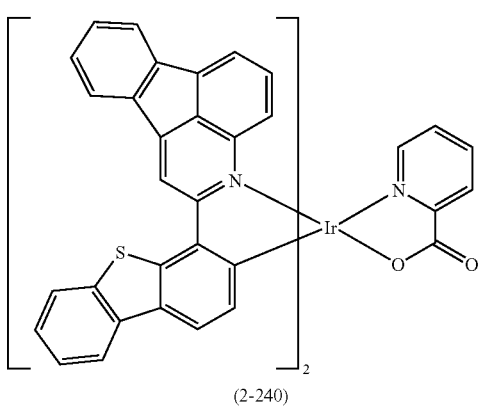
(2-240)
TABLE 14
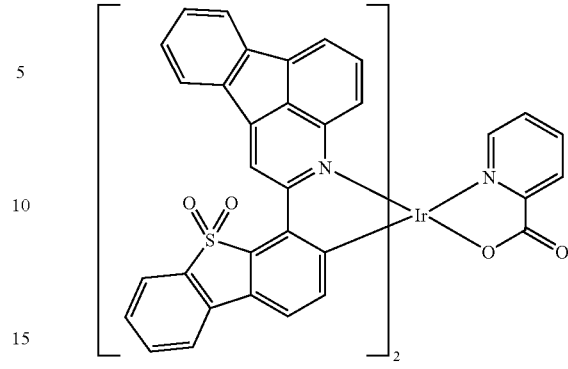
(2-241)
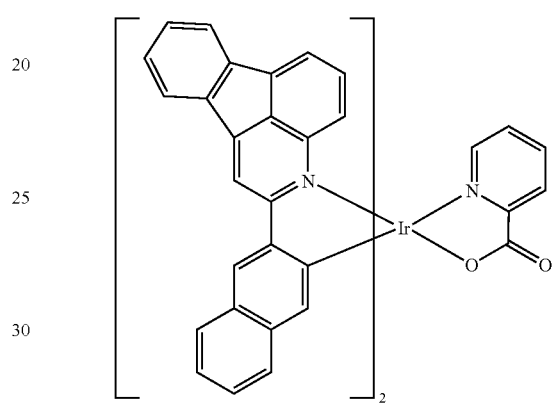
(2-242)
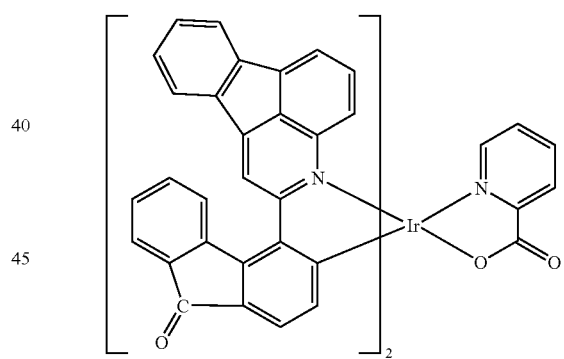
(2-243)
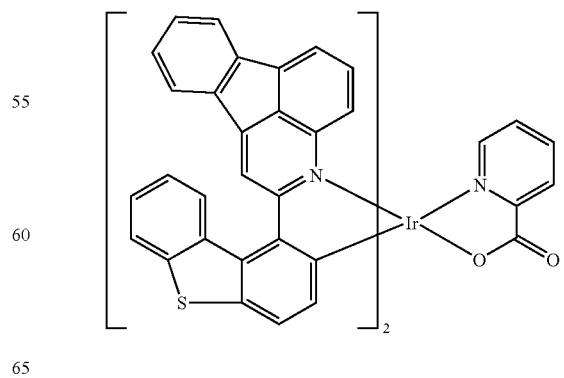
(2-244)

TABLE 14-continued
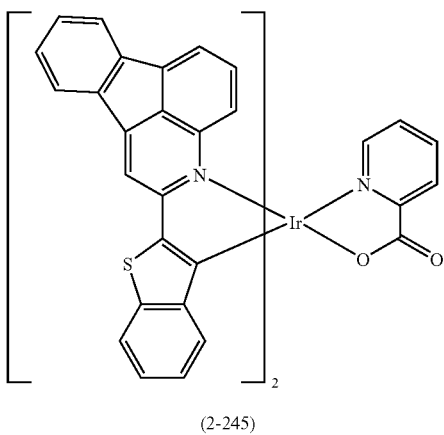
(2-245)
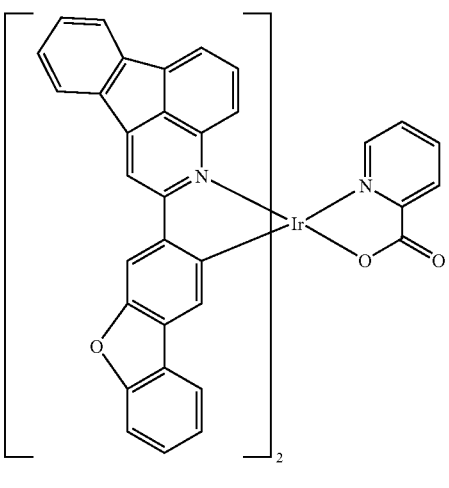
(2-246)
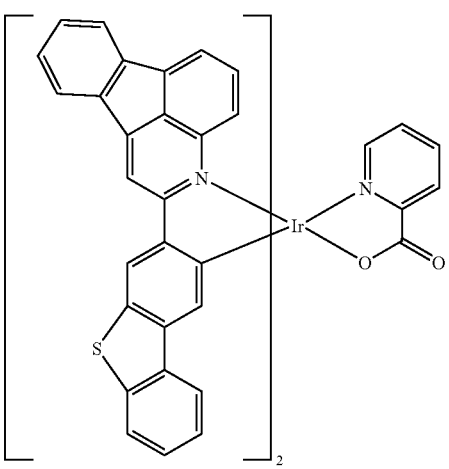
(2-247)
TABLE 14-continued
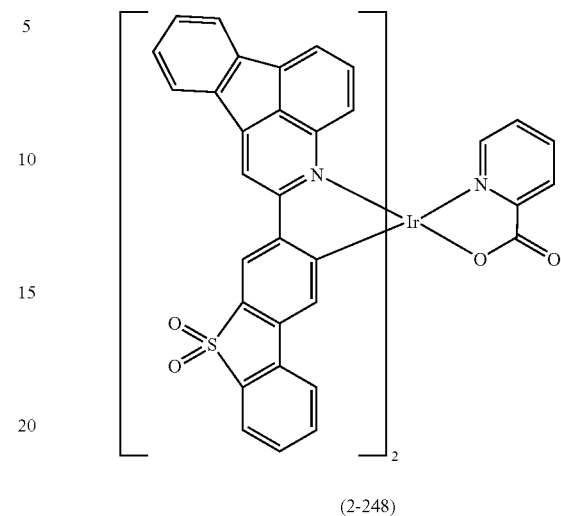
(2-248)
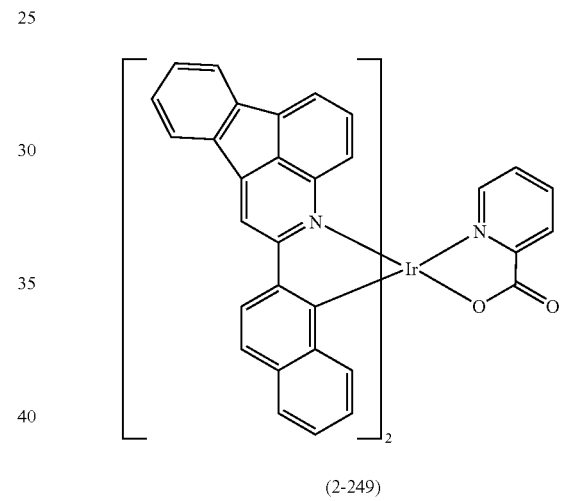
(2-249)
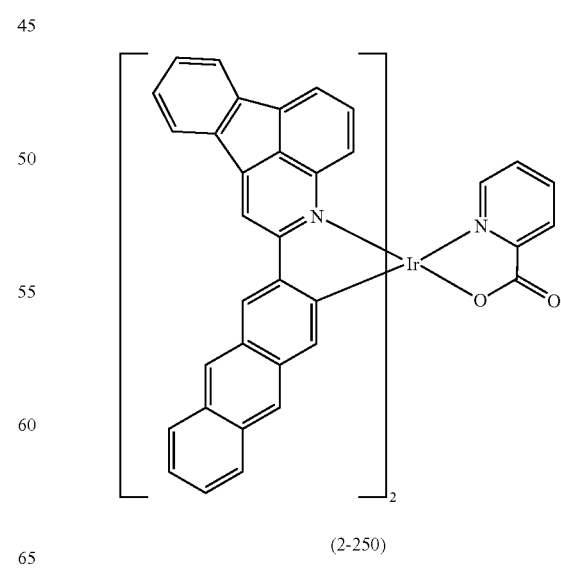
(2-250)

TABLE 14-continued
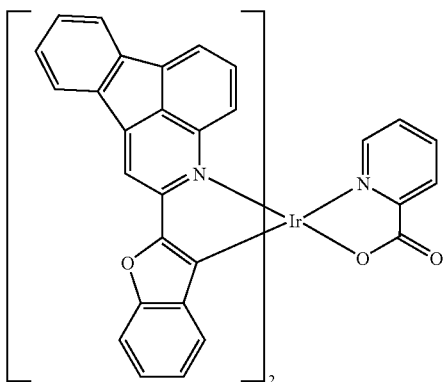
(2-251)
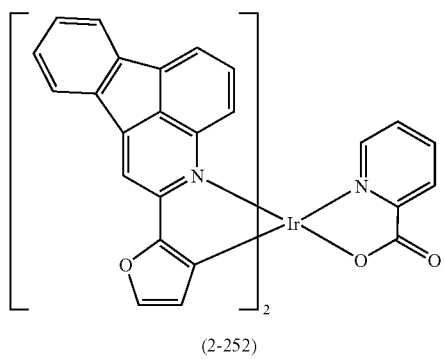
(2-252)
TABLE 15
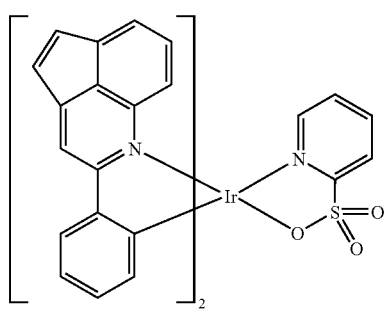
(2-253)
TABLE 15-continued
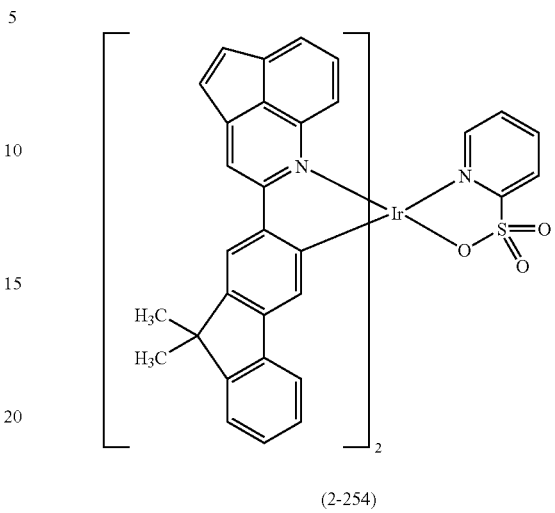
(2-254)
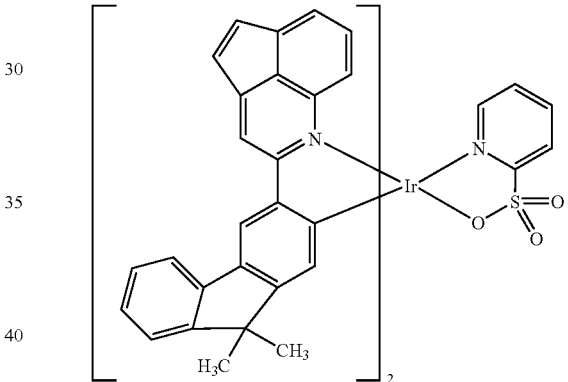
(2-255)
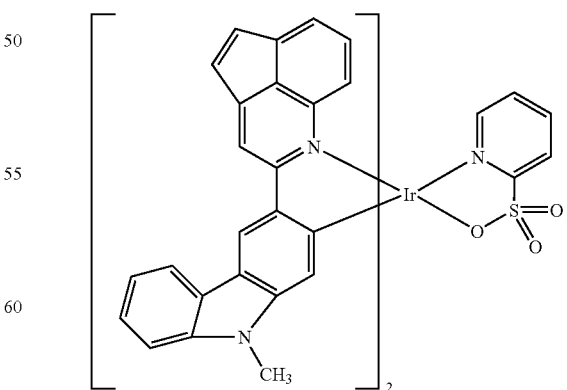
(2-256)

TABLE 15-continued
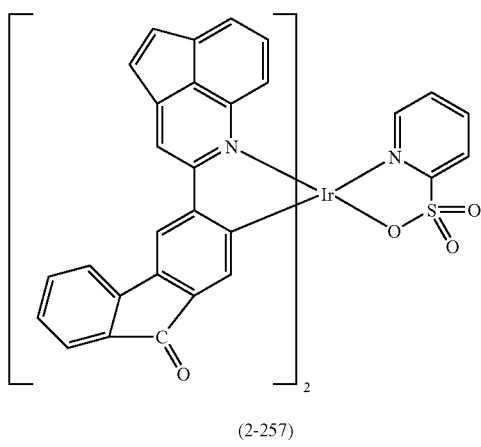
(2-257)
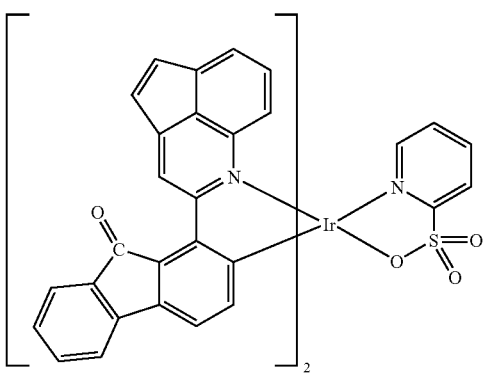
(2-258)
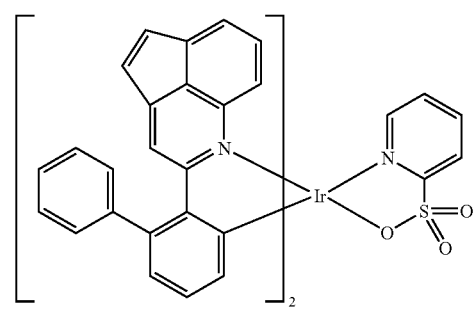
(2-259)
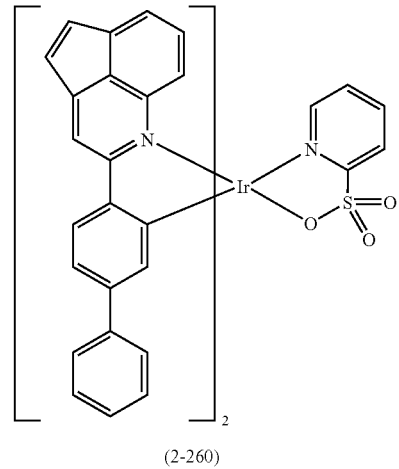
(2-260)
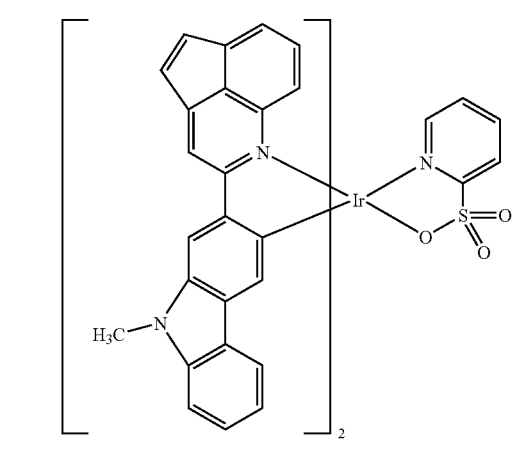
(2-261)
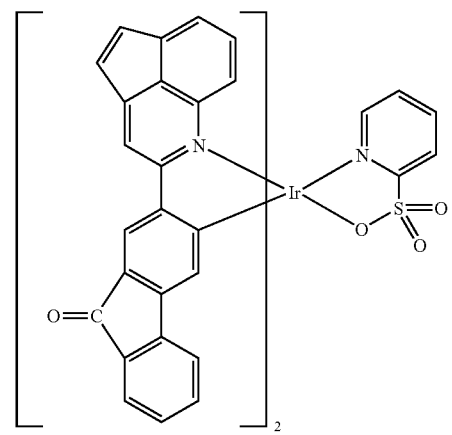
(2-262)

TABLE 15-continued
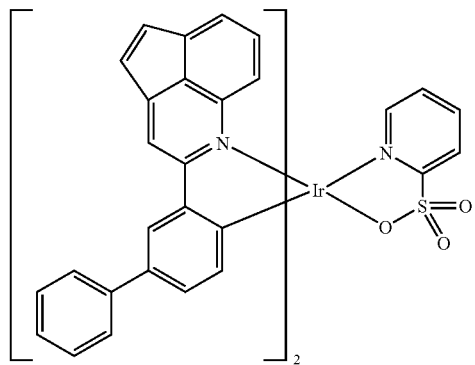
(2-263)
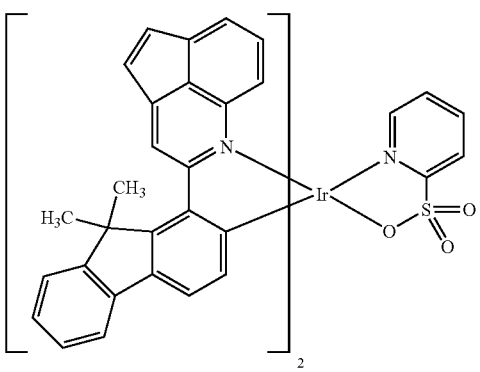
(2-264)
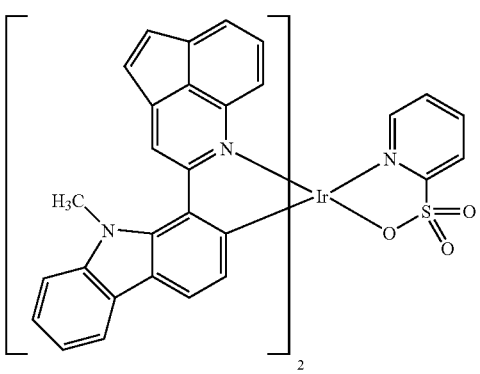
(2-265)
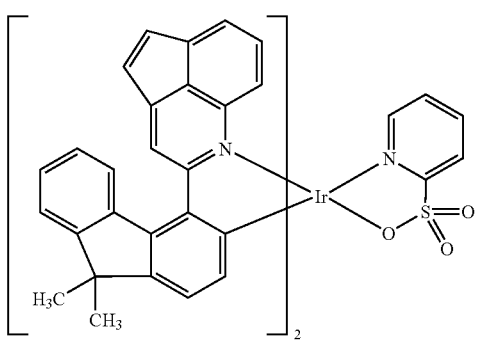
(2-266)
TABLE 15-continued
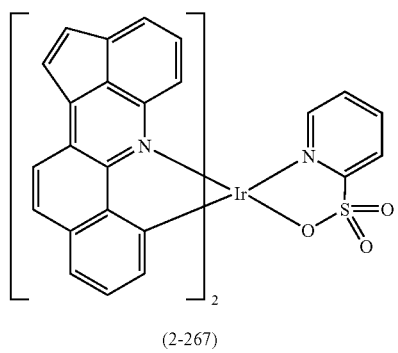
(2-267)
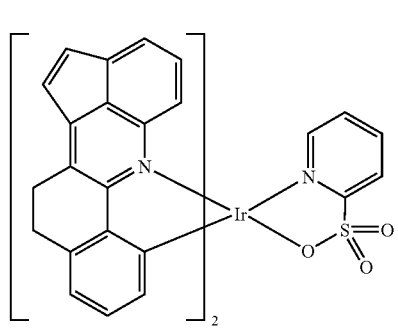
(2-268)
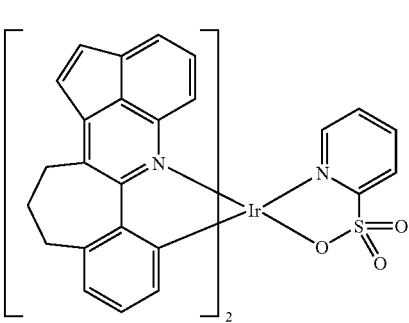
(2-269)
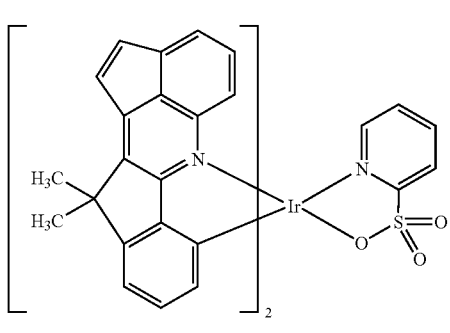
(2-270)

TABLE 15-continued
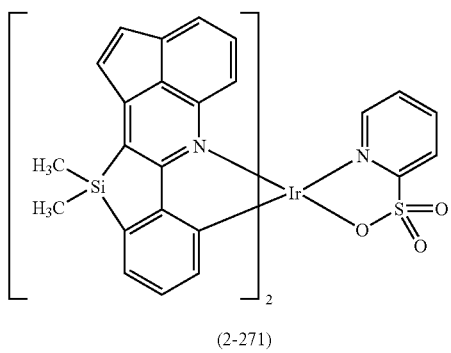
(2-271)
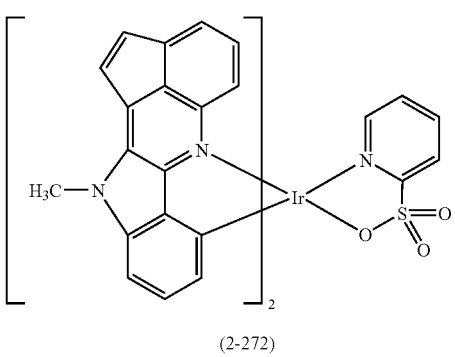
(2-272)
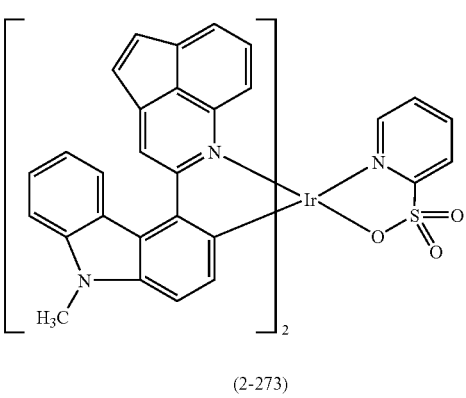
(2-273)
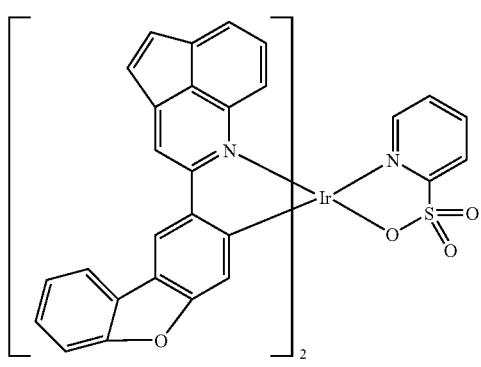
(2-274)
TABLE 15-continued
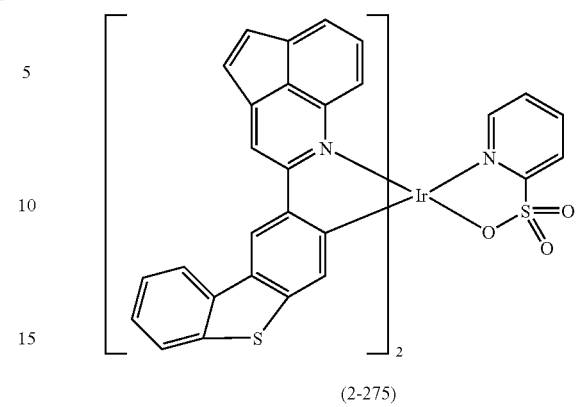
(2-275)
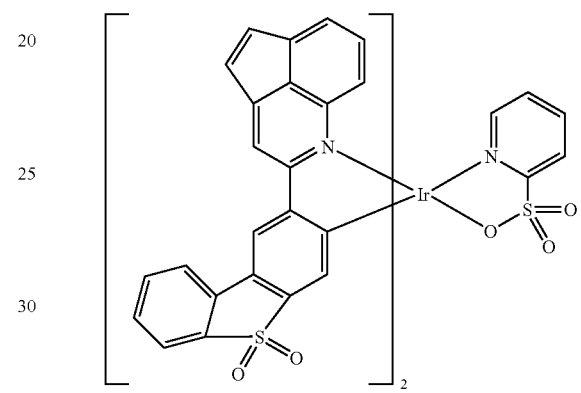
(2-276)
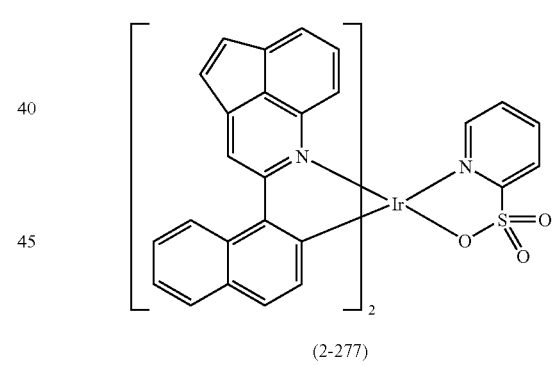
(2-277)
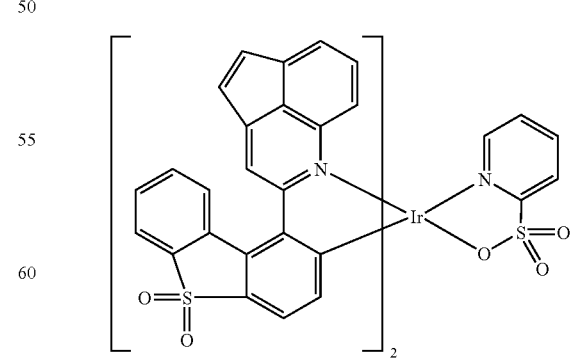
(2-278)

TABLE 15-continued
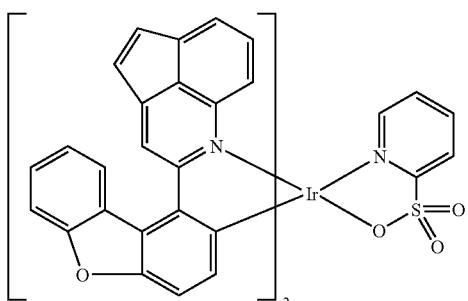
(2-279)
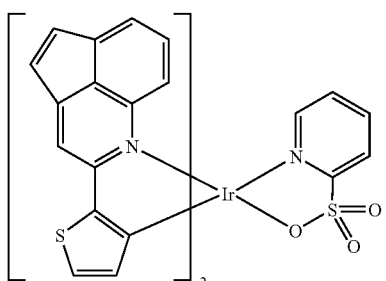
(2-280)
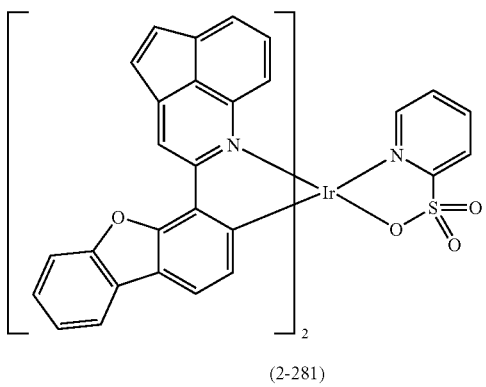
(2-281)
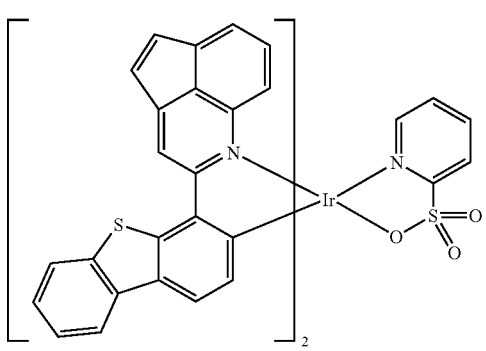
(2-282)
TABLE 15-continued
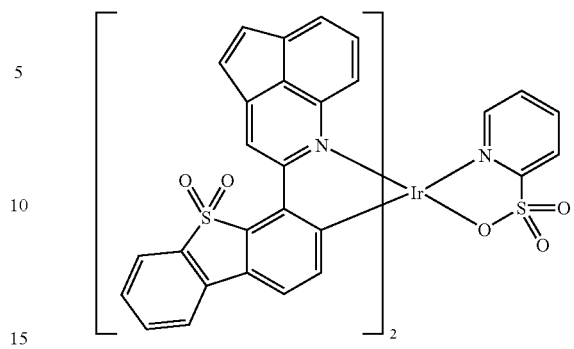
(2-283)
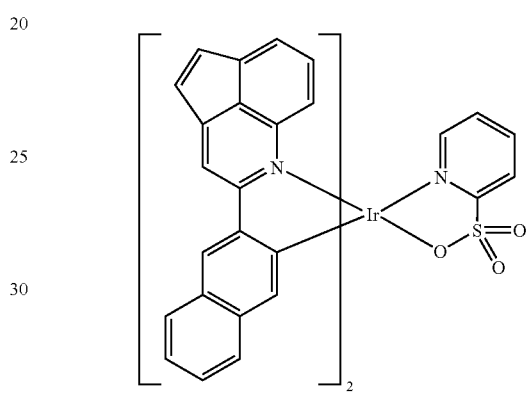
(2-284)
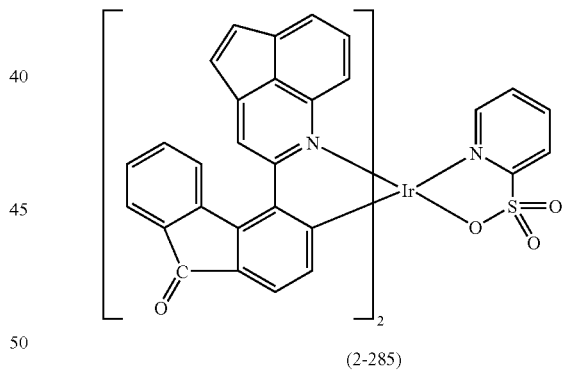
(2-285)
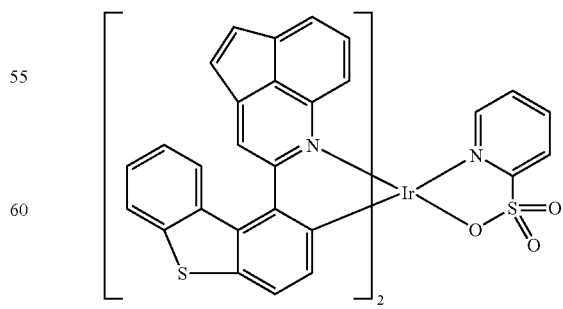
(2-286)

TABLE 15-continued
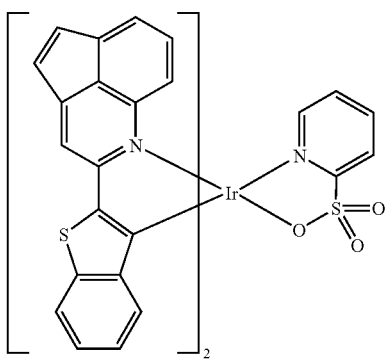
(2-287)
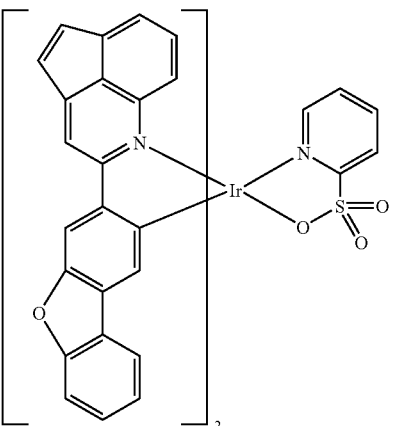
(2-288)
TABLE 16
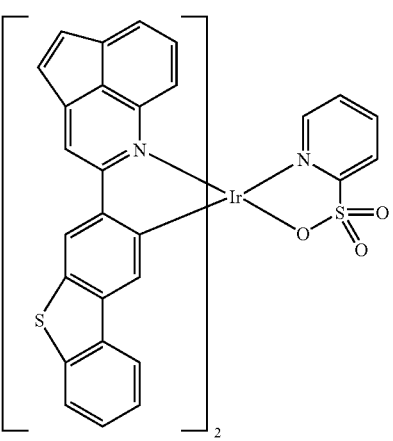
(2-289)
TABLE 16-continued
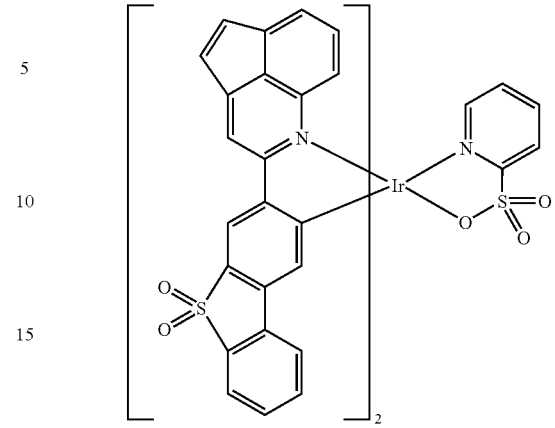
(2-290)
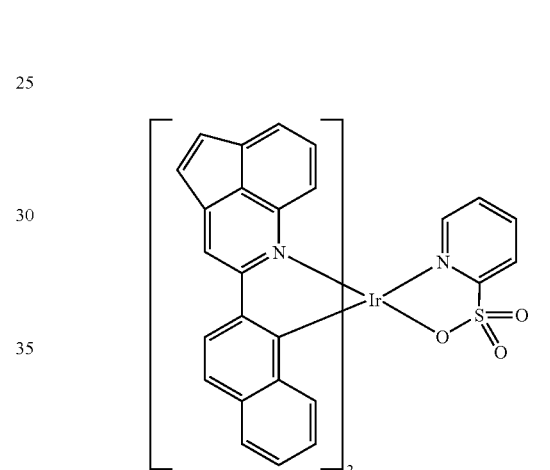
(2-291)
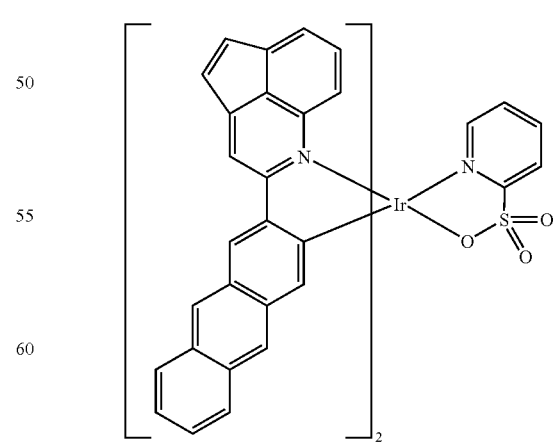
(2-292)

TABLE 16-continued
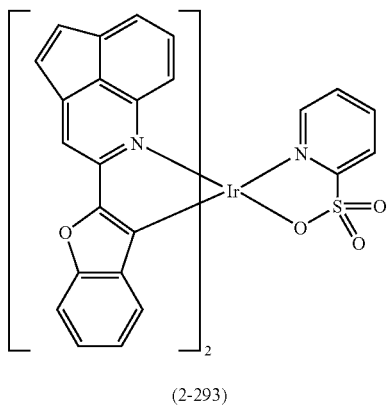
(2-293)
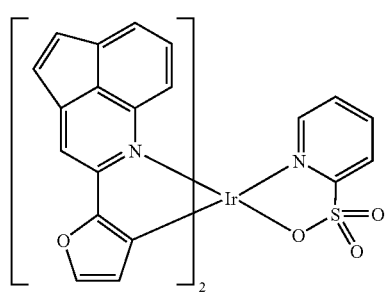
(2-294)
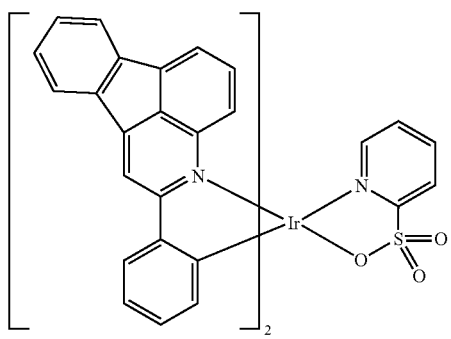
(2-295)
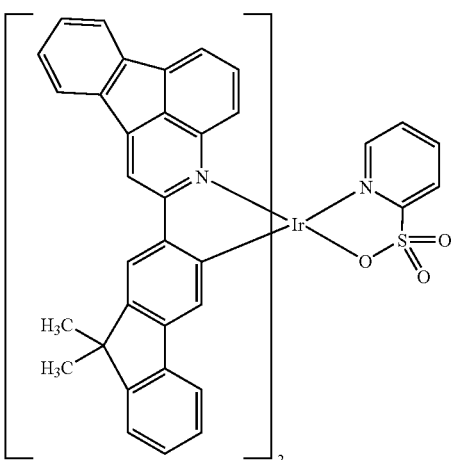
(2-296)
TABLE 16-continued
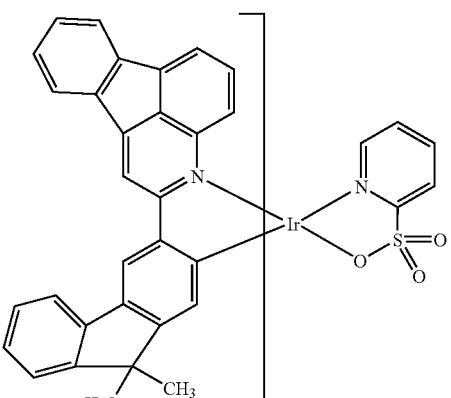
(2-297)
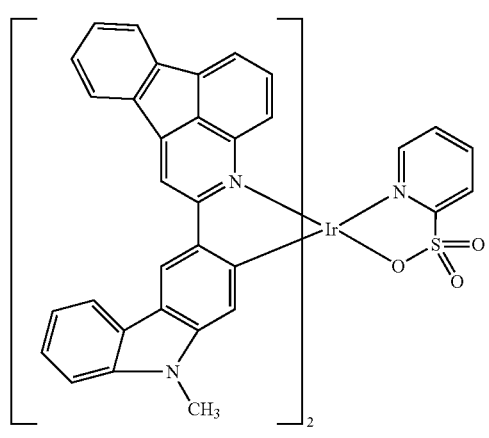
(2-298)
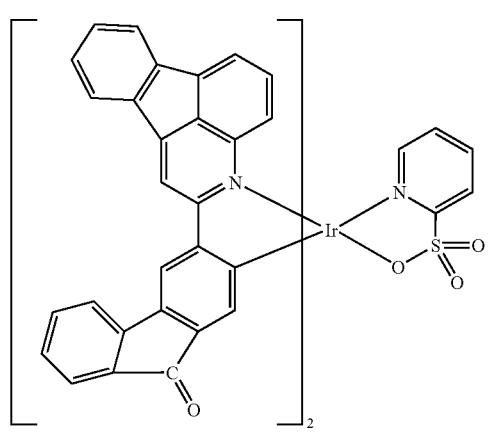
(2-299)

TABLE 16-continued
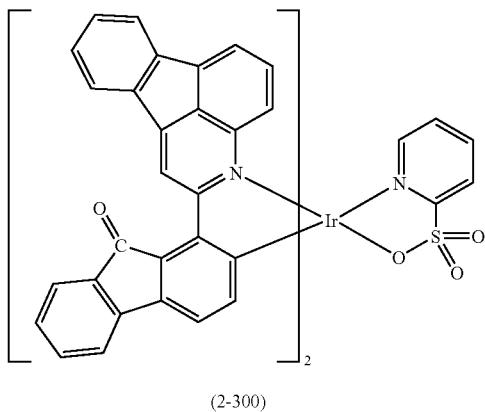
(2-300)
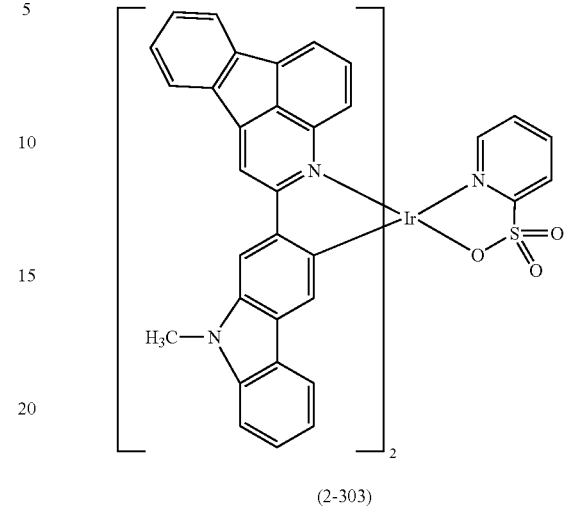
(2-303)
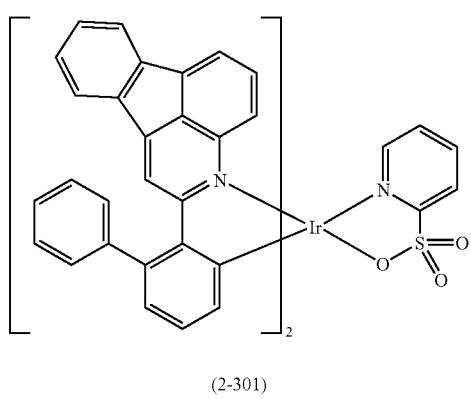
(2-301)
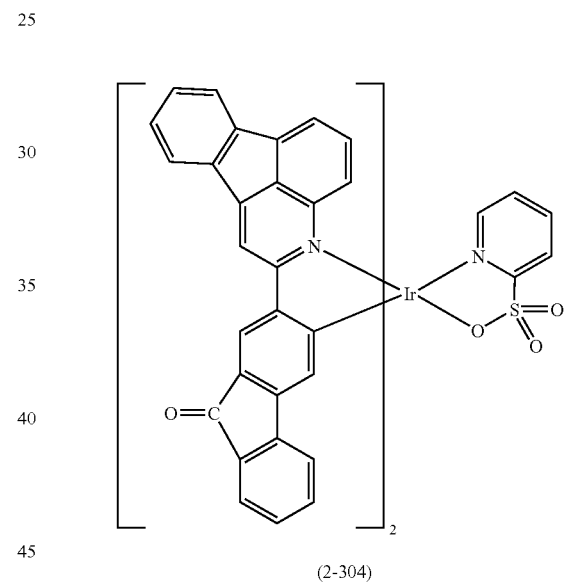
(2-304)
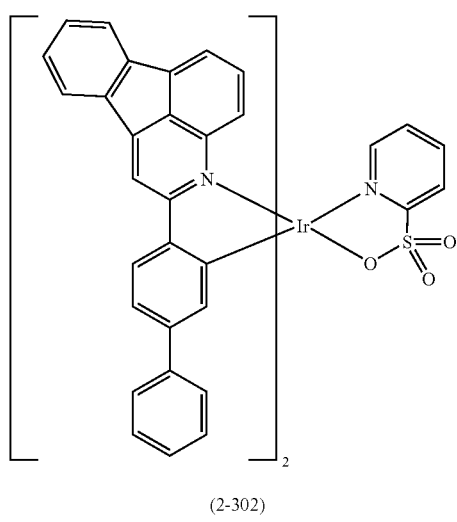
(2-302)
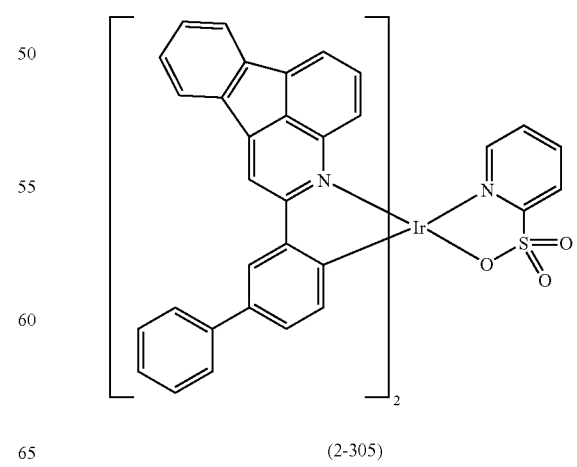
(2-305)

TABLE 16-continued
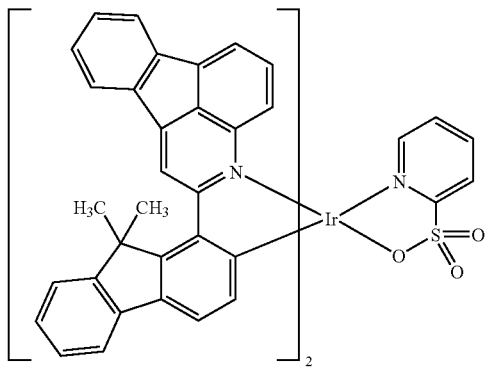
(2-306)
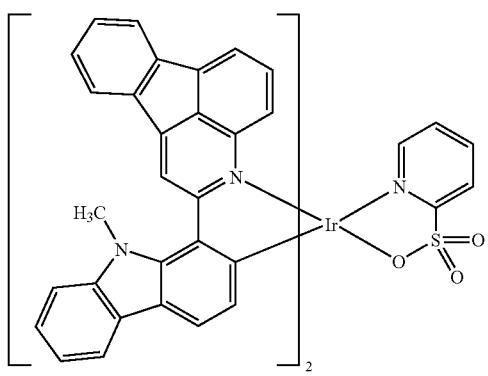
(2-307)
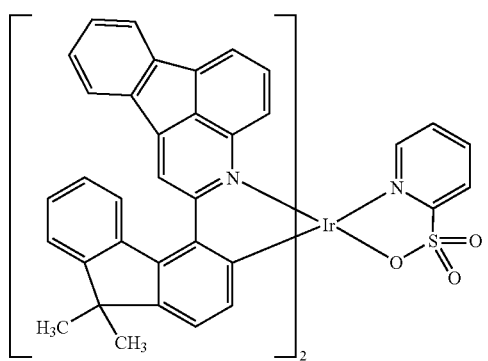
(2-308)
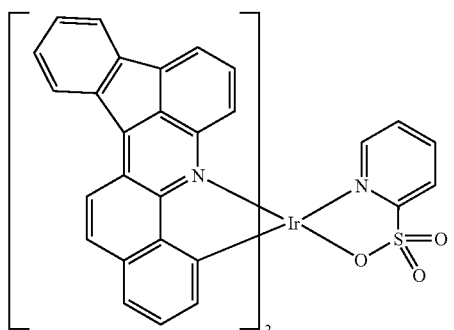
(2-309)
TABLE 16-continued
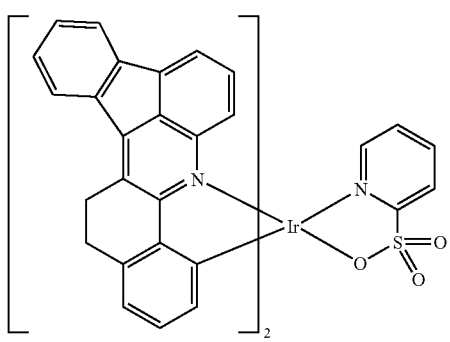
(2-310)
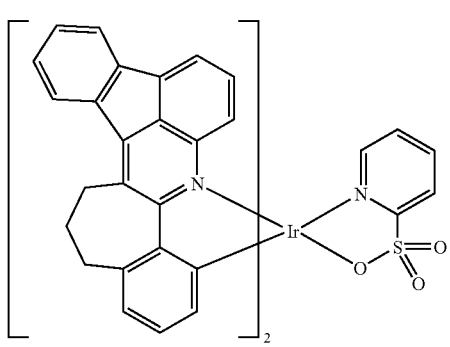
(2-311)
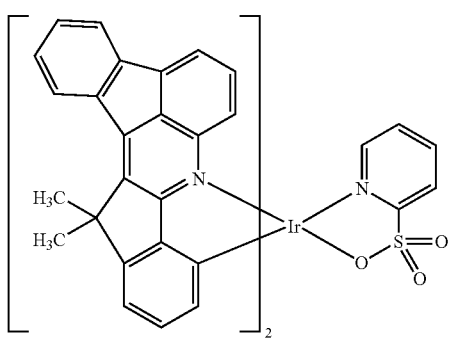
(2-312)
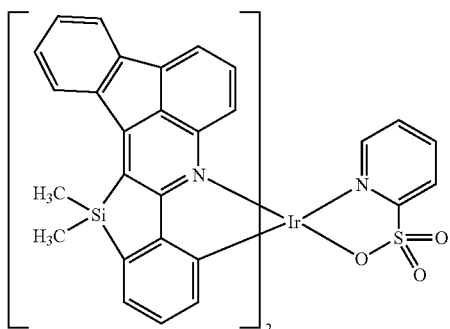
(2-313)

TABLE 16-continued
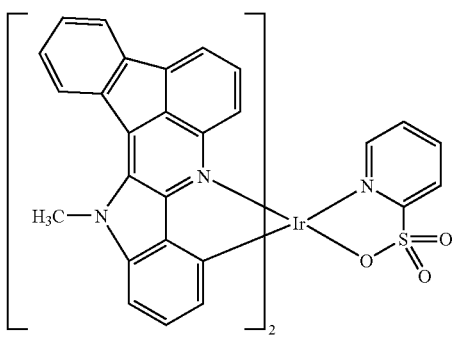
(2-314)
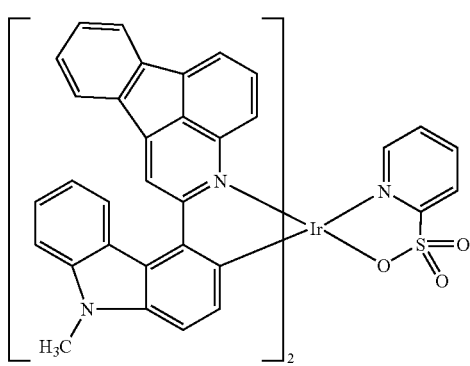
(2-315)
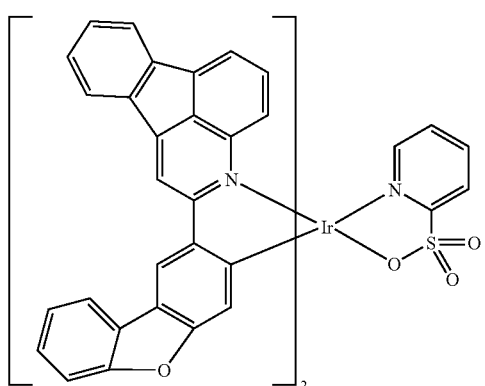
(2-316)
TABLE 16-continued
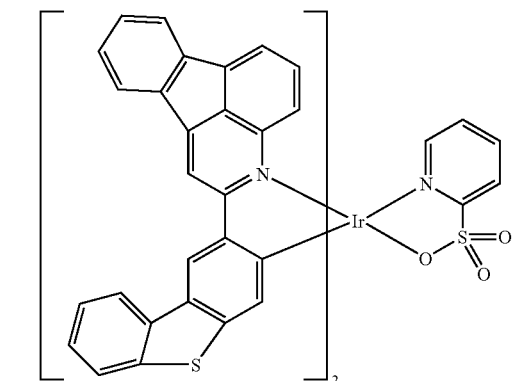
(2-317)
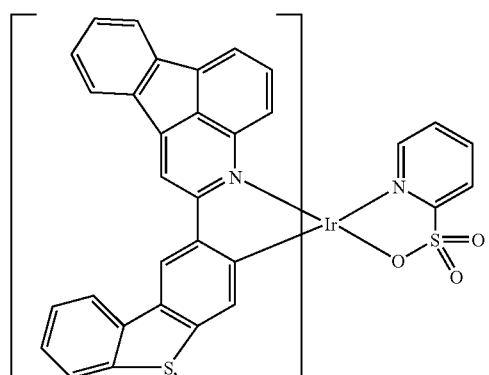
(2-318)
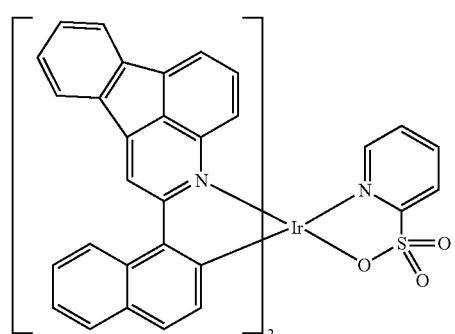
(2-319)

TABLE 16-continued
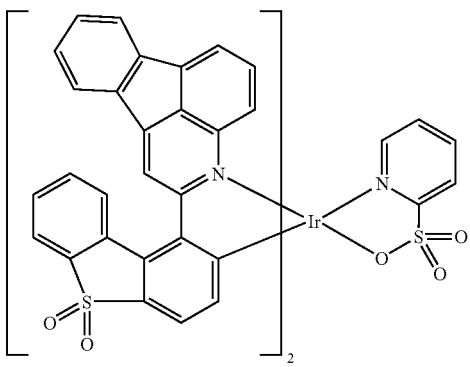
(2-320)
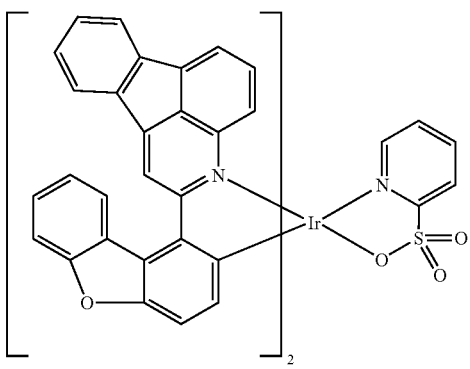
(2-321)
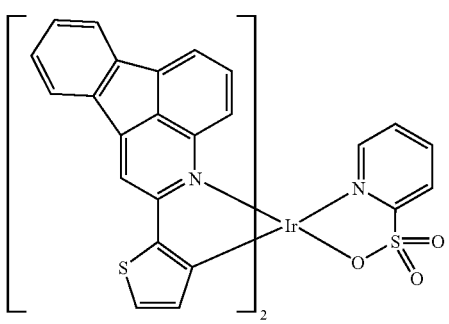
(2-322)
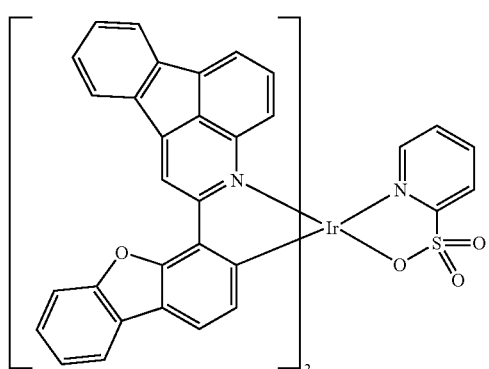
(2-323)
TABLE 16-continued
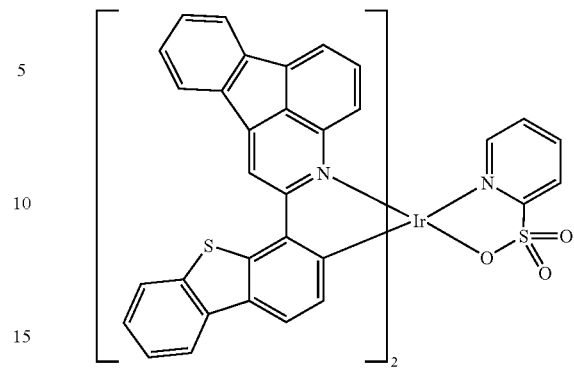
(2-324)
TABLE 17
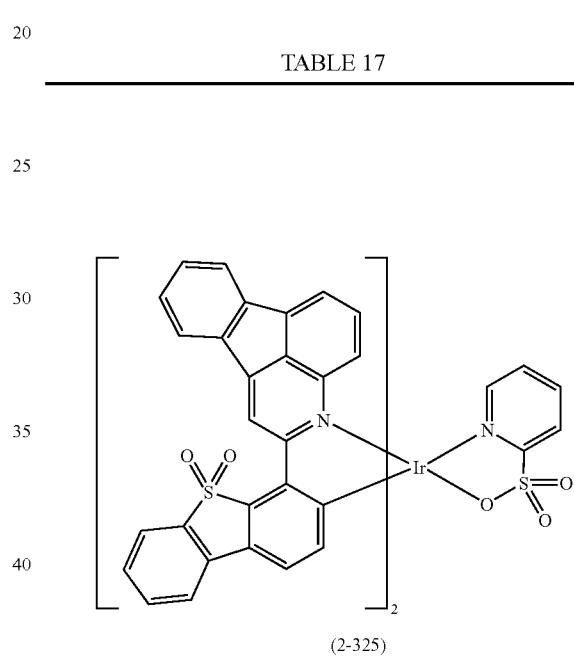
(2-325)
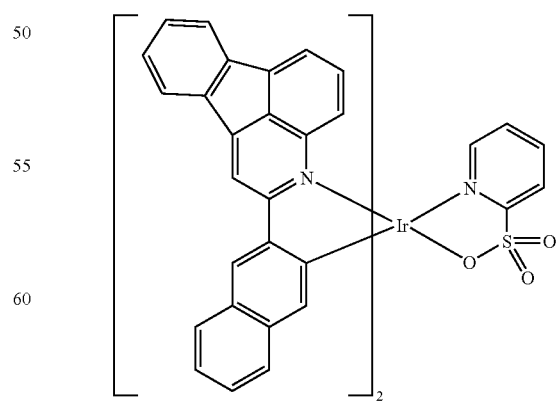
(2-326)

TABLE 17-continued
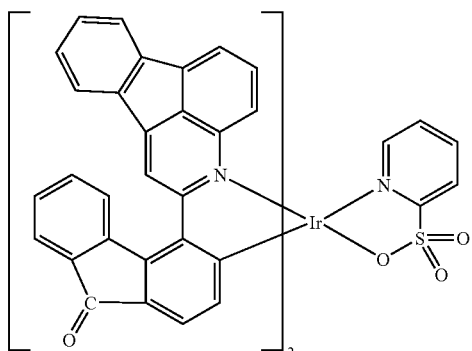
(2-327)
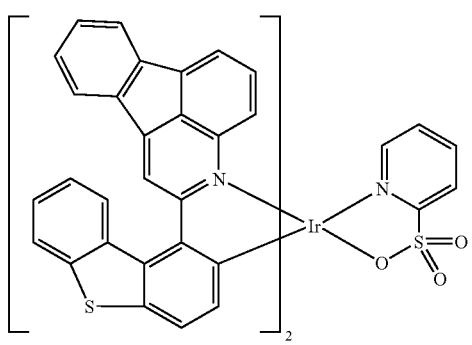
(2-328)
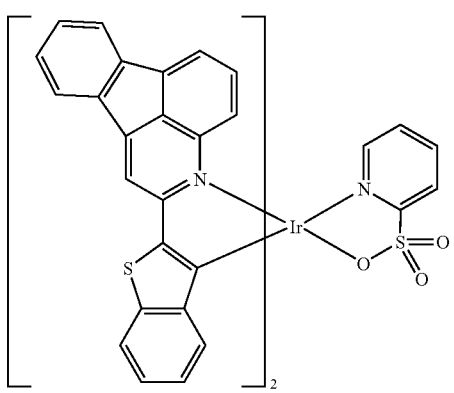
(2-329)
TABLE 17-continued
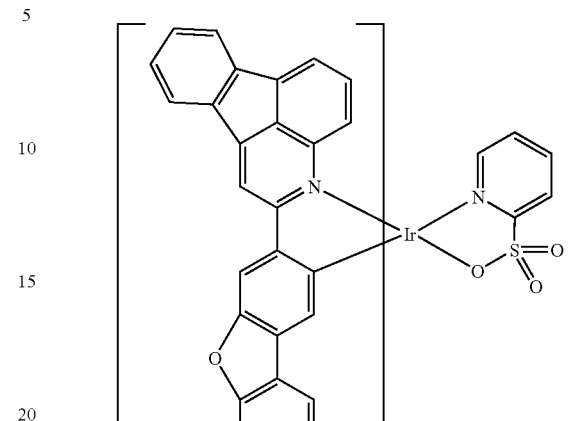
(2-330)
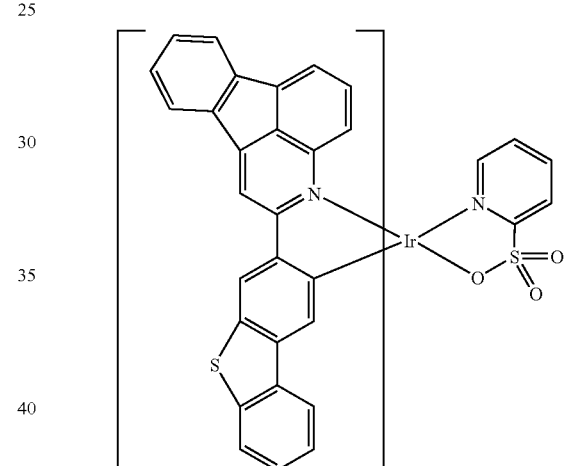
(2-331)
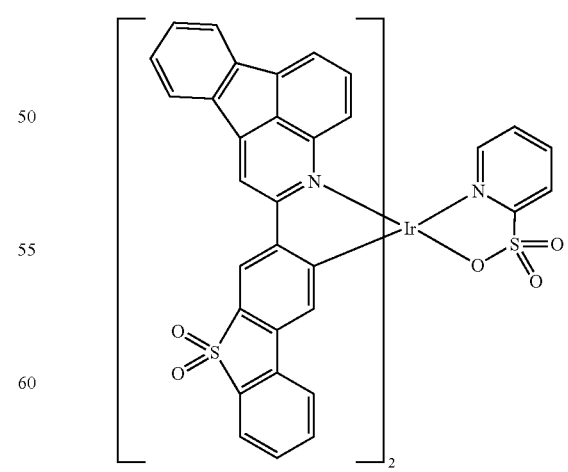
(2-332)

TABLE 17-continued
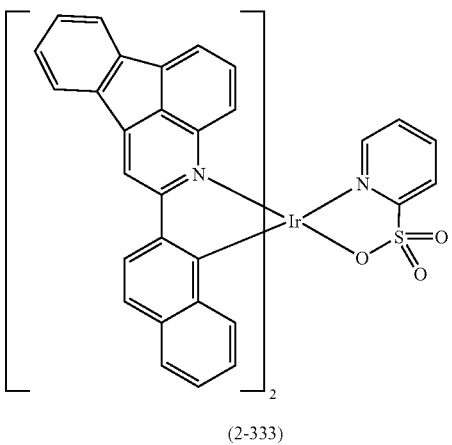
(2-333)
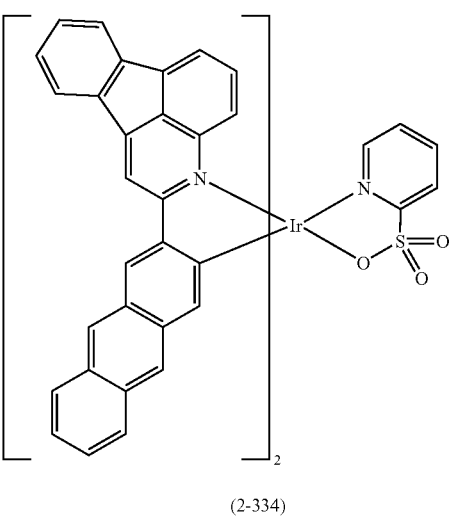
(2-334)
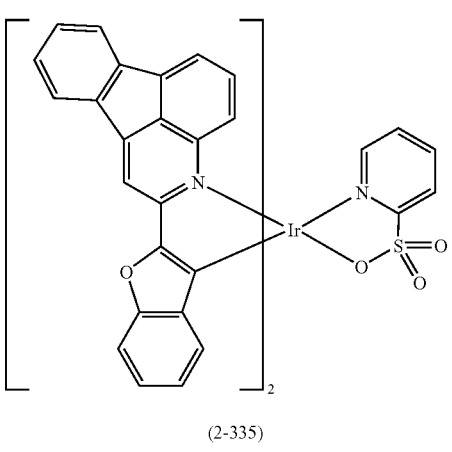
(2-335)
TABLE 17-continued
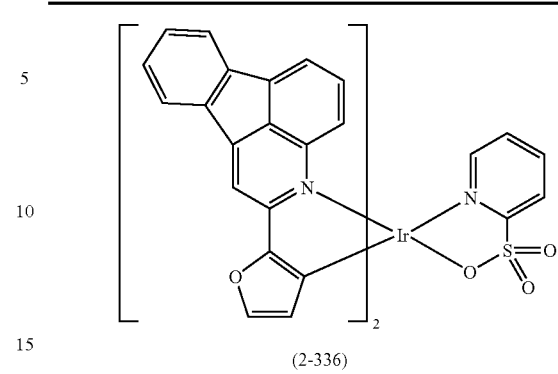
(2-336)
TABLE 18
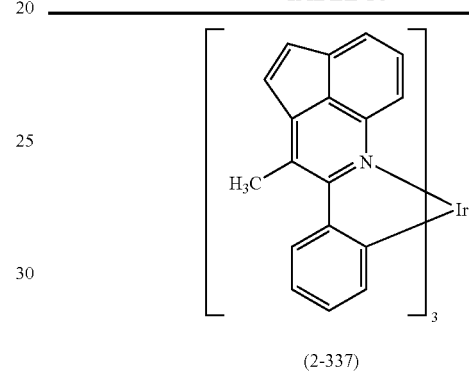
(2-337)
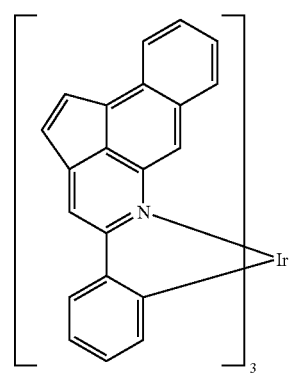
(2-338)
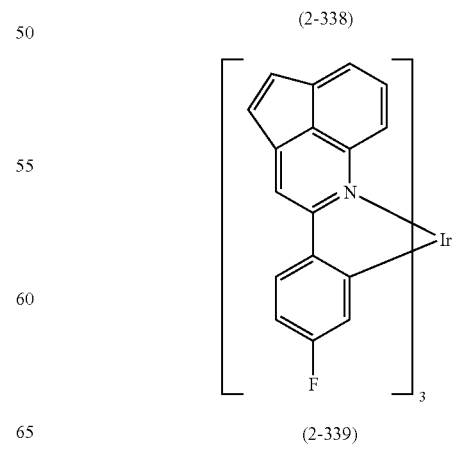
(2-339)

TABLE 18-continued
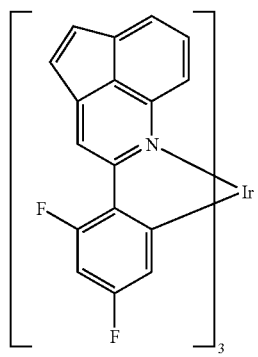
(2-340)
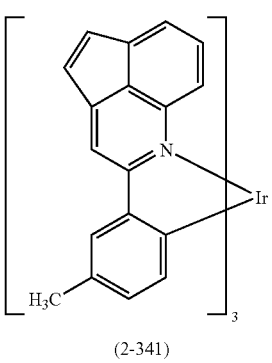
(2-341)
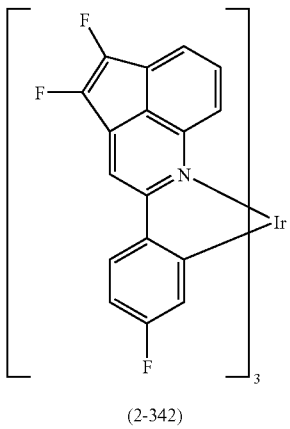
(2-342)
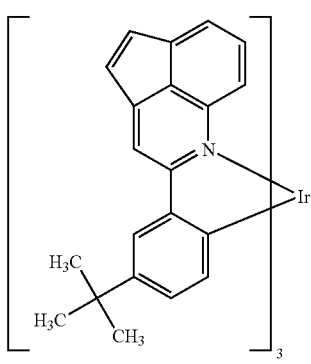
(2-343)
TABLE 18-continued
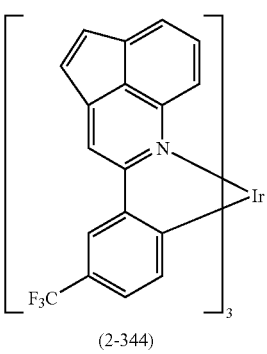
(2-344)
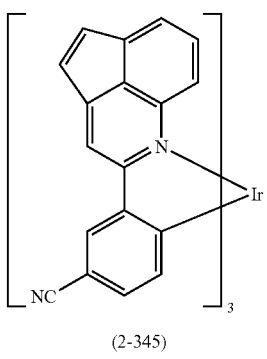
(2-345)
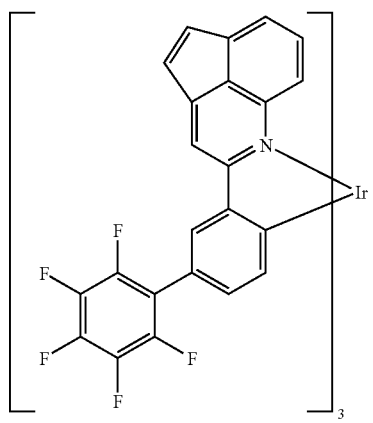
(2-346)
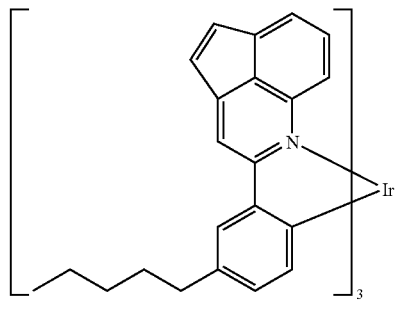
(2-347)

TABLE 18-continued
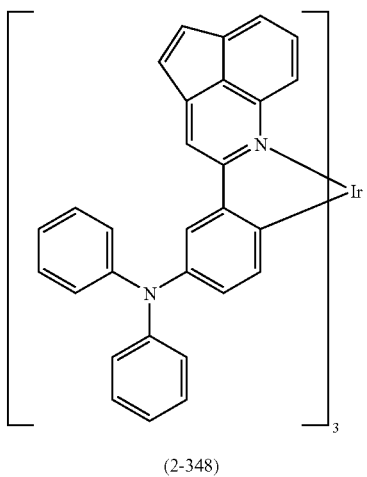
(2-348)
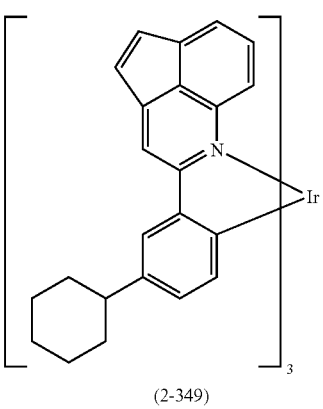
(2-349)
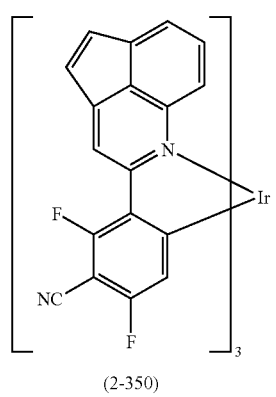
(2-350)
TABLE 18-continued
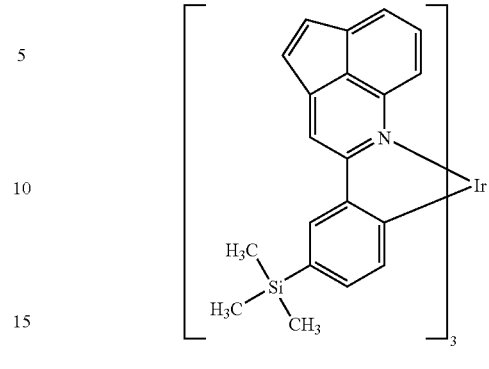
(2-351)
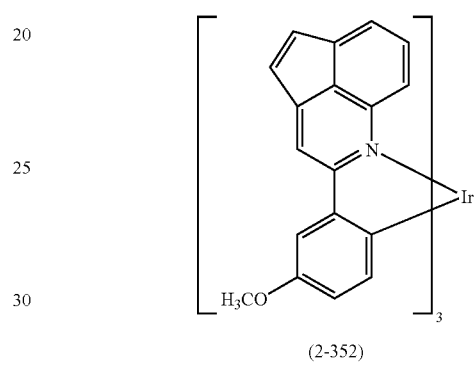
(2-352)
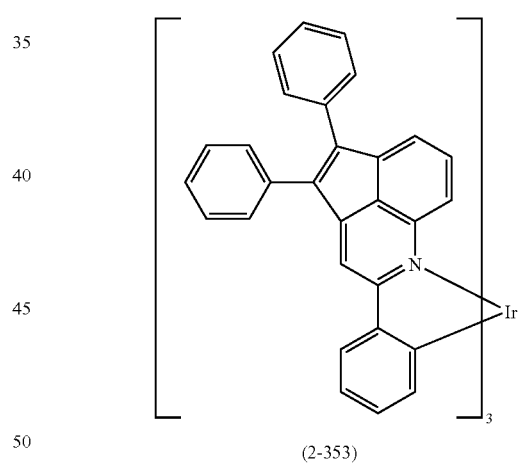
(2-353)
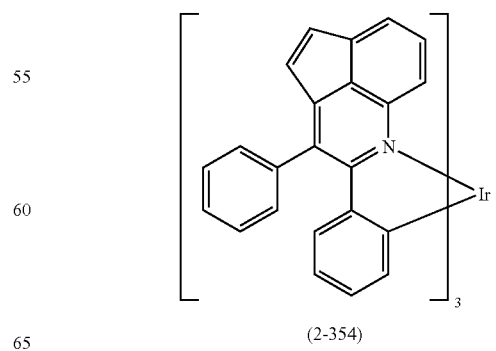
(2-354)

TABLE 18-continued
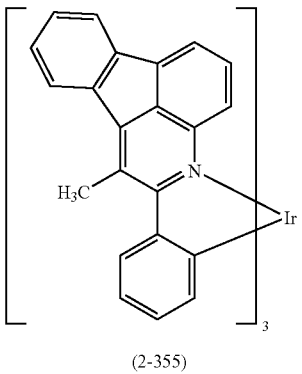
(2-355)
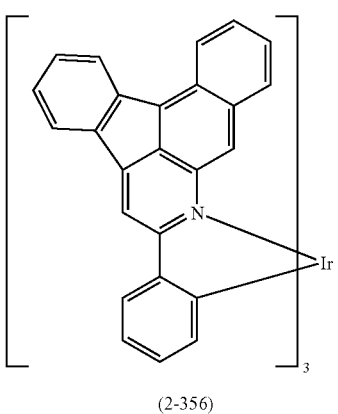
(2-356)
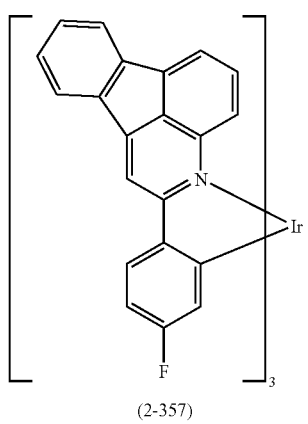
(2-357)
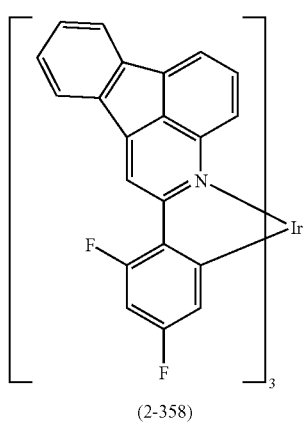
(2-358)
TABLE 18-continued
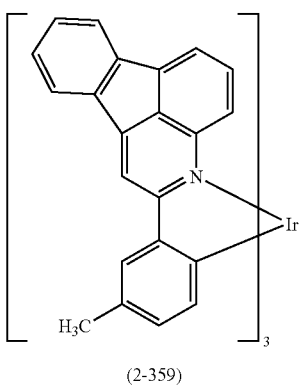
(2-359)
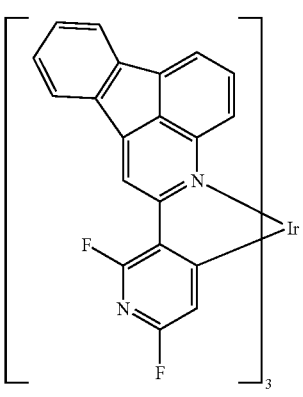
(2-360)
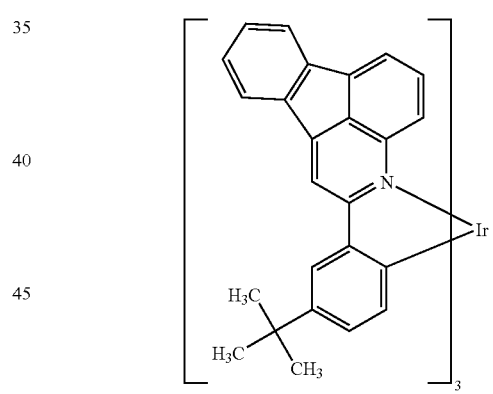
(2-361)
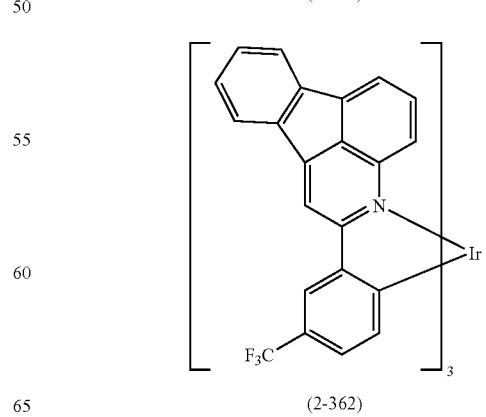
(2-362)

TABLE 18-continued
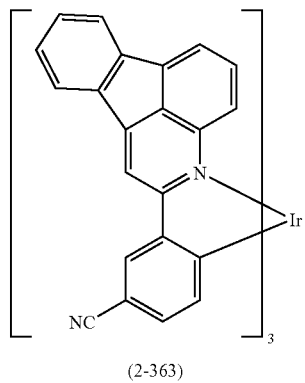
(2-363)
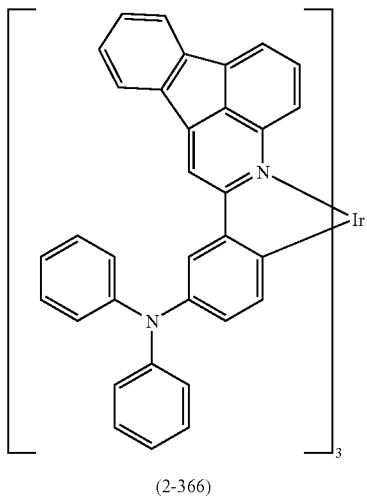
(2-366)
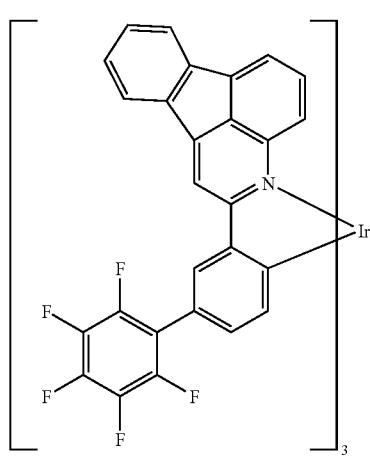
(2-364)
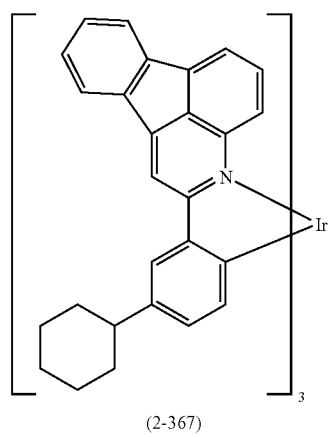
(2-367)
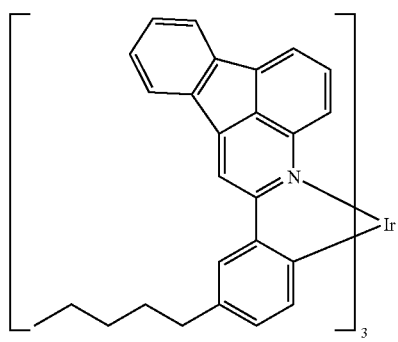
(2-365)
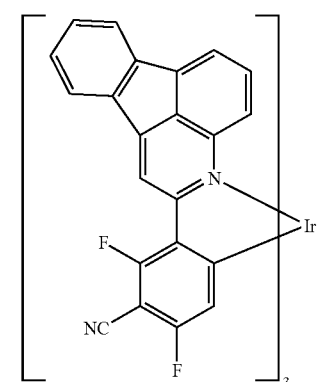
(2-368)

TABLE 18-continued
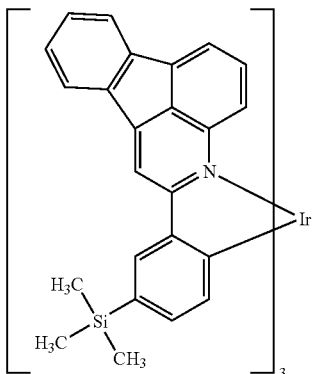
(2-369)
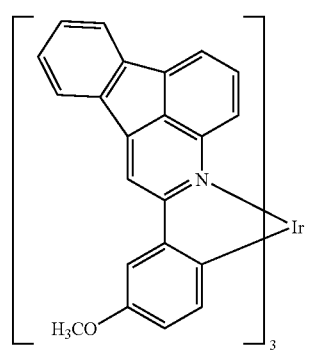
(2-370)
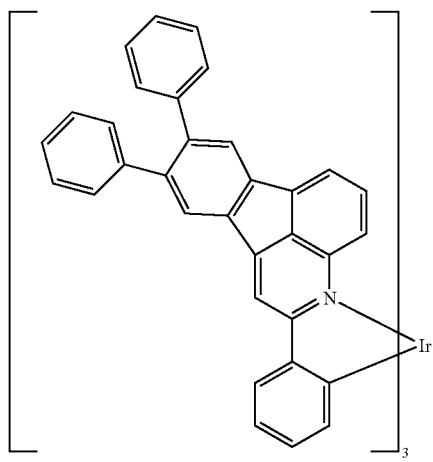
(2-371)
TABLE 18-continued
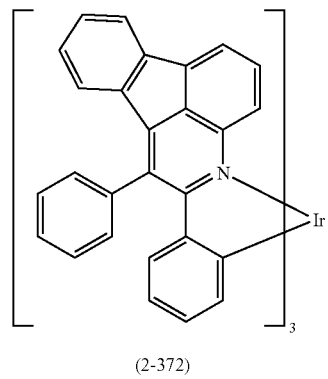
(2-372)
TABLE 19
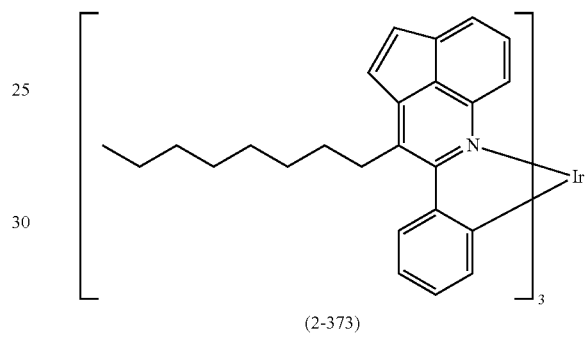
(2-373)
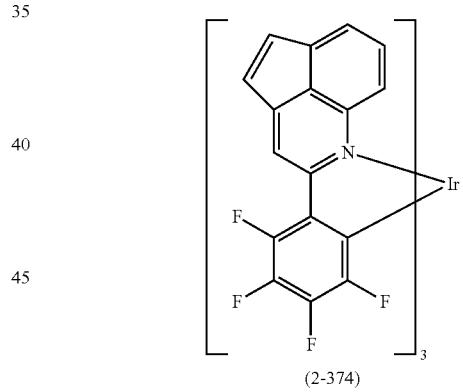
(2-374)
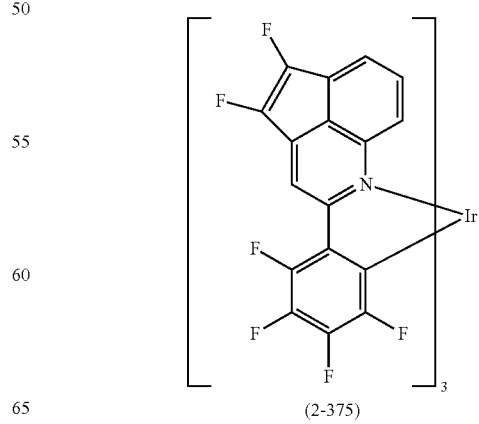
(2-375)

TABLE 19-continued
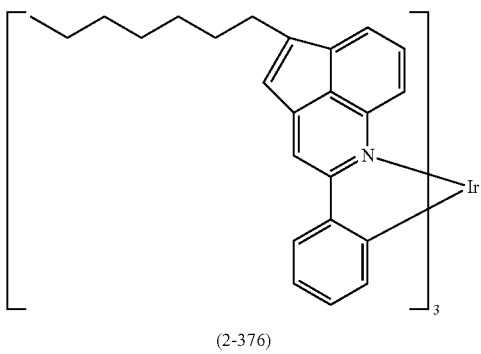
(2-376)
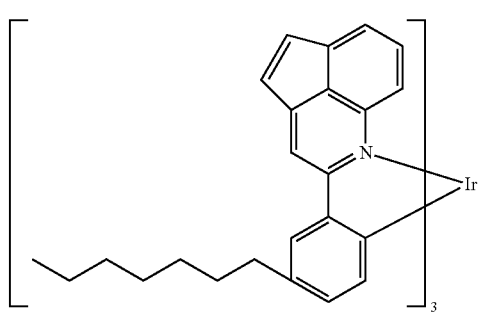
(2-377)
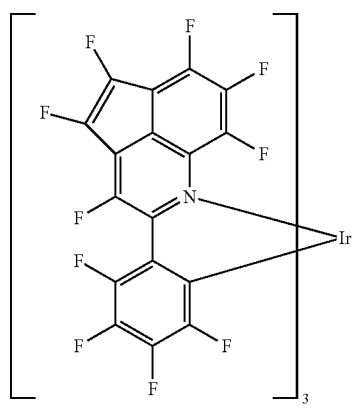
(2-378)
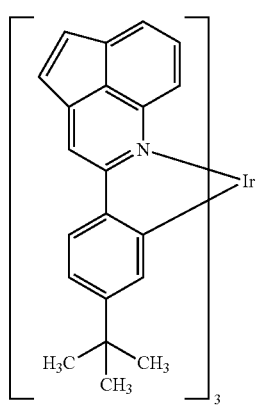
(2-379)
TABLE 19-continued
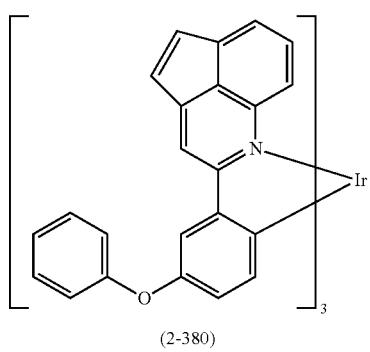
(2-380)
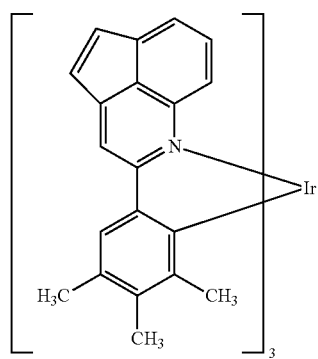
(2-381)
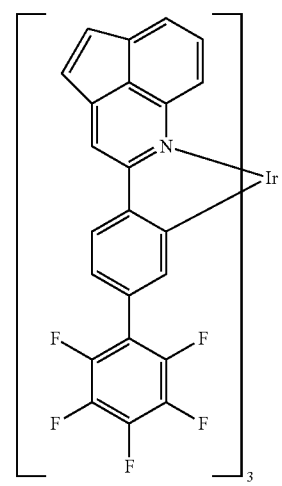
(2-382)

TABLE 19-continued
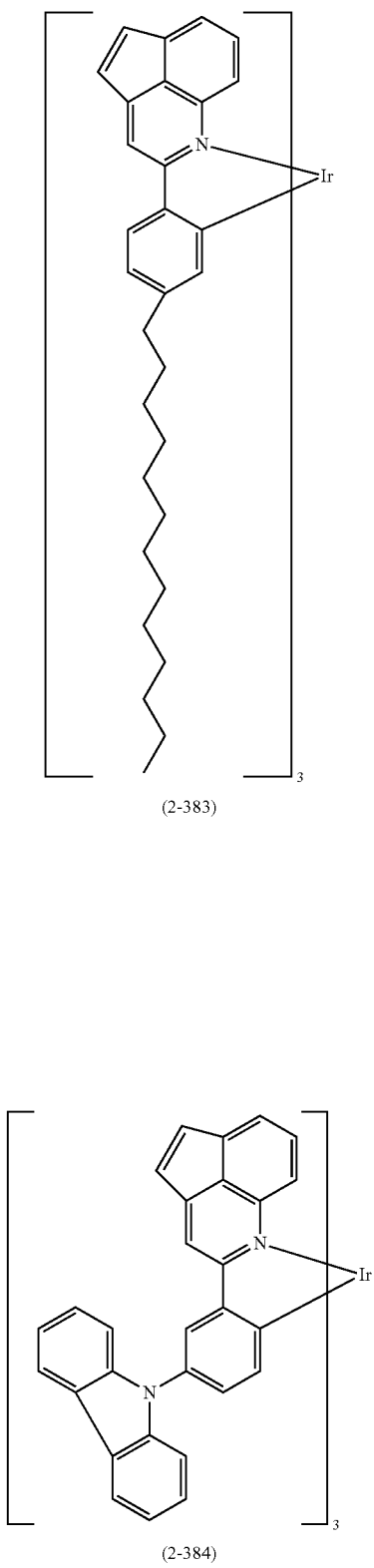
(2-383)
(2-384)
TABLE 19-continued
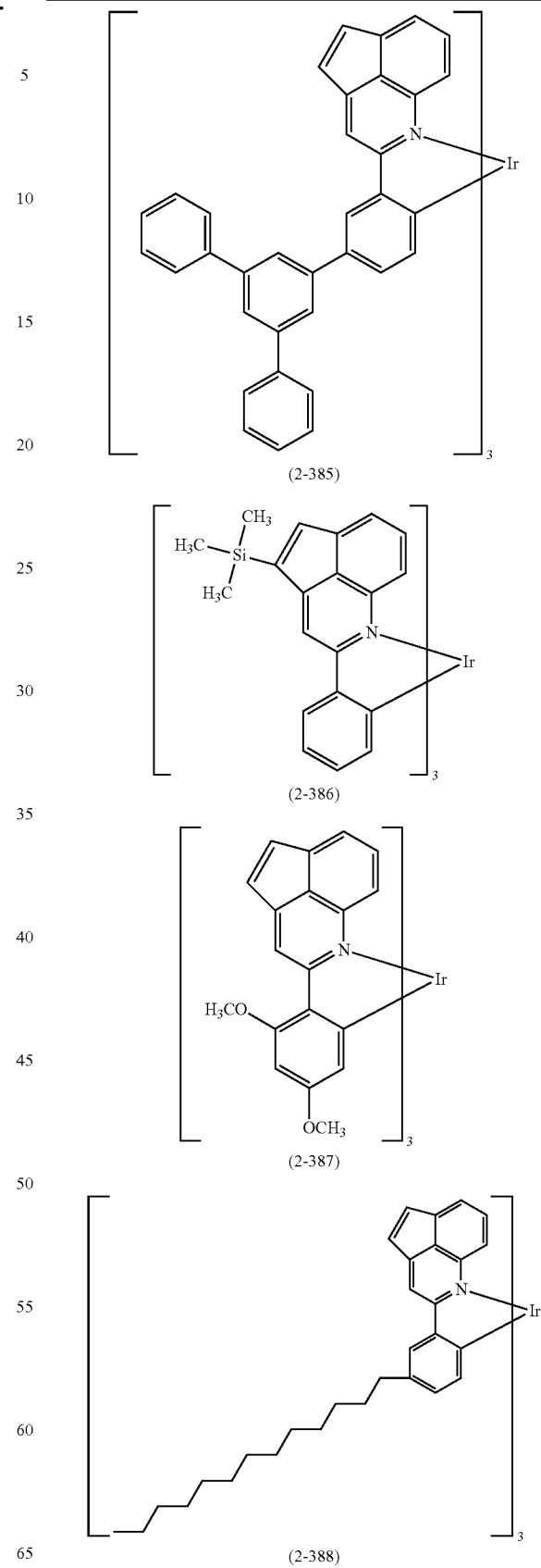
(2-385)
(2-386)
(2-387)
(2-388)

TABLE 19-continued
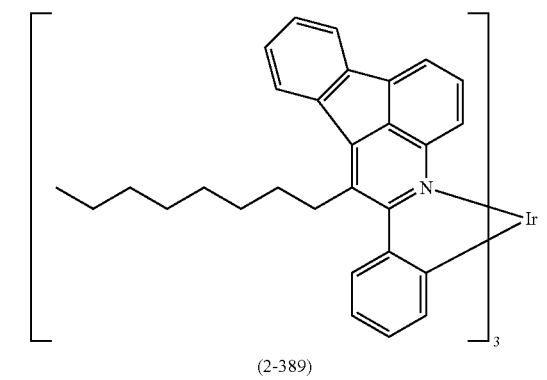
(2-389)
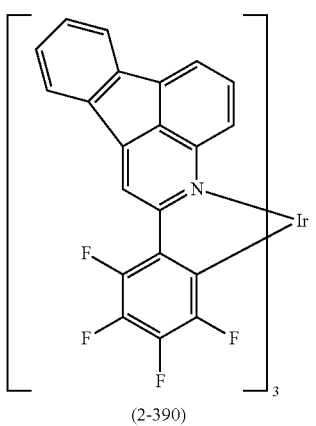
(2-390)
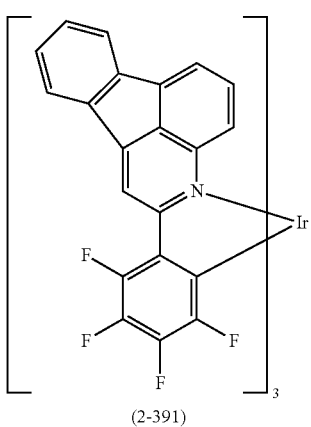
(2-391)
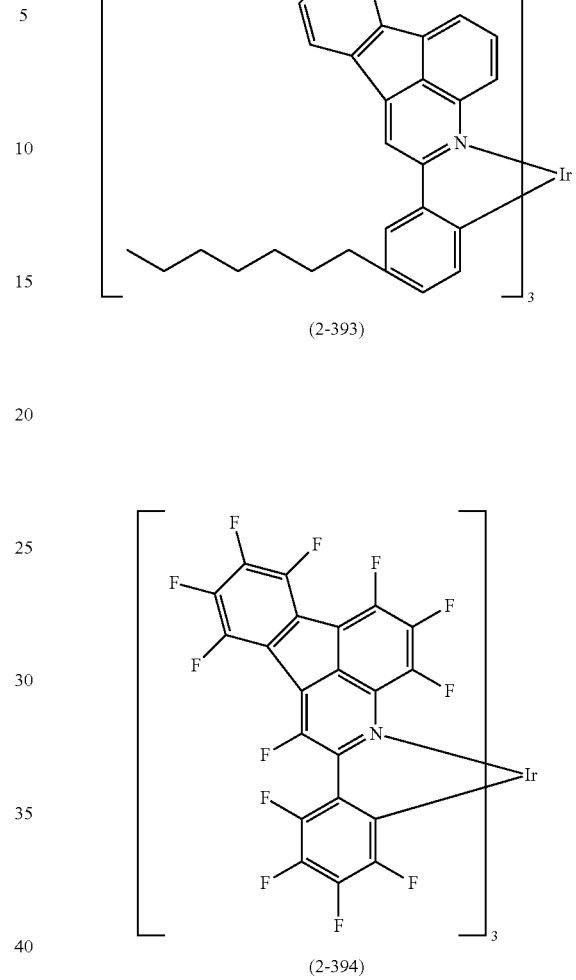
(2-392)
TABLE 19-continued
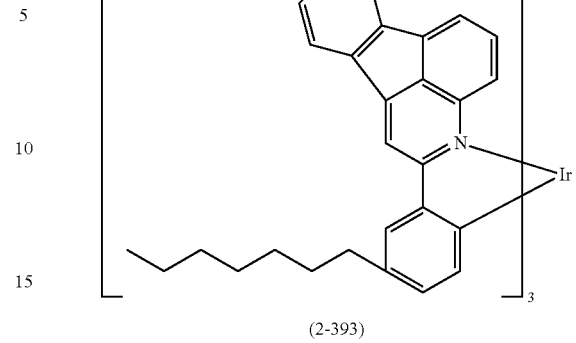
(2-393)
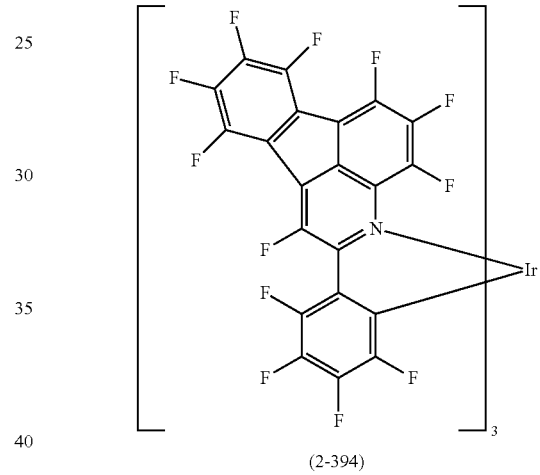
(2-394)
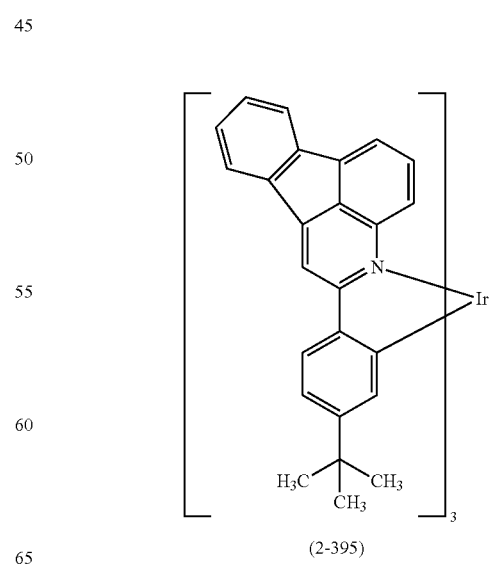
(2-395)

TABLE 19-continued
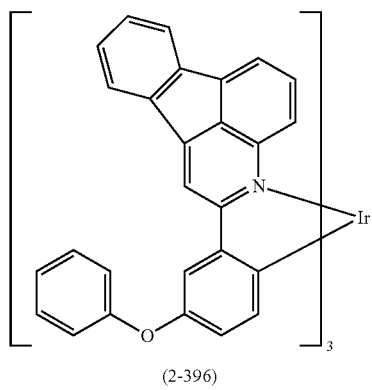
(2-396)
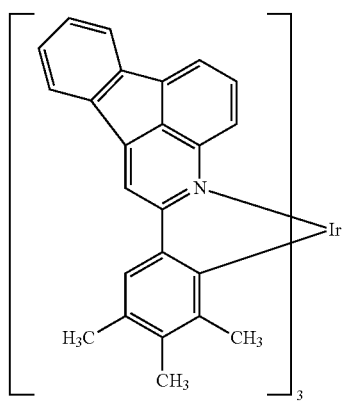
(2-397)
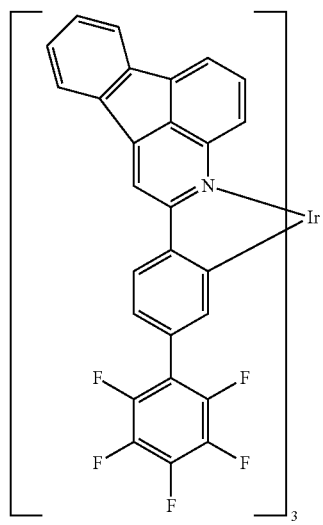
(2-398)
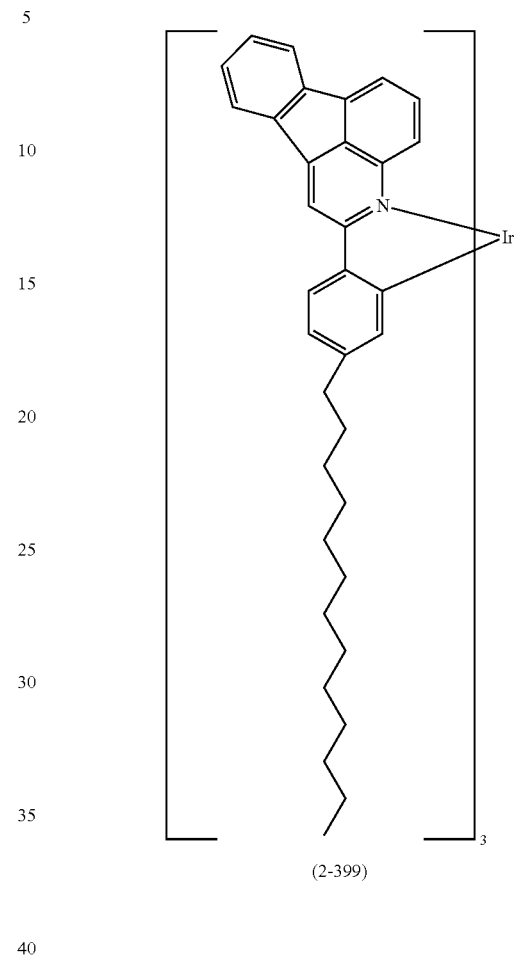
(2-399)
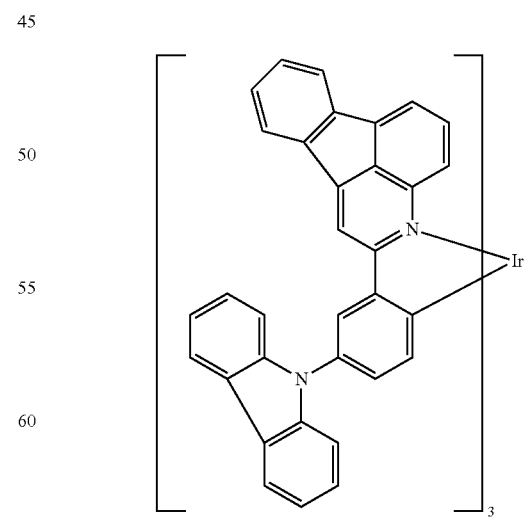
(2-400)

TABLE 19-continued
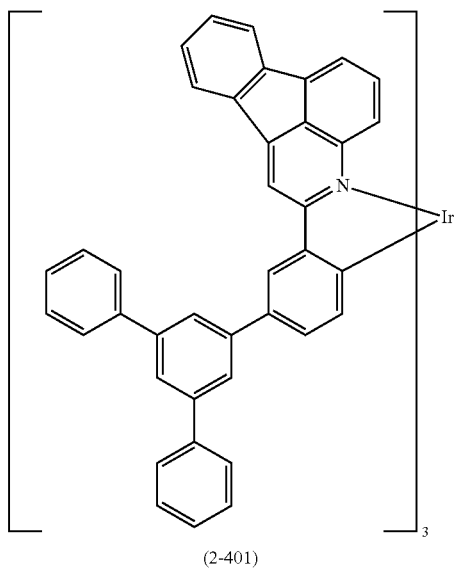
(2-401)
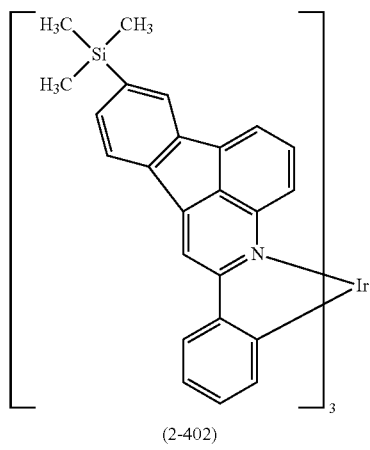
(2-402)
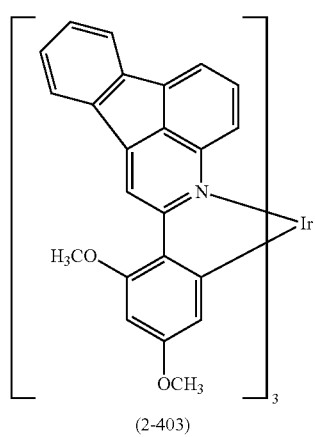
(2-403)
TABLE 19-continued
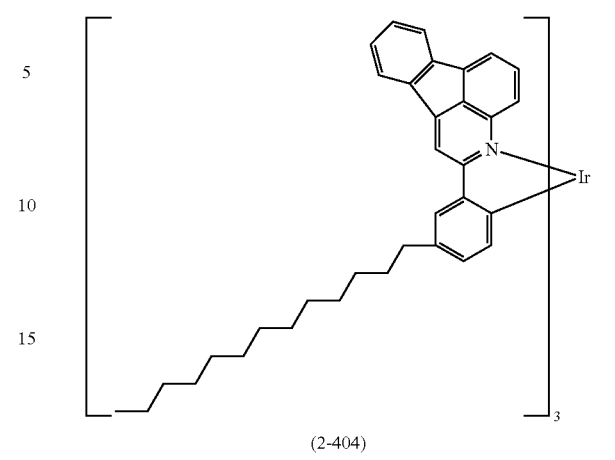
(2-404)
TABLE 20
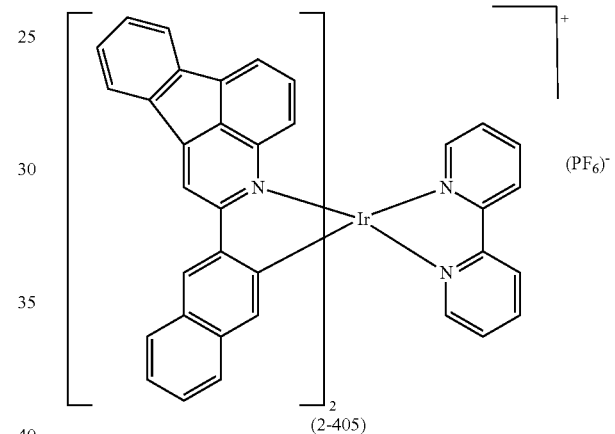
(2-405)
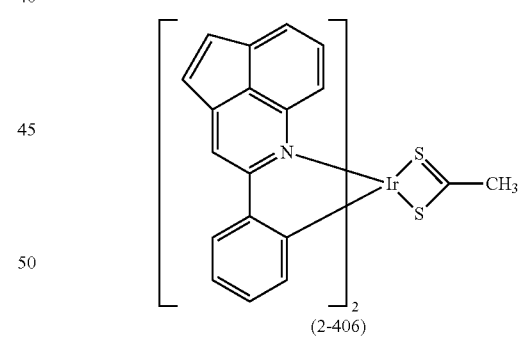
(2-406)
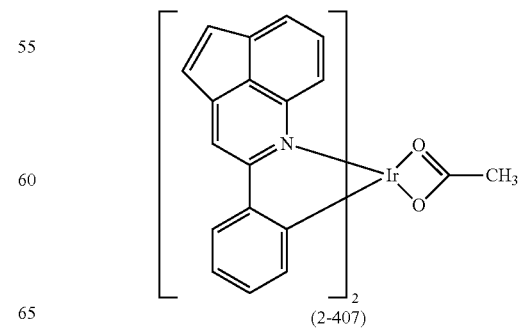
(2-407)

TABLE 20-continued
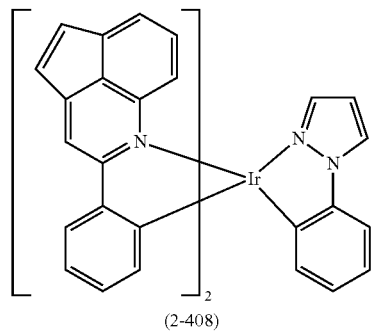
(2-408)
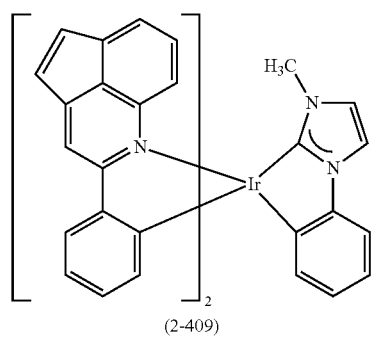
(2-409)
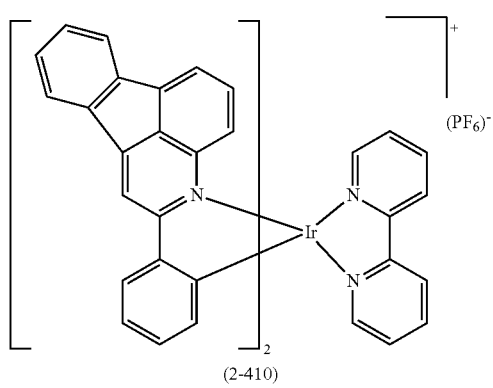
(2-410)
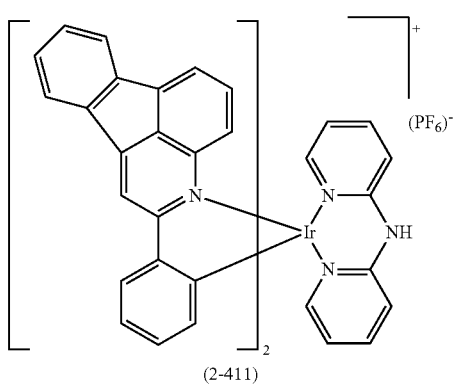
(2-411)
TABLE 20-continued
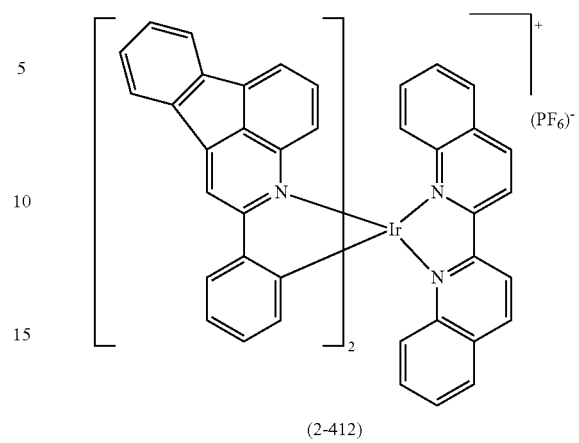
(2-412)
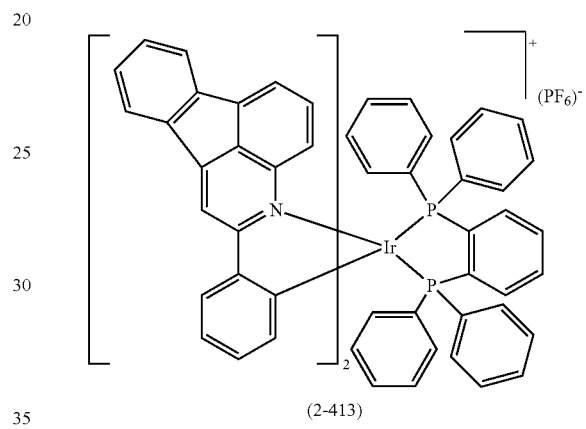
(2-413)
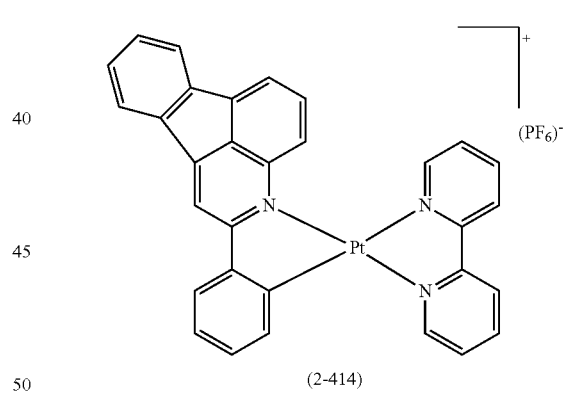
(2-414)
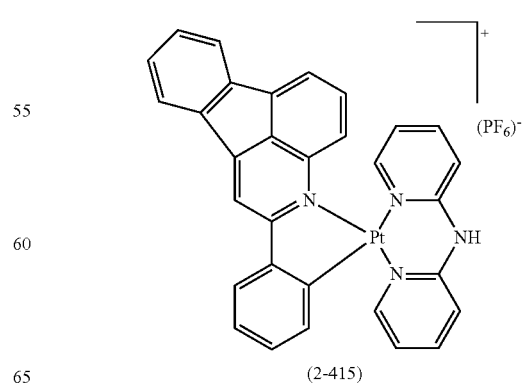
(2-415)

TABLE 20-continued
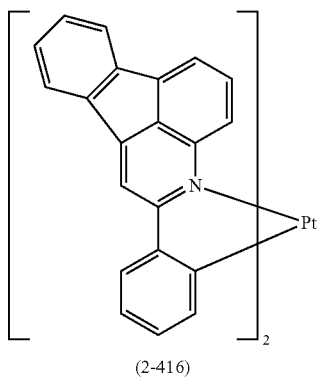
(2-416)
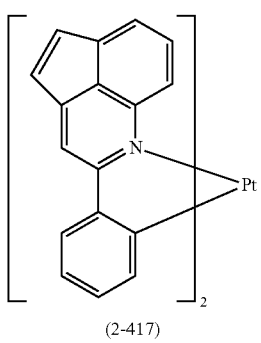
(2-417)
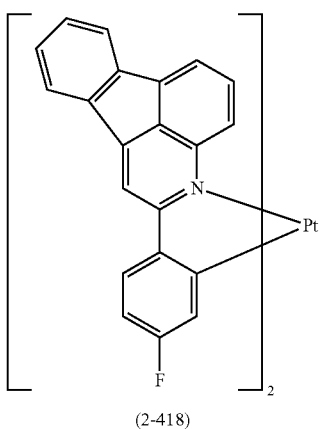
(2-418)
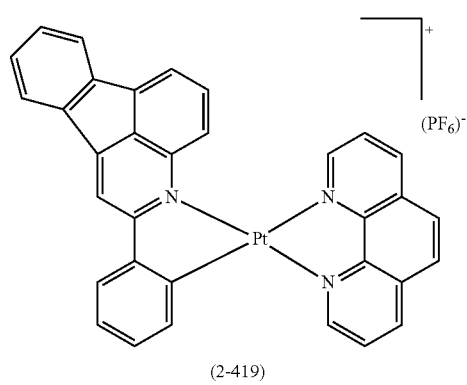
(2-419)
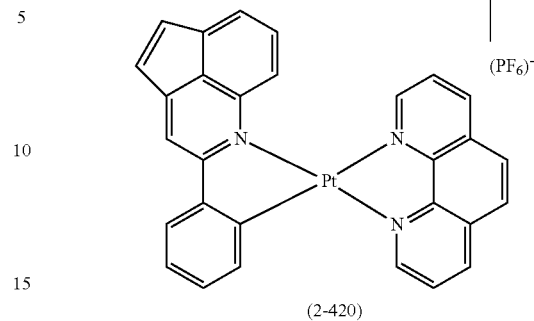
(2-420)
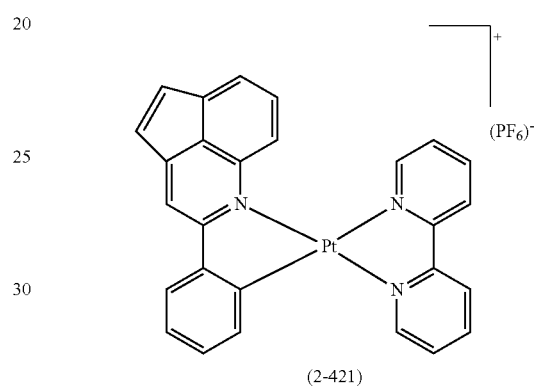
(2-421)
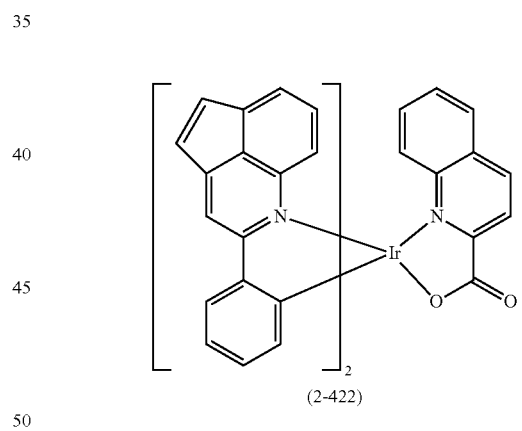
(2-422)
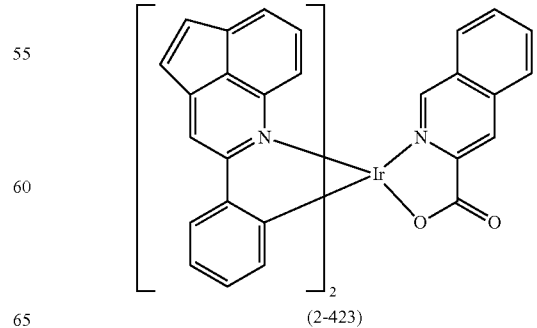
(2-423)

TABLE 20-continued
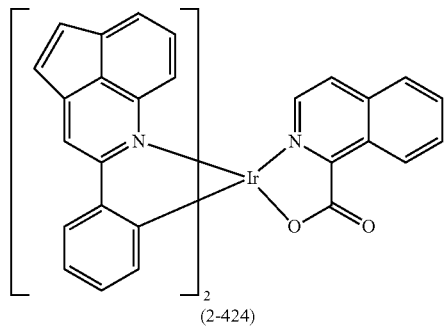
(2-424)
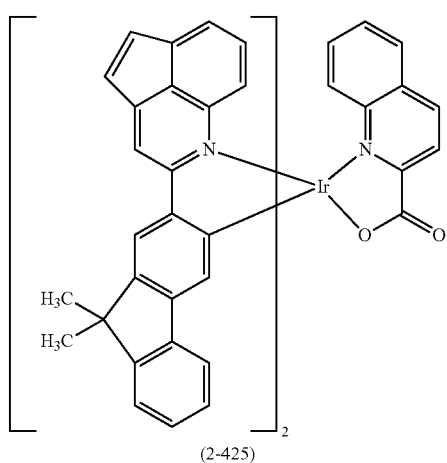
(2-425)
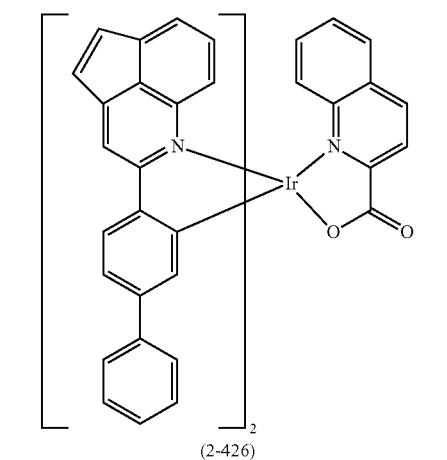
(2-426)
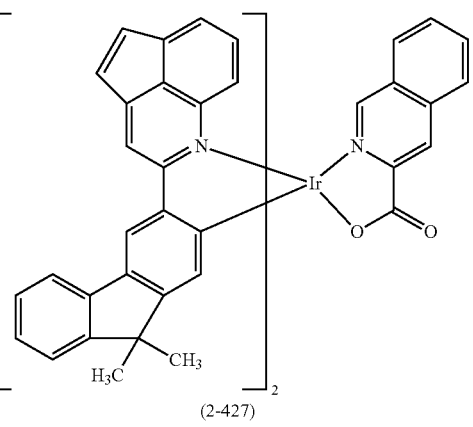
(2-427)
TABLE 20-continued
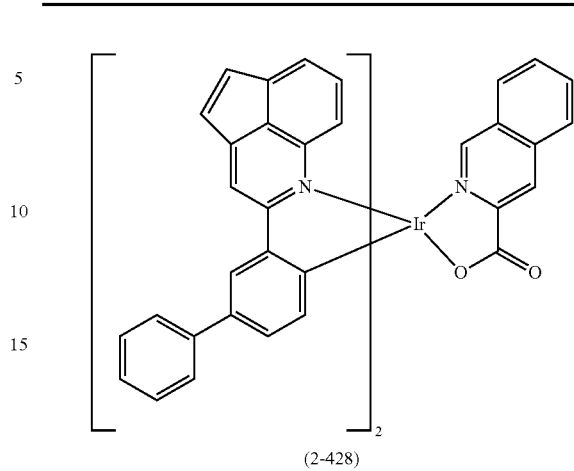
(2-428)
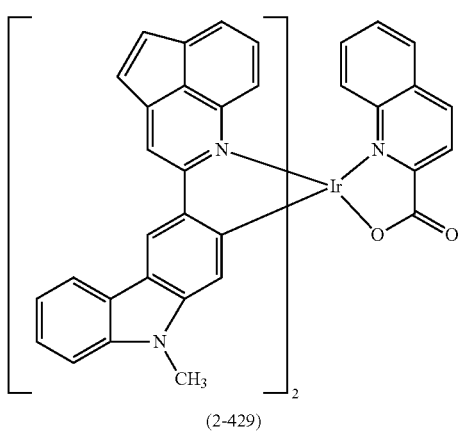
(2-429)
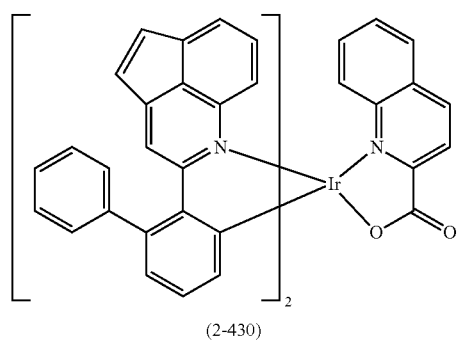
(2-430)
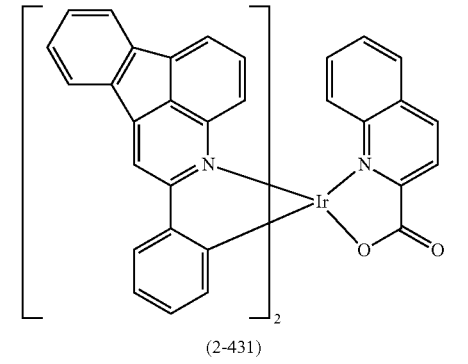
(2-431)

TABLE 20-continued
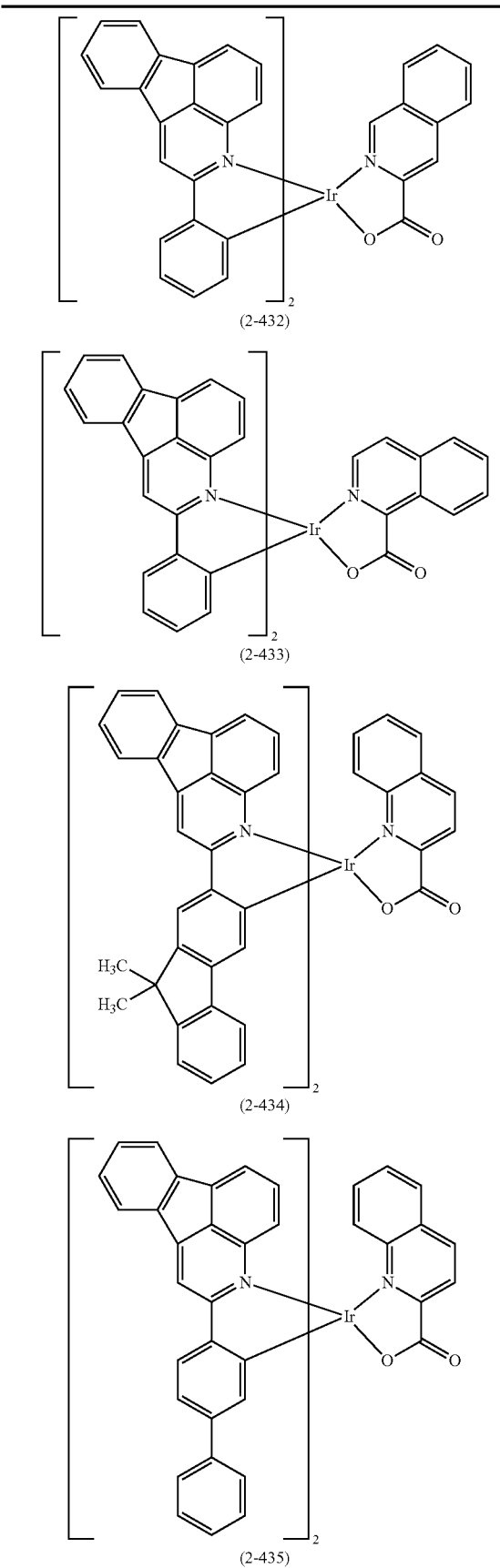
(2-432)
(2-433)
(2-434)
(2-435)
TABLE 20-continued
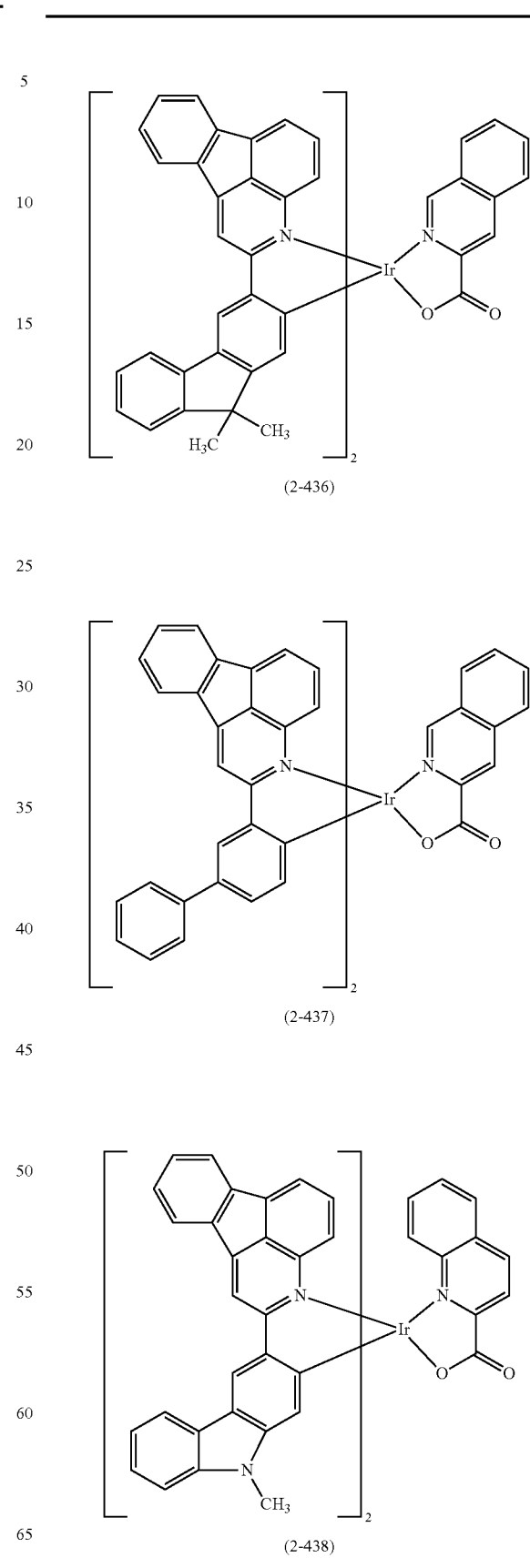
(2-436)
(2-437)
(2-438)

TABLE 20-continued
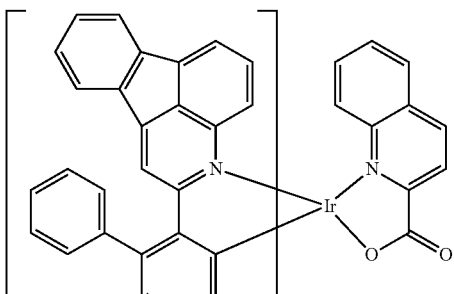
(2-439)
TABLE 21
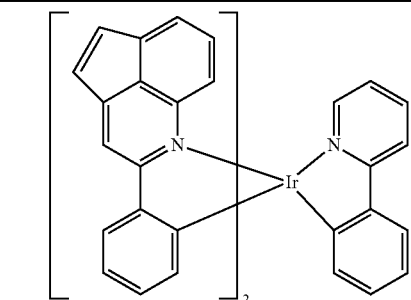
(2-440)
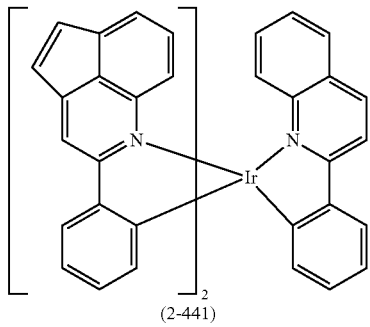
(2-441)
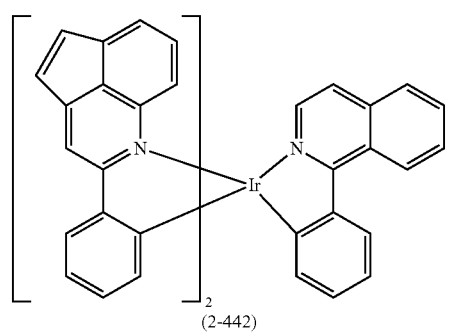
(2-442)
TABLE 21-continued
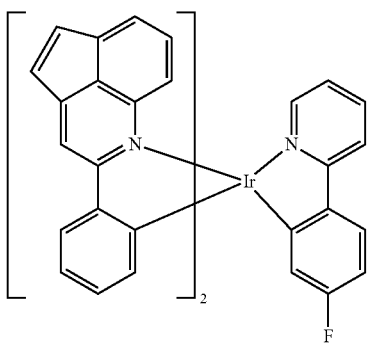
(2-443)
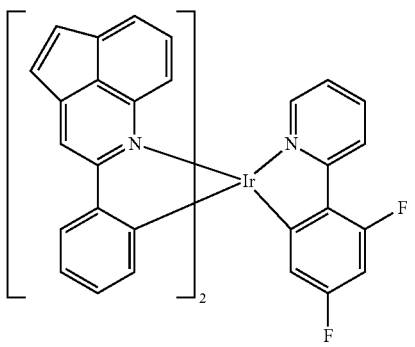
(2-444)
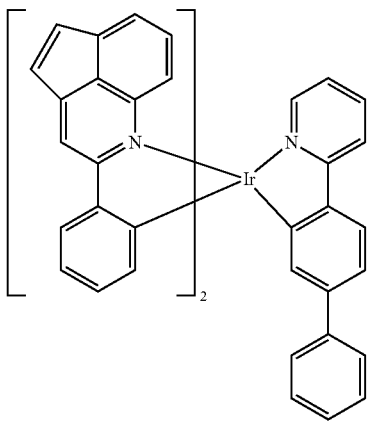
(2-445)
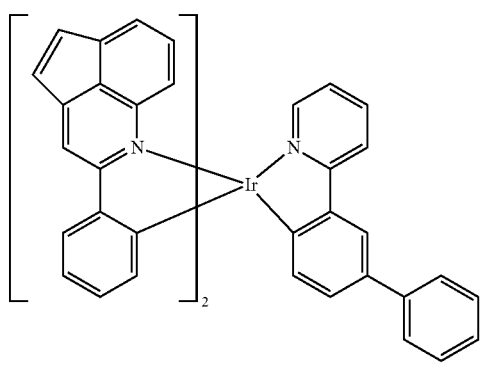
(2-446)

TABLE 21-continued
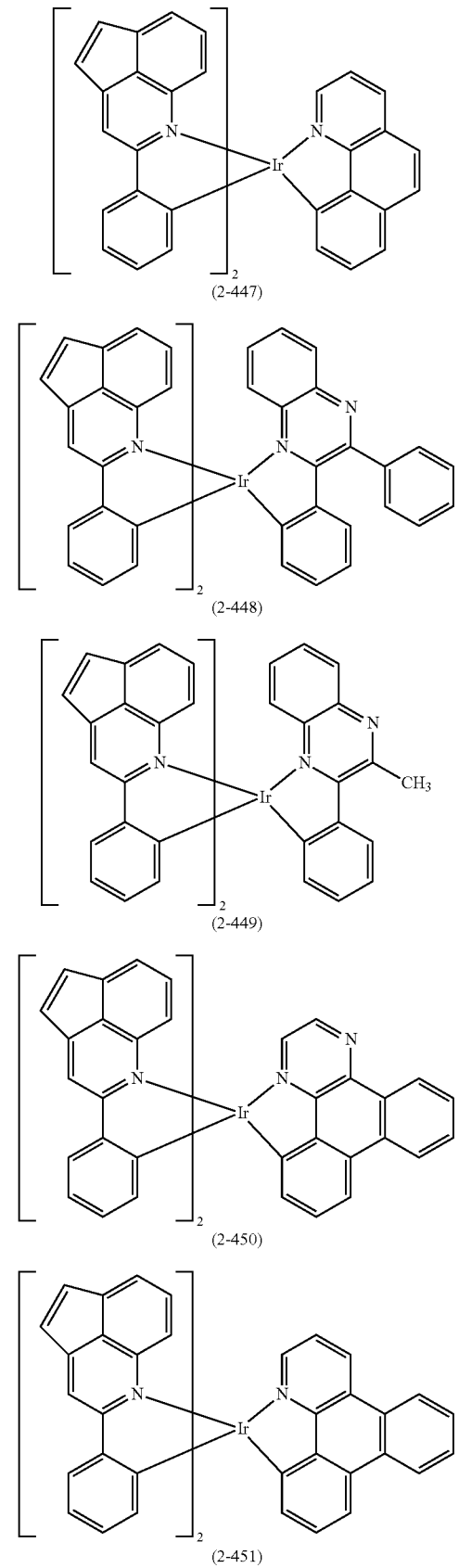
(2-447)
(2-448)
(2-449)
(2-450)
(2-451)
TABLE 21-continued
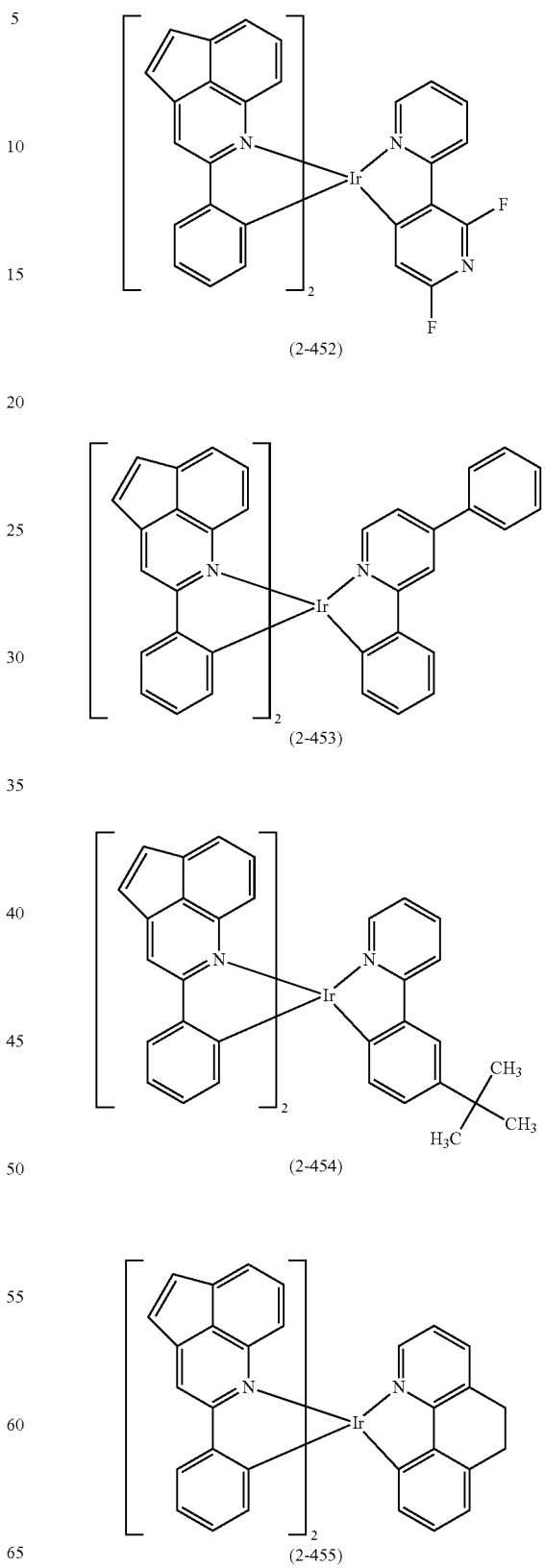
(2-452)
(2-453)
(2-454)
(2-455)

TABLE 21-continued
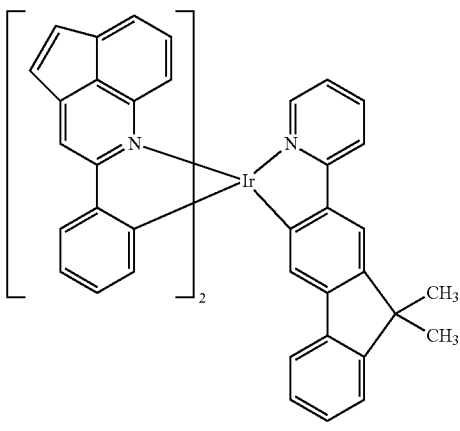
(2-456)
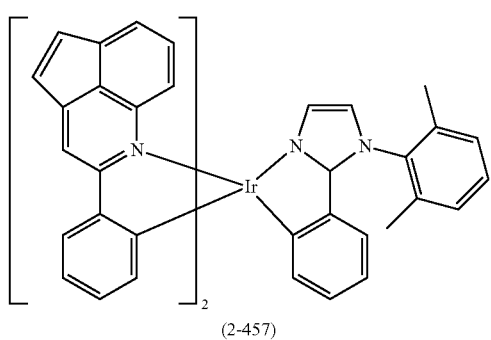
(2-457)
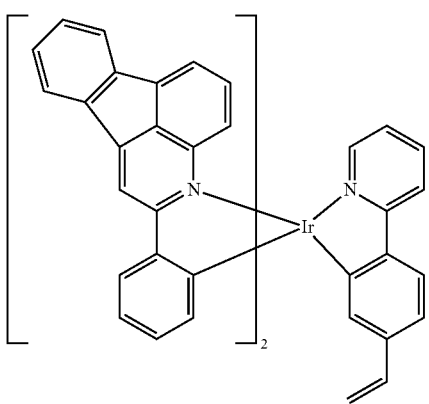
(2-458)
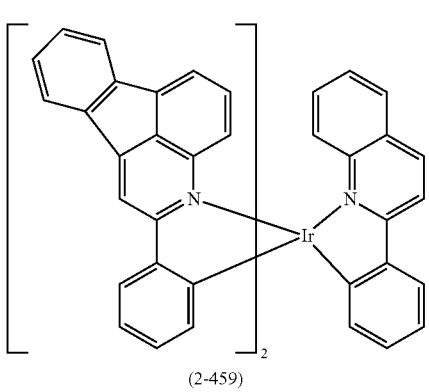
(2-459)
TABLE 21-continued
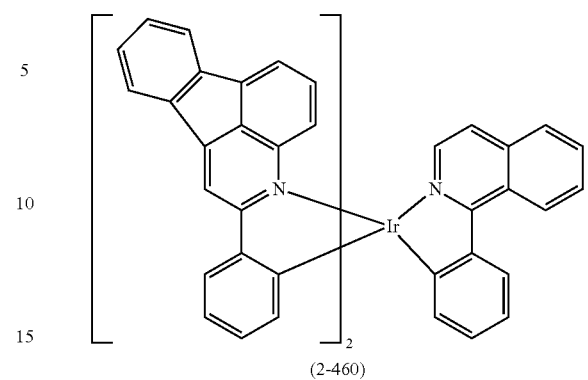
(2-460)
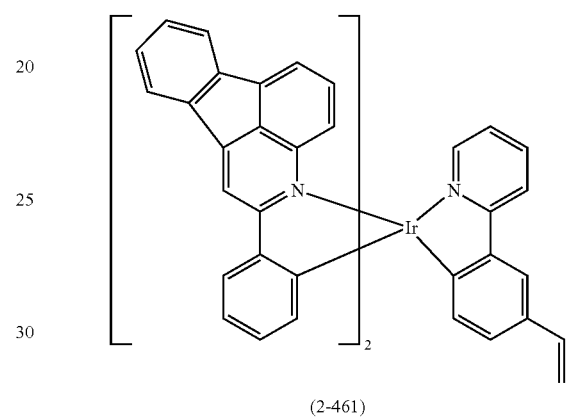
(2-461)
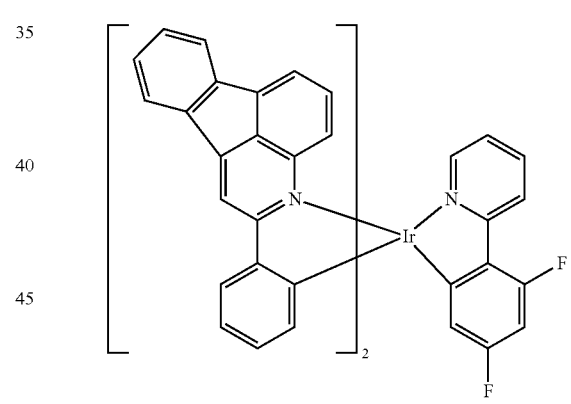
(2-462)
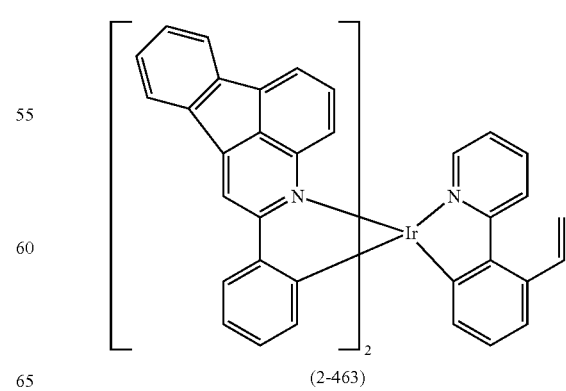
(2-463)

TABLE 21-continued
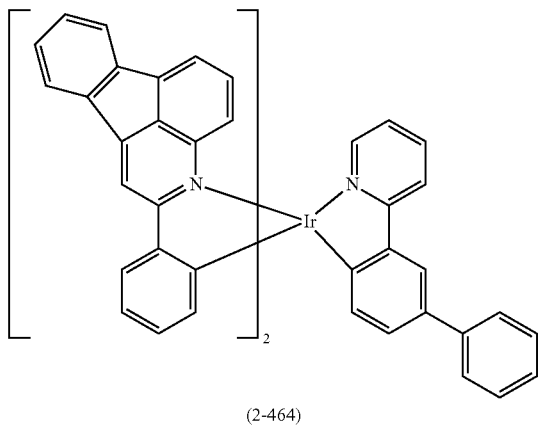
(2-464)
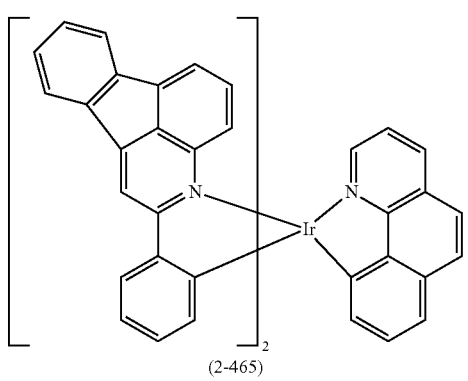
(2-465)
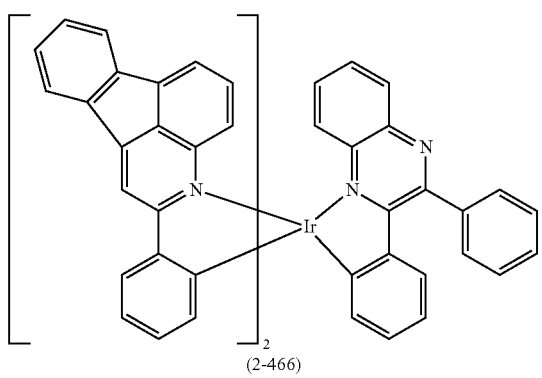
(2-466)
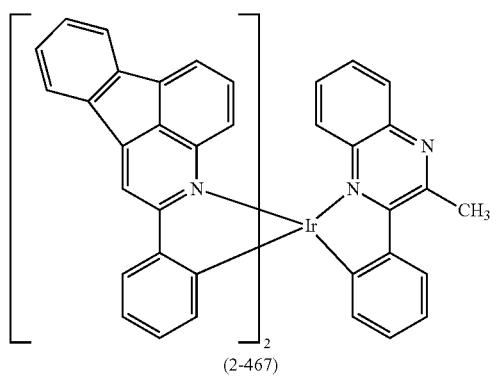
(2-467)
TABLE 21-continued
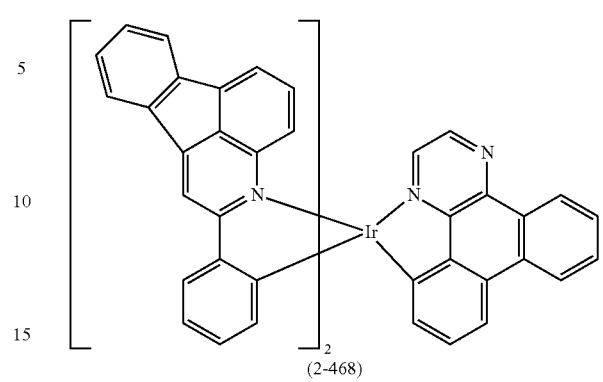
(2-468)
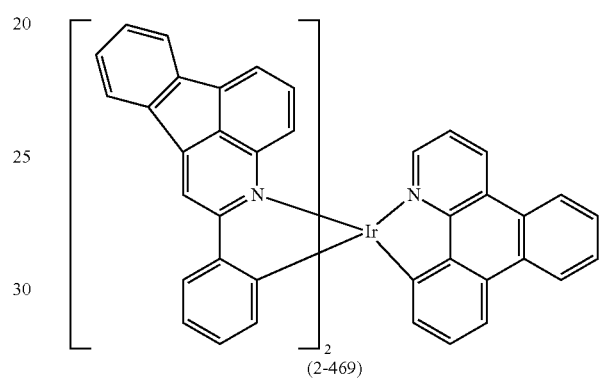
(2-469)
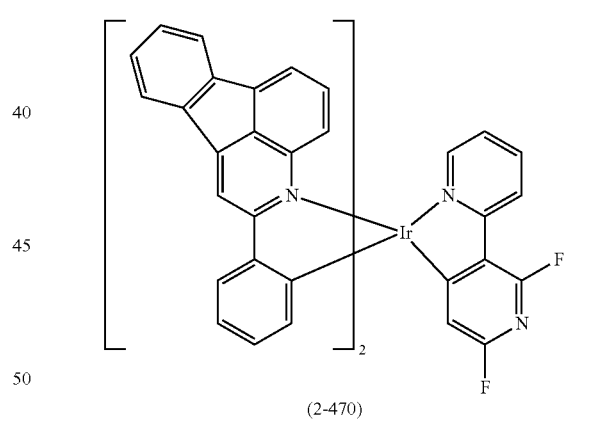
(2-470)
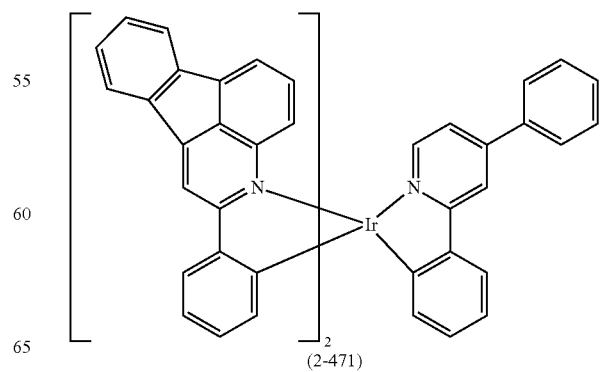
(2-471)

TABLE 21-continued
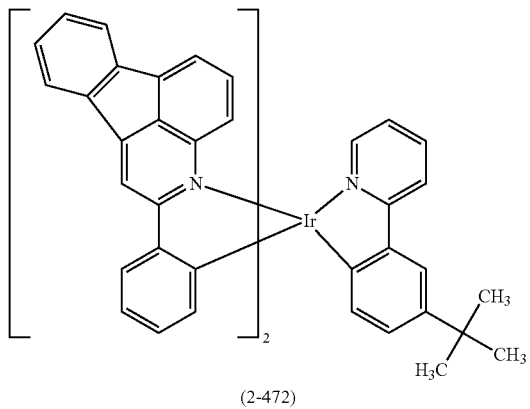
(2-472)
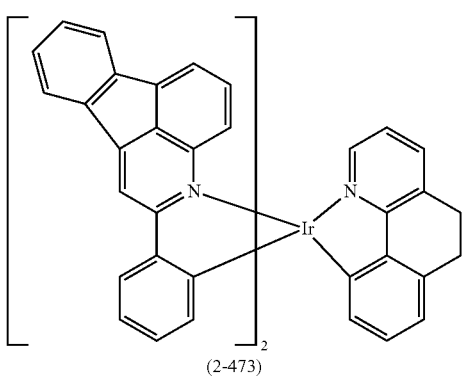
(2-473)
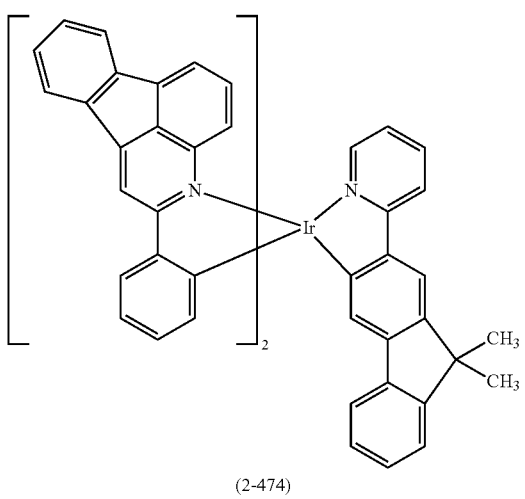
(2-474)
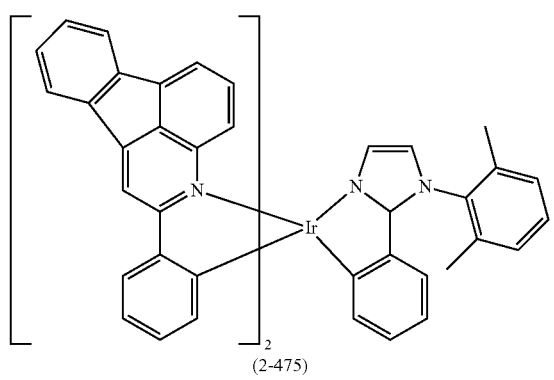
(2-475)
TABLE 22
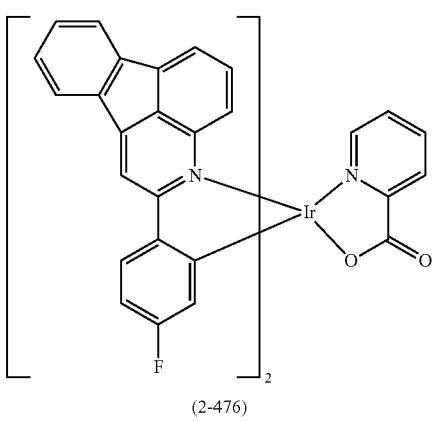
(2-476)
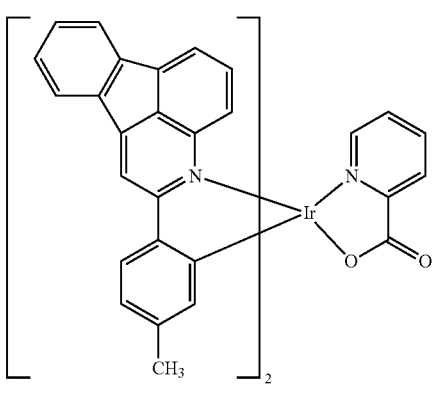
(2-477)
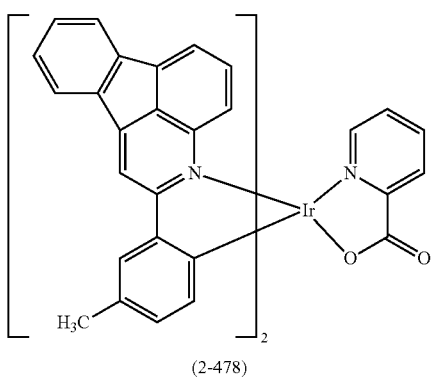
(2-478)
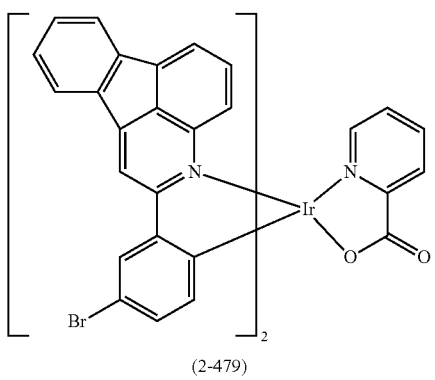
(2-479)

TABLE 22-continued
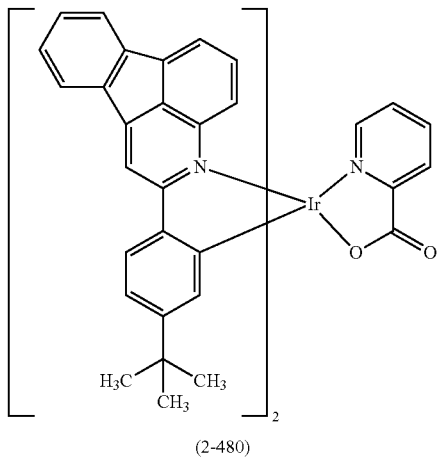
(2-480)
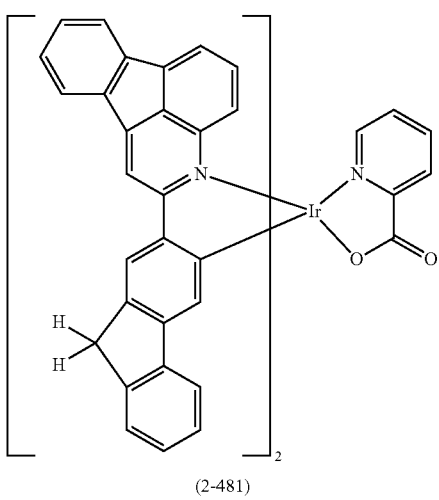
(2-481)
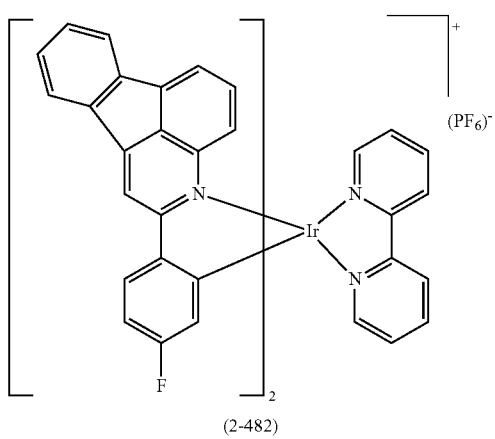
(2-482)
TABLE 22-continued
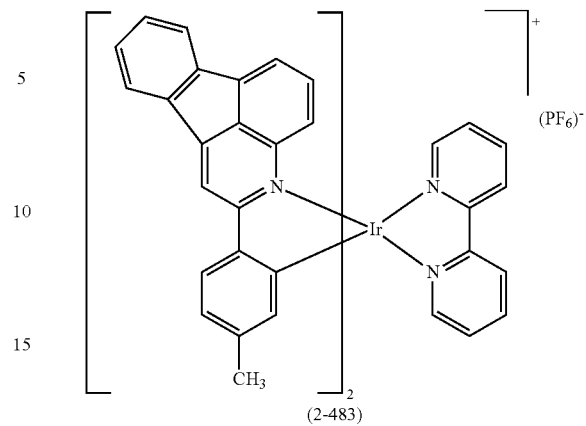
(2-483)
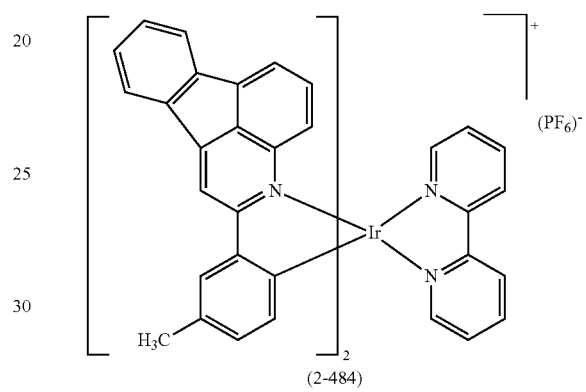
(2-484)
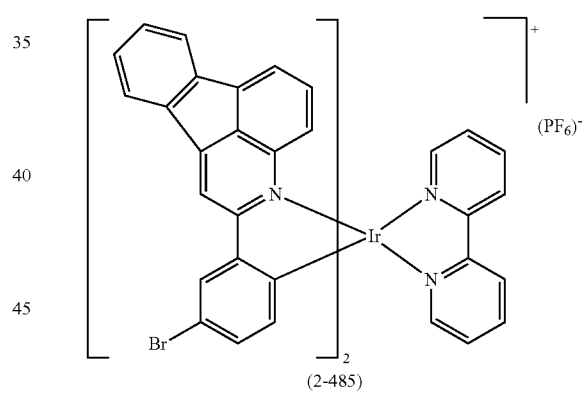
(2-485)
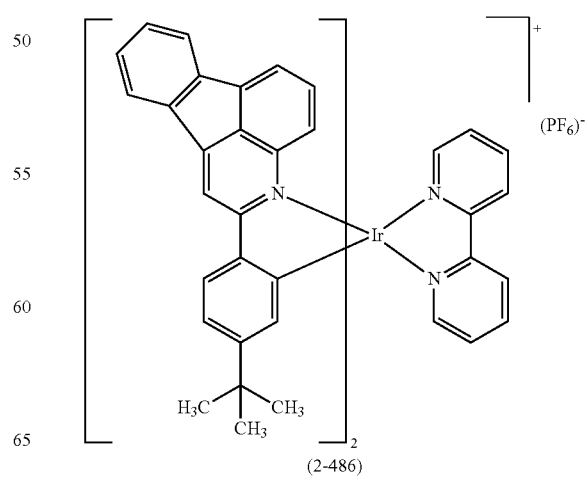
(2-486)

TABLE 22-continued
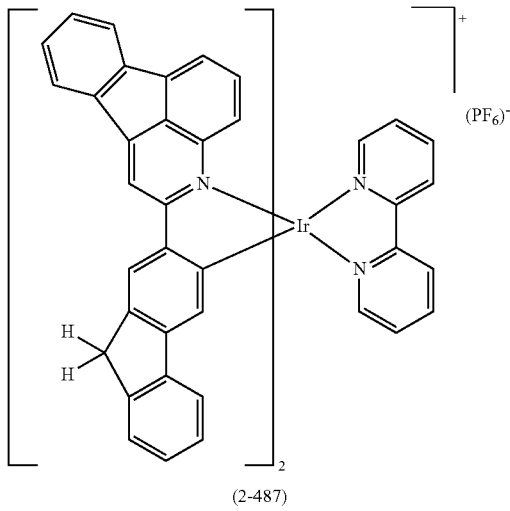
(2-487)
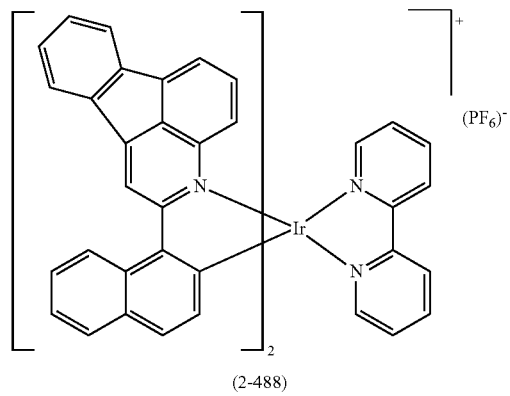
(2-488)
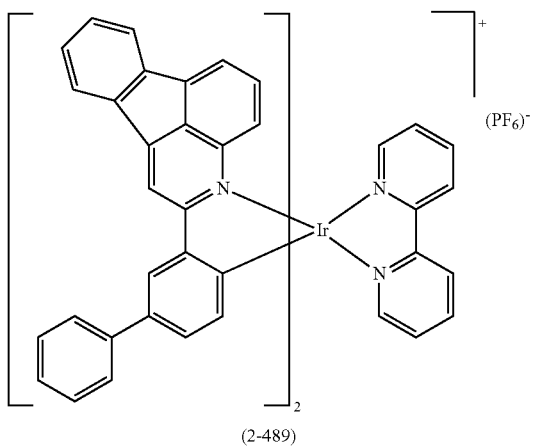
(2-489)
TABLE 22-continued
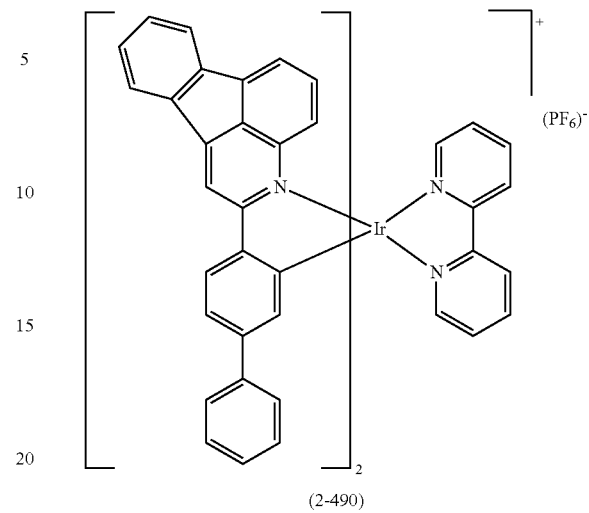
(2-490)
TABLE 23
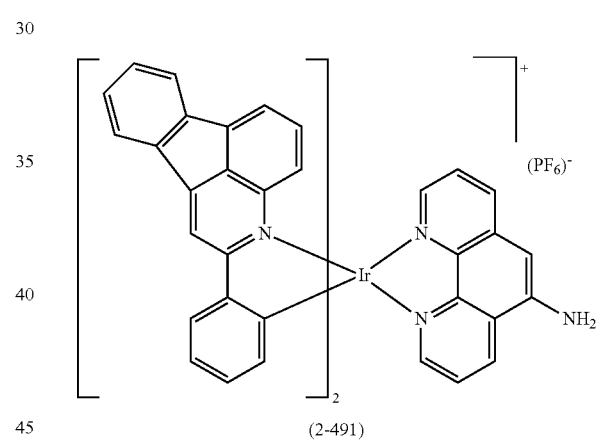
(2-491)
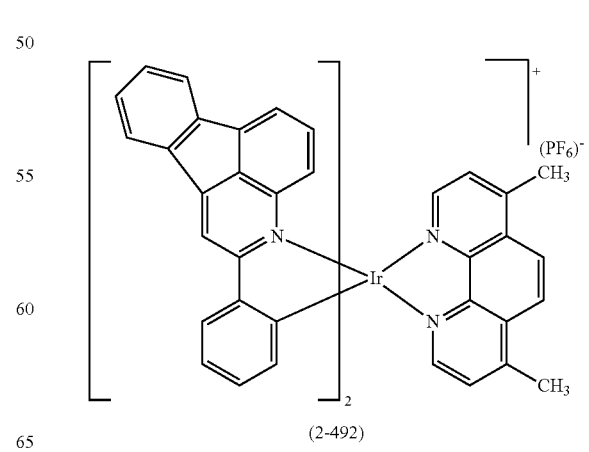
(2-492)

TABLE 23-continued
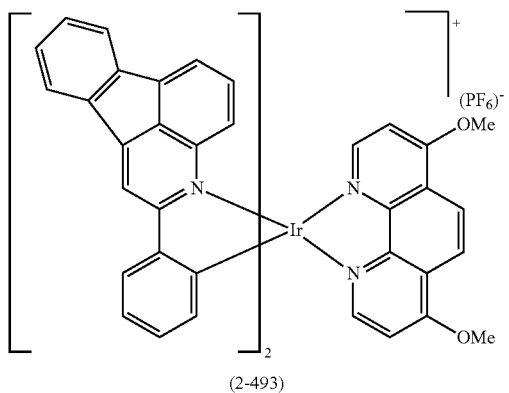
(2-493)
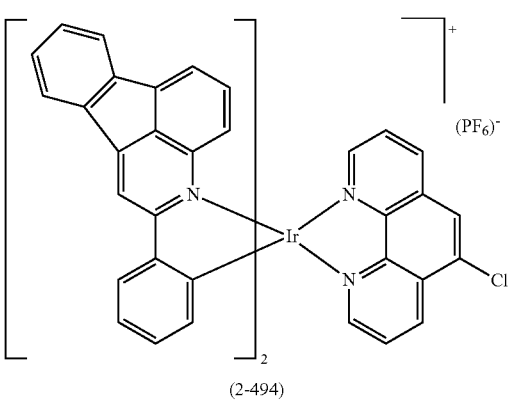
(2-494)
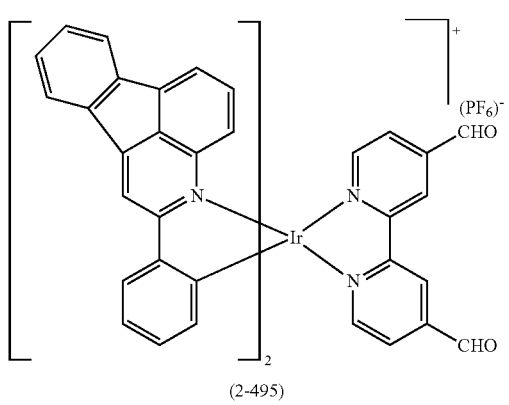
(2-495)
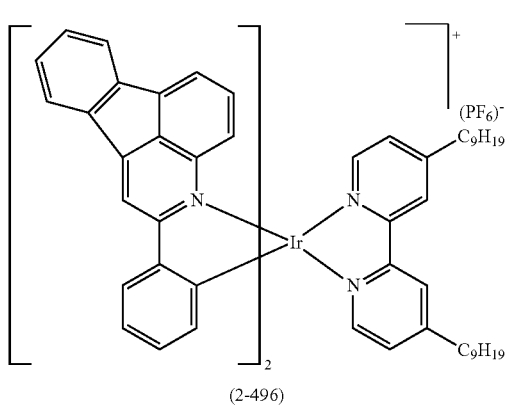
(2-496)
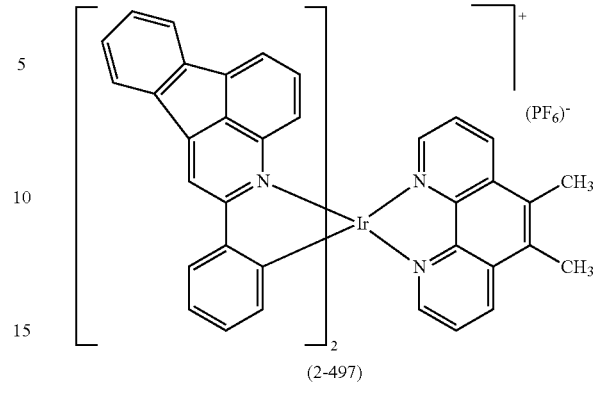
(2-497)
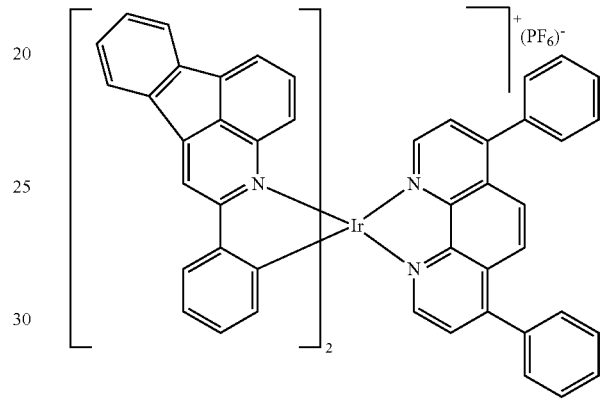
(2-498)
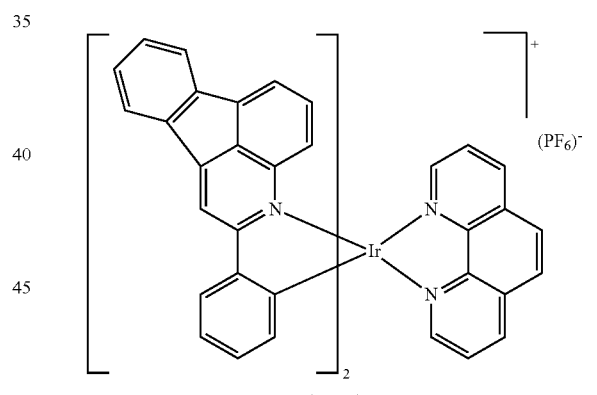
(2-499)
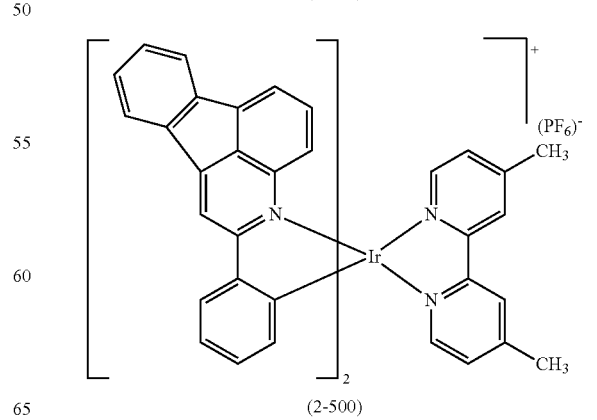
(2-500)

TABLE 23-continued
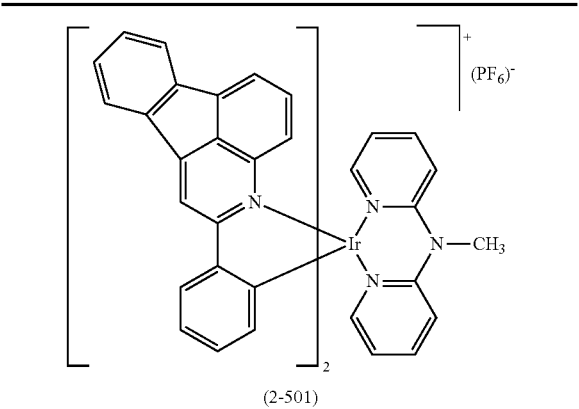
(2-501)
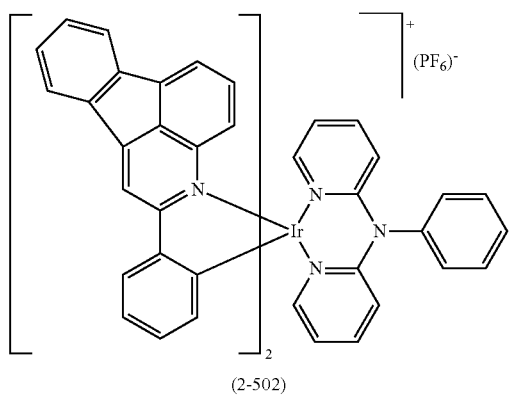
(2-502)
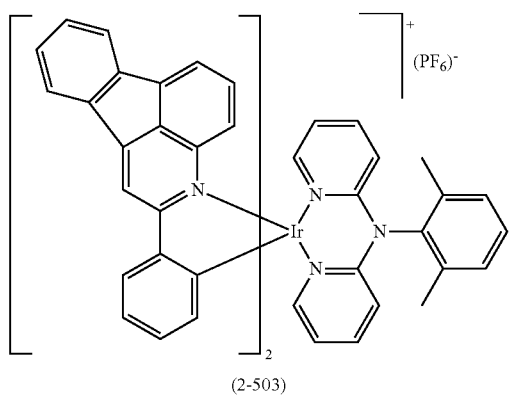
(2-503)
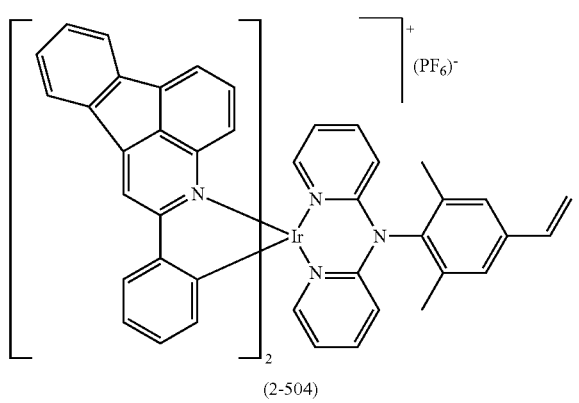
(2-504)
TABLE 23-continued
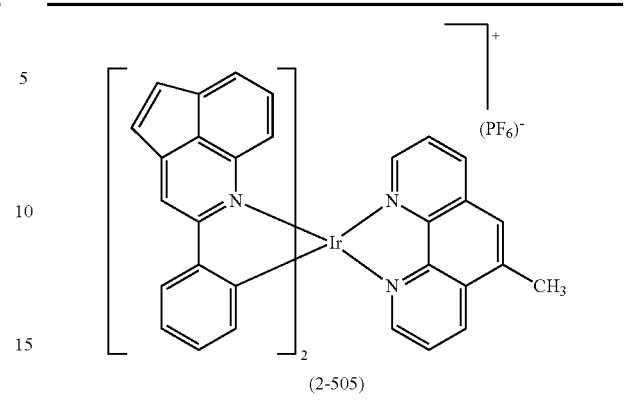
(2-505)
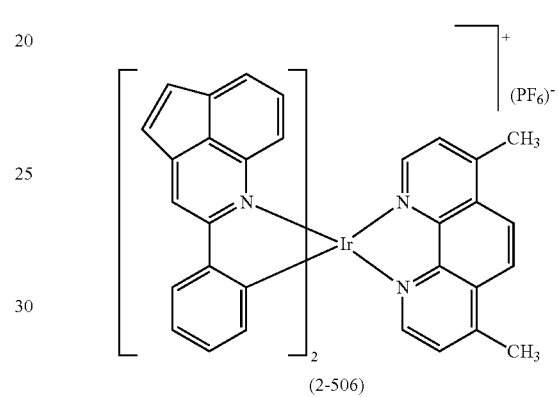
(2-506)
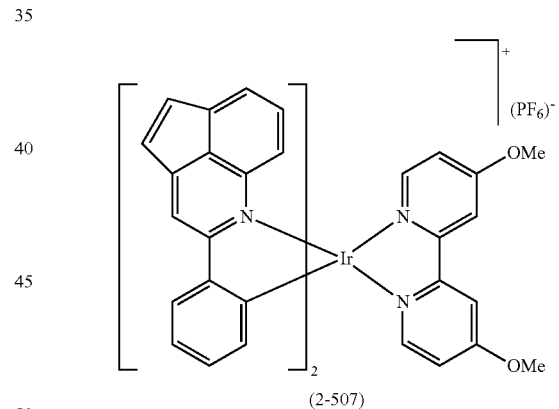
(2-507)
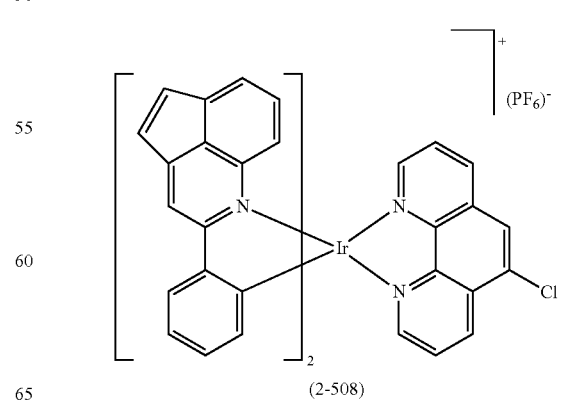
(2-508)

TABLE 23-continued
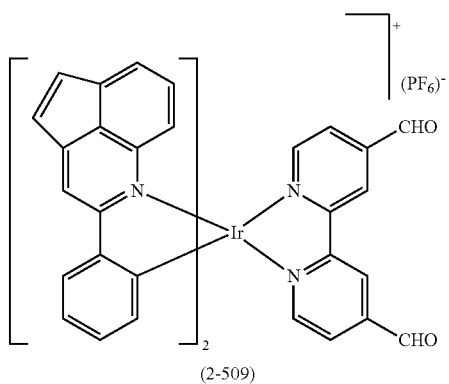
(2-509)
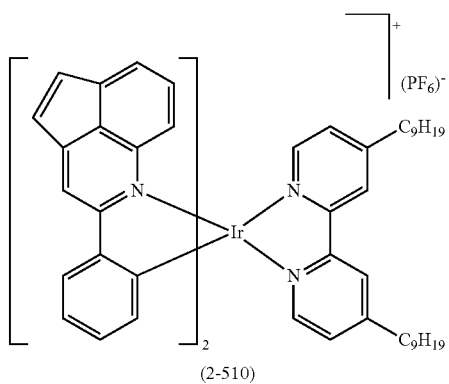
(2-510)
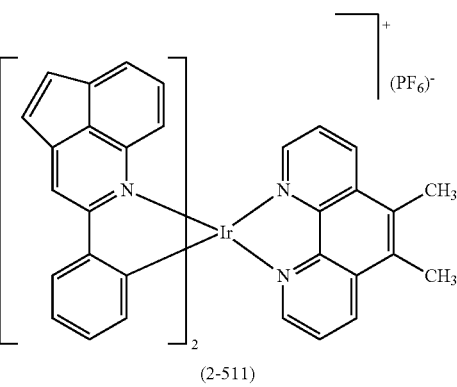
(2-511)
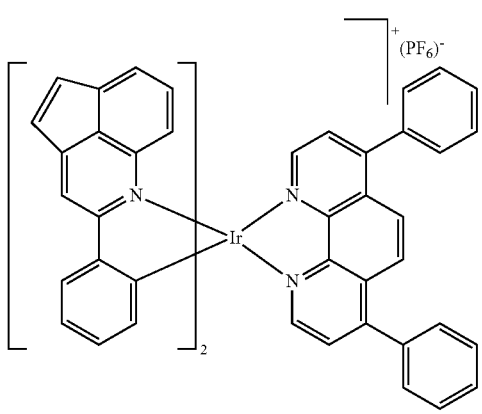
(2-512)
TABLE 23-continued
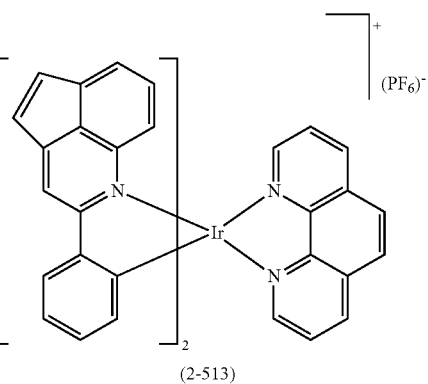
(2-513)
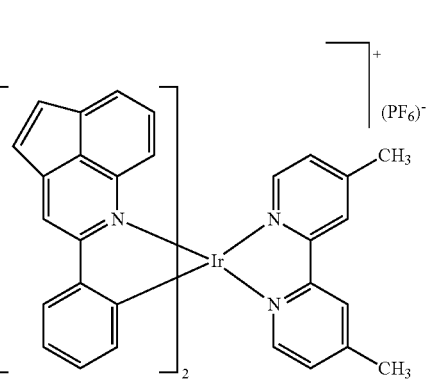
(2-514)
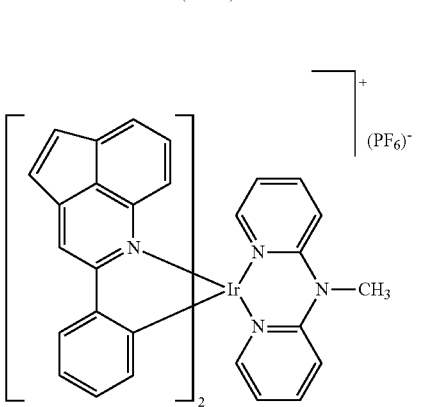
(2-515)
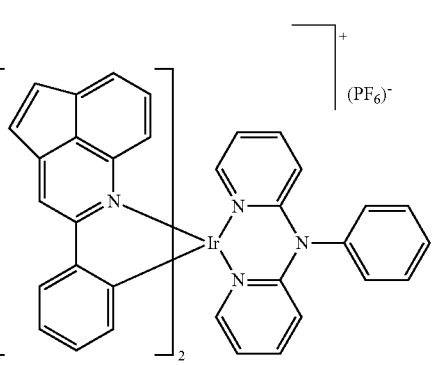
(2-516)

TABLE 23-continued
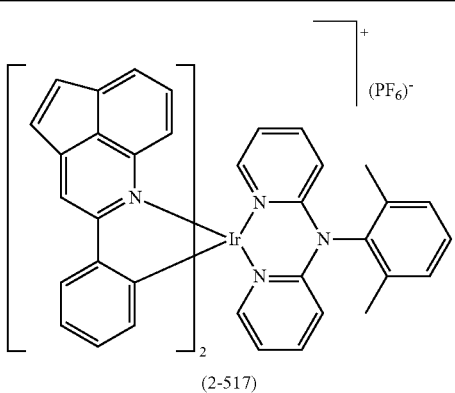
(2-517)
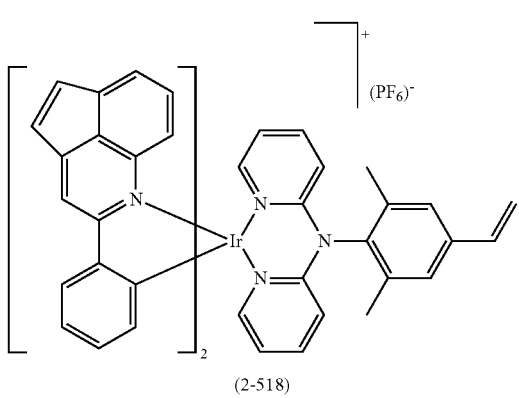
(2-518)
TABLE 24
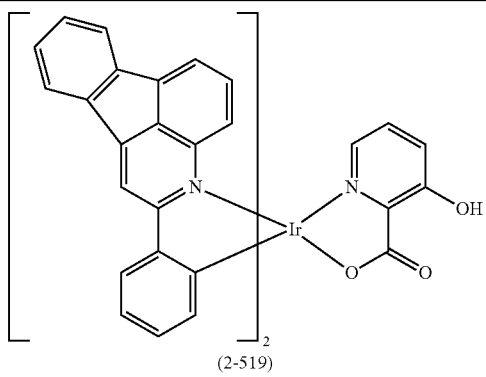
(2-519)
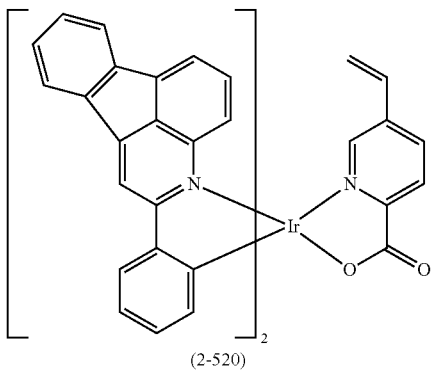
(2-520)
TABLE 24-continued
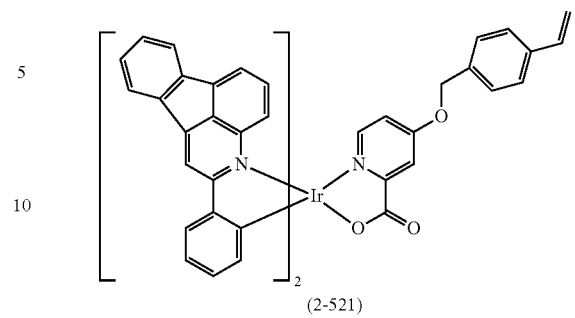
(2-521)
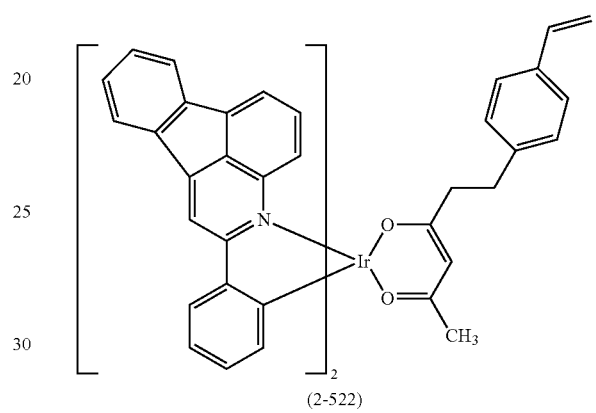
(2-522)
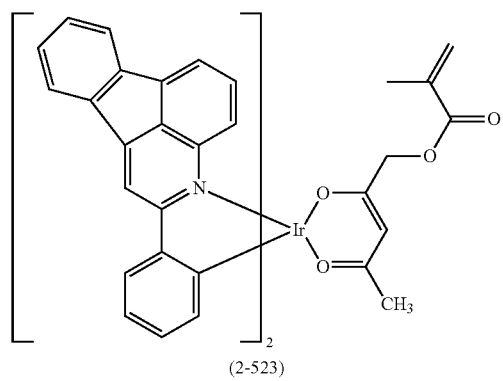
(2-523)
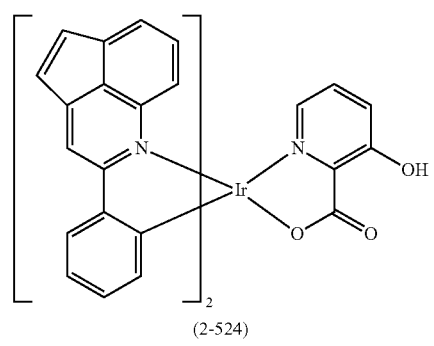
(2-524)

TABLE 24-continued
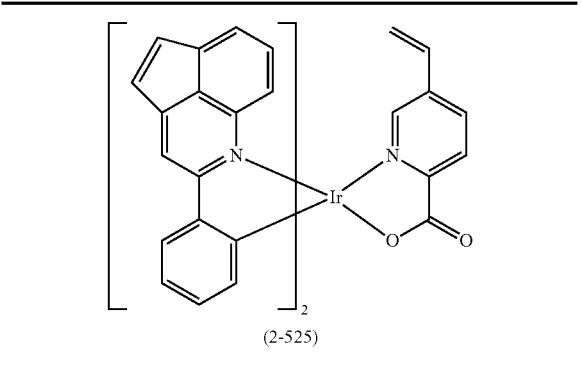
(2-525)
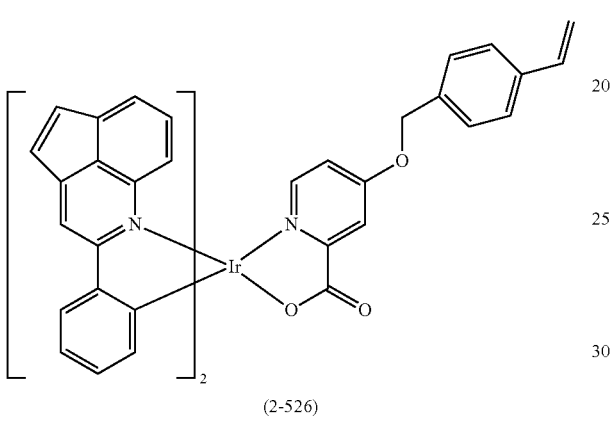
(2-526)
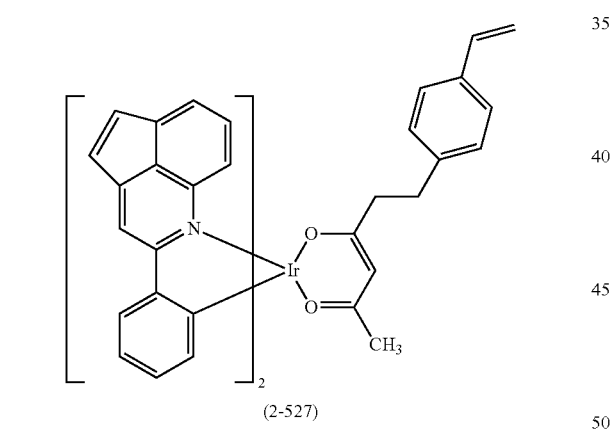
(2-527)
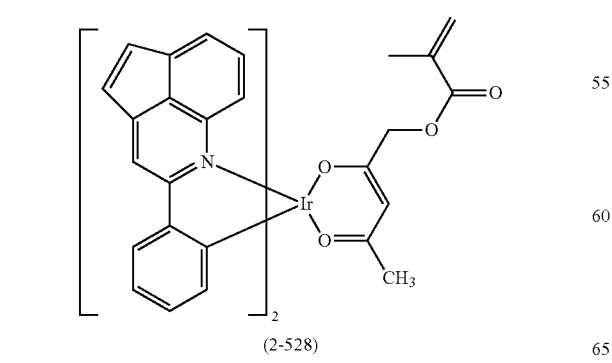
(2-528)
TABLE 24-continued
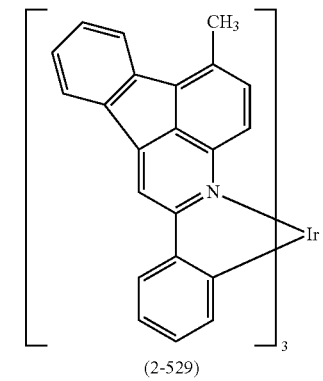
(2-529)
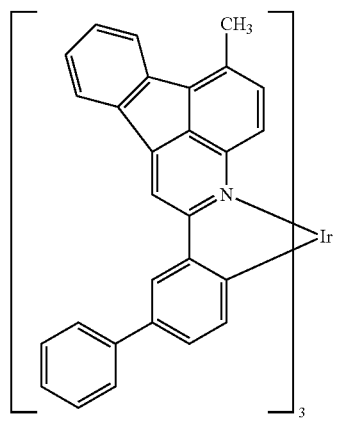
(2-530)
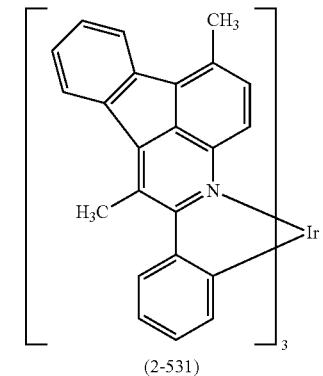
(2-531)
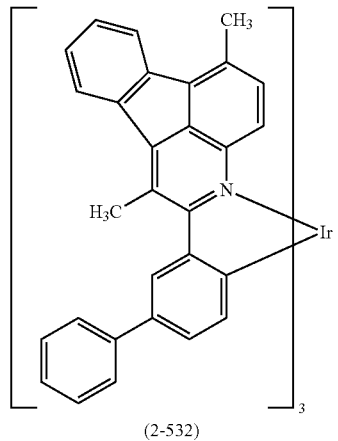
(2-532)

TABLE 24-continued
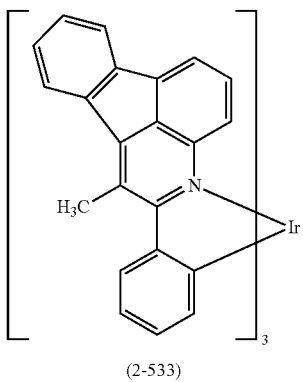
(2-533)
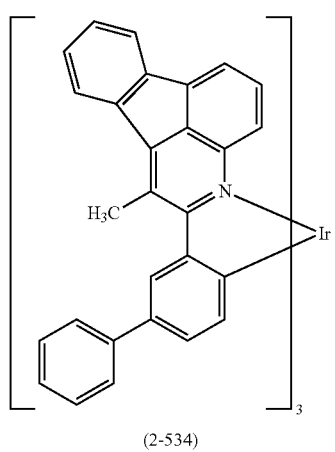
(2-534)
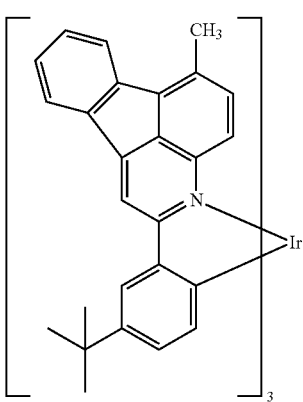
(2-535)
TABLE 24-continued
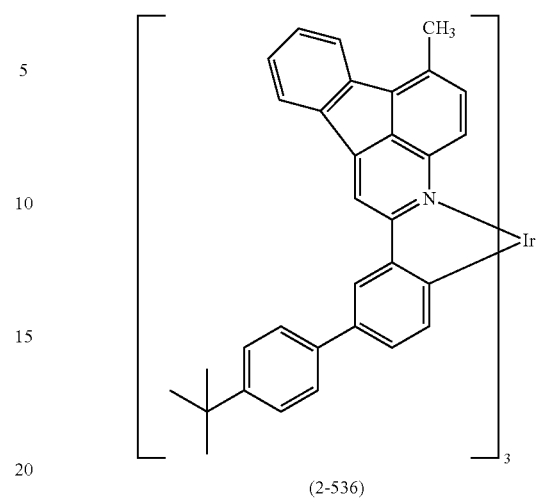
(2-536)
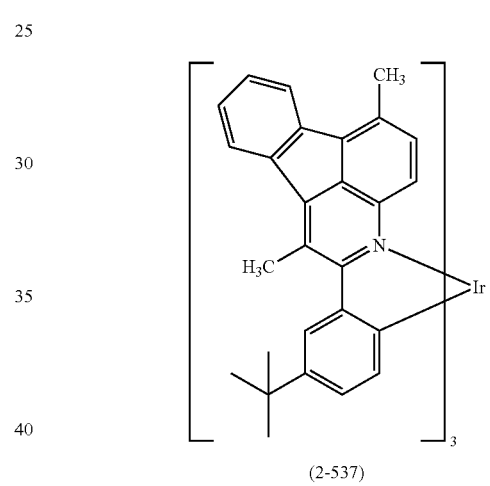
(2-537)
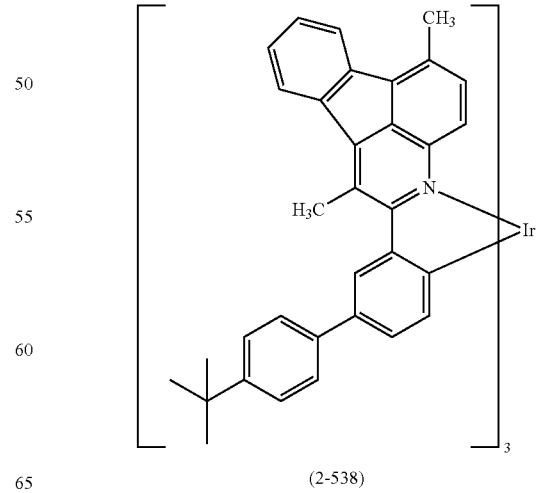
(2-538)

TABLE 24-continued
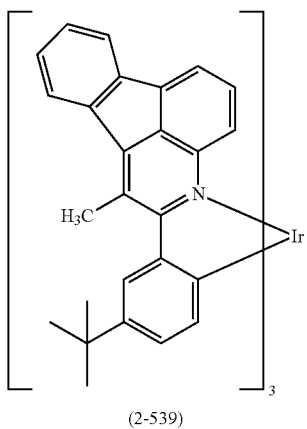
(2-539)
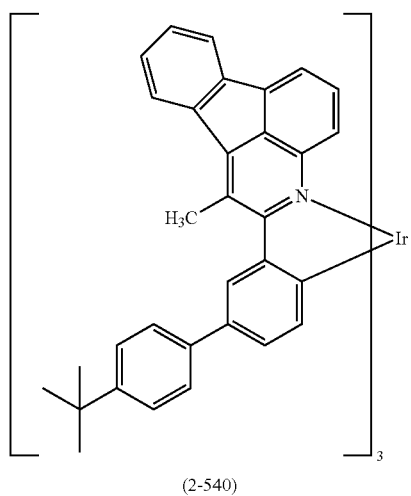
(2-540)
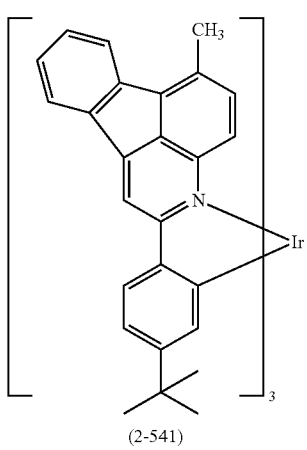
(2-541)
TABLE 24-continued
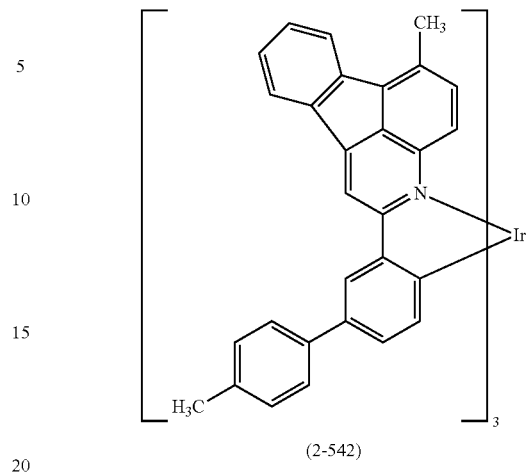
(2-542)
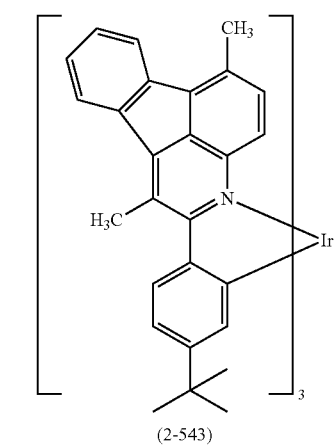
(2-543)
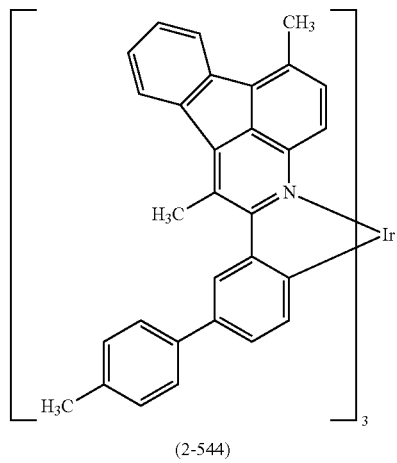
(2-544)

TABLE 24-continued
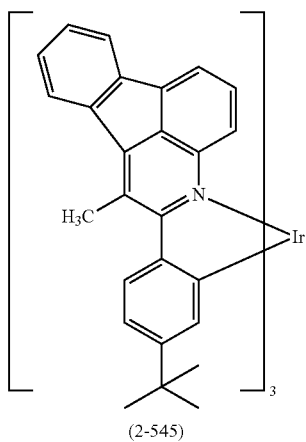
(2-545)
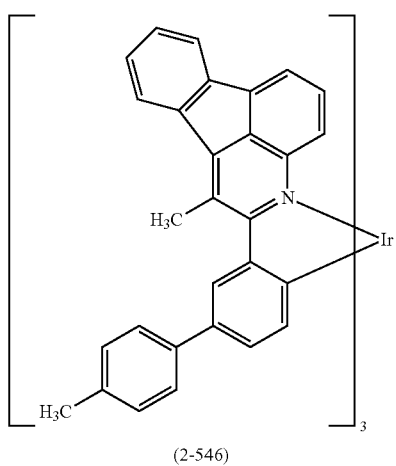
(2-546)
TABLE 25
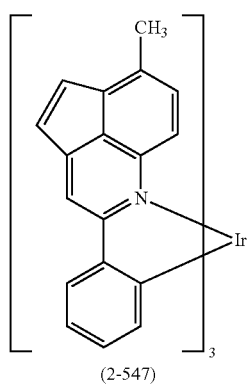
(2-547)
TABLE 25-continued
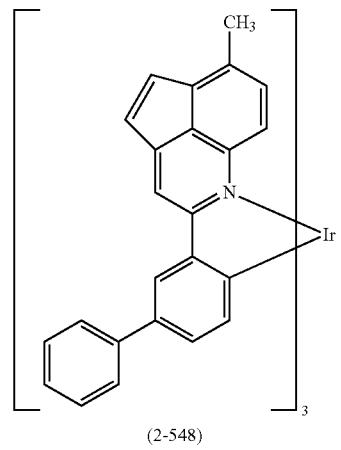
(2-548)
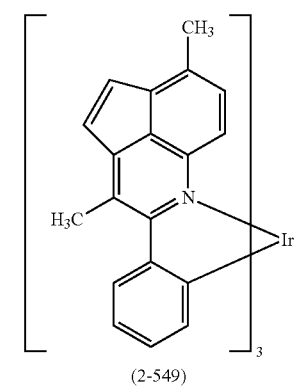
(2-549)
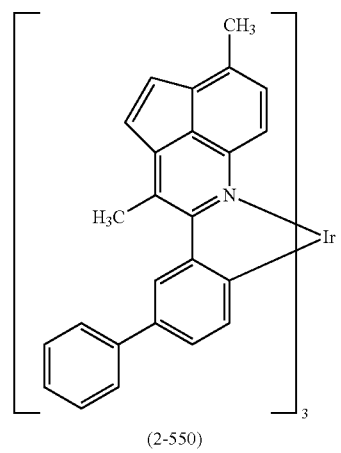
(2-550)
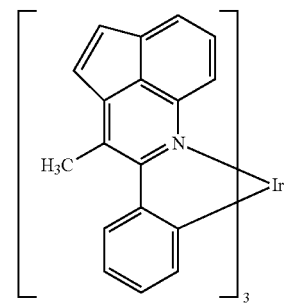
(2-551)

TABLE 25-continued
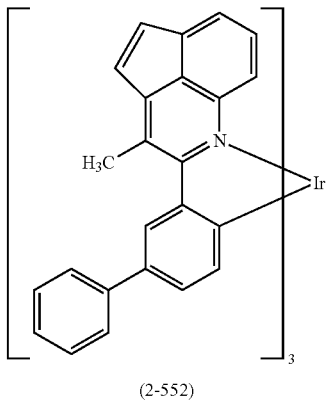
(2-552)
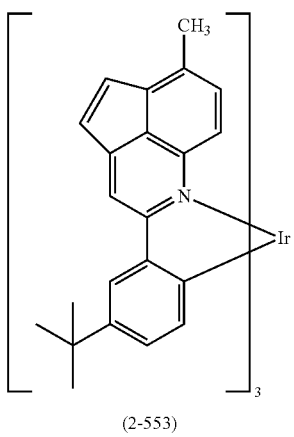
(2-553)
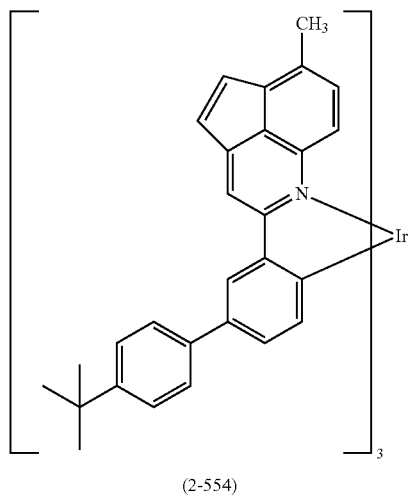
(2-554)
TABLE 25-continued
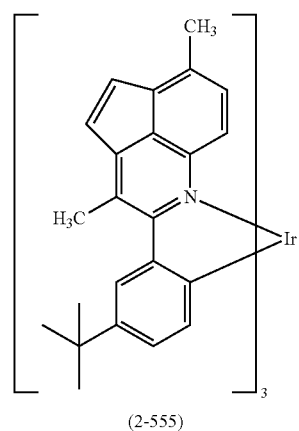
(2-555)
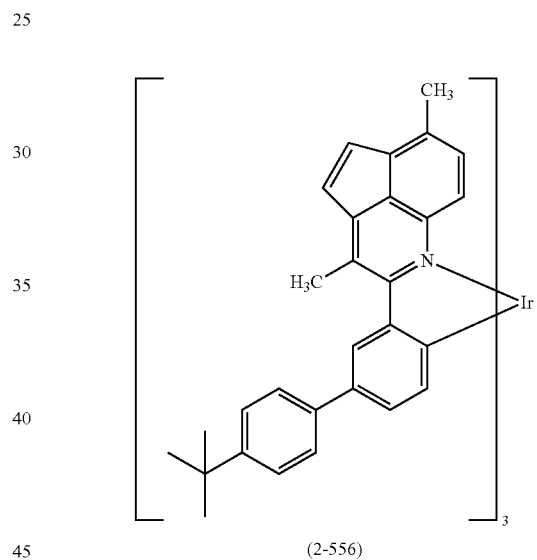
(2-556)
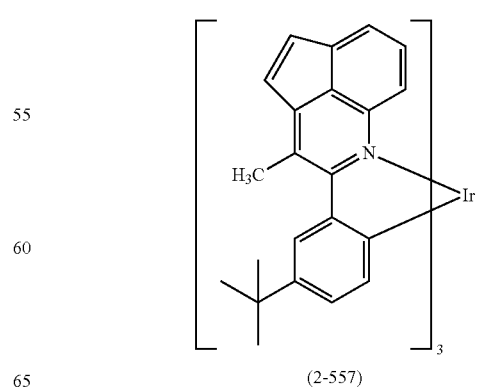
(2-557)

TABLE 25-continued
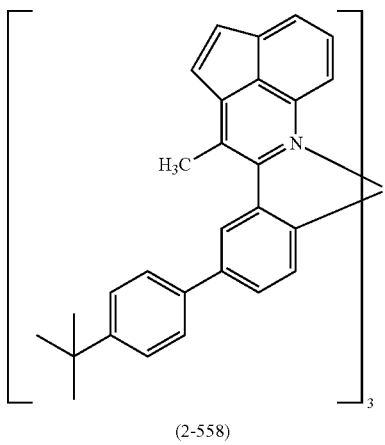
(2-558)
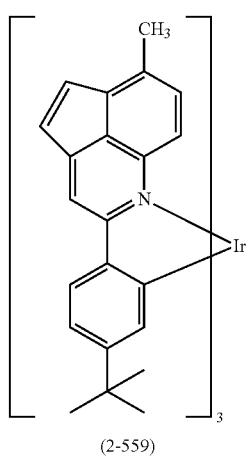
(2-559)
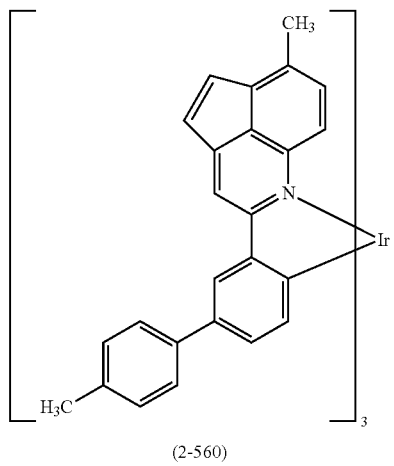
(2-560)
TABLE 25-continued
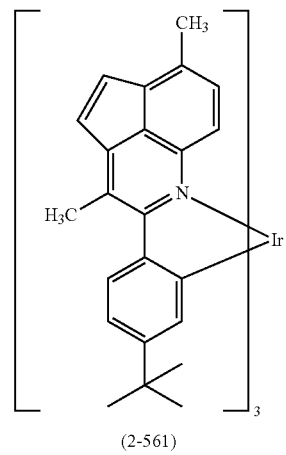
(2-561)
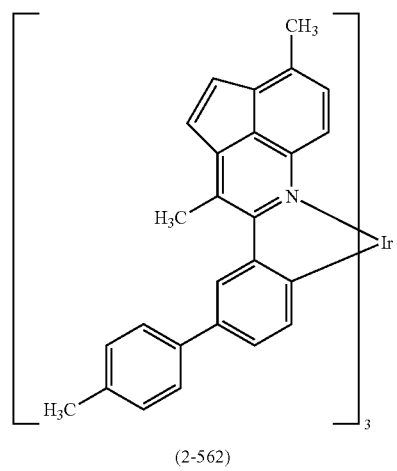
(2-562)
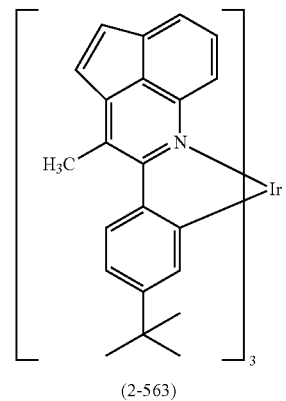
(2-563)

TABLE 25-continued
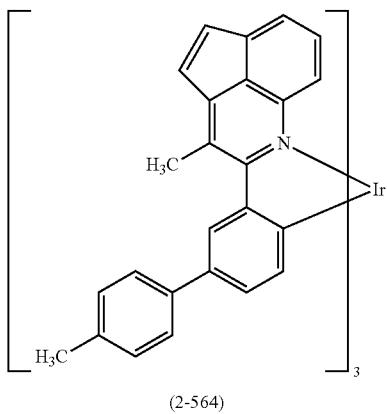
(2-564)
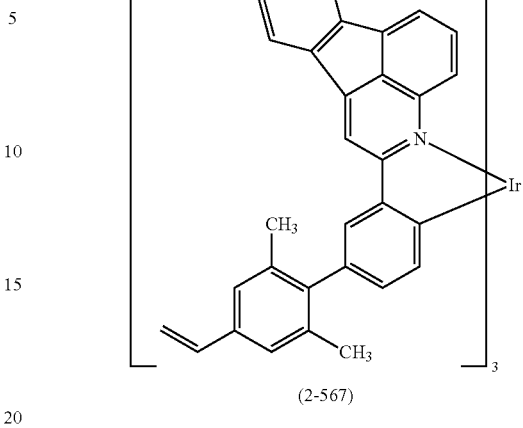
(2-567)
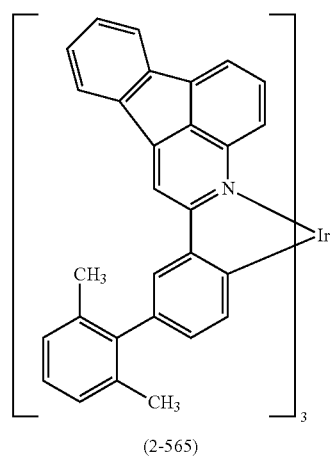
(2-565)
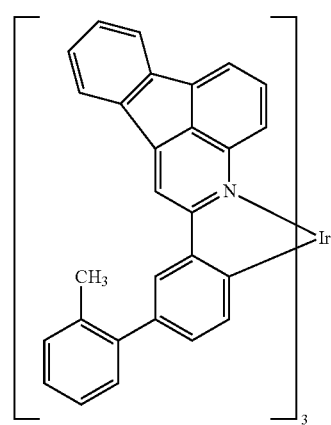
(2-568)
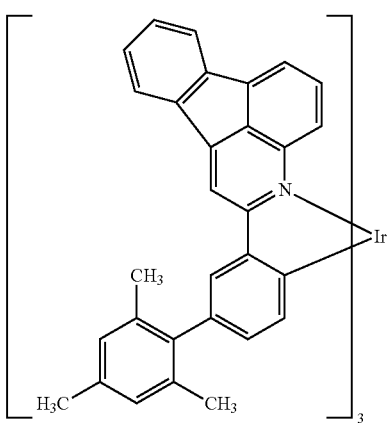
(2-566)
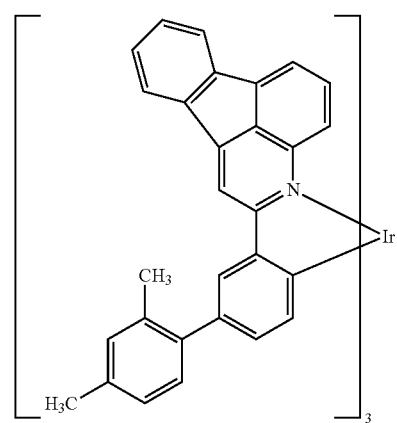
(2-569)

TABLE 25-continued
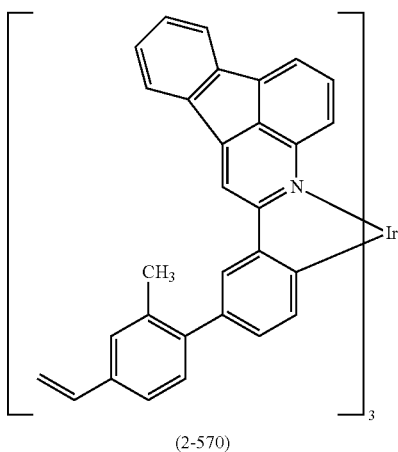
(2-570)
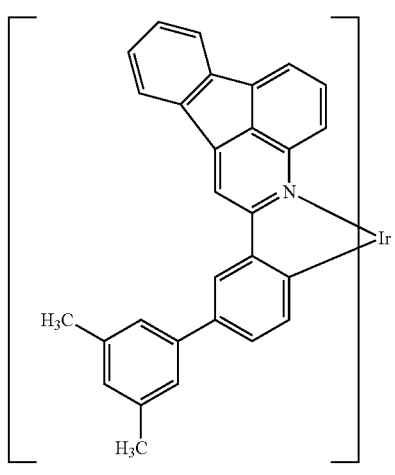
(2-571)
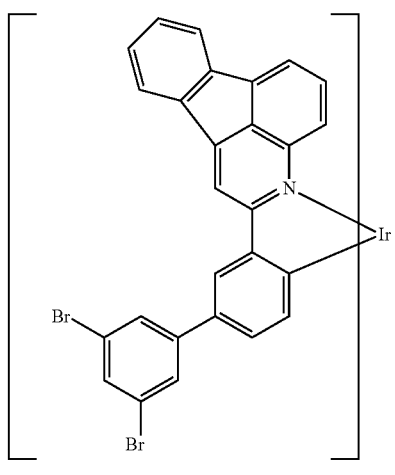
(2-572)
TABLE 25-continued
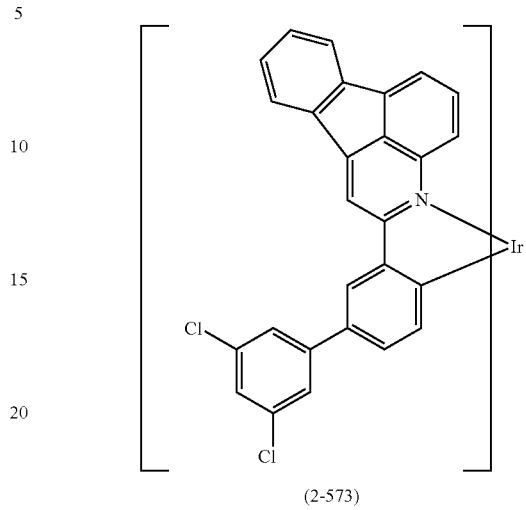
(2-573)
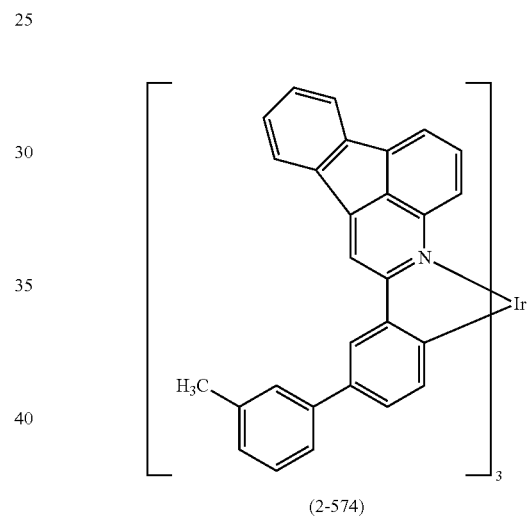
(2-574)
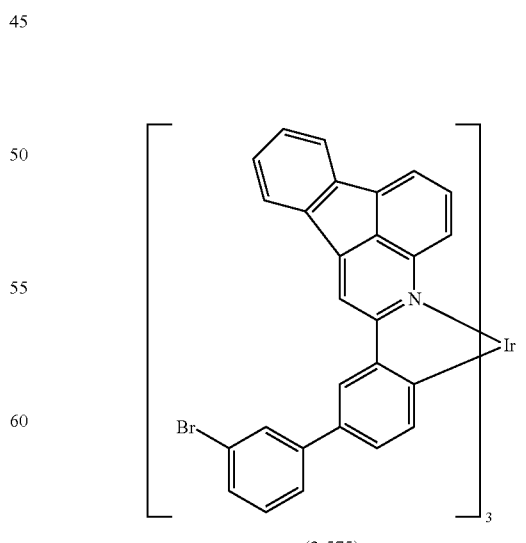
(2-575)

TABLE 25-continued
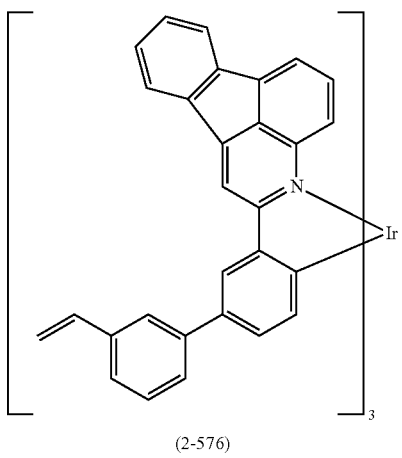
(2-576)
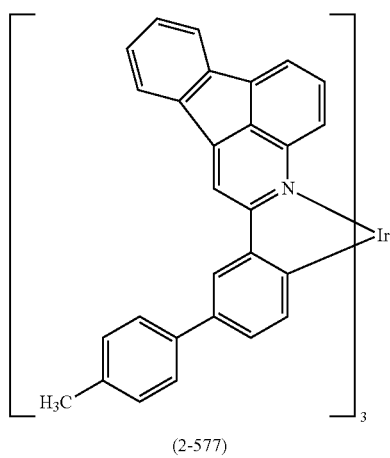
(2-577)
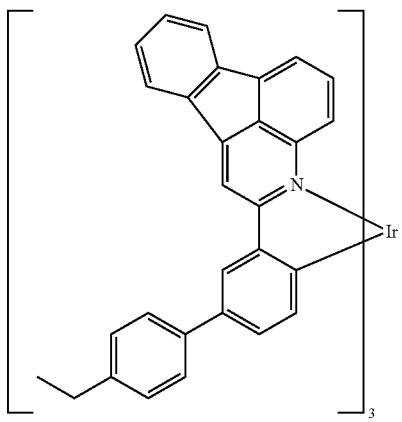
(2-578)
TABLE 25-continued
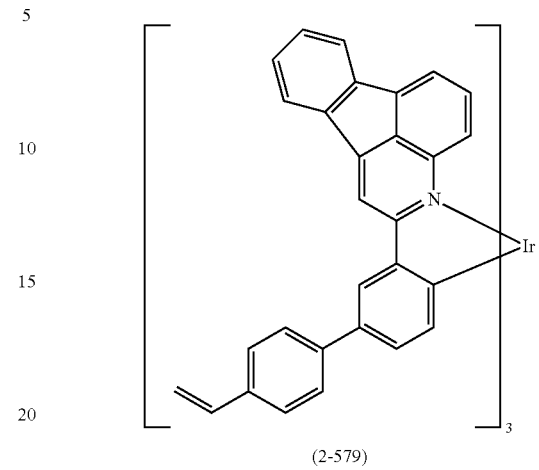
(2-579)
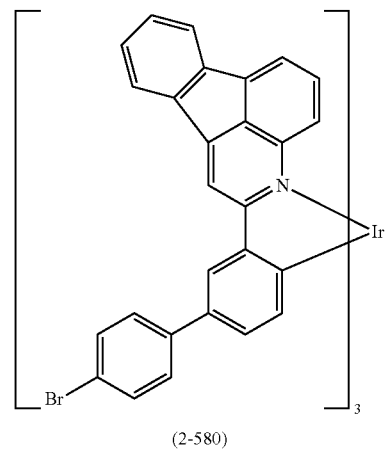
(2-580)
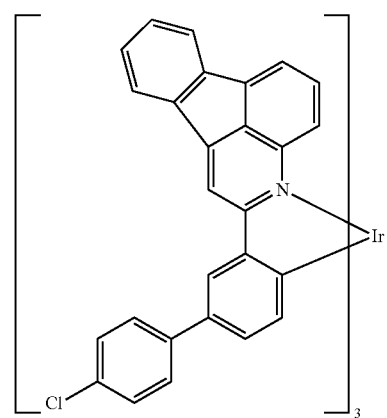
(2-581)

TABLE 25-continued
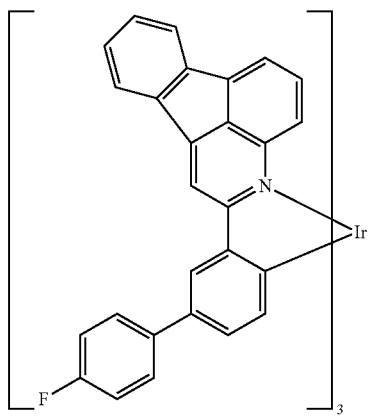
(2-582)
TABLE 26
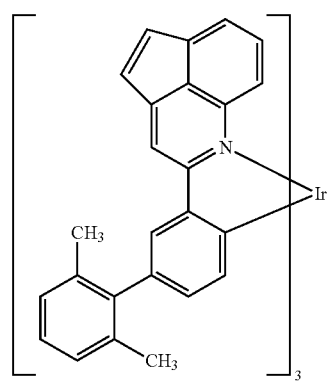
(2-583)
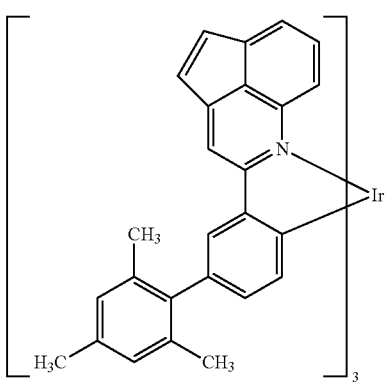
(2-584)
TABLE 26-continued
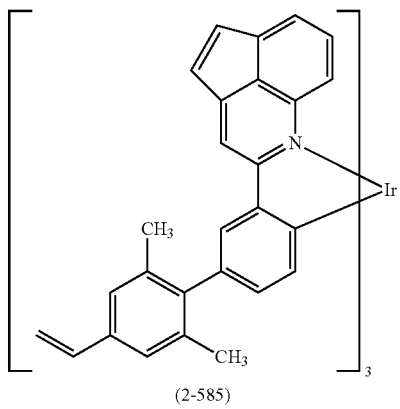
(2-585)
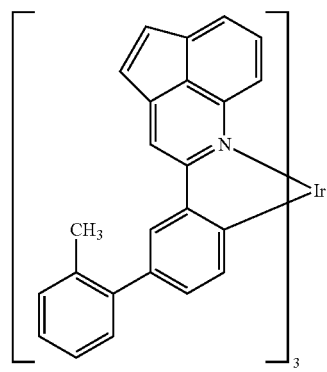
(2-586)
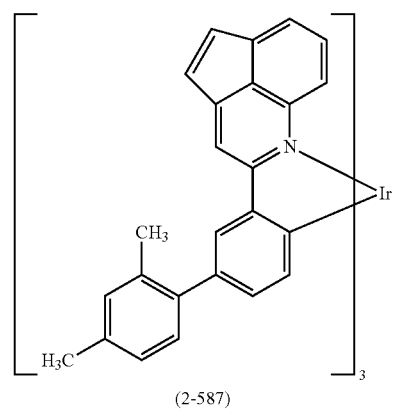
(2-587)
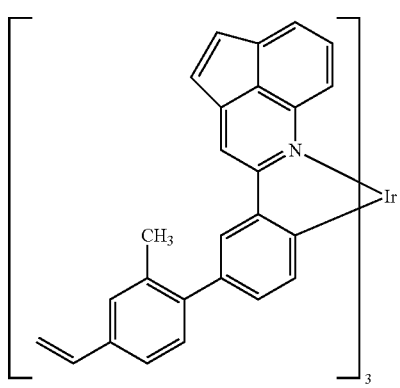
(2-588)

TABLE 26-continued
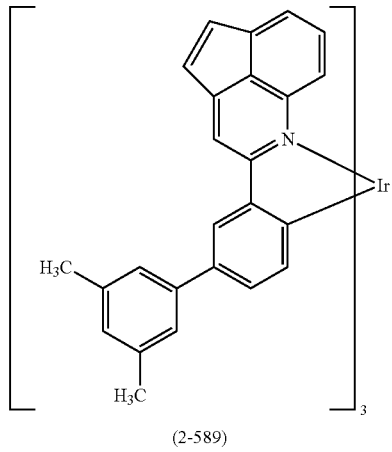
(2-589)
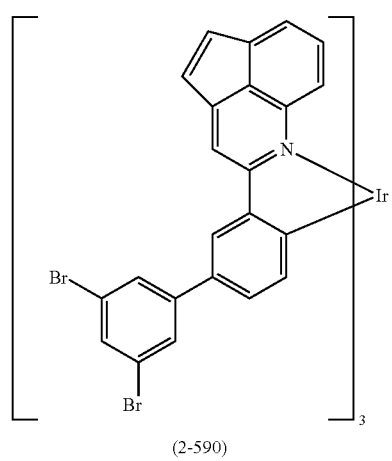
(2-590)
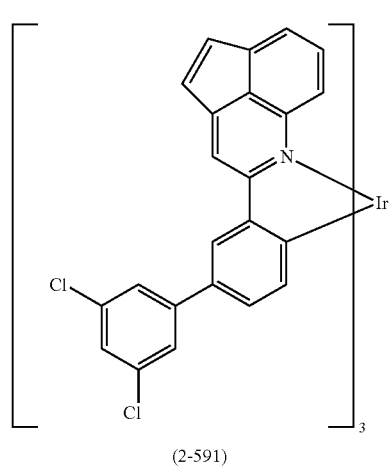
(2-591)
TABLE 26-continued
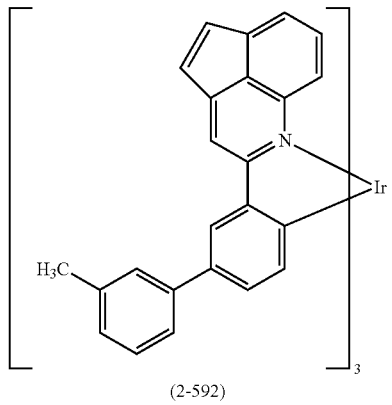
(2-592)
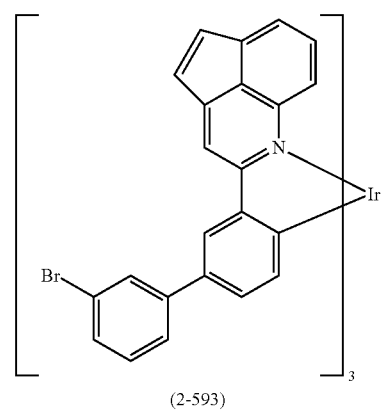
(2-593)
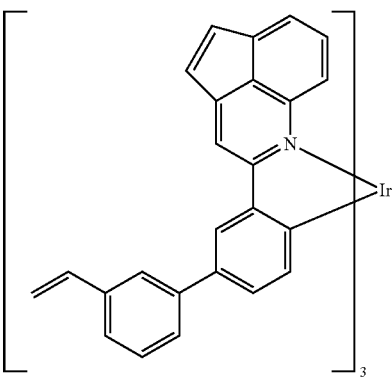
(2-594)
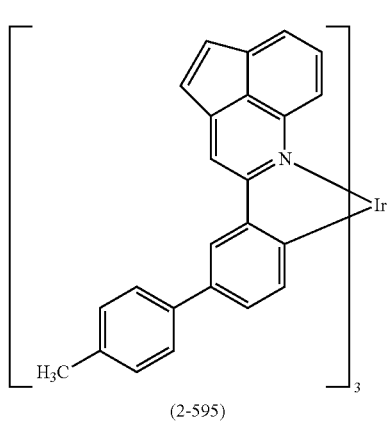
(2-595)

TABLE 26-continued
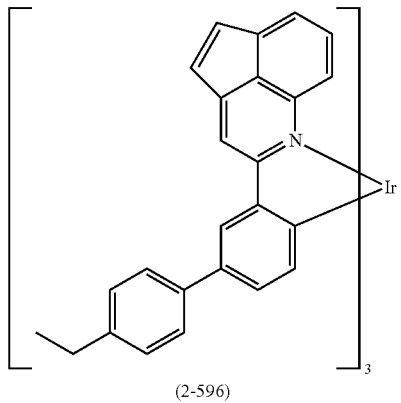
(2-596)
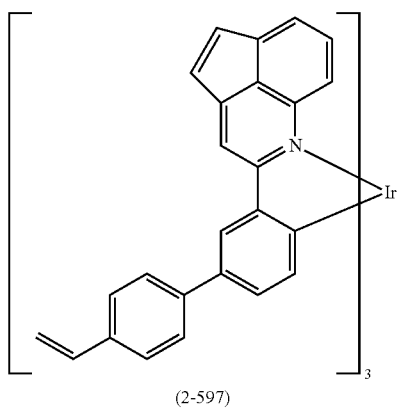
(2-597)
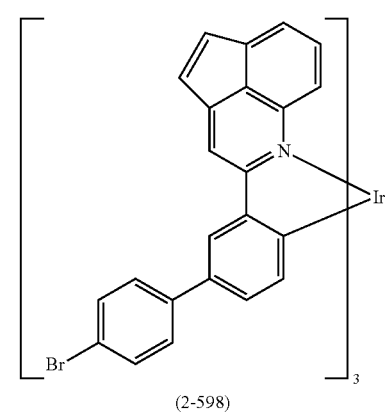
(2-598)
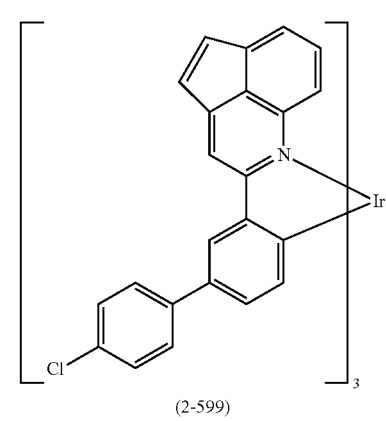
(2-599)
TABLE 26-continued
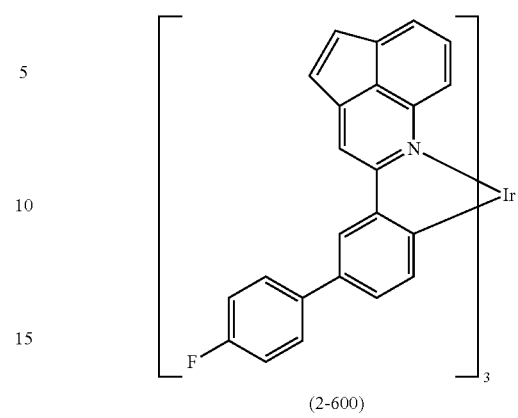
(2-600)
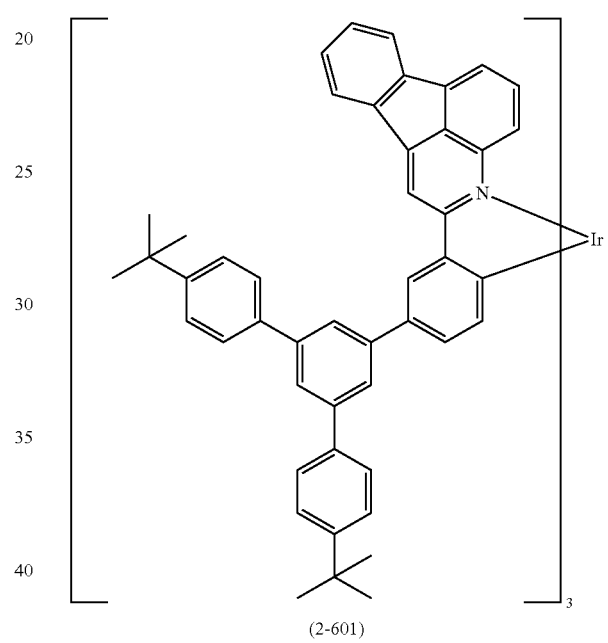
(2-601)
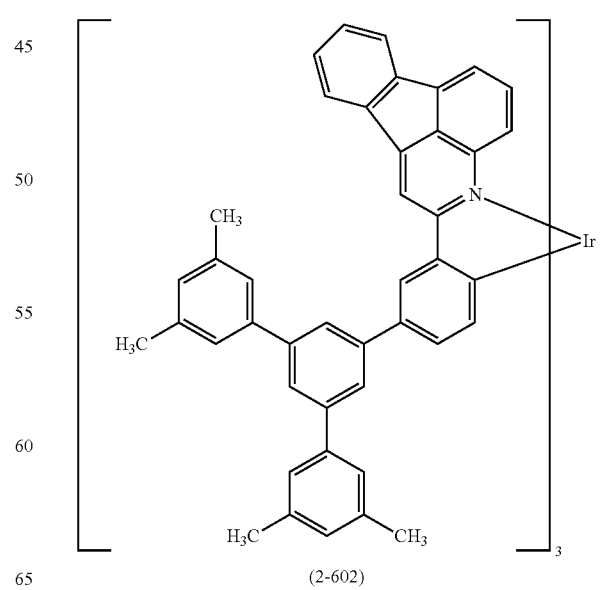
(2-602)

TABLE 26-continued
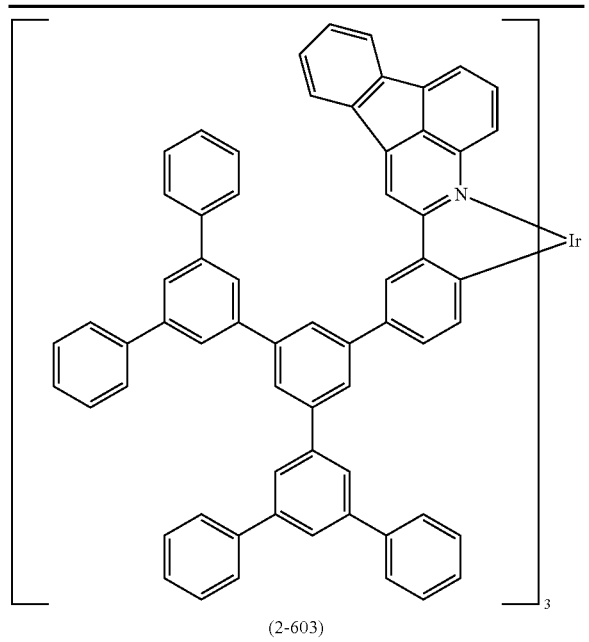
(2-603)
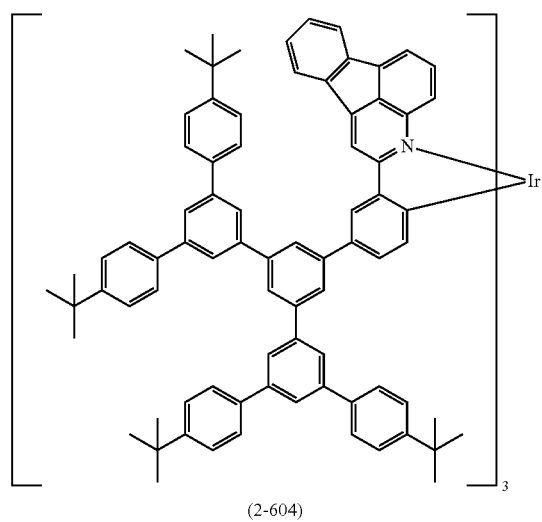
(2-604)
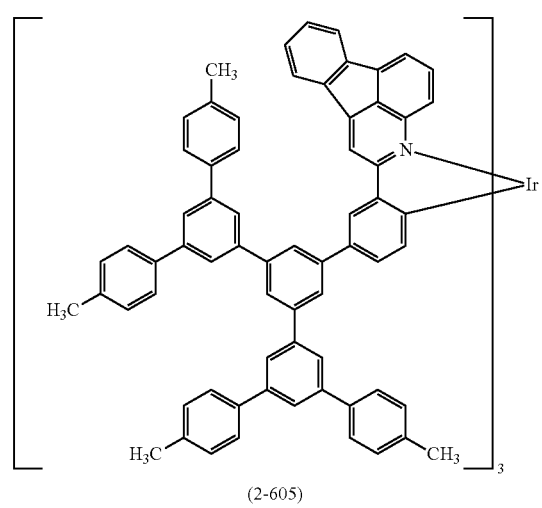
(2-605)
TABLE 27
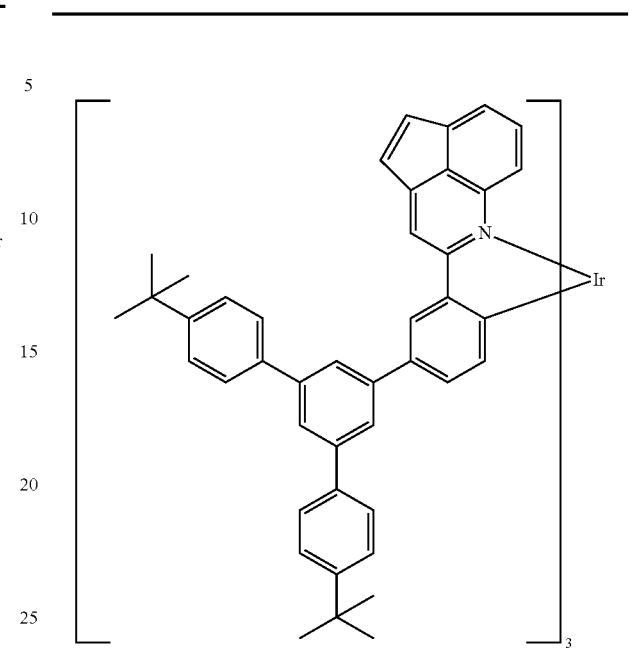
(2-606)
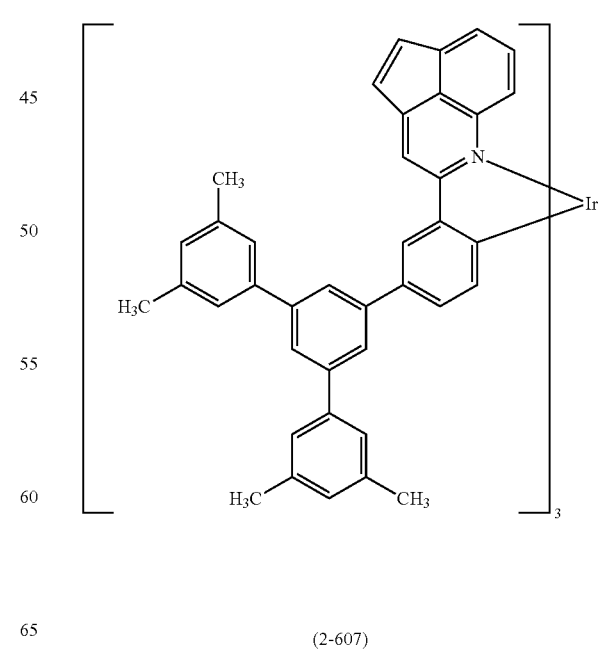
(2-607)

TABLE 27-continued
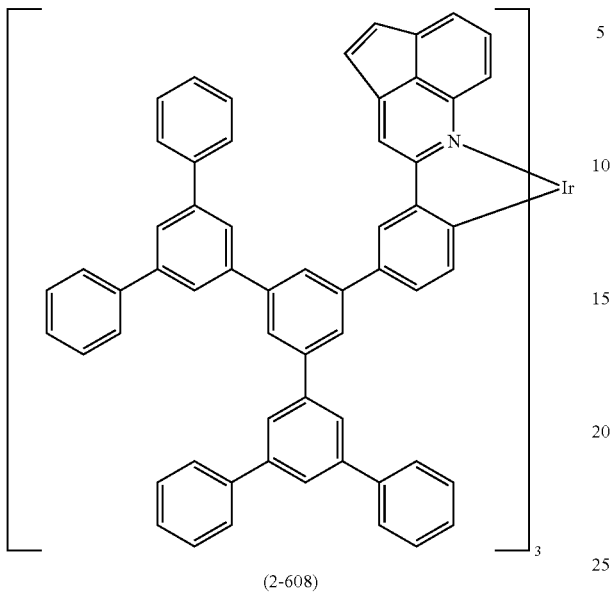
(2-608)
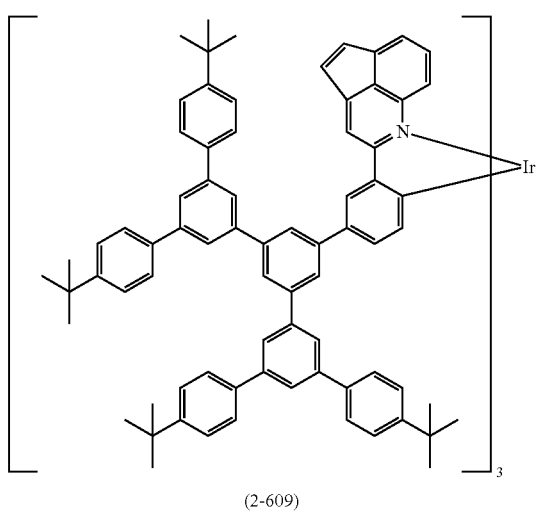
(2-609)
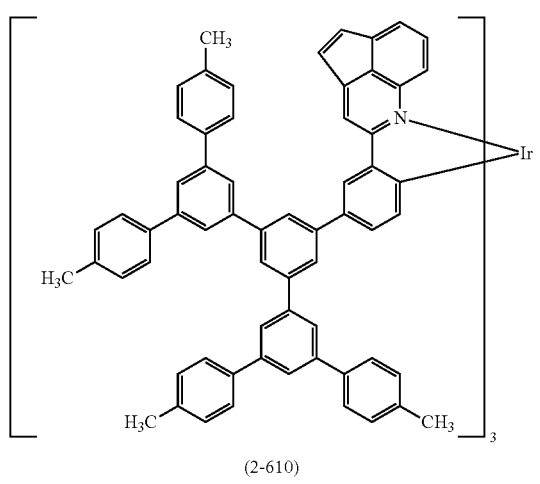
(2-610)
TABLE 27-continued
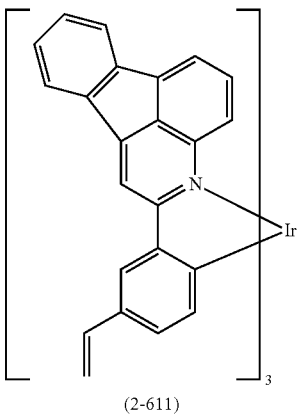
(2-611)
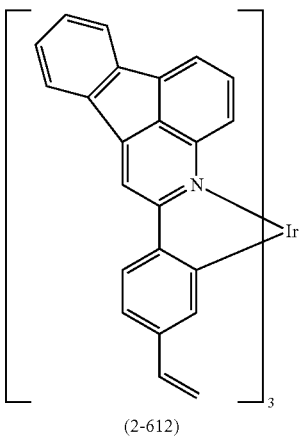
(2-612)
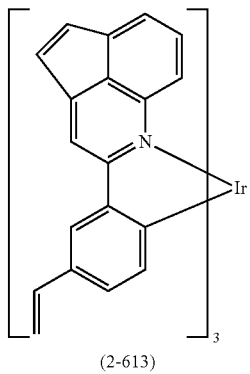
(2-613)
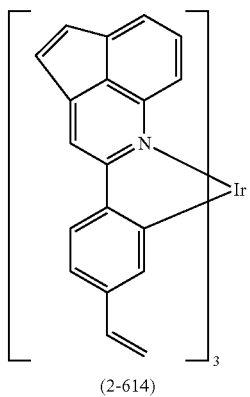
(2-614)

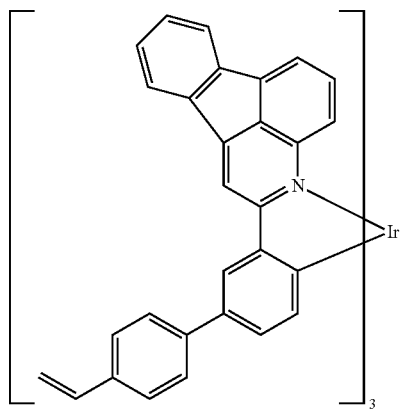
(2-615)
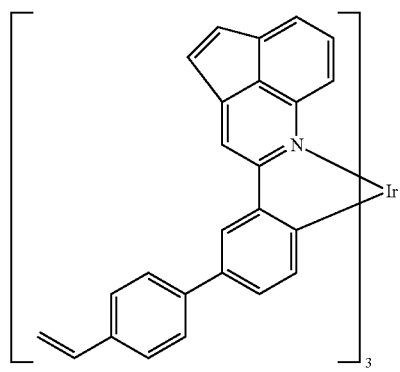
(2-616)
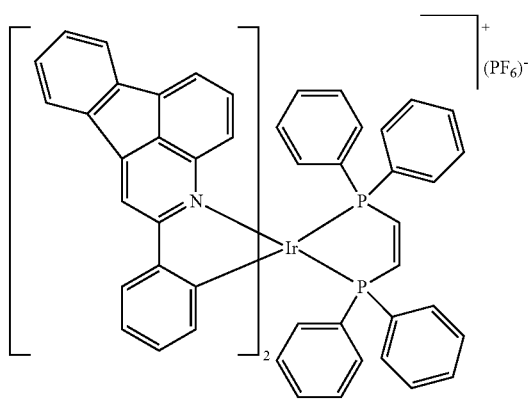
(2-617)
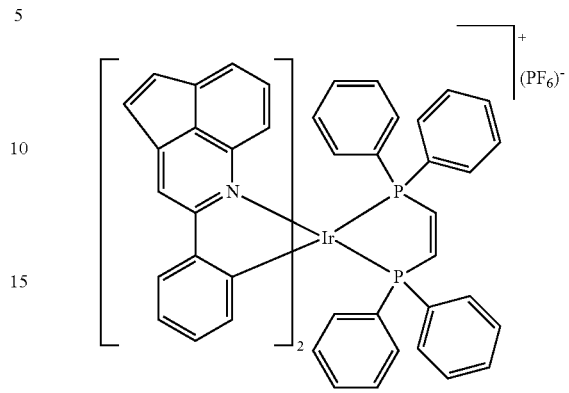
(2-618)
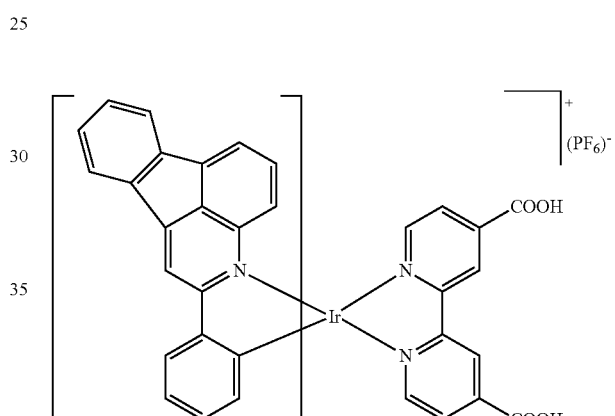
(2-619)
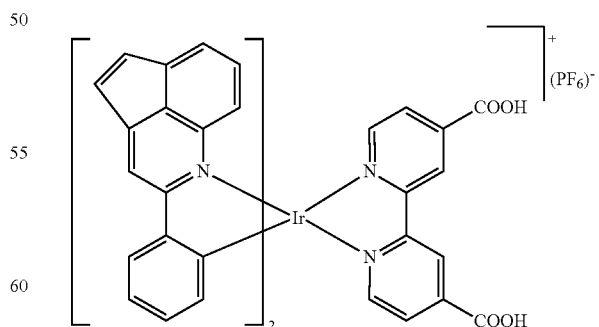
(2-620)

TABLE 28
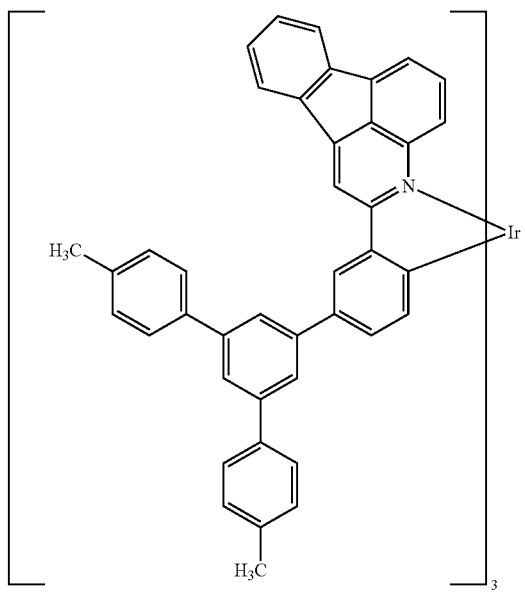
(2-621)
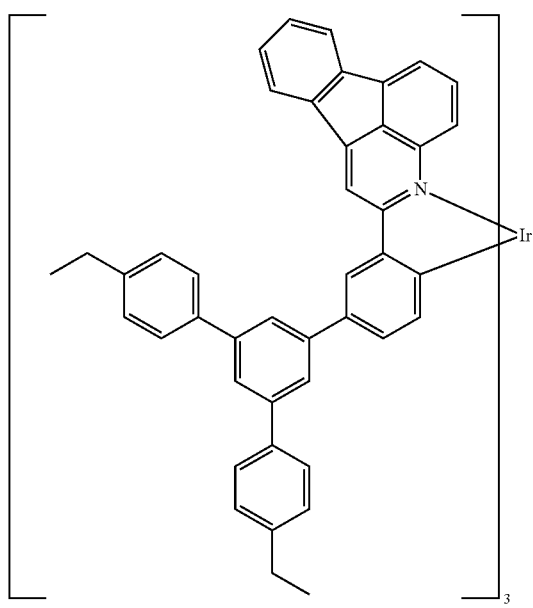
(2-622)

TABLE 28-continued
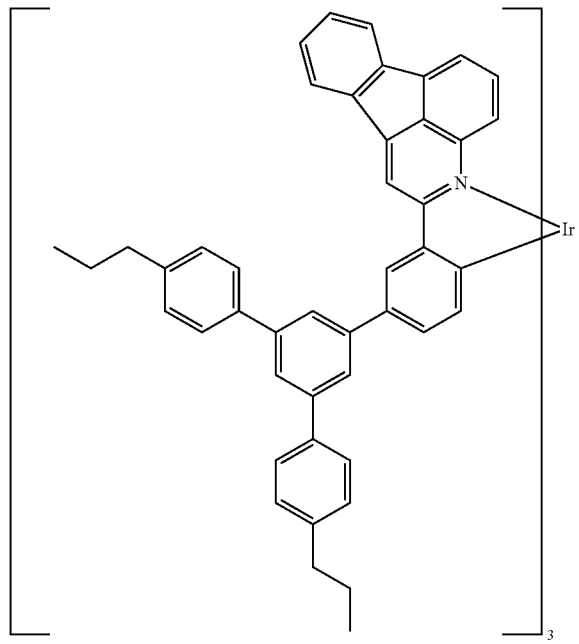
(2-623)
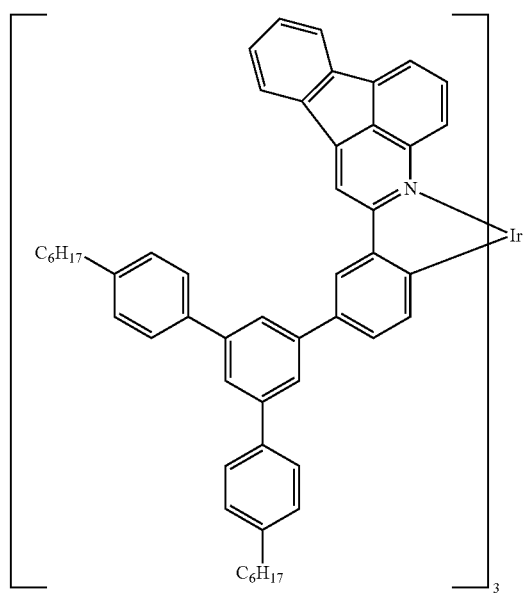
(2-624)

TABLE 28-continued
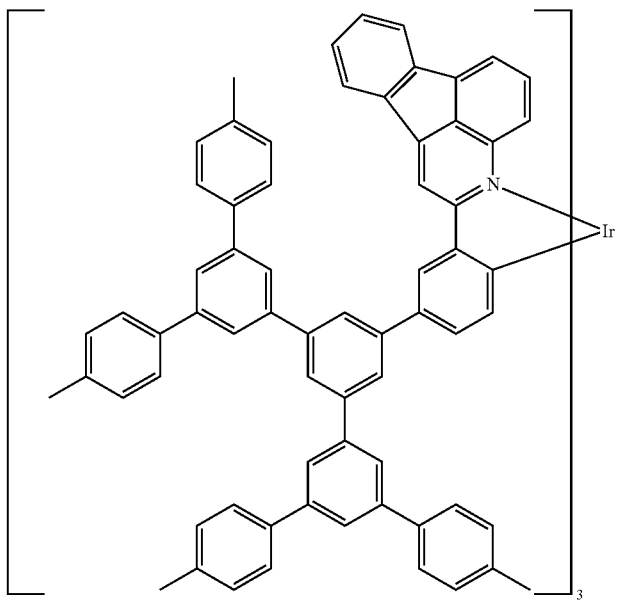
(2-625)
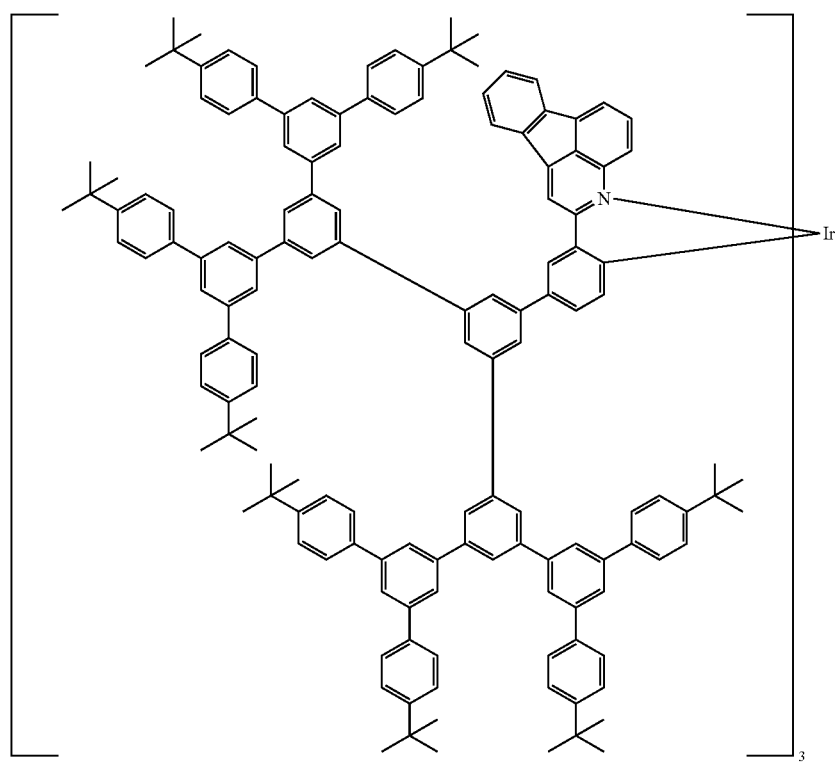
(2-626)

TABLE 28-continued
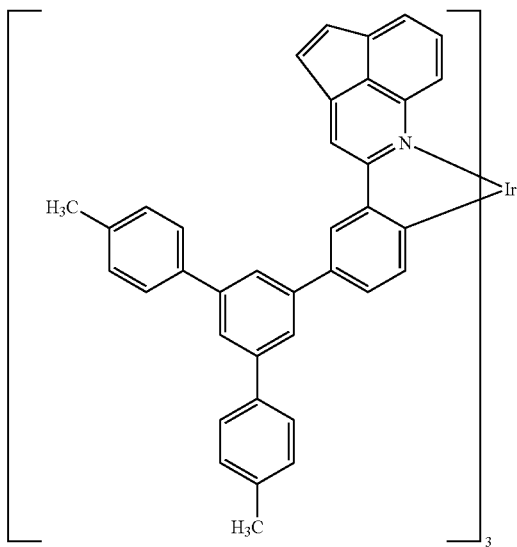
(2-627)
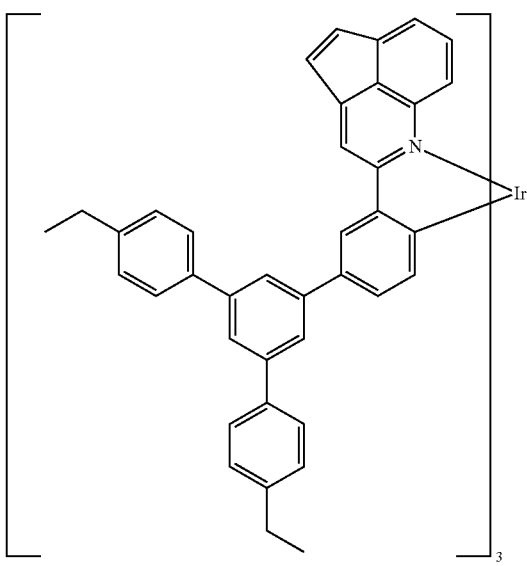
(2-628)

TABLE 28-continued
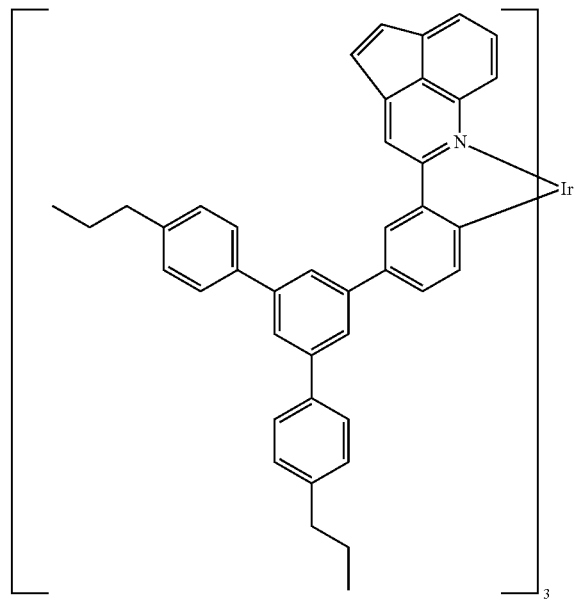
(2-629)
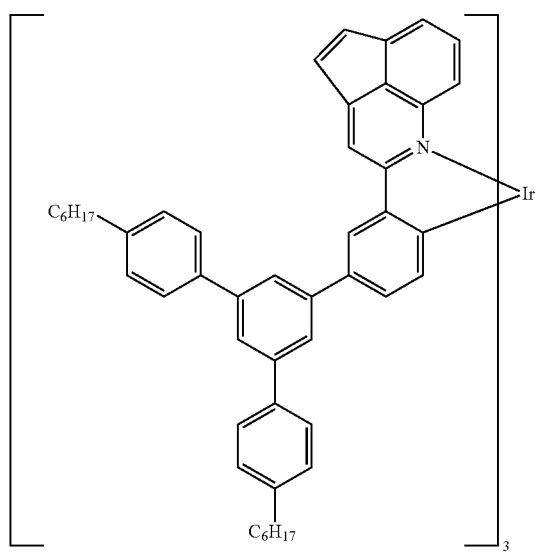
(2-630)

TABLE 28-continued

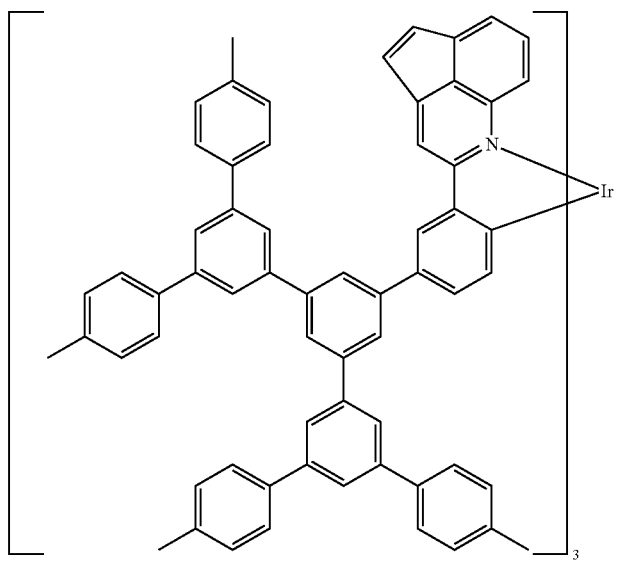

(2-631)

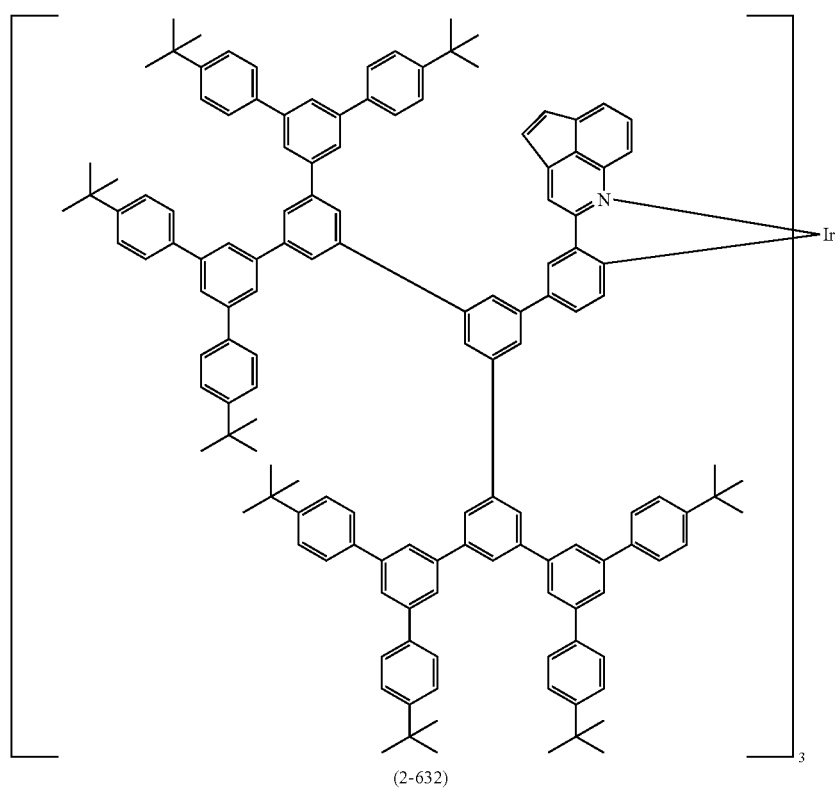

(2-632)

EXAMPLES

The present invention will be described in more detail based on the following examples, but the invention is not intended to be limited thereto. Hereinafter, methods of preparing the compounds of the present invention will be described.

Example 1

Synthesis of Compound (3-43) of the Present Invention

In a round-bottomed flask, 9.0 mmol of acetophenone, 3.0 mmol of 1-amino-9-fluorenone (manufactured by Aldrich), and 1.5 mmol of diphenyl phosphate were placed, and the resultant mixture was irradiated with microwave (2,450 MHz) for 10 minutes under argon atmosphere. The reaction solution was cooled to room temperature, concentrated, and then separated and purified by silica gel column chromatography (eluant: dichloromethane and methanol), to give 2-phenylindeno[1,2,3-de]quinoline. The isolation yield was 45%.

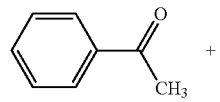

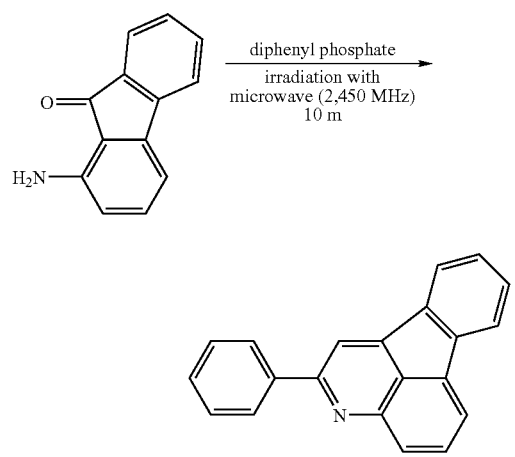

$^1$H-NMR (in CDCl$_3$) δ 8.23 (s, 1H), 8.20 (d, 2H), 8.05 (d, 1H), 7.99 (d, 1H), 7.89 (d, 1H), 7.85 (d, 1H), 7.77 (t, 1H), 7.55-7.59 (m, 2H), 7.47-7.52 (m, 2H), 7.42 (t, 1H).

In a two-necked flask, 1.76×10$^{-1}$ mmol of iridium trichloride trihydrate, 5.63×10$^{-1}$ mmol of 2-phenylindeno[1,2,3-de]quinoline, 10 ml of 2-ethoxyethanol, and 3 ml of water were placed, and the resultant mixture was heated under reflux under argon atmosphere for 15 hours. The reaction solution was cooled to room temperature, concentrated under reduced pressure, and precipitated by addition of water, and the thus-formed dark brown solid was collected by filtration. The dark brown solid was washed with water, to give a target iridium complex (3-43). The isolation yield was 94%.

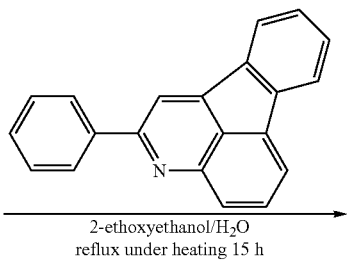

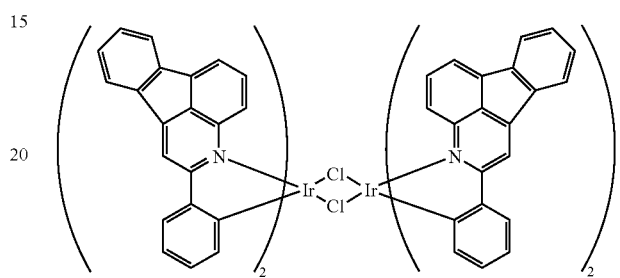

$^1$H-NMR (in CDCl$_3$) δ 8.35 (d, 4H), 8.25 (s, 4H), 8.08 (d, 4H), 7.78 (d, 4H), 7.60 (t, 4H), 7.54 (t, 4H), 7.47 (d, 4H), 6.77 (t, 4H), 6.62 (t, 4H), 6.52 (d, 4H), 6.28 (t, 4H), 5.88 (d, 4H).

Example 2

Synthesis of Compound (2-127) of the Present Invention

In a round-bottomed flask, 1.27×10$^{-2}$ mmol of the compound (3-43) of the present invention, 3.82×10$^{-2}$ mmol of acetylacetonatosodium, and 10 ml of 2-ethoxyethanol were placed, and the resultant mixture was irradiated with microwave (2,450 MHz) under argon atmosphere for 15 minutes. The reaction solution was cooled to room temperature, concentrated under reduced pressure to remove the solvent, to give a black brown solid. The black brown solid was recrystallized from dichloromethane-hexane, to give a target iridium complex (2-127). The isolation yield was 73%.

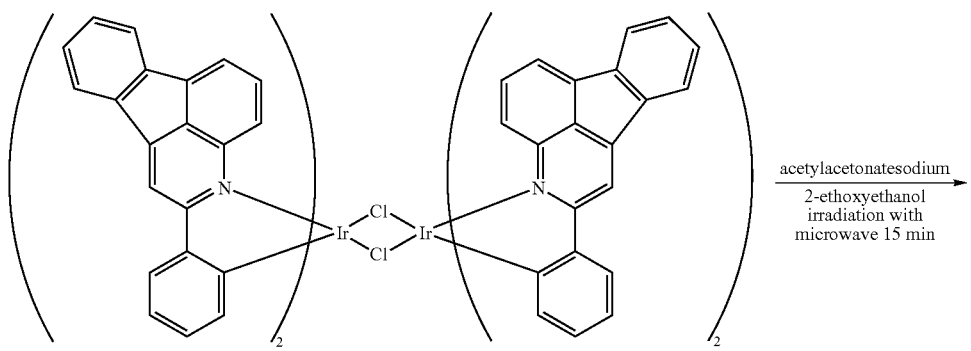

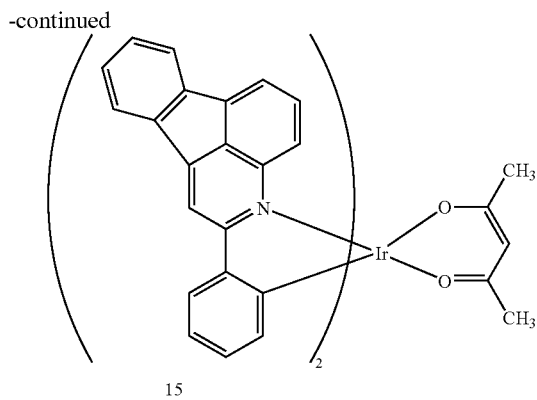

$^1$H-NMR (in CD$_2$Cl$_2$) δ 8.55 (s, 2H), 8.16 (d, 2H), 8.13 (d, 2H), 8.03 (d, 2H), 7.93 (d, 2H), 7.85 (d, 2H), 7.48-7.59 (m, 6H), 7.00 (t, 2H), 6.63 (t, 2H), 6.51 (d, 2H), 4.90 (s, 1H), 1.63 (s, 6H).

Example 3

Synthesis of Compound (2-211) of the Present Invention

In a round-bottomed flask, 6.42×10$^{-3}$ mmol of the compound (3-43) of the present invention, 1.65×10$^{-2}$ mmol of sodium picolinate, and 10 ml of 2-ethoxyethanol were placed, the resultant mixture was irradiated with microwave (2,450 MHz) under argon atmosphere for 15 minutes. The reaction solution was cooled to room temperature, concentrated under reduced pressure to remove the solvent, to give a black brown solid. The black brown solid was recrystallized from dichloromethane-hexane, to give a target iridium complex (2-211). The isolation yield was 45%.

$^1$H-NMR (in CD$_2$Cl$_2$) δ 8.71 (s, 1H), 8.70 (s, 1H), 8.60 (d, 1H), 8.29 (d, 1H), 8.16-8.23 (m, 3H), 8.07 (d, 1H), 7.97-8.00 (m, 3H), 7.89 (d, 1H), 7.82 (t, 1H), 7.78 (d, 1H), 7.70 (dd, 1H), 7.57-7.64 (m, 4H), 7.42 (dd, 1H), 7.24 (t, 1H), 7.14-7.18 (m, 2H), 6.94 (d, 1H), 6.88 (t, 1H), 6.84 (d, 1H), 6.79 (t, 1H), 6.40 (d, 1H).

Example 4

Synthesis of Compound (2-295) of the Present Invention

In a round-bottomed flask, 1.27×10$^{-2}$ mmol of the compound (3-43) of the present invention, 3.82×10$^{-2}$ mmol of pyridine-2-sulfonic acid, 1.27×10$^{-1}$ mmol of sodium carbonate, and 10 ml of 2-ethoxyethanol were placed, the resultant mixture was irradiated with microwave (2,450 MHz) under argon atmosphere for 15 minutes. The reaction solution was cooled to room temperature and concentrated under reduced pressure to remove the solvent, to give a brown solid. The brown solid was recrystallized from dichloromethane-hexane, to give a target iridium complex (2-295). The isolation yield was 60%.

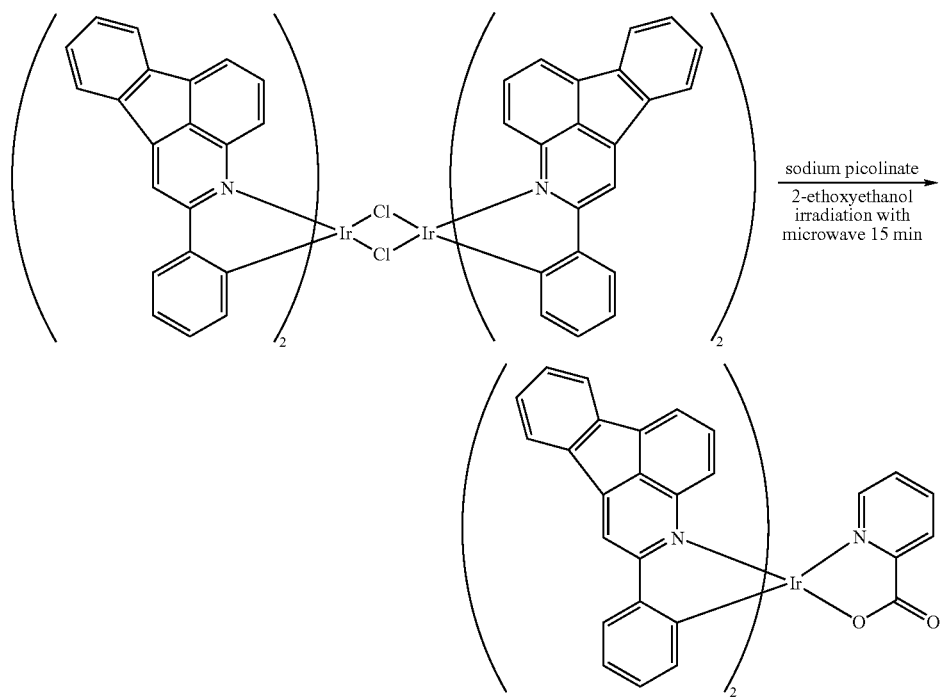

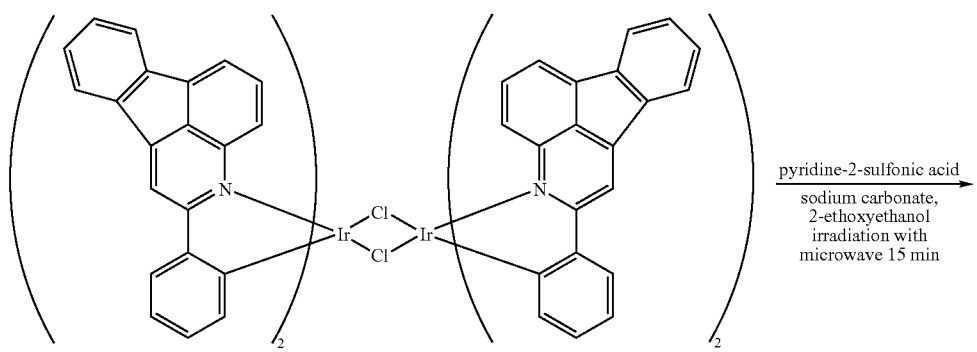

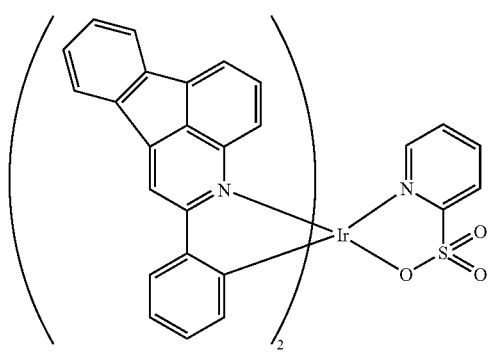

¹H-NMR (in CD$_2$Cl$_2$) δ 8.83 (d, 1H), 8.64 (s, 1H), 8.57 (s, 1H), 8.17 (d, 1H), 8.11 (t, 2H), 8.04 (d, 1H), 7.94 (d, 1H), 7.87-7.90 (m, 2H), 7.77-7.82 (m, 2H), 7.68-7.72 (m, 2H), 7.63 (dd, 1H), 7.48-7.55 (m, 4H), 7.27 (dd, 1H), 7.05-7.14 (m, 3H), 6.74-6.78 (m, 3H), 6.69 (t, 1H), 6.20 (d, 1H).

Example 5

Synthesis of Compound (2-411) of the Present Invention

In a round-bottomed flask, 6.54×10⁻³ mmol of the compound (3-43) of the present invention, 1.64×10⁻² mmol of 2,2'-dipyridylamine, and 10 ml of 2-ethoxyethanol were placed, the resultant mixture was irradiated with microwave (2,450 MHz) under argon atmosphere for 15 minutes. The reaction solution was cooled to room temperature, concentrated under reduced pressure to remove the solvent, and precipitated by addition of saturated aqueous NH$_4$PF$_6$ solution, and the red brown solid thus obtained was recrystallized from dichloromethane-hexane. Analysis by proton NMR and electrospray ionization mass spectrometry (ESI-MS) showed that the compound obtained was a target iridium complex (2-411), and the isolation yield was 78%.

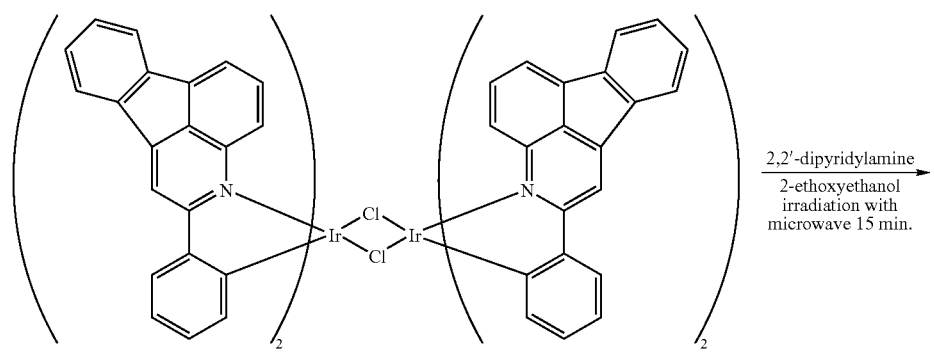

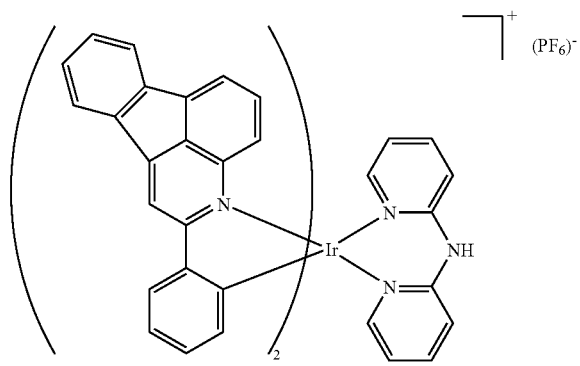

¹H-NMR (in CD$_2$Cl$_2$) δ 8.42 (s, 2H), 8.12 (brs, 1H), 8.01 (d, 2H), 7.92 (d, 2H), 7.83 (d, 2H), 7.71 (d, 2H), 7.54 (m, 2H), 7.49 (t, 2H), 7.43 (t, 2H), 7.25 (d, 2H), 7.14-7.19 (m, 4H), 7.00 (t, 2H), 6.91 (d, 2H), 6.71 (t, 2H), 6.52 (t, 2H), 6.40 (d, 2H). ESI-MS (m/z): 921

Example 6

Synthesis of Compound (2-410) of the Present Invention

In a round-bottomed flask, $6.42 \times 10^{-3}$ mmol of the compound (3-43) of the present invention, $1.66 \times 10^{-2}$ mmol of 2,2'-bipyridine, and 10 ml of 2-ethoxyethanol were placed, and the resultant mixture was irradiated with microwave (2,450 MHz) under argon atmosphere for 15 minutes. The reaction solution was cooled to room temperature, concentrated under reduced pressure to remove the solvent, and precipitated by addition of saturated aqueous NH$_4$PF$_6$ solution, to give a red brown solid. The red brown solid was recrystallized from dichloromethane-hexane. Analysis by proton NMR and electrospray ionization mass spectrometry (ESI-MS) showed that the compound obtained was a target iridium complex (2-410). The isolation yield was 59%.

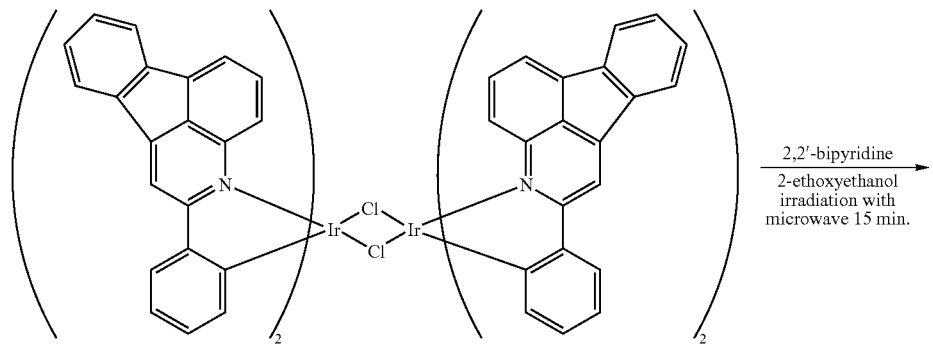

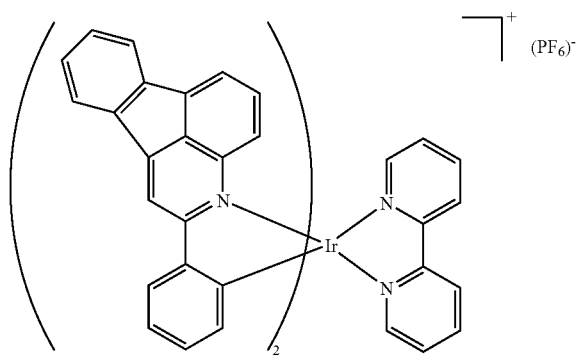

$^1$H-NMR (in CDCl$_3$) δ 8.56 (s, 2H), 8.45 (d, 2H), 8.16 (d, 2H), 8.12 (d, 2H), 8.02-8.06 (m, 4H), 7.81 (d, 2H), 7.66 (d, 2H), 7.51 (t, 2H), 7.46 (t, 2H), 7.39 (t, 2H), 7.18 (t, 2H), 7.11 (dd, 2H), 6.82 (t, 2H), 6.62 (d, 2H), 6.49 (d, 2H).

ESI-MS (m/z): 906

Example 7

Synthesis of Compound (2-413) of the Present Invention

In a round-bottomed flask, $1.28 \times 10^{-2}$ mmol of the compound (3-43) of the present invention, $3.87 \times 10^{-2}$ mmol of 1,2-bisdiphenylphosphino benzene, and 10 ml of 2-ethoxyethanol were placed, the resultant mixture was irradiated with microwave (2,450 MHz) under argon atmosphere for 15 minutes. The reaction solution was cooled to room temperature, concentrated under reduced pressure to remove the solvent, precipitated by addition of saturated aqueous NH$_4$PF$_6$ solution, and the brown solid thus obtained was recrystallized from dichloromethane-hexane. Analysis by electrospray ionization mass spectrometry (ESI-MS) identified the parent ion peak (m/z=1196) of the target iridium complex (2-413). The isolation yield was 50%.

Example 8

Synthesis of Compound (2-412) of the Present Invention

In a round-bottomed flask, $1.28 \times 10^{-2}$ mmol of the compound (3-43) of the present invention, $1.66 \times 10^{-2}$ mmol of 2,2'-biquinoline, and 10 ml of 2-ethoxyethanol were placed, and the resultant mixture was irradiated with microwave (2,450 MHz) under argon atmosphere for 15 minutes. The reaction solution was cooled to room temperature, concentrated under reduced pressure to remove the solvent, and precipitated by addition of saturated aqueous NH$_4$PF$_6$ solution, to give a brown solid. The brown solid was recrystallized from dichloromethane-hexane. Analysis by electrospray ionization mass spectrometry (ESI-MS) identified the parent ion peak (m/z=1006) of the target iridium complex (2-412). The isolation yield was 55%.

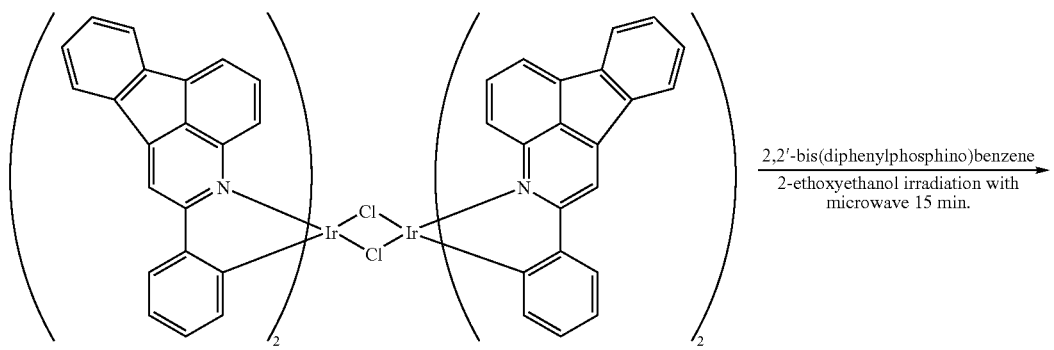

2,2'-bis(diphenylphosphino)benzene
2-ethoxyethanol irradiation with microwave 15 min.

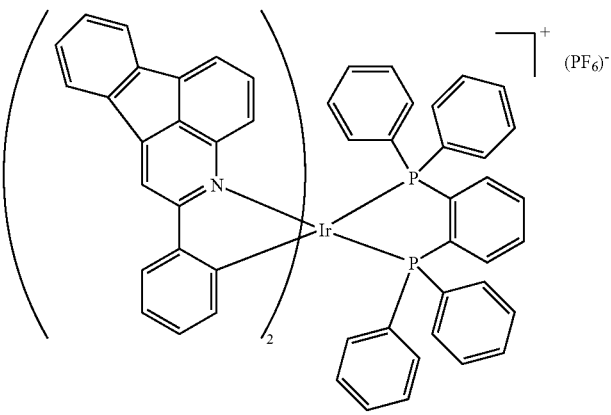

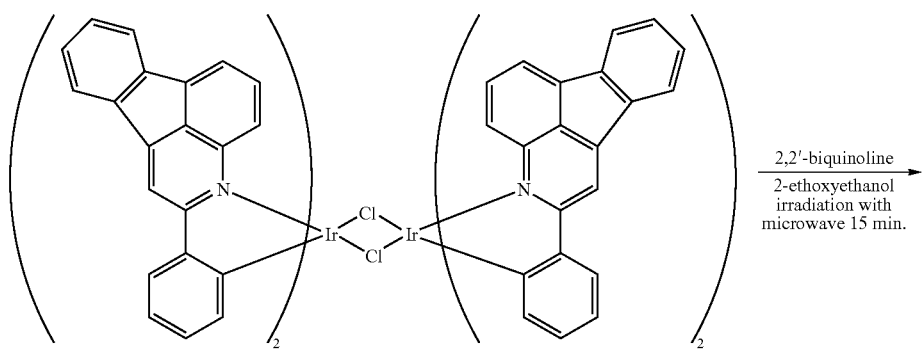

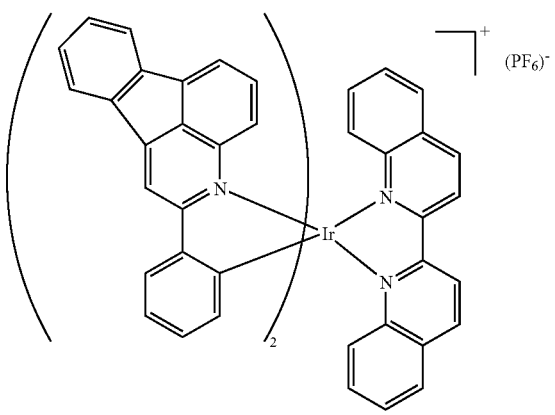

Example 9

Synthesis of Compound (3-95) of the Present Invention

In a two-necked flask, $1.76 \times 10^{-1}$ mmol of potassium tetrachloroplatinate n-hydrate, $5.63 \times 10^{-1}$ mmol of 2-phenylindeno[1,2,3-de]quinoline, 10 ml of 2-ethoxyethanol, and 3 ml of water were placed, the resultant mixture was heated under argon atmosphere at 80° C. for 15.5 hours. The reaction solution was cooled to room temperature, concentrated, and precipitated by addition of water, to give a brownish-red solid. The brownish-red solid was washed with water, to give a target platinum complex (3-91).

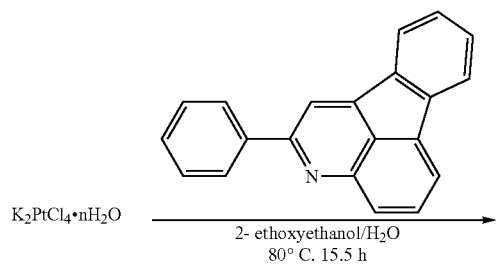

-continued

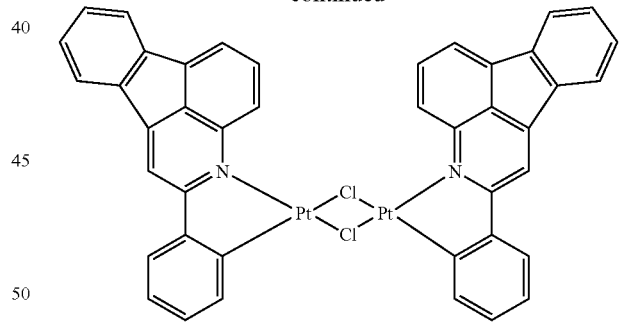

Example 10

Synthesis of Compound (2-414) of the Present Invention

In a round-bottomed flask, $6.42 \times 10^{-3}$ mmol of the compound (3-91) of the present invention, $1.66 \times 10^{-2}$ mmol of 2,2'-bipyridine, and 10 ml of 2-ethoxyethanol were placed, the resultant mixture was irradiated with microwave (2,450 MHz) under argon atmosphere for 5 minutes. The reaction solution was cooled to room temperature, concentrated under reduced pressure to remove the solvent, and precipitated by addition of saturated aqueous $NH_4PF_6$ solution, to give a red brown solid. The red brown solid was recrystallized from dichloromethane-hexane. Analysis by electrospray ionization mass spectrometry (ESI-MS) identified the parent ion peak (m/z=629) of the target platinum complex (2-414).

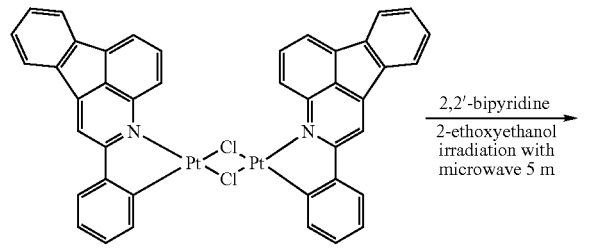

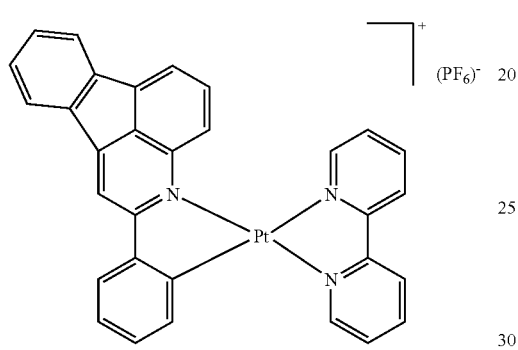

Example 11

Synthesis of Compound (2-415) of the Present Invention

In a round-bottomed flask, $6.42 \times 10^{-3}$ mmol of the compound (3-91) of the present invention, $1.66 \times 10^{-2}$ mmol of 2,2'-bipyridine, and 10 ml of 2-ethoxyethanol were placed, the resultant mixture was irradiated with microwave (2,450 MHz) under argon atmosphere for 5 minutes. The reaction solution was cooled to room temperature, concentrated under reduced pressure to remove the solvent, and precipitated by addition of saturated aqueous NH$_4$PF$_6$ solution, to give a red brown solid. The red brown solid was recrystallized from dichloromethane-hexane. Analysis by electrospray ionization mass spectrometry (ESI-MS) identified the parent ion peak (m/z=644) of the target platinum complex (2-415).

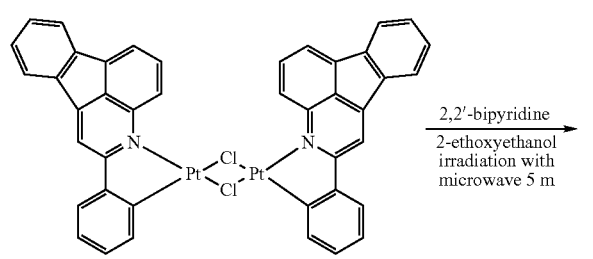

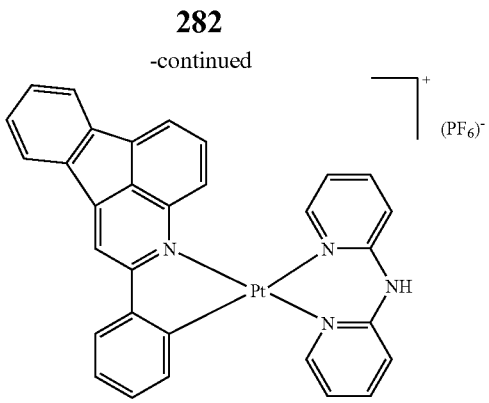

Example 12

Synthesis of Compound (2-43) of the Present Invention

In a two-necked flask, 0.205 mmol of iridium trisacetylacetonate, 1.02 mmol of 2-phenylindeno[1,2,3-de]quinoline, and 10 ml of glycerin were placed, the resultant mixture was allowed to react under heating under argon atmosphere at 210° C. for 15 hours. The reaction solution was cooled to room temperature and precipitated by addition of 60 ml of 1M hydrochloric acid solution, and the dark brown solid thus obtained was collected by filtration. The dark brown solid was recrystallized three times from dichloromethane-methanol, to give a target iridium complex (2-43). The isolation yield was 21%.

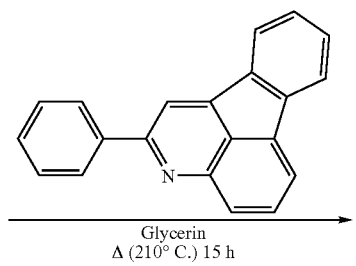

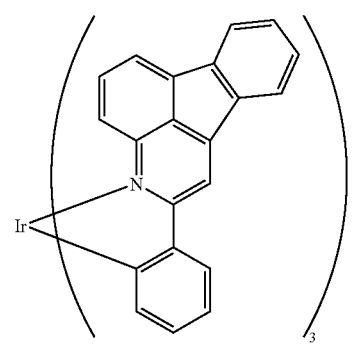

$^1$H-NMR (in CD$_2$Cl$_2$) δ 8.61 (s, 3H), 8.03 (d, 3H), 8.00 (d, 3H), 7.80 (d, 3H), 7.55 (d, 3H), 7.41-7.49 (m, 6H), 7.37 (d, 3H), 6.93 (t, 3H), 6.86 (dd, 3H), 6.71 (t, 3H), 6.48 (d, 3H).

Example 13

Synthesis of Compound (2-431) of the Present Invention

In a round-bottomed flask, $6.42\times10^{-3}$ mmol of the compound (3-43) of the present invention, $1.65\times10^{-2}$ mmol of sodium quinaldinate and 10 ml of 2-ethoxyethanol were placed, the resultant mixture was irradiated with microwave (2,450 MHz) under argon atmosphere for 15 minutes. The reaction solution was cooled to room temperature and concentrated under reduced pressure to remove the solvent, to give a red brown solid. The red brown solid was recrystallized from dichloromethane-hexane, to give a target iridium complex (2-431). The isolation yield was 65%.

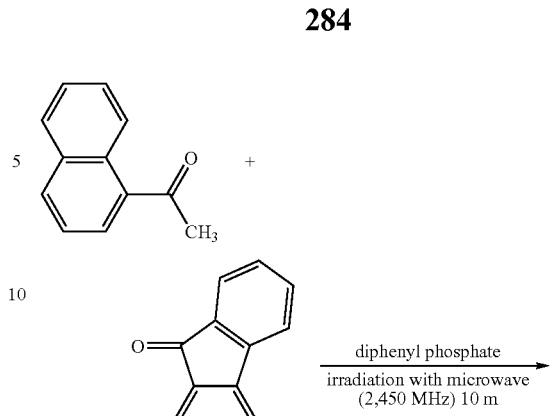

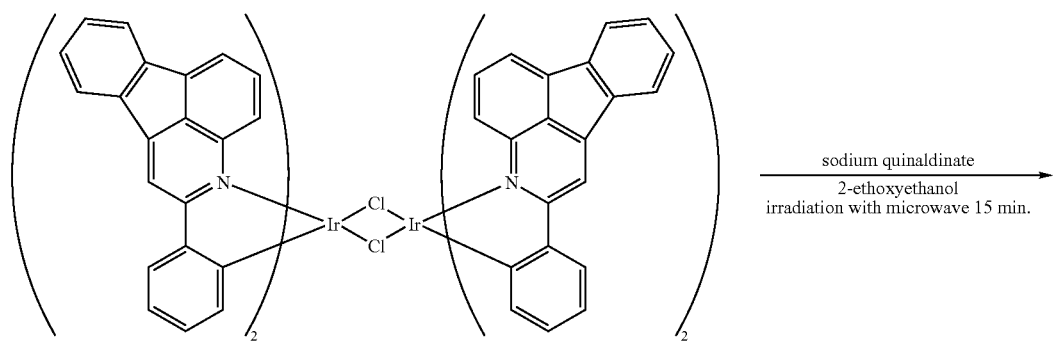

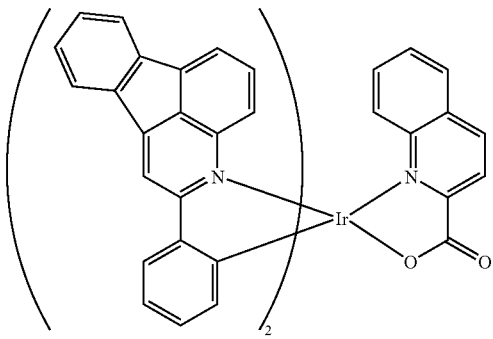

$^1$H-NMR (in $CD_2Cl_2$) δ 8.60 (d, 1H), 8.59 (s, 1H), 8.48 (s, 1H), 8.16 (d, 2H), 8.12 (d, 1H), 8.05 (d, 1H), 8.04 (d, 1H), 8.00 (d, 1H), 7.85 (d, 1H), 7.79-7.82 (m, 2H), 7.75 (d, 1H), 7.72 (d, 1H), 7.60 (d, 1H), 7.42-7.57 (m, 6H), 7.28 (dd, 1H), 7.15 (dd, 1H), 7.13 (d, 1H), 7.04 (dd, 1H), 6.74-6.82 (m, 3H), 6.69 (dd, 1H), 6.16 (d, 1H).

Example 14

Synthesis of Compound (3-67) of the Present Invention 2-(Naphthalen-4-yl)indeno[1,2,3-de]quinoline was prepared in the same manner as in Example 1, except that acetophenone used in preparation of 2-phenylindeno[1,2,3-de]quinoline in Example 1 was replaced with 1-(naphthalen-4-yl)ethanone.

-continued

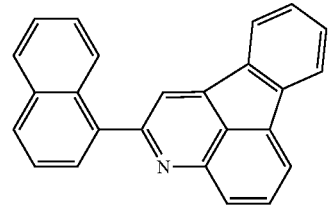

In a two-necked flask, $1.76\times10^{-1}$ mmol of iridium trichloride trihydrate, $5.63\times10^{-1}$ mmol of the 2-(naphthalen-4-yl)indeno[1,2,3-de]quinoline thus prepared, 10 ml of 2-ethoxyethanol, and 3 ml of water were placed, the resultant mixture was heated under reflux under argon atmosphere for 15 hours. The reaction solution was cooled to room temperature, concentrated under reduced pressure, and precipitated by addition of water, and the dark brown solid thus obtained was collected by filtration. The dark brown solid was washed with water, to give a target iridium complex (3-67). The isolation yield was 88%.

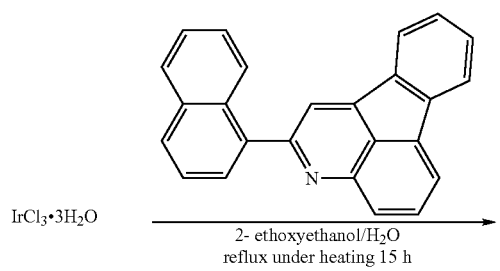

$^1$H-NMR (in CDCl$_3$) δ 8.96 (s, 4H), 8.70 (d, 4H), 8.15 (d, 4H), 8.09 (d, 4H), 7.50-7.58 (m, 24H), 6.58-6.65 (m, 12H), 5.82 (d, 4H).

Example 15

Synthesis of Compound (2-488) of the Present Invention

In a round-bottomed flask, $6.42 \times 10^{-3}$ mmol of the compound (3-67) of the present invention, $1.66 \times 10^{-2}$ mmol of 2,2'-bipyridine, and 10 ml of 2-ethoxyethanol were placed, the resultant mixture was irradiated with microwave (2,450 MHz) under argon atmosphere for 5 minutes. The reaction solution was cooled to room temperature, concentrated under reduced pressure to remove the solvent, and precipitated by addition of saturated aqueous NH$_4$PF$_6$ solution, to give a red brown solid. The red brown solid was recrystallized from dichloromethane-hexane. Analysis by electrospray ionization mass spectrometry (ESI-MS) identified the parent ion peak (m/z=1006) of the target iridium complex (2-488). The isolation yield was 60%.

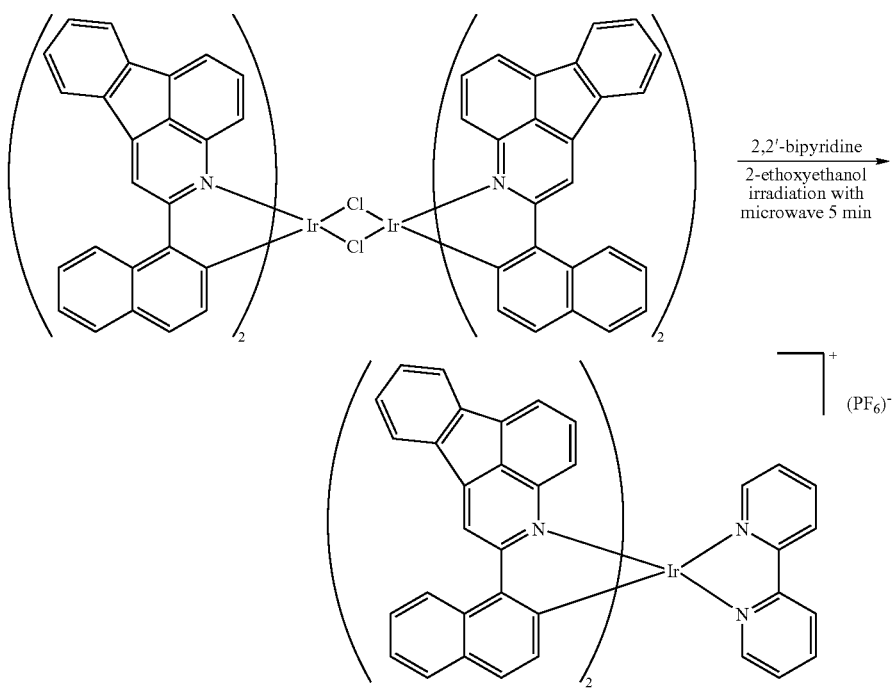

$^1$H-NMR (in CD$_2$Cl$_2$) δ 9.12 (s, 2H), 8.82 (d, 2H), 8.27 (d, 2H), 8.13 (d, 4H), 7.94 (dd, 2H), 7.86 (d, 2H), 7.80 (d, 2H), 7.71 (dd, 2H), 7.68 (d, 2H), 7.48-7.57 (m, 6H), 7.36 (t, 2H), 7.24 (d, 2H), 7.08 (t, 2H), 6.77 (d, 2H), 6.64 (d, 2H).

Example 16

Synthesis of Compound (3-74) of the Present Invention 2-(Naphthalen-2-yl)indeno[1,2,3-de]quinoline was prepared in the same manner as in Example 1, except that acetophenone used in preparation of 2-phenylindeno[1,2,3-de]quinoline in Example 1 was replaced with 1-(naphthalen-3-yl)ethanone.

-continued

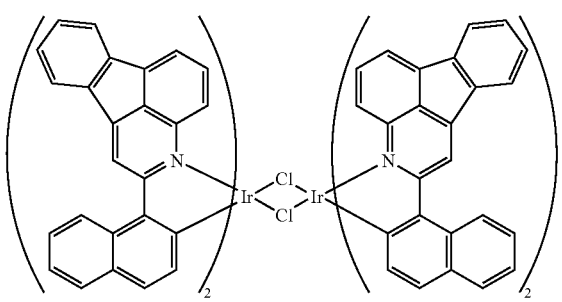

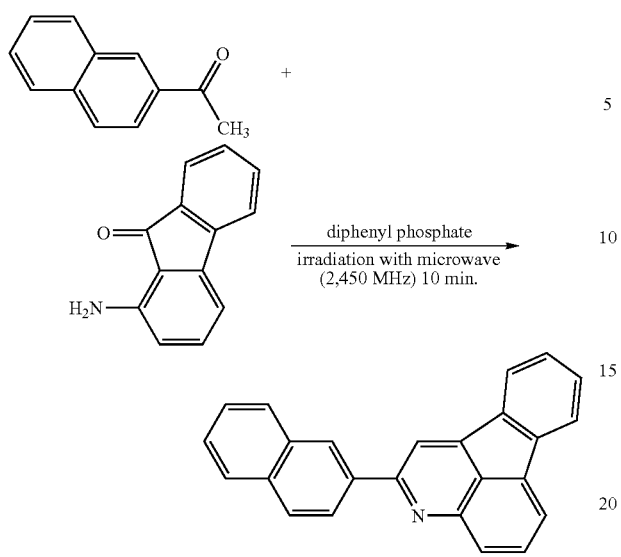

In a two-necked flask, $1.76 \times 10^{-1}$ mmol of iridium trichloride trihydrate, $5.63 \times 10^{-1}$ mmol of 2-(naphthalene-2-yl)indeno[1,2,3-de]quinoline thus prepared, 10 ml of 2-ethoxyethanol, and 3 ml of water were placed, and the resultant mixture was heated under reflux under argon atmosphere for 15 hours. The reaction solution was cooled to room temperature, concentrated under reduced pressure, and precipitated by addition of water, and the thus-formed dark brown solid was collected by filtration. The dark brown solid was washed with water, to give a target iridium complex (3-74). The isolation yield was 79%.

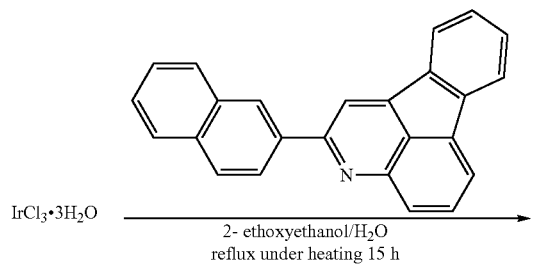

$^1$H-NMR (in CDCl$_3$) δ 8.48 (s, 4H), 8.41 (d, 4H), 8.32 (s, 4H), 8.16 (d, 4H), 7.62-7.69 (m, 8H), 7.59 (t, 4H), 7.51 (d, 4H), 7.05 (t, 4H), 6.94 (t, 4H), 6.66 (d, 4H), 6.61 (t, 4H), 6.55 (d, 4H), 6.15 (s, 4H).

Example 17

Synthesis of Compound (2-242) of the Present Invention

In a round-bottomed flask, $6.42 \times 10^{-3}$ mmol of the compound (3-74) of the present invention, $1.65 \times 10^{-2}$ mmol of sodium picolinate, and 10 ml of 2-ethoxyethanol were placed, and the resultant mixture was irradiated with microwave (2,450 MHz) under argon atmosphere for 15 minutes. The reaction solution was cooled to room temperature, concentrated under reduced pressure to remove the solvent, to give a black brown solid. The black brown solid was recrystallized from dichloromethane-hexane, to give a target iridium complex (2-242). The isolation yield was 55%.

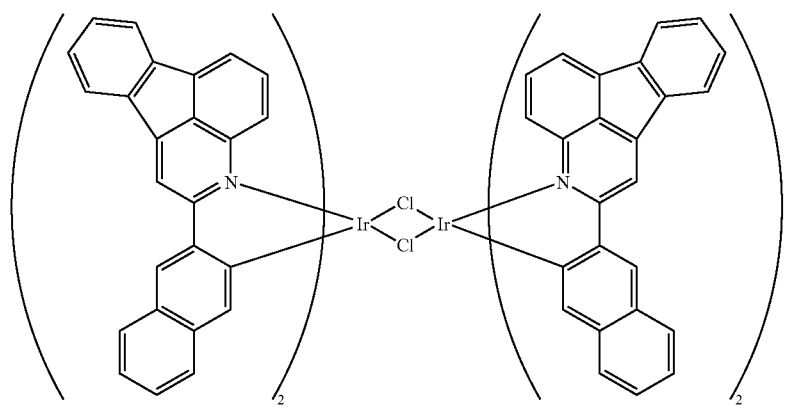

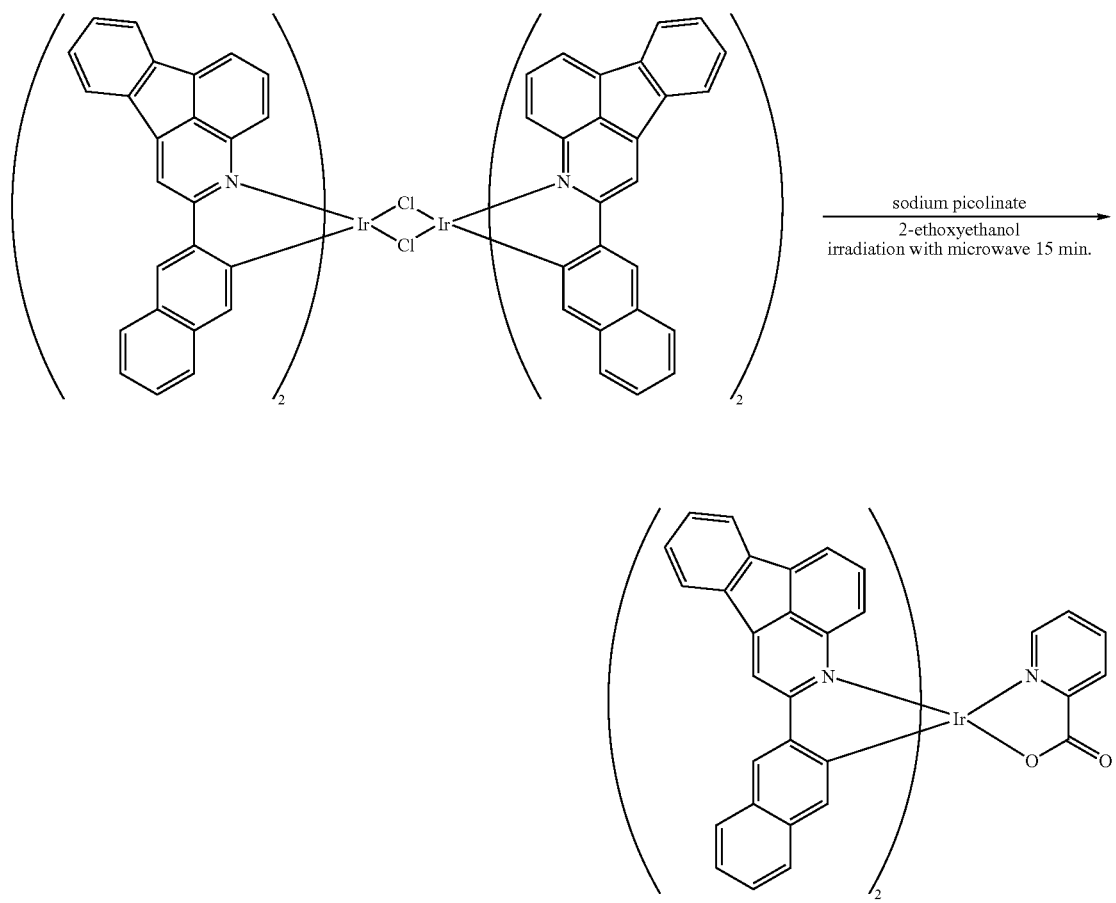

Example 18

Synthesis of Compound (2-405) of the Present Invention

In a round-bottomed flask, $6.42 \times 10^{-3}$ mmol of the compound (3-74) of the present invention, $1.66 \times 10^{-2}$ mmol of 2,2'-bipyridine, and 10 ml of 2-ethoxyethanol were placed, the resultant mixture was irradiated with microwave (2,450 MHz) under argon atmosphere for 15 minutes. The reaction solution was cooled to room temperature, concentrated under reduced pressure to remove the solvent, and precipitated by addition of saturated aqueous $NH_4PF_6$ solution, to give a red brown solid. The red brown solid was recrystallized from dichloromethane-hexane. Analysis by electrospray ionization mass spectrometry (ESI-MS) identified the parent ion peak (m/z=1006) of the target iridium complex (2-405). The isolation yield was 63%.

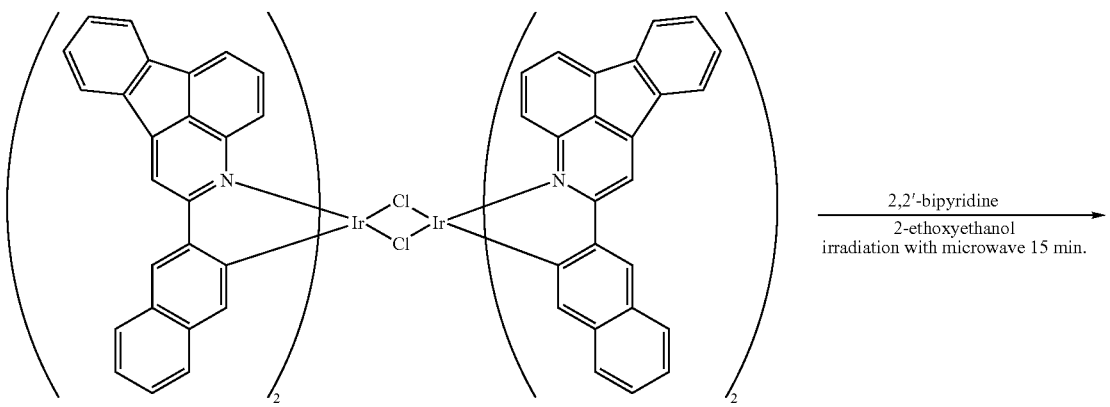

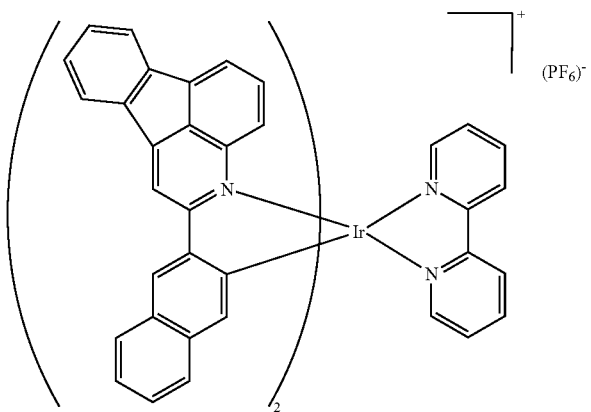

Example 19

Synthesis of Compound (3-101) of the Present Invention 2-(4-Fluorophenyl)indeno[1,2,3-de]quinoline was prepared in the same manner as in Example 1, except that acetophenone used in preparation of 2-phenylindeno[1,2,3-de]quinoline in Example 1 was replaced with 1-(4-fluorophenyl)ethanone.

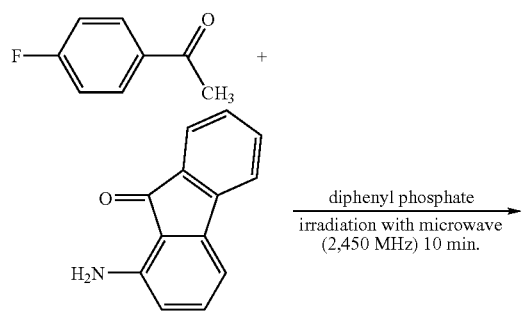

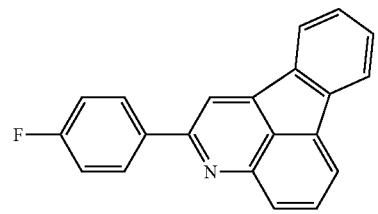

$^1$H-NMR (in CD$_2$Cl$_2$) δ 8.21-8.25 (m, 3H), 8.07 (d, 1H), 8.03 (d, 1H), 7.90 (d, 1H), 7.88 (d, 1H), 7.79 (t, 1H), 7.53 (t, 1H), 7.45 (t, 1H), 7.26 (t, 2H).

In a two-necked flask, 1.76×10$^{-1}$ mmol of iridium trichloride trihydrate, 5.63×10$^{-1}$ mmol of 2-(4-fluorophenyl)indeno[1,2,3-de]quinoline, 10 ml of 2-ethoxyethanol, and 3 ml of water were placed, and the resultant mixture was heated under reflux under argon atmosphere for 15 hours. The reaction solution was cooled to room temperature, concentrated under reduced pressure, and precipitated by addition of water, and the thus-formed dark brown solid was collected by filtration. The dark brown solid was washed with water, to give a target iridium complex (3-101). The isolation yield was 90%.

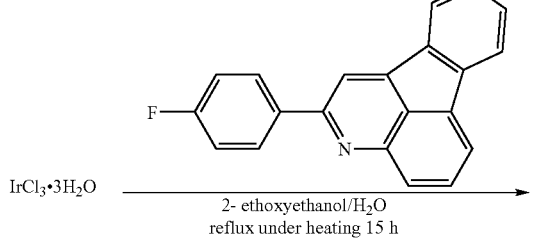

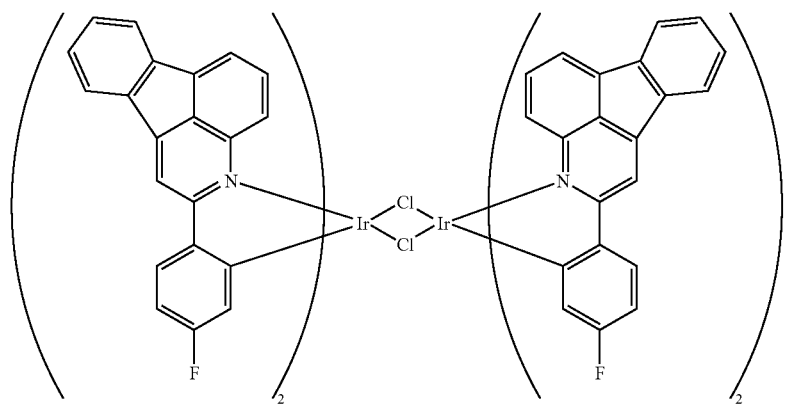

$^1$H-NMR (in CDCl$_3$) δ 8.27 (d, 4H), 8.18 (s, 4H), 8.07 (d, 4H), 7.78 (dd, 4H), 7.61 (t, 4H), 7.56 (t, 4H), 7.47 (d, 4H), 6.65 (t, 4H), 6.52-6.56 (m, 8H), 5.50 (d, 4H).

Example 20

Synthesis of Compound (2-476) of the Present Invention

In a round-bottomed flask, 6.42×10$^{-3}$ mmol of the compound (3-101) of the present invention, 1.65×10$^{-2}$ mmol of sodium picolinate, and 10 ml of 2-ethoxyethanol were placed, and the resultant mixture was irradiated with microwave (2,450 MHz) under argon atmosphere for 15 minutes. The reaction solution was cooled to room temperature, concentrated under reduced pressure to remove the solvent, to give a brown solid. The brown solid was recrystallized from dichloromethane-hexane, to give a target iridium complex (2-476). The isolation yield was 40%.

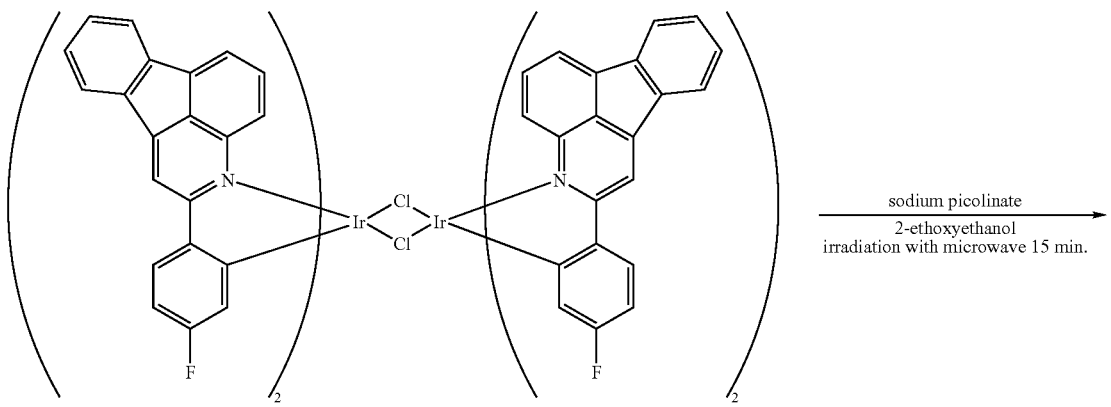

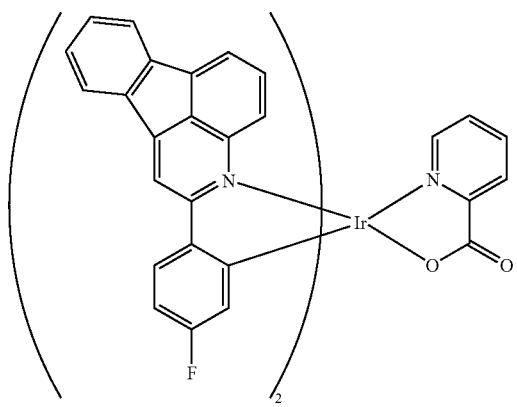

$^1$H-NMR (in CD$_2$Cl$_2$) δ 8.53 (s, 1H), 8.51 (s, 1H), 8.46 (d, 1H), 8.19 (dd, 1H), 8.06-8.09 (m, 3H), 7.98 (d, 1H), 7.83-7.91 (m, 3H), 7.73-7.79 (m, 2H), 7.67 (d, 1H), 7.62 (t, 1H), 7.44-7.53 (m, 4H), 7.35 (t, 1H), 7.07 (t, 1H), 6.89 (dd, 1H), 6.76 (dd, 1H), 6.67 (d, 1H), 6.46 (d, 1H), 5.94 (d, 1H).

Example 21

Synthesis of Compound (2-482) of the Present Invention

In a round-bottomed flask, 6.42×10$^{-3}$ mmol of the compound (3-101) of the present invention, 1.66×10$^{-2}$ mmol of 2,2'-bipyridine, and 10 ml of 2-ethoxyethanol were placed, the resultant mixture was irradiated with microwave (2,450 MHz) under argon atmosphere for 5 minutes. The reaction solution was cooled to room temperature, concentrated under reduced pressure to remove the solvent, and precipitated by addition of saturated aqueous NH$_4$PF$_6$ solution, to give a red brown solid. The red brown solid was recrystallized from dichloromethane-hexane. Analysis by electrospray ionization mass spectrometry (ESI-MS) identified the parent ion peak (m/z=942) of the target iridium complex (2-482).

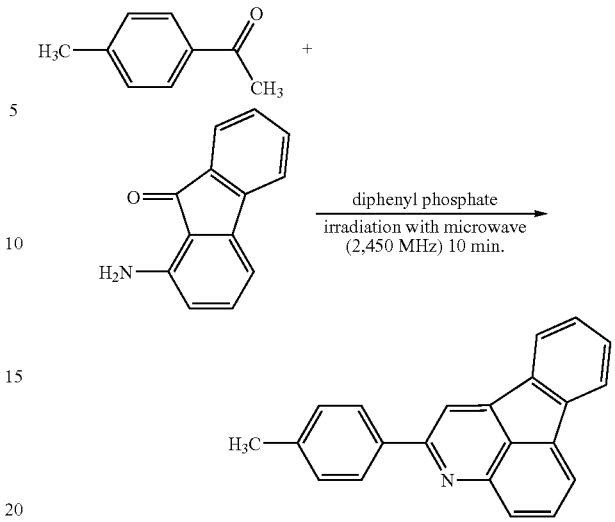

$^1$H-NMR (in CDCl$_3$) δ 8.21 (s, 1H), 8.09 (d, 2H), 8.03 (d, 1H), 7.98 (d, 1H), 7.88 (d, 1H), 7.84 (d, 1H), 7.76 (t, 1H), 7.49 (t, 1H), 7.41 (t, 1H), 7.37 (d, 2H), 2.46 (s, 3H).

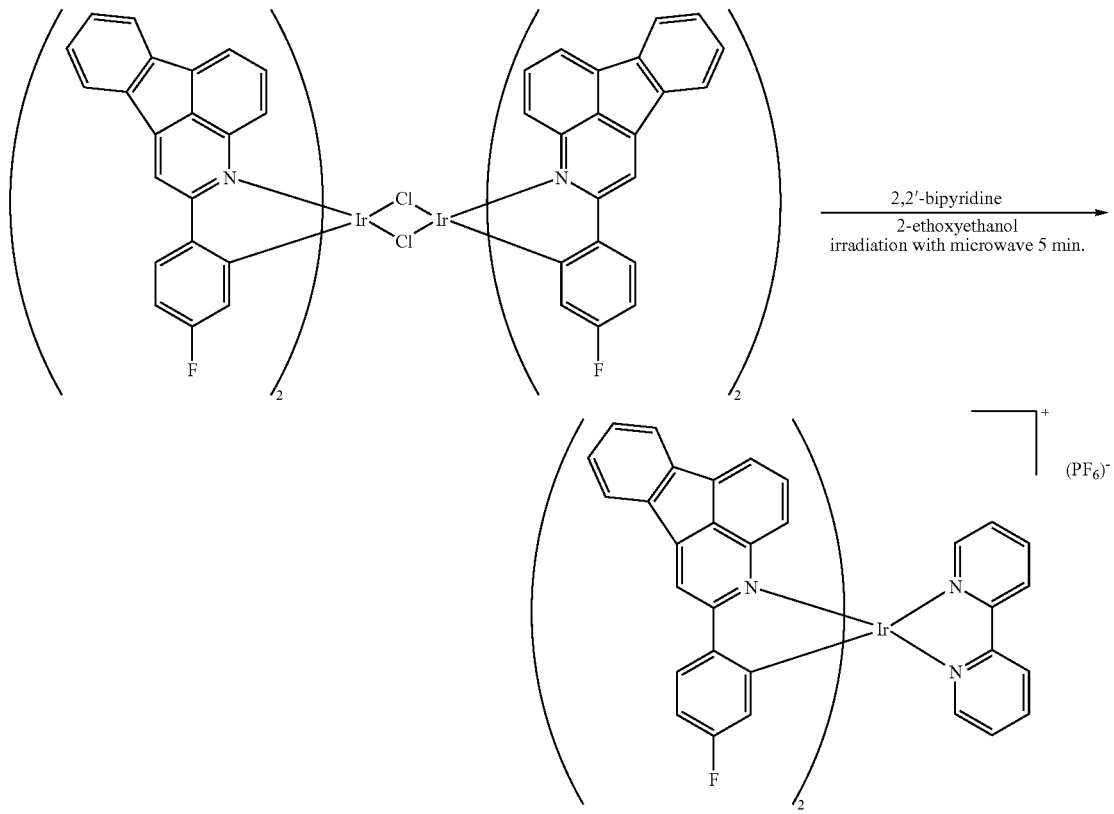

Example 22

Synthesis of Compound (3-102) of the Present Invention 2-para-tolylindeno[1,2,3-de]quinoline was prepared in the same manner as in Example 1, except that acetophenone used in preparation of 2-phenylindeno[1,2,3-de]quinoline in Example 1 was replaced with 1-para-tolylethanone.

In a two-necked flask, 1.76×10$^{-1}$ mmol of iridium trichloride trihydrate, 5.63×10$^{-1}$ mmol of 2-para-tolylindeno[1,2,3-de]quinoline, 10 ml of 2-ethoxyethanol, and 3 ml of water were placed, and the resultant mixture was heated under reflux under argon atmosphere for 15 hours. The reaction solution was cooled to room temperature, concentrated under reduced pressure, and precipitated by addition of water, and the thus-formed dark brown solid was collected by filtration. The dark brown solid was washed with water, to give a target iridium complex (3-102). The isolation yield was 79%.

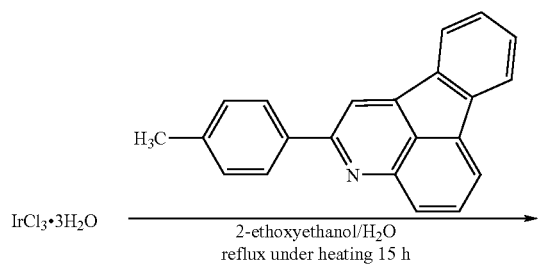

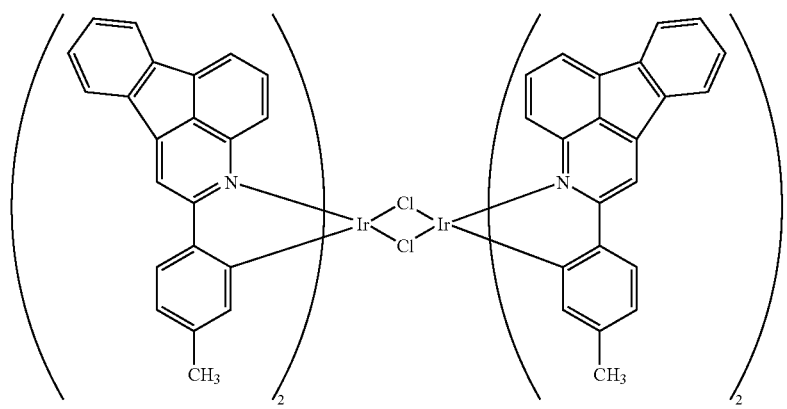

$^1$H-NMR (in CDCl$_3$) δ 8.31 (d, 4H), 8.20 (s, 4H), 8.06 (d, 4H), 7.65 (d, 4H), 7.59 (t, 4H), 7.53 (t, 4H), 7.46 (d, 4H), 6.57-6.61 (m, 8H), 6.49 (d, 4H), 5.70 (s, 4H), 1.60 (s, 12H).

Example 23

Synthesis of Compound (2-477) of the Present Invention

In a round-bottomed flask, 6.42×10$^{-3}$ mmol of the compound (3-102) of the present invention, 1.65×10$^{-2}$ mmol of sodium picolinate, and 10 ml of 2-ethoxyethanol were placed, and the resultant mixture was irradiated with microwave (2,450 MHz) under argon atmosphere for 15 minutes. The reaction solution was cooled to room temperature, concentrated under reduced pressure to remove the solvent, to give a brown solid. The brown solid was recrystallized from dichloromethane-hexane, to give a target iridium complex (2-477). The isolation yield was 48%.

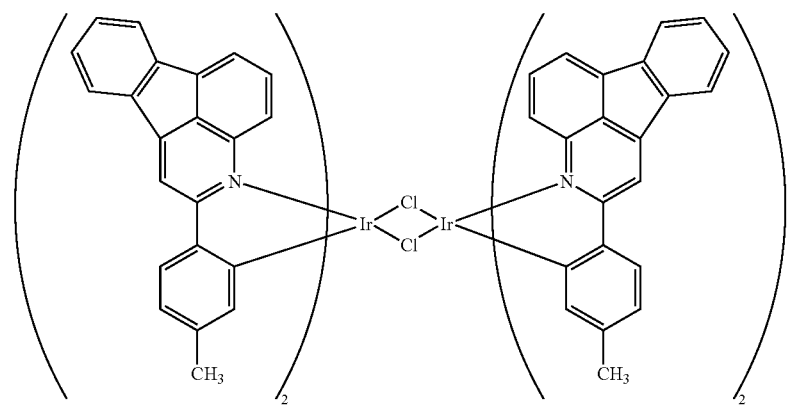

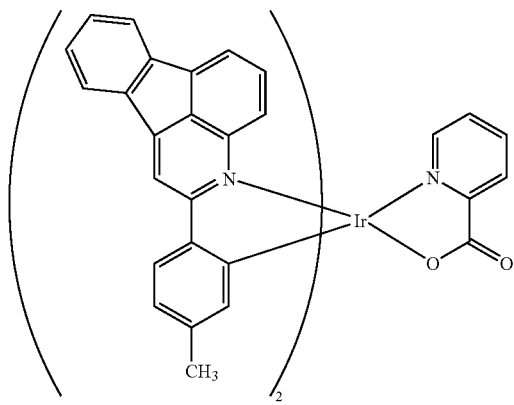

$^1$H-NMR (in CD$_2$Cl$_2$) δ 8.56 (s, 1H), 8.53 (s, 1H), 8.44 (d, 1H), 8.05-8.11 (m, 3H), 7.94-7.97 (m, 2H), 7.86 (d, 3H), 7.75 (d, 1H), 7.70 (t, 1H), 7.64 (d, 1H), 7.58 (t, 1H), 7.44-7.53 (m, 4H), 7.29 (t, 1H), 7.03 (t, 1H), 6.97 (d, 1H), 6.88 (d, 1H), 6.70 (d, 1H), 6.66 (s, 1H), 6.14 (s, 1H), 2.05 (s, 3H), 1.93 (s, 3H).

Example 24

Synthesis of Compound (2-483) of the Present Invention

In a round-bottomed flask, 6.42×10$^{-3}$ mmol of the compound (3-102) of the present invention, 1.66×10$^{-2}$ mmol of 2,2'-bipyridine, and 10 ml of 2-ethoxyethanol were placed, the resultant mixture was irradiated with microwave (2,450 MHz) under argon atmosphere for 5 minutes. The reaction solution was cooled to room temperature, concentrated under reduced pressure to remove the solvent, and precipitated by addition of saturated aqueous NH$_4$PF$_6$ solution, to give a red brown solid. The red brown solid was recrystallized from dichloromethane-hexane. Analysis by electrospray ionization mass spectrometry (ESI-MS) identified the parent ion peak (m/z=934) of the target iridium complex (2-483).

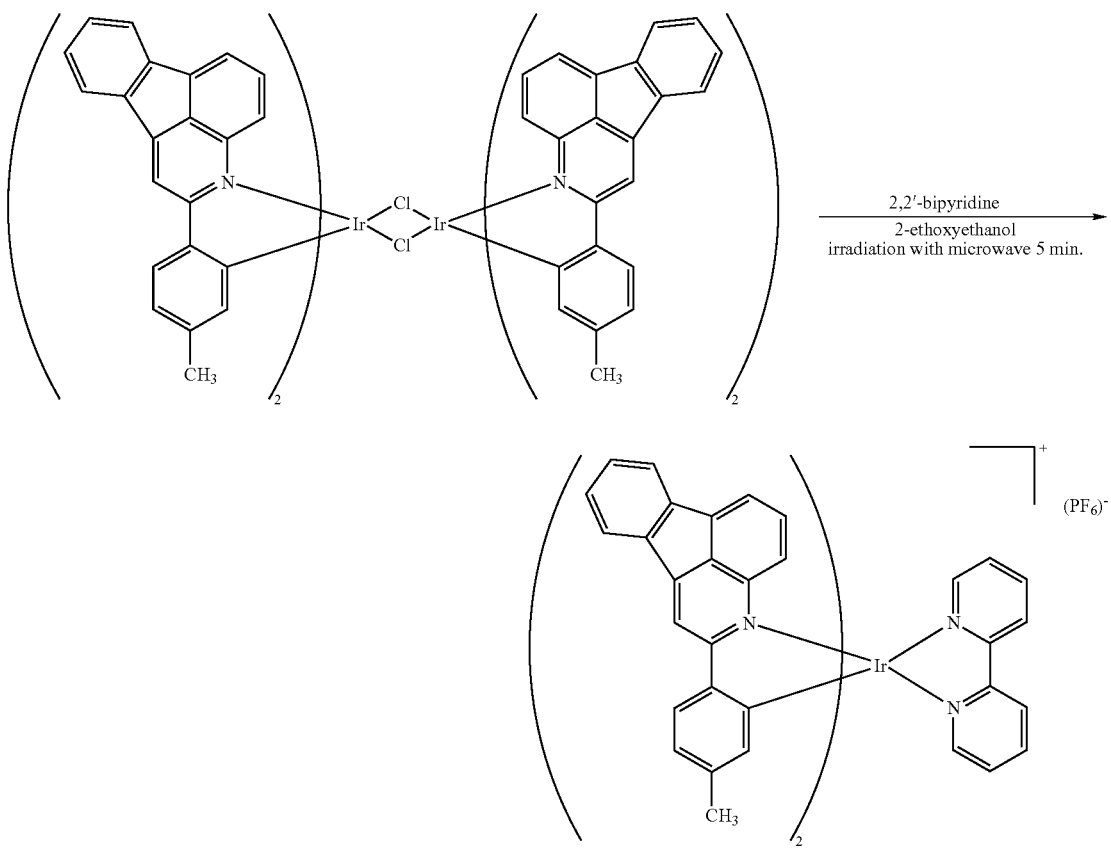

¹H-NMR (in CD₂Cl₂) δ 8.59 (s, 2H), 8.23 (d, 2H), 8.08-8.15 (m, 6H), 7.95 (t, 2H), 7.84 (d, 2H), 7.65 (d, 2H), 7.42-7.55 (m, 6H), 7.05-7.10 (m, 4H), 6.63 (d, 2H), 6.36 (m, 2H), 2.02 (s, 6H).

Example 25

Synthesis of Compound (3-103) of the Present Invention 2-meta-tolylindeno[1,2,3-de]quinoline was prepared in the same manner as in Example 1, except that acetophenone used in preparation of 2-phenylindeno[1,2,3-de]quinoline in Example 1 was replaced with 1-meta-tolylethanone.

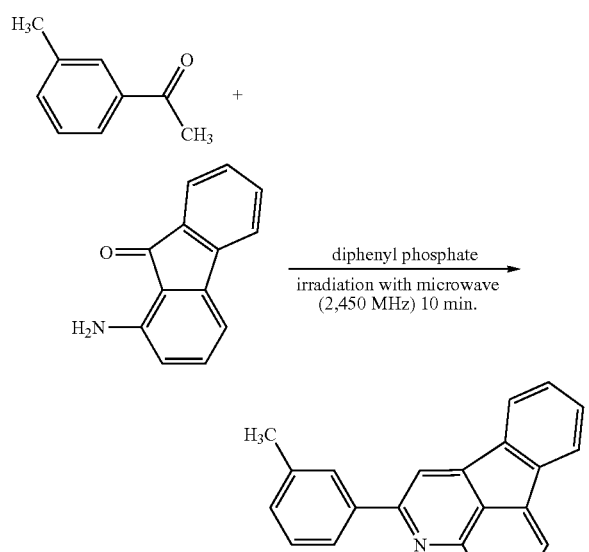

¹H-NMR (in CDCl₃) δ 8.23 (s, 1H), 8.05 (d, 1H), 8.04 (s, 1H), 8.00 (d, 1H), 7.97 (d, 1H), 7.89 (d, 1H), 7.85 (d, 1H), 7.77 (t, 1H), 7.40-7.51 (m, 3H), 7.32 (d, 1H), 2.51 (s, 3H).

In a two-necked flask, 1.76×10⁻¹ mmol of iridium trichloride trihydrate, 5.63×10⁻¹ mmol of 2-meta-tolylindeno[1,2,3-de]quinoline, 10 ml of 2-ethoxyethanol, and 3 ml of water were placed, and the resultant mixture was heated under reflux under argon atmosphere for 15 hours. The reaction solution was cooled to room temperature, concentrated under reduced pressure, and precipitated by addition of water, and the thus-formed dark brown solid was collected by filtration. The dark brown solid was washed with water, to give a target iridium complex (3-103). The isolation yield was 83%.

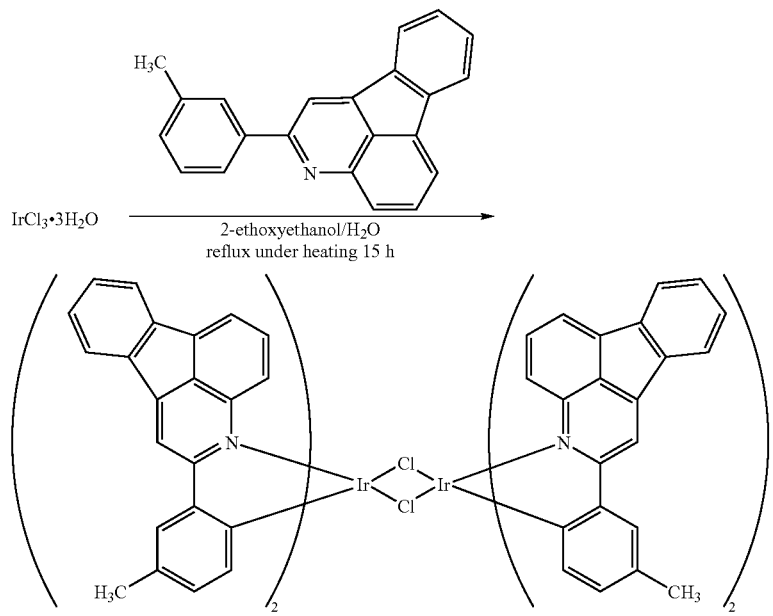

¹H-NMR (in CDCl₃) δ 8.35 (d, 4H), 8.23 (s, 4H), 8.08 (d, 4H), 7.57-7.60 (m, 8H), 7.54 (t, 4H), 7.46 (d, 4H), 6.59 (t, 4H), 6.50 (d, 4H), 6.11 (d, 4H), 5.76 (d, 4H), 2.14 (s, 12H).

Example 26

Synthesis of Compound (2-484) of the Present Invention

In a round-bottomed flask, 6.42×10⁻³ mmol of the compound (3-103) of the present invention, 1.66×10⁻² mmol of 2,2'-bipyridine, and 10 ml of 2-ethoxyethanol were placed, the resultant mixture was irradiated with microwave (2,450 MHz) under argon atmosphere for 5 minutes. The reaction solution was cooled to room temperature, concentrated under reduced pressure to remove the solvent, and precipitated by addition of saturated aqueous NH₄PF₆ solution, to give a red brown solid. The red brown solid was recrystallized from dichloromethane-hexane. Analysis by electrospray ionization mass spectrometry (ESI-MS) identified the parent ion peak (m/z=934) of the target iridium complex (2-484).

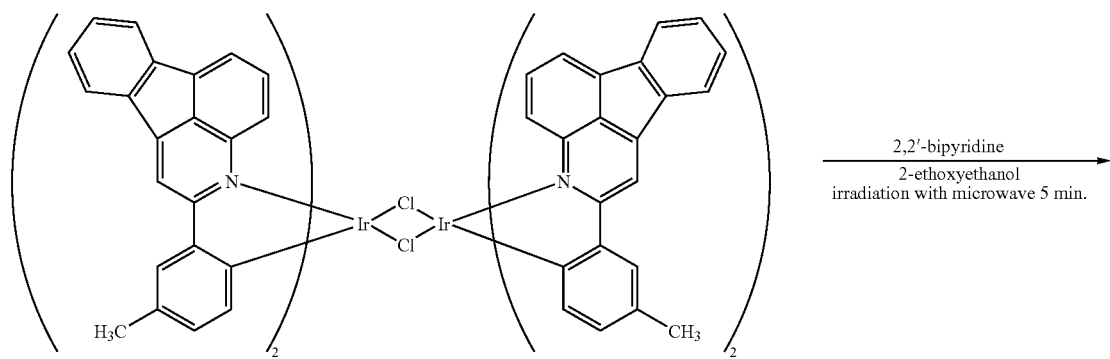

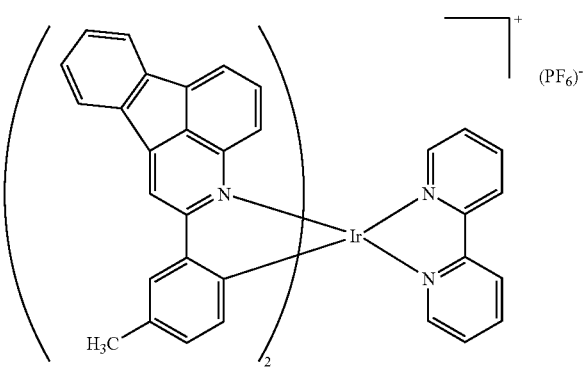

¹H-NMR (in CD$_2$Cl$_2$) δ 8.62 (s, 2H), 8.24 (d, 2H), 8.16 (d, 2H), 8.10 (d, 2H), 8.04 (s, 2H), 7.96 (t, 2H), 7.84 (d, 2H), 7.67 (d, 2H), 7.48-7.55 (m, 4H), 7.44 (t, 2H), 7.10 (t, 2H), 6.68 (d, 2H), 6.64 (d, 2H), 6.38 (d, 2H), 2.38 (s, 6H).

Example 27

Synthesis of Compound (3-104) of the Present Invention 2-(4-tert-butylphenyl)indeno[1,2,3-de]quinoline was prepared in the same manner as in Example 1, except that acetophenone used in preparation of 2-phenylindeno[1,2,3-de]quinoline in Example 1 was replaced with 1-(4-tert-butylphenyl)ethanone.

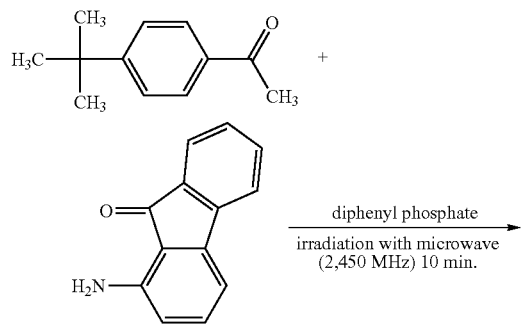

-continued

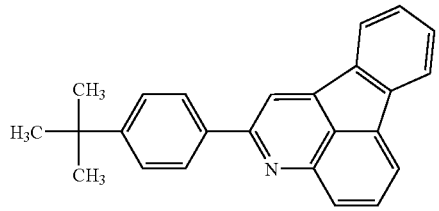

In a two-necked flask, $1.76 \times 10^{-1}$ mmol of iridium trichloride trihydrate, $5.63 \times 10^{-1}$ mmol of 2-(4-tert-butylphenyl)indeno[1,2,3-de]quinoline, 10 ml of 2-ethoxyethanol, and 3 ml of water were placed, and the resultant mixture was heated under reflux under argon atmosphere for 15 hours. The reaction solution was cooled to room temperature, concentrated under reduced pressure, and precipitated by addition of water, and the thus-formed dark brown solid was collected by filtration. The dark brown solid was washed with water, to give a target iridium complex (3-104). The isolation yield was 61%.

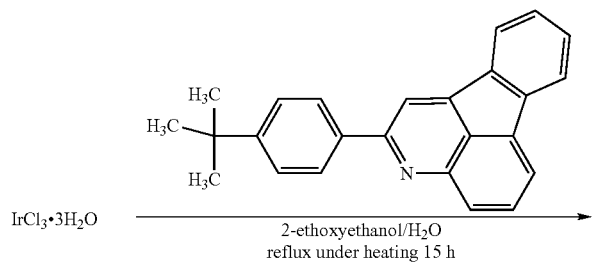

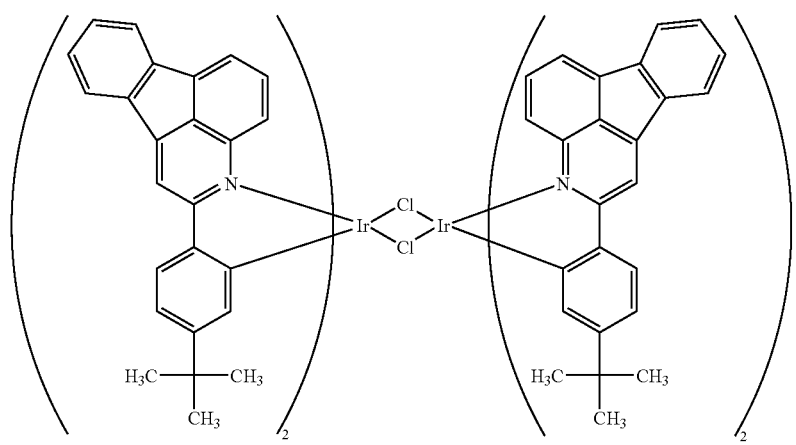

$^1$H-NMR (in CDCl$_3$) δ 8.37 (d, 4H), 8.20 (s, 4H), 8.06 (d, 4H), 7.71 (d, 4H), 7.60 (t, 4H), 7.53 (t, 4H), 7.46 (d, 4H), 6.82 (d, 4H), 6.57 (t, 4H), 6.46 (d, 4H), 6.00 (s, 4H), 0.56 (s, 36H).

Example 28

Synthesis of Compound (2-480) of the Present Invention

In a round-bottomed flask, 6.42×10$^{-3}$ mmol of the compound (3-104) of the present invention, 1.66×10$^{-2}$ mmol of 2,2'-bipyridine, and 10 ml of 2-ethoxyethanol were placed, the resultant mixture was irradiated with microwave (2,450 MHz) under argon atmosphere for 5 minutes. The reaction solution was cooled to room temperature, concentrated under reduced pressure to remove the solvent, and precipitated by addition of saturated aqueous NH$_4$PF$_6$ solution, to give a red brown solid. The red brown solid was recrystallized from dichloromethane-hexane. Analysis by electrospray ionization mass spectrometry (ESI-MS) identified the parent ion peak (m/z=1018) of the target iridium complex (2-480).

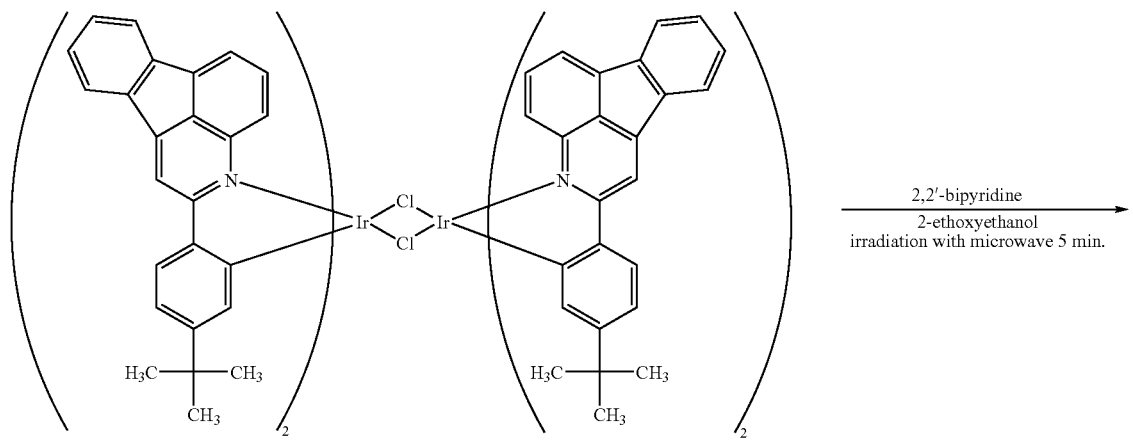

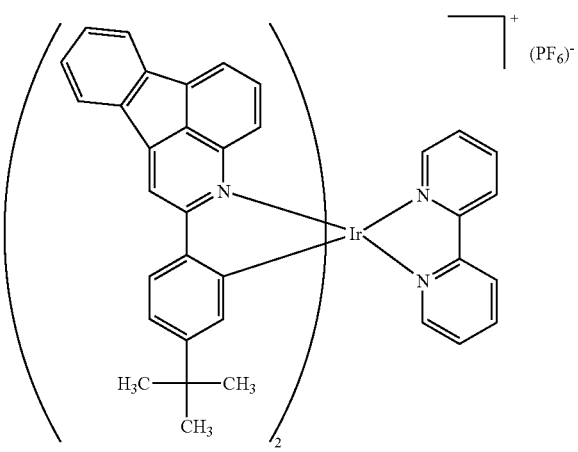

Example 29

Synthesis of Compound (3-106) of the Present Invention 2-(2,4-difluorophenyl)indeno[1,2,3-de]quinoline was prepared in the same manner as in Example 1, except that acetophenone used in preparation of 2-phenylindeno[1,2,3-de]quinoline in Example 1 was replaced with 1-(2,4-difluorophenyl)ethanone.

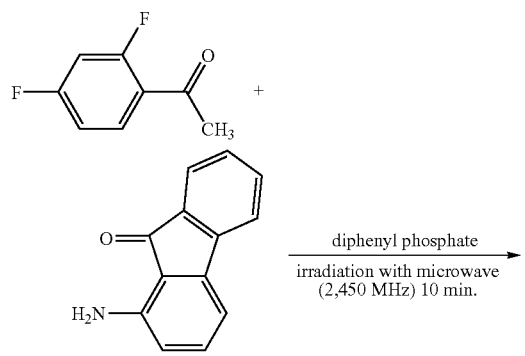

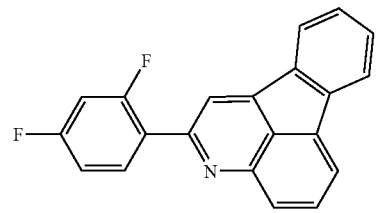

In a two-necked flask, $1.76 \times 10^{-1}$ mmol of iridium trichloride trihydrate, $5.63 \times 10^{-1}$ mmol of 2-(2,4-difluorophenyl)indeno[1,2,3-de]quinoline, 10 ml of 2-ethoxyethanol, and 3 ml of water were placed, and the resultant mixture was heated under reflux under argon atmosphere for 15 hours. The reaction solution was cooled to room temperature, concentrated under reduced pressure, and precipitated by addition of water, and the thus-formed dark brown solid was collected by filtration. The dark brown solid was washed with water, to give a target iridium complex (3-106). The isolation yield was 73%.

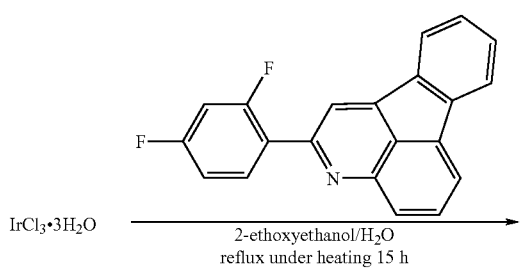

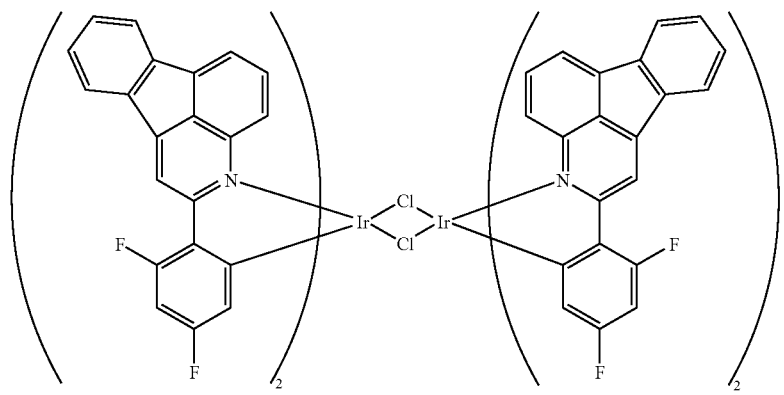

Example 30

Synthesis of Compound (3-105) of the Present Invention 2-(3-bromophenyl)indeno[1,2,3-de]quinoline was prepared in the same manner as in Example 1, except that acetophenone used in preparation of 2-phenylindeno[1,2,3-de]quinoline in Example 1 was replaced with 1-(3-bromophenyl)ethanone.

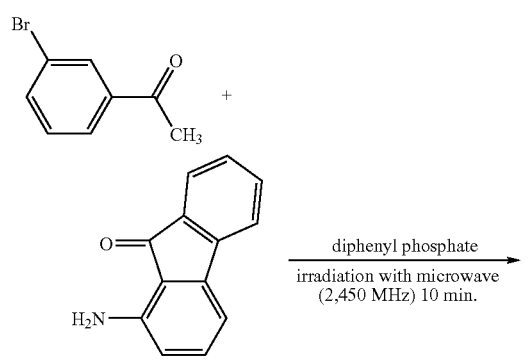

-continued

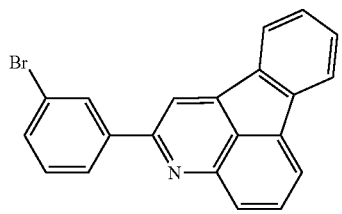

In a two-necked flask, $1.76 \times 10^{-1}$ mmol of iridium trichloride trihydrate, $5.63 \times 10^{-1}$ mmol of 2-(3-bromophenyl)indeno[1,2,3-de]quinoline, 10 ml of 2-ethoxyethanol, and 3 ml of water were placed, and the resultant mixture was heated under reflux under argon atmosphere for 15 hours. The reaction solution was cooled to room temperature, concentrated under reduced pressure, and precipitated by addition of water, and the thus-formed dark brown solid was collected by filtration. The dark brown solid was washed with water, to give a target iridium complex (3-105). The isolation yield was 83%.

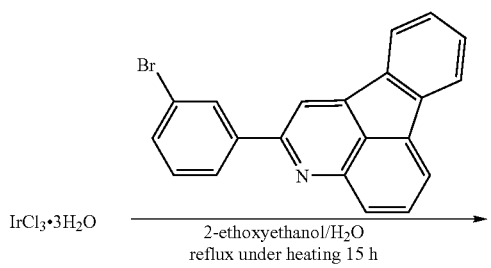

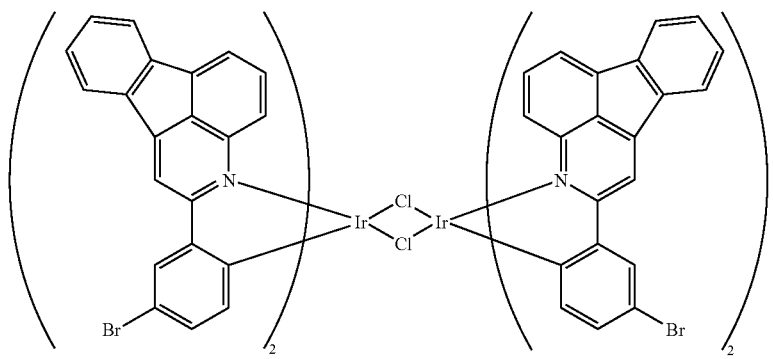

Example 31

Synthesis of Compound (3-53) of the Present Invention 2-(3-biphenyl)indeno[1,2,3-de]quinoline was prepared in the same manner as in Example 1, except that acetophenone used in preparation of 2-phenylindeno[1,2,3-de]quinoline in Example 1 was replaced with 3-acetylbiphenyl.

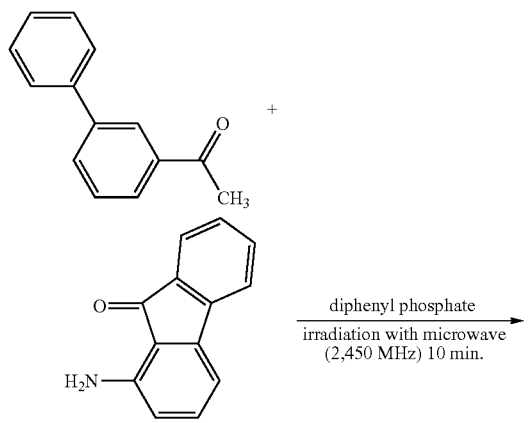

In a two-necked flask, $1.76 \times 10^{-1}$ mmol of iridium trichloride trihydrate, $5.63 \times 10^{-1}$ mmol of 2-(3-biphenyl)indeno[1,2,3-de]quinoline, 10 ml of 2-ethoxyethanol, and 3 ml of water were placed, and the resultant mixture was heated under reflux under argon atmosphere for 15 hours. The reaction solution was cooled to room temperature, concentrated under reduced pressure, and precipitated by addition of water, and the thus-formed dark brown solid was collected by filtration. The dark brown solid was washed with water, to give a target iridium complex (3-53). The isolation yield was 80%.

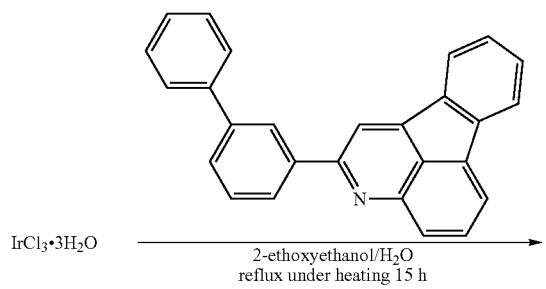

-continued

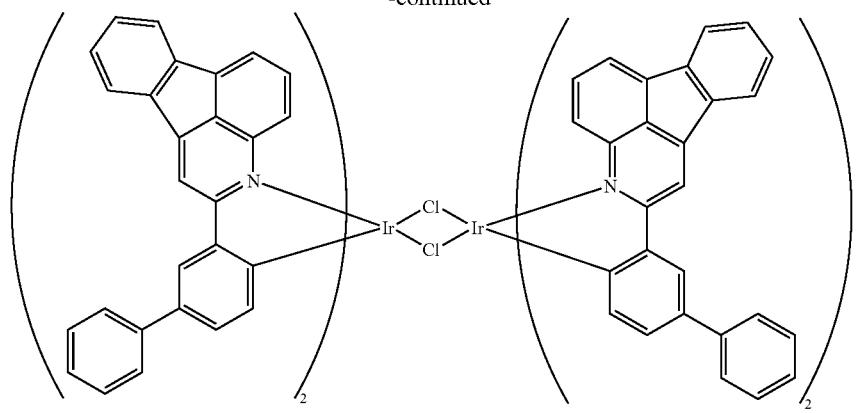

Example 32

Synthesis of Compound (3-70) of the Present Invention 2-(thiophene-2-yl)indeno[1,2,3-de]quinoline was prepared in the same manner as in Example 1, except that acetophenone used in preparation of 2-phenylindeno[1,2,3-de]quinoline in Example 1 was replaced with 1-(thiophene-2-yl)ethanone.

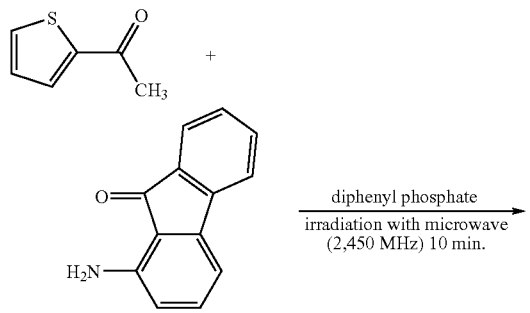

-continued

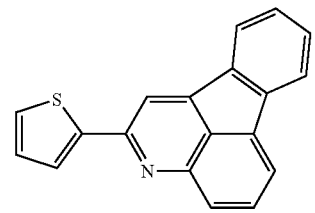

In a two-necked flask, $1.76 \times 10^{-1}$ mmol of iridium trichloride trihydrate, $5.63 \times 10^{-1}$ mmol of 2-(thiophene-2-yl)indeno[1,2,3-de]quinoline, 10 ml of 2-ethoxyethanol, and 3 ml of water were placed, and the resultant mixture was heated under reflux under argon atmosphere for 15 hours. The reaction solution was cooled to room temperature, concentrated under reduced pressure, and precipitated by addition of water, and the thus-formed dark brown solid was collected by filtration. The dark brown solid was washed with water, to give a target iridium complex (3-70). The isolation yield was 74%.

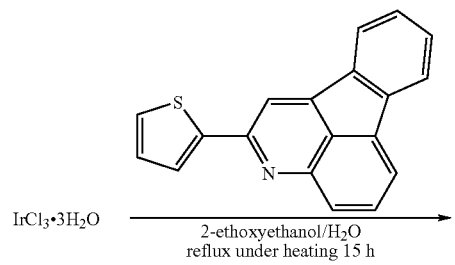

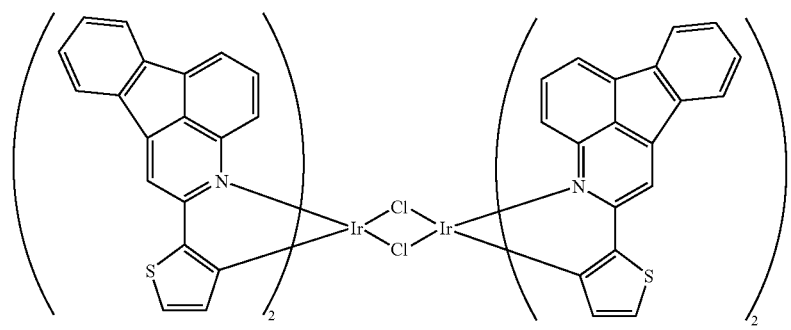

Example 33

Synthesis of Compound (3-44) of the Present Invention 2-(9H-fluorene-2-yl)indeno[1,2,3-de]quinoline was prepared in the same manner as in Example 1, except that acetophenone used in preparation of 2-phenylindeno[1,2,3-de]quinoline in Example 1 was replaced with 1-(9H-fluorene-2-yl)ethanone.

In a two-necked flask, $1.76 \times 10^{-1}$ mmol of iridium trichloride trihydrate, $5.63 \times 10^{-1}$ mmol of 2-(9H-fluorene-2-yl)indeno[1,2,3-de]quinoline, 10 ml of 2-ethoxyethanol, and 3 ml of water were placed, and the resultant mixture was heated under reflux under argon atmosphere for 15 hours. The reaction solution was cooled to room temperature, concentrated under reduced pressure, and precipitated by addition of water, and the thus-formed dark brown solid was collected by filtration. The dark brown solid was washed with water, to give a target iridium complex (3-44). The isolation yield was 79%.

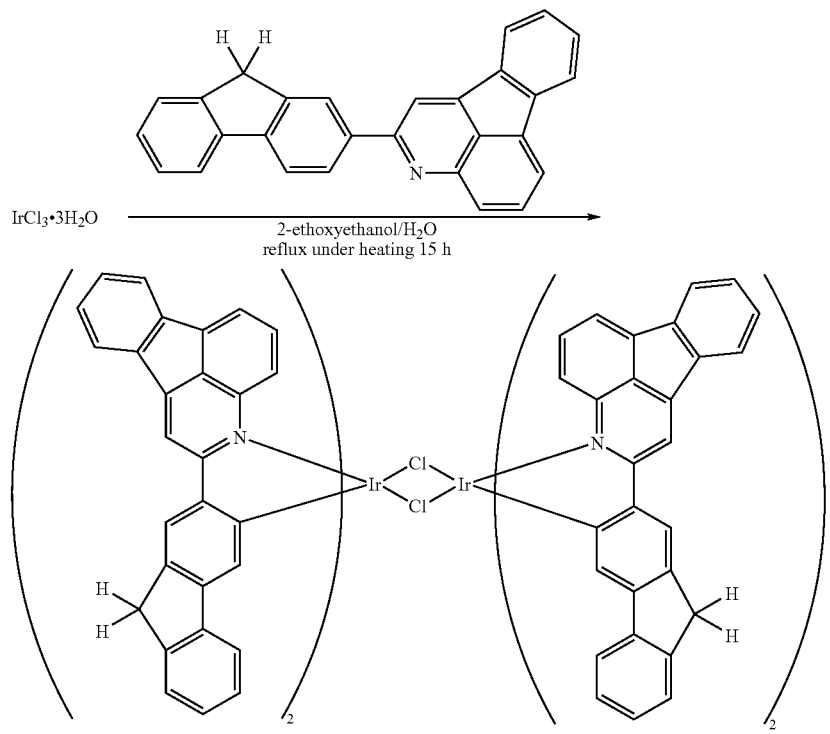

Example 34

Synthesis of Compound (3-50) of the Present Invention 2-(4-biphenyl)indeno[1,2,3-de]quinoline was prepared in the same manner as in Example 1, except that acetophenone used in preparation of 2-phenylindeno[1,2,3-de]quinoline in Example 1 was replaced with 4-acetylbiphenyl.

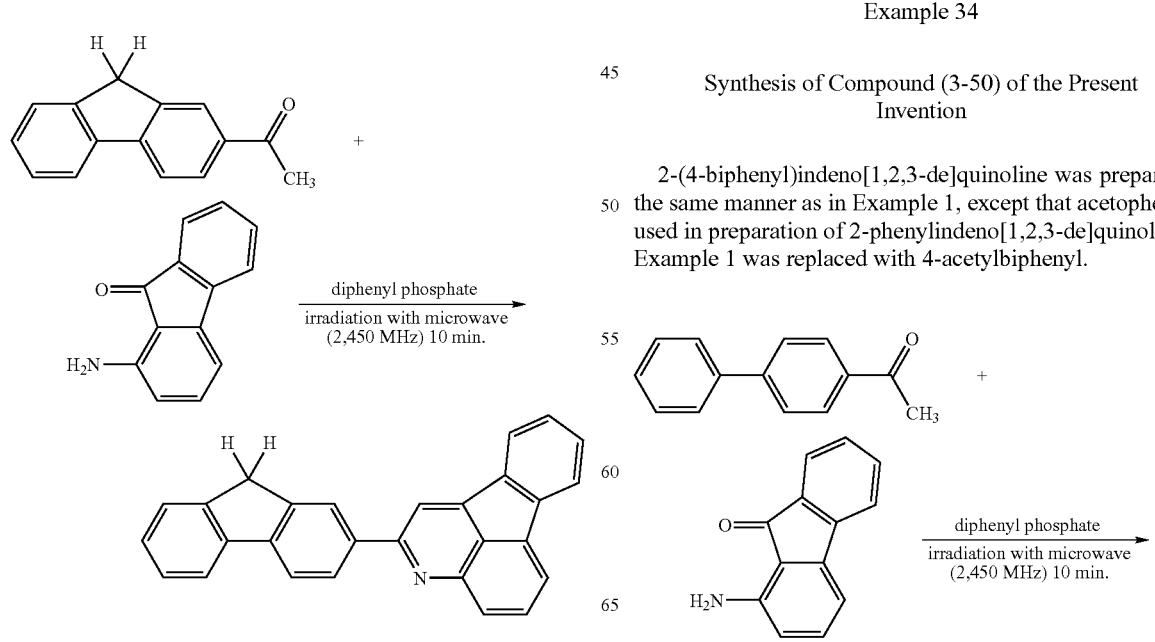

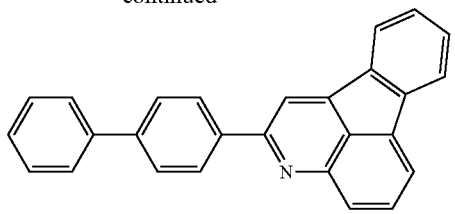

In a two-necked flask, $1.76 \times 10^{-1}$ mmol of iridium trichloride trihydrate, $5.63 \times 10^{-1}$ mmol of 2-(4-biphenyl)indeno[1,2,3-de]quinoline, 10 ml of 2-ethoxyethanol, and 3 ml of water were placed, and the resultant mixture was heated under reflux under argon atmosphere for 15 hours. The reaction solution was cooled to room temperature, concentrated under reduced pressure, and precipitated by addition of water, and the thus-formed dark brown solid was collected by filtration. The dark brown solid was washed with water, to give a target iridium complex (3-50). The isolation yield was 88%.

Example 35

Synthesis of Compound (2-490) of the Present Invention

In a round-bottomed flask, $6.42 \times 10^{-3}$ mmol of the compound (3-50) of the present invention, $1.66 \times 10^{-2}$ mmol of 2,2'-bipyridine, and 10 ml of 2-ethoxyethanol were placed, the resultant mixture was heated under reflux under argon atmosphere for 1 hour. The reaction solution was cooled to room temperature, concentrated under reduced pressure to remove the solvent, and precipitated by addition of saturated aqueous $NH_4PF_6$ solution, to give a red brown solid. The red brown solid was recrystallized from dichloromethane-hexane. Analysis by electrospray ionization mass spectrometry (ESI-MS) identified the parent ion peak (m/z=1058) of the target iridium complex (2-480).

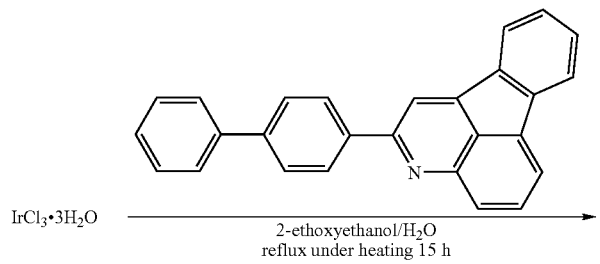

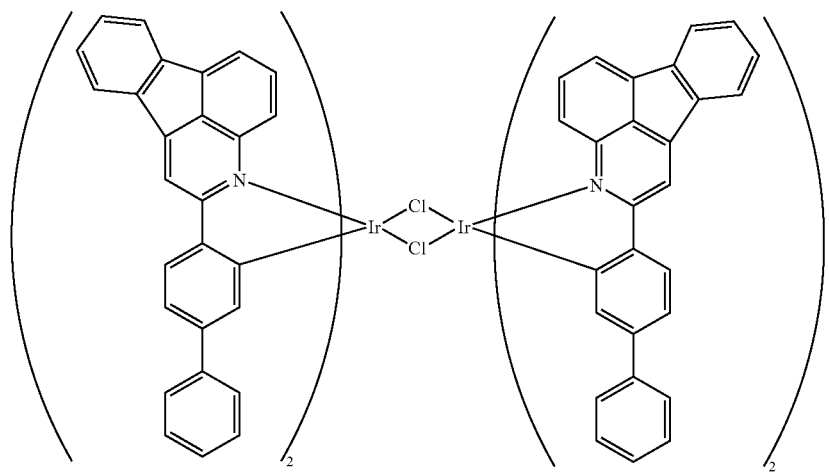

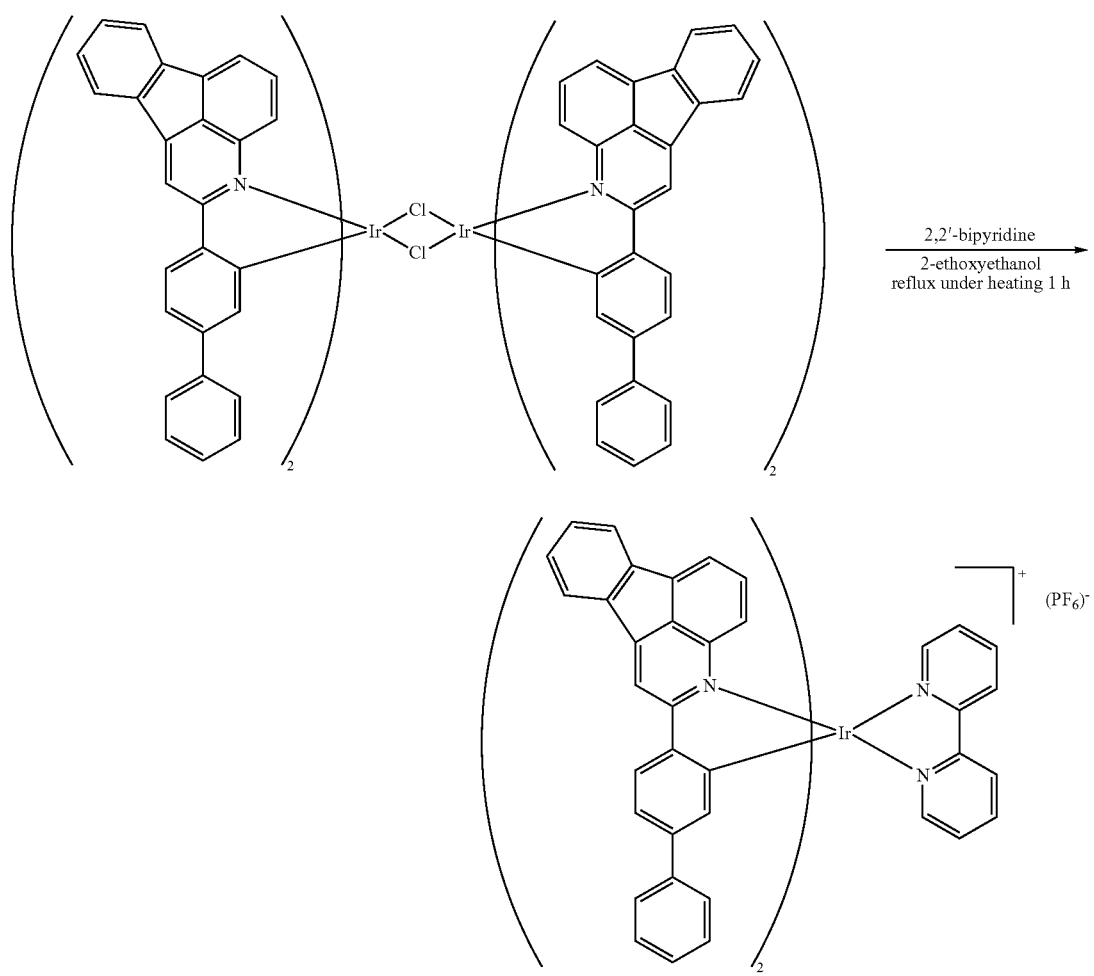

Example 36

Synthesis of Compound (3-111) of the Present Invention 2-(3,5-bis(trifluoromethyl)phenyl)indeno[1,2,3-de]quinoline was prepared in the same manner as in Example 1, except that acetophenone used in preparation of 2-phenylindeno[1,2,3-de]quinoline in Example 1 was replaced with 1-(3,5-bis(trifluoromethyl)phenyl)ethanone.

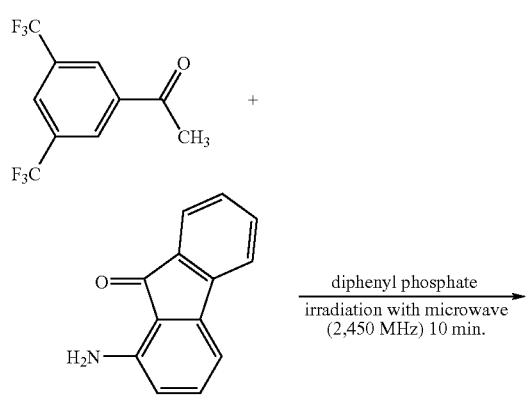

-continued

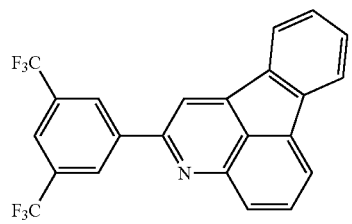

In a two-necked flask, $1.76 \times 10^{-1}$ mmol of iridium trichloride trihydrate, $5.63 \times 10^{-1}$ mmol of 2-(3,5-bis(trifluoromethyl)phenyl)indeno[1,2,3-de]quinoline, 10 ml of 2-ethoxyethanol, and 3 ml of water were placed, and the resultant mixture was heated under reflux under argon atmosphere for 15 hours. The reaction solution was cooled to room temperature, concentrated under reduced pressure, and precipitated by addition of water, and the thus-formed dark brown solid was collected by filtration. The dark brown solid was washed with water, to give a target iridium complex (3-111). The isolation yield was 73%.

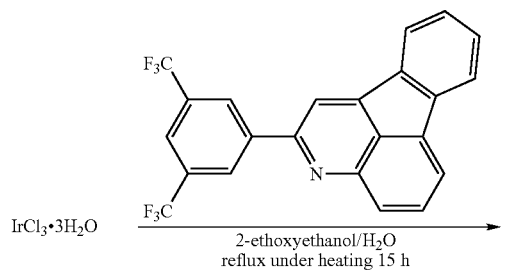

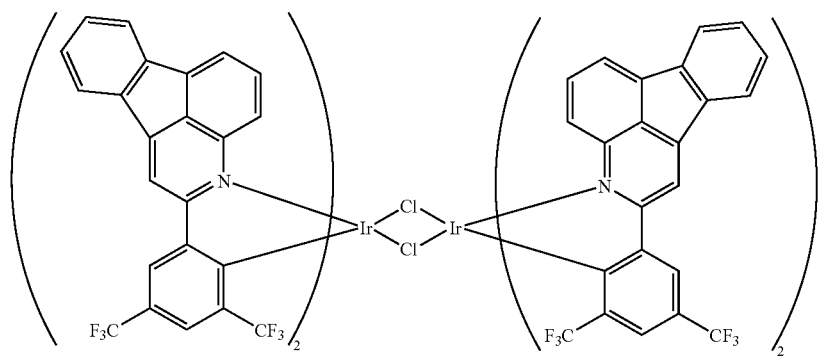

Example 37

Synthesis of Compound (3-83) of the Present Invention 2-(benzofuran-2-yl)indeno[1,2,3-de]quinoline was prepared in the same manner as in Example 1, except that acetophenone used in preparation of 2-phenylindeno[1,2,3-de]quinoline in Example 1 was replaced with 1-(benzofuran-2-yl)ethanone.

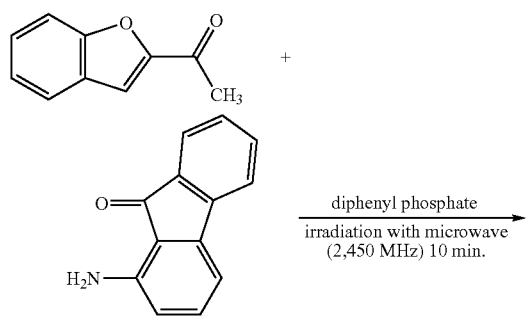

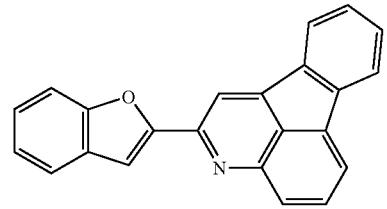

In a two-necked flask, $1.76 \times 10^{-1}$ mmol of iridium trichloride trihydrate, $5.63 \times 10^{-1}$ mmol of 2-(benzofuran-2-yl)indeno[1,2,3-de]quinoline, 10 ml of 2-ethoxyethanol, and 3 ml of water were placed, and the resultant mixture was heated under reflux under argon atmosphere for 15 hours. The reaction solution was cooled to room temperature, concentrated under reduced pressure, and precipitated by addition of water, and the thus-formed dark brown solid was collected by filtration. The dark brown solid was washed with water, to give a target iridium complex (3-83). The isolation yield was 50%.

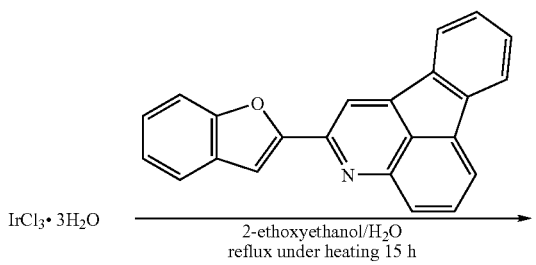

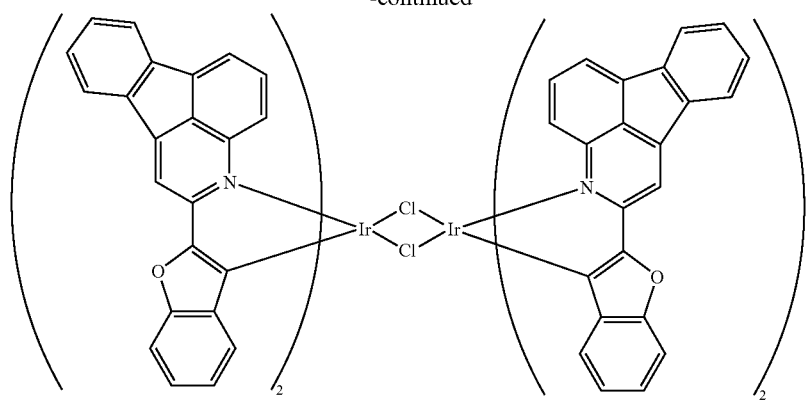

Example 38

Synthesis of Compound (2-357) of the Present Invention

In a two-necked flask, 0.205 mmol of iridium trisacetylacetonate, 0.82 mmol of 2-(4-fluorophenyl)indeno[1,2,3-de]quinoline, and 10 ml of glycerin were placed, the resultant mixture was allowed to react under heating under argon atmosphere at 195° C. for 7 hours. The reaction solution was cooled to room temperature and precipitated by addition of 60 ml of 1M hydrochloric acid solution, and the dark brown solid thus obtained was collected by filtration. The dark brown solid was washed with water and separated and purified by silica gel column chromatography (eluant: mixed solvent of dichloromethane and hexane), to give a target iridium complex (2-357). The isolation yield was 35%.

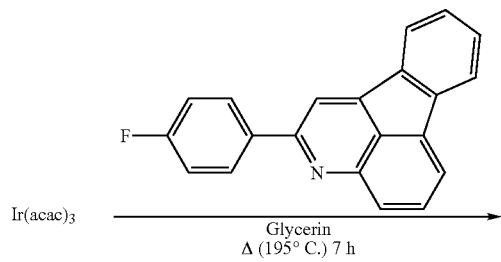

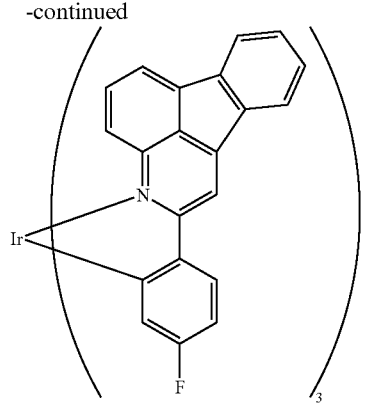

$^1$H-NMR (in CDCl$_3$) δ 8.46 (s, 3H), 7.97 (d, 3H), 7.93 (t, 3H), 7.76 (d, 3H), 7.49 (d, 3H), 7.40-7.46 (m, 6H), 7.29 (d, 3H), 6.82 (t, 3H), 6.63 (dd, 3H), 6.18 (d, 3H).

Example 39

Synthesis of Compound (2-491) of the Present Invention

The compound (2-491) of the present invention was prepared in the same manner as in Example 6, except that 2,2'-bipyridine was replaced with 1,10-phenanthroline-5-amine. Analysis by electrospray ionization mass spectrometry (ESI-MS) identified the parent ion peak (m/z=944) of the target iridium complex (2-491).

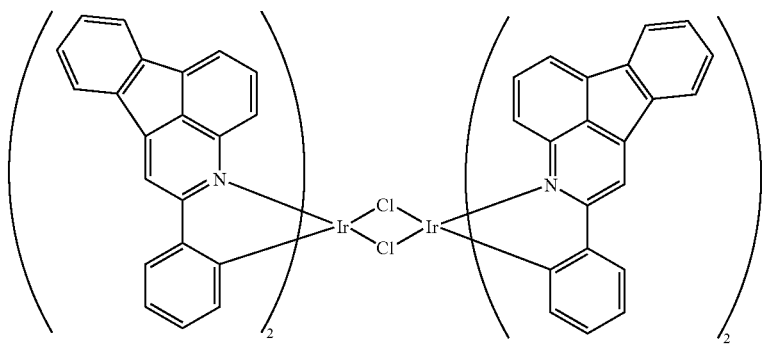
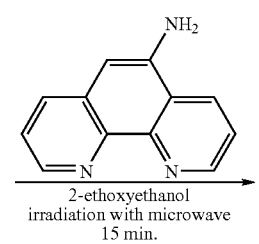

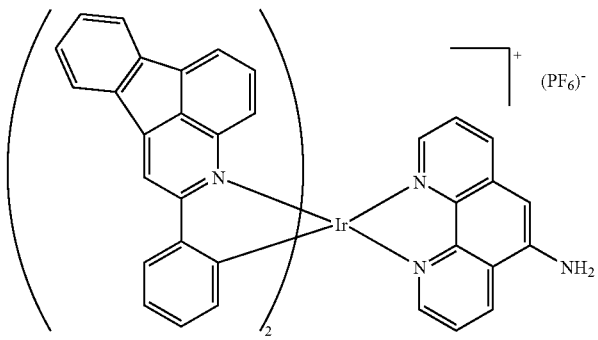

Example 40

Synthesis of Compound (2-492) of the Present Invention

The compound (2-492) of the present invention was prepared in the same manner as in Example 6, except that 2,2'-bipyridine was replaced with 4,7-dimethyl-1,10-phenanthroline. Analysis by electrospray ionization mass spectrometry (ESI-MS) identified the parent ion peak (m/z=957) of the target iridium complex (2-492).

Example 41

Synthesis of Compound (2-493) of the Present Invention

The compound (2-493) of the present invention was prepared in the same manner as in Example 6, except that 2,2'-bipyridine was replaced with 4,4'-dimethoxy-2,2'-bipyridine. Analysis by electrospray ionization mass spectrometry (ESI-MS) identified the parent ion peak (m/z=965) of the target iridium complex (2-493).

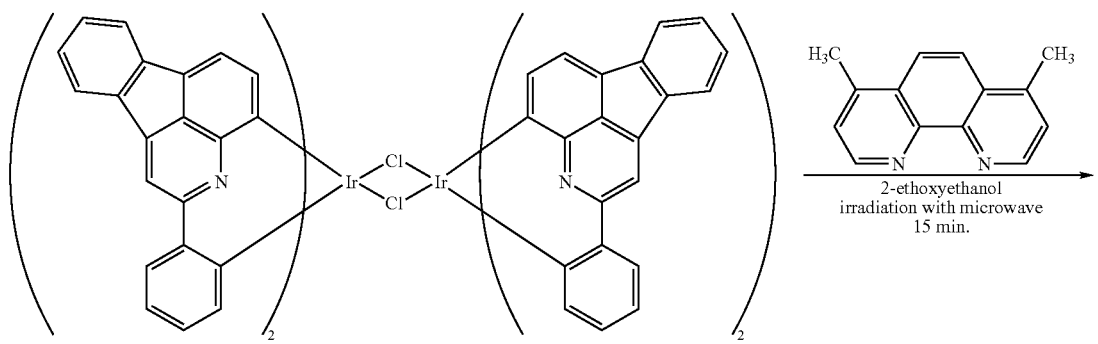

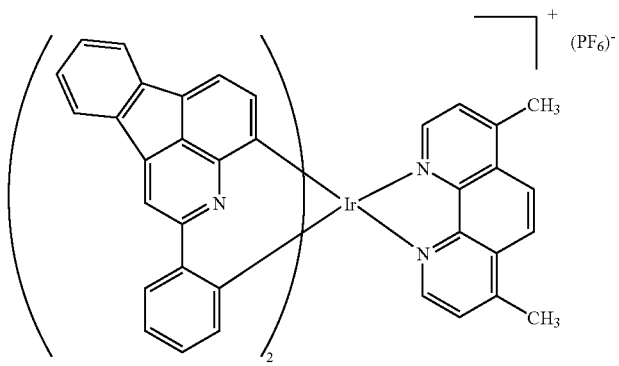

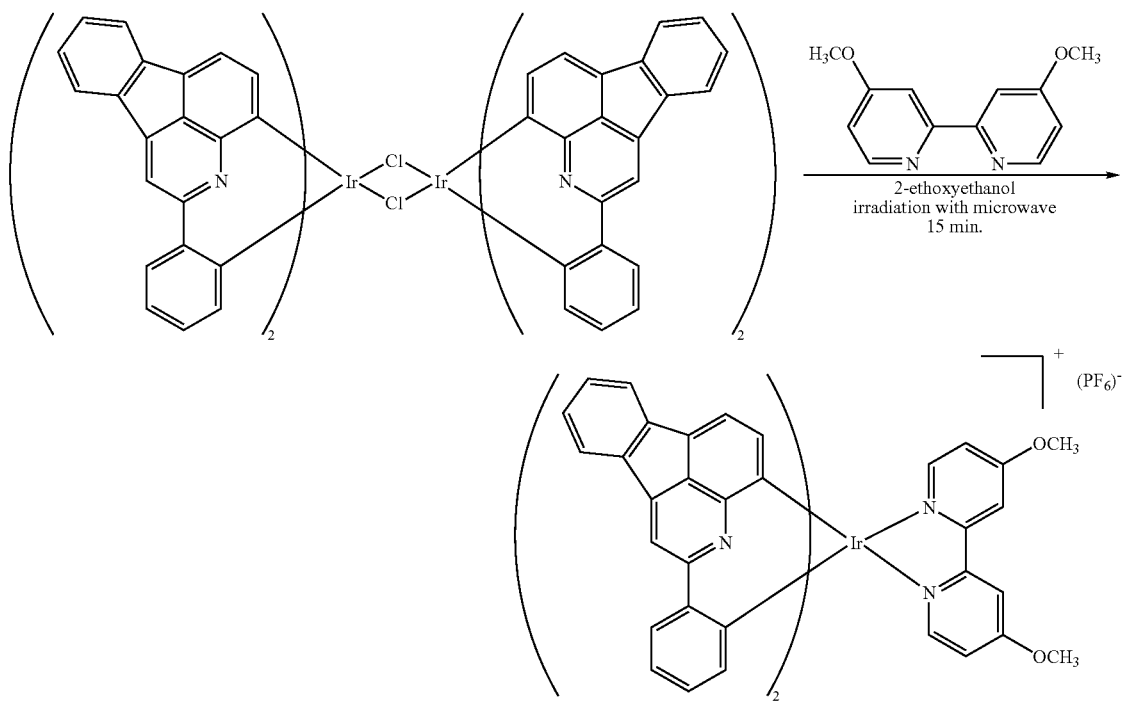
Example 42
Synthesis of Compound (2-494) of the Present Invention
The compound (2-494) of the present invention was prepared in the same manner as in Example 6, except that 2,2'-bipyridine was replaced with 5-chloro-1,10-phenanthroline. Analysis by electrospray ionization mass spectrometry (ESI-MS) identified the parent ion peak (m/z=964) of the target iridium complex (2-494).
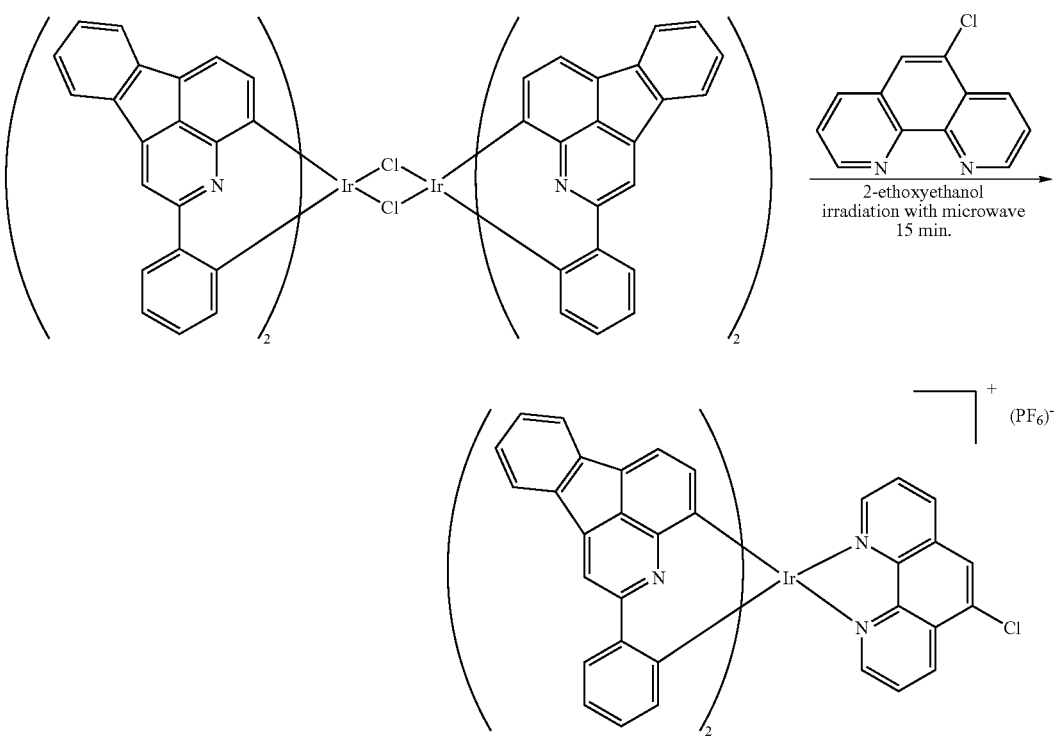

Example 43

Synthesis of Compound (2-495) of the Present Invention

The compound (2-495) of the present invention was prepared in the same manner as in Example 6, except that 2,2'-bipyridine was replaced with 2,2'-bipyridine-4,4'-dicarboxylic aldehyde. Analysis by electrospray ionization mass spectrometry (ESI-MS) identified the parent ion peak (m/z=961) of the target iridium complex (2-495).

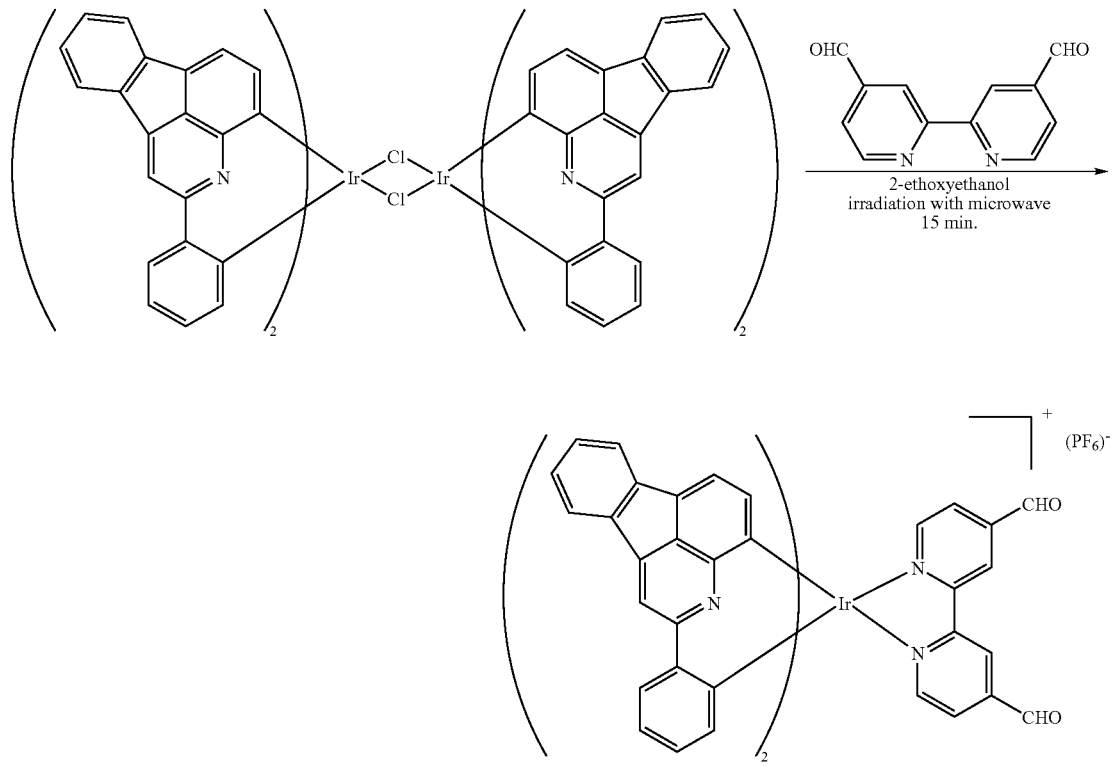

Example 44

Synthesis of Compound (2-496) of the Present Invention

The compound (2-496) of the present invention was prepared in the same manner as in Example 6, except that 2,2'-bipyridine was replaced with 4,4'-dinonyl-2,2'-dipyridyl. Analysis by electrospray ionization mass spectrometry (ESI-MS) identified the parent ion peak (m/z=1158) of the target iridium complex (2-496).

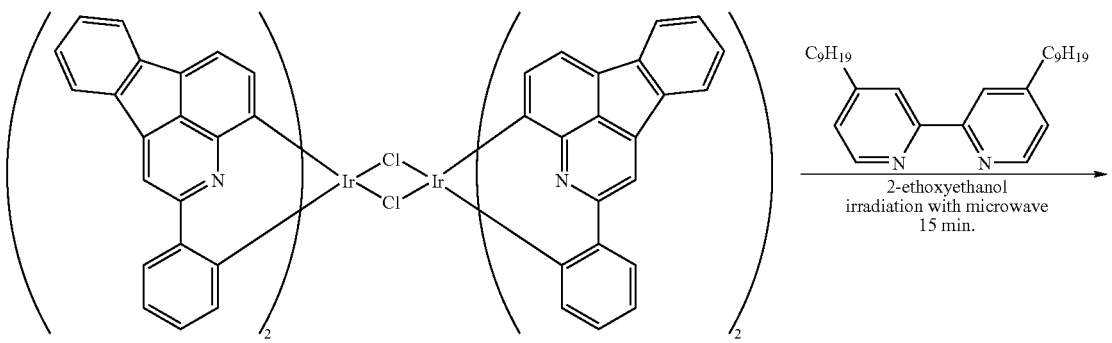

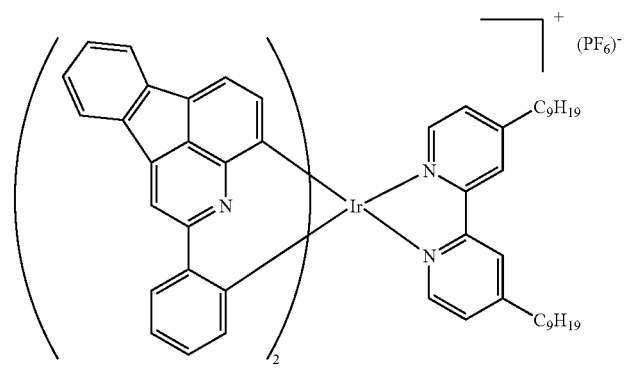

Example 45

Synthesis of Compound (2-497) of the Present Invention

The compound (2-497) of the present invention was prepared in the same manner as in Example 6, except that 2,2'-bipyridine was replaced with 5,6-dimethyl-1,10-phenanthroline. Analysis by electrospray ionization mass spectrometry (ESI-MS) identified the parent ion peak (m/z=957) of the target iridium complex (2-497).

Example 46

Synthesis of Compound (2-498) of the Present Invention

The compound (2-498) of the present invention was prepared in the same manner as in Example 6, except that 2,2'-bipyridine was replaced with bathophenanthroline. Analysis by electrospray ionization mass spectrometry (ESI-MS) identified the parent ion peak (m/z=1081) of the target iridium complex (2-498).

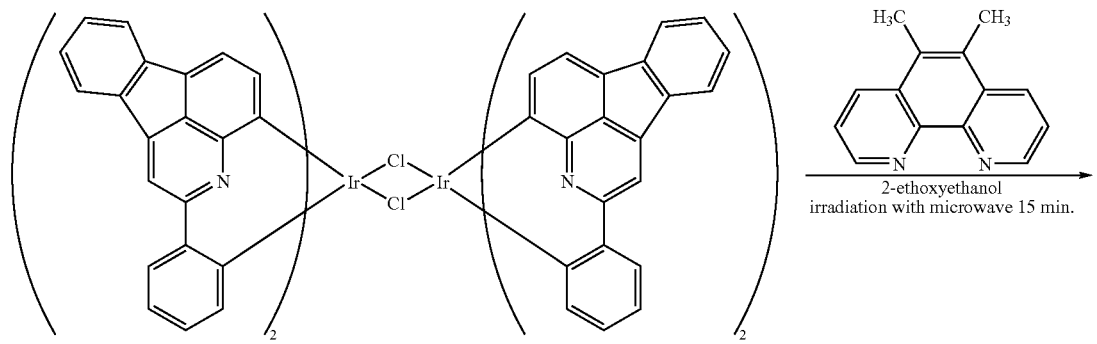

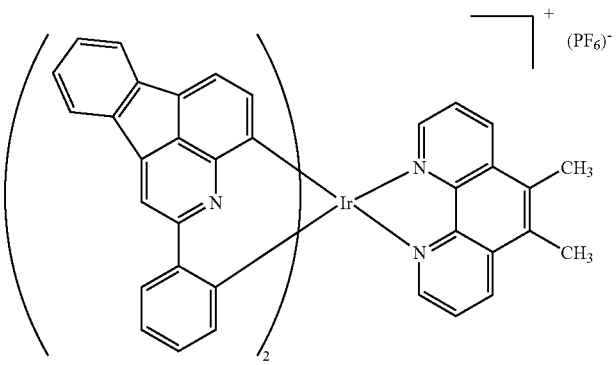

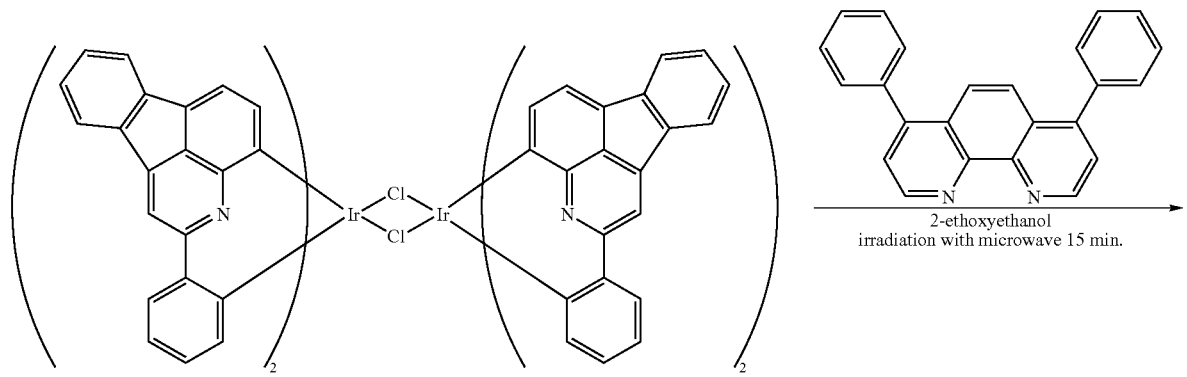
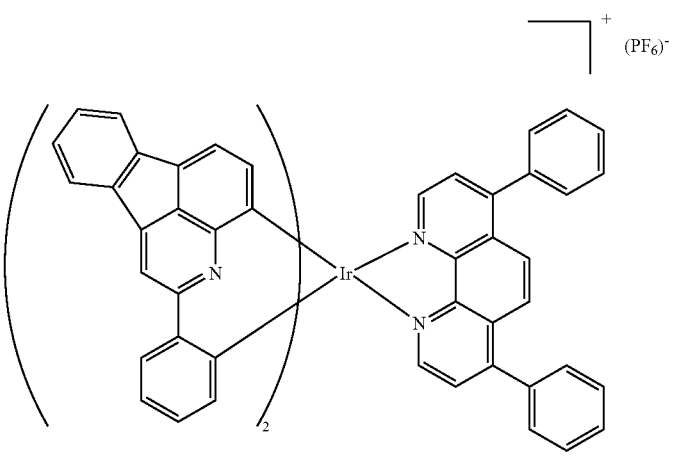
Example 47
Synthesis of Compound (2-499) of the Present Invention
The compound (2-499) of the present invention was prepared in the same manner as in Example 6, except that 2,2'-bipyridine was replaced with 1,10-phenanthroline. Analysis by electrospray ionization mass spectrometry (ESI-MS) identified the parent ion peak (m/z=929) of the target iridium complex (2-499).
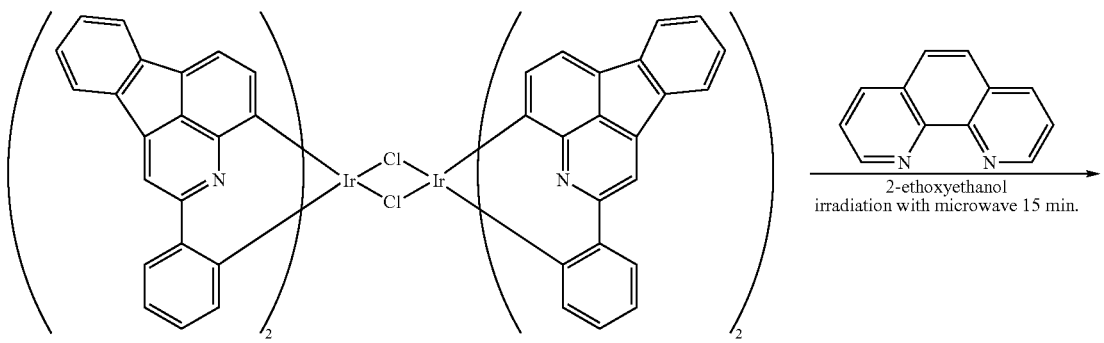

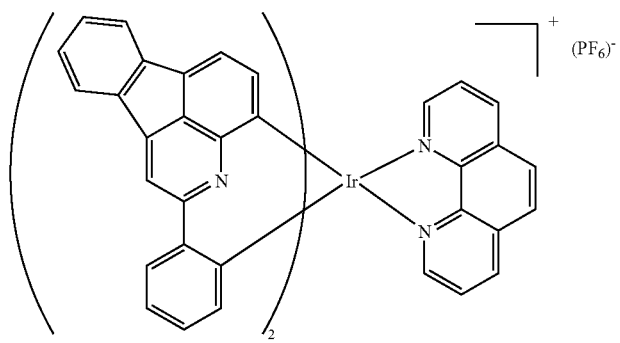

Example 48

Synthesis of Compound (2-500) of the Present Invention

The compound (2-500) of the present invention was prepared in the same manner as in Example 6, except that 2,2'-bipyridine was replaced with 4,4'-dimethyl-2,2'-dipyridyl. Analysis by electrospray ionization mass spectrometry (ESI-MS) identified the parent ion peak (m/z=933) of the target iridium complex (2-500).

Example 49

Synthesis of Compound (2-501) of the Present Invention

The compound (2-501) of the present invention was prepared in the same manner as in Example 6, except that 2,2'-bipyridine was replaced with N-methyl-N-(pyridine-2-yl)pyridine-2-amine. Analysis by electrospray ionization mass spectrometry (ESI-MS) identified the parent ion peak (m/z=934) of the target iridium complex (2-501).

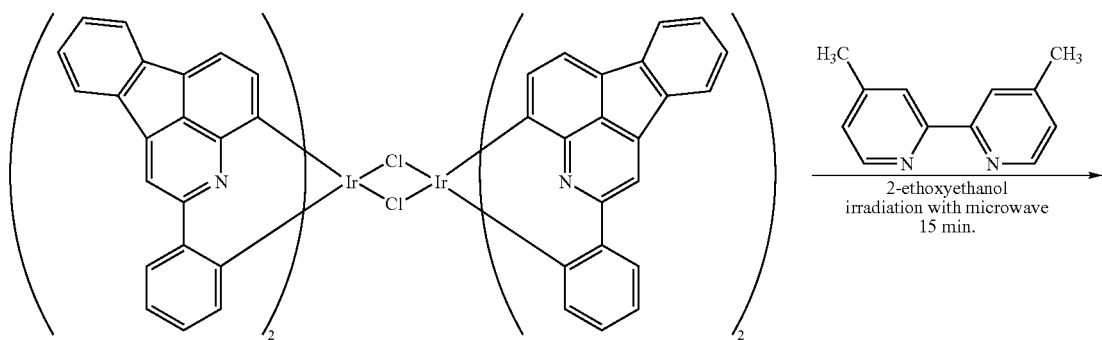

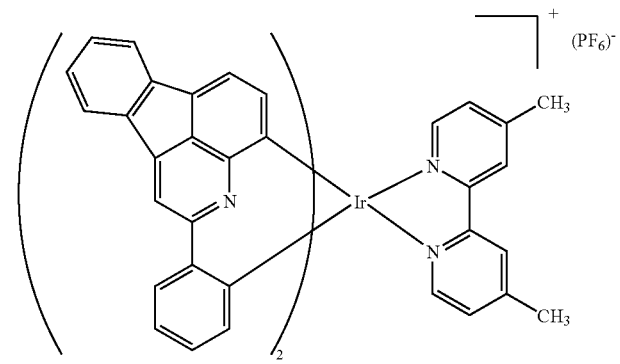

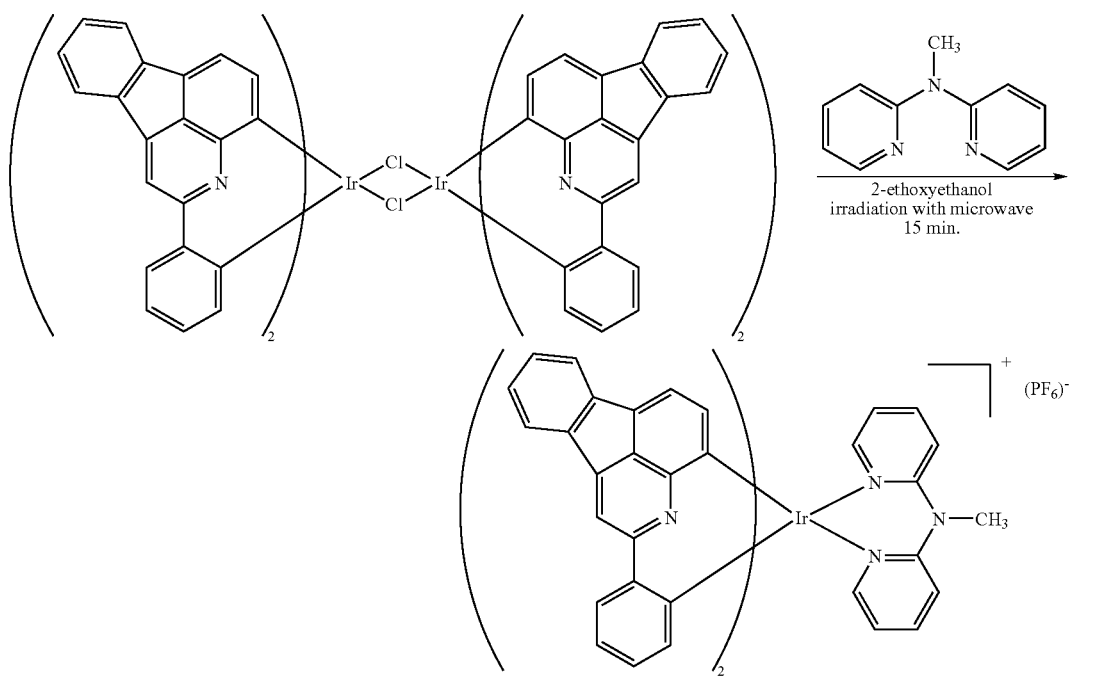
Example 50
Synthesis of Compound (2-617) of the Present Invention
The compound (2-617) of the present invention was prepared in the same manner as in Example 6, except that 2,2'-bipyridine was replaced with cis-1,2-bis(diphenylphosphino) ethylene. Analysis by electrospray ionization mass spectrometry (ESI-MS) identified the parent ion peak (m/z=1145) of the target iridium complex (2-617).
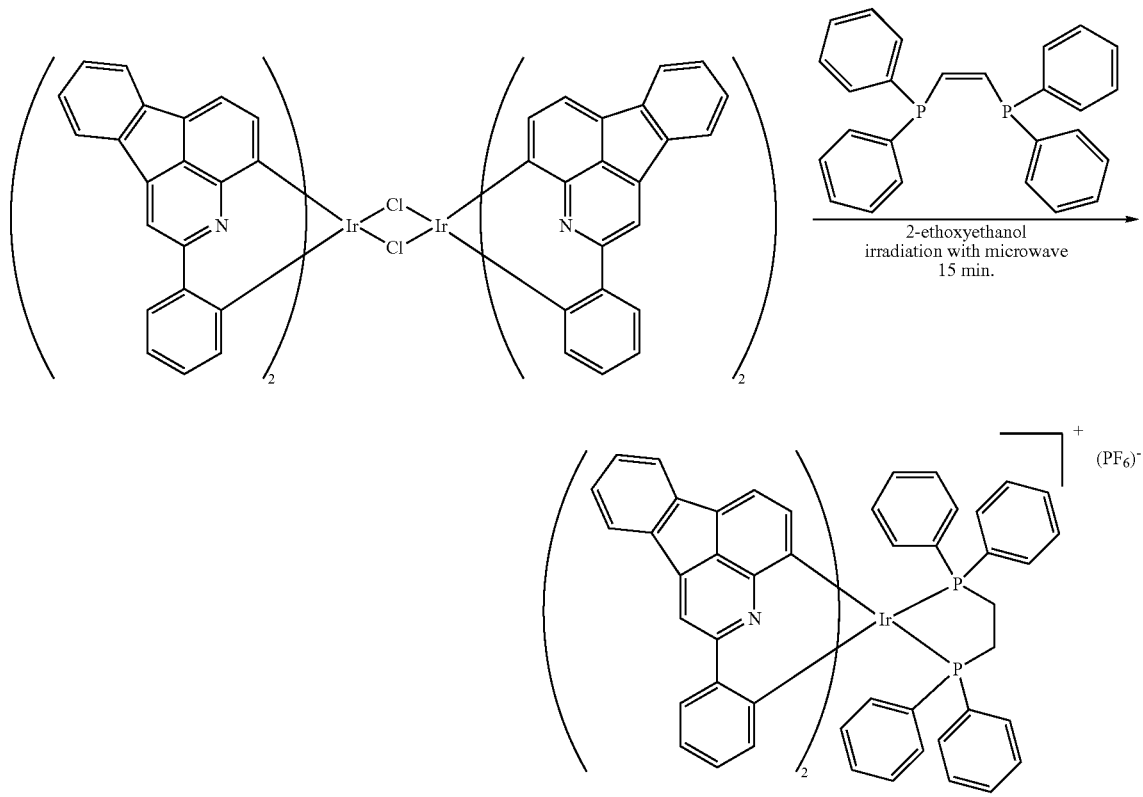

Emission characteristics of the compounds of the present invention will be described below.

Example 51

Emission of Compound (3-43) of the Present Invention

The compound (3-43) of the present invention was dissolved in THF, the resultant solution was purged with argon gas, and thus the emission spectrum of the compound (excitation wavelength: 340 nm) was determined at room temperature, by using RF-5300PC, manufactured by Shimadzu Corp. The compound showed strong red emission (maximum emission wavelength: 674 nm). The emission quantum yield was determined to be 0.13 (as a standard, using the quantum yield 0.546 of quinine sulfate salt in 0.5M sulfuric acid solution), according to the method described in "New Experimental Chemistry Lectures 4, Basic Techniques 3, Photochemistry (II), Chapter 8, Measurement of fluorescence and phosphorescence" (published by Maruzen Co., Ltd.).

Example 52

Emission of Compound (2-211) of the Present Invention

The compound (2-211) of the present invention was dissolved in THF, the resultant solution was purged with argon gas, and thus the emission spectrum of the compound (excitation wavelength: 340 nm) was determined at room temperature, by using RF-5300PC, manufactured by Shimadzu Corp. The compound showed strong red emission (maximum emission wavelength: 694 nm). The mission quantum yield was determined to be 0.18 (as a standard, using the quantum yield 0.546 of quinine sulfate salt in 0.5M sulfuric acid solution), according to the method described in "New Experimental Chemistry Lectures 4, Basic Techniques 3, Photochemistry (II), Chapter 8, Measurement of fluorescence and phosphorescence" (published by Maruzen Co., Ltd.).

Example 53

Emission of Compound (2-295) of the Present Invention

The compound (2-295) of the present invention was dissolved in THF, the resultant solution was purged with argon gas, and thus the emission spectrum of the compound (excitation wavelength: 340 nm) was determined at room temperature, by using RF-5300PC, manufactured by Shimadzu Corp. The compound showed strong red emission (maximum emission wavelength: 653 nm). The emission quantum yield was determined to be 0.54 (as a standard, using the quantum yield 0.546 of quinine sulfate salt in 0.5M sulfuric acid solution), according to the method described in "New Experimental Chemistry Lectures 4, Basic Techniques 3, Photochemistry (II), Chapter 8, Measurement of fluorescence and phosphorescence" (published by Maruzen Co., Ltd.).

Example 54

Emission of Compound (2-411) of the Present Invention

The compound (2-411) of the present invention was dissolved in THF, the resultant solution was purged with argon gas, and thus the emission spectrum of the compound (excitation wavelength: 340 nm) was determined at room temperature, by using RF-5300PC, manufactured by Shimadzu Corp. The compound showed strong red emission (maximum emission wavelength: 650 nm). The emission quantum yield was determined to be 0.49 (as a standard, using the quantum yield 0.546 of quinine sulfate salt in 0.5M sulfuric acid solution), according to the method described in "New Experimental Chemistry Lectures 4, Basic Techniques 3, Photochemistry (II), Chapter 8, Measurement of fluorescence and phosphorescence" (published by Maruzen Co., Ltd.).

Example 55

Emission of Compound (2-410) of the Present Invention

The compound (2-410) of the present invention was dissolved in THF, the resultant solution was purged with argon gas, and thus the emission spectrum of the compound (excitation wavelength: 340 nm) was determined at room temperature, by using RF-5300PC, manufactured by Shimadzu Corp. The compound showed strong red emission (maximum emission wavelength: 650 nm). The emission quantum yield was determined to be 0.60 (as a standard, using the quantum yield 0.546 of quinine sulfate salt in 0.5M sulfuric acid solution), according to the method described in "New Experimental Chemistry Lectures 4, Basic Techniques 3, Photochemistry (II), Chapter 8, Measurement of fluorescence and phosphorescence" (published by Maruzen Co., Ltd.).

Example 56

Emission of Compound (2-413) of the Present Invention

The compound (2-413) of the present invention was dissolved in THF, the resultant solution was purged with argon gas, and thus the emission spectrum of the compound (excitation wavelength: 340 nm) was determined at room temperature, by using RF-5300PC, manufactured by Shimadzu Corp. The compound showed strong red emission (maximum emission wavelength: 597 nm, 648 nm). The emission quantum yield was determined to be 0.07 (as a standard, using the quantum yield 0.546 of quinine sulfate salt in 0.5M sulfuric acid solution), according to the method described in "New Experimental Chemistry Lectures 4, Basic Techniques 3, Photochemistry (II), Chapter 8, Measurement of fluorescence and phosphorescence" (published by Maruzen Co., Ltd.).

Example 57

Emission of Compound (2-431) of the Present Invention

The compound (2-431) of the present invention was dissolved in THF, the resultant solution was purged with argon gas, and thus the emission spectrum of the compound (excitation wavelength: 340 nm) was determined at room temperature, by using RF-5300PC, manufactured by Shimadzu Corp. The compound showed strong red emission (maximum emission wavelength: 683 nm). The emission quantum yield was determined to be 0.28 (as a standard, using the quantum yield 0.546 of quinine sulfate salt in 0.5M sulfuric acid solution), according to the method described in "New Experimental Chemistry Lectures 4, Basic Techniques 3, Photochemistry (II), Chapter 8, Measurement of fluorescence and phosphorescence" (published by Maruzen Co., Ltd.).

Example 58

Emission of Compound (3-74) of the Present Invention

The compound (3-74) of the present invention was dissolved in THF, the resultant solution was purged with argon gas, and thus the emission spectrum of the compound (excitation wavelength: 340 nm) was determined at room temperature, by using RF-5300PC, manufactured by Shimadzu Corp. The compound showed strong red emission (maximum emission wavelength: 400 nm). The emission quantum yield was determined to be 0.13 (as a standard, using the quantum yield 0.546 of quinine sulfate salt in 0.5M sulfuric acid solution), according to the method described in "New Experimental Chemistry Lectures 4, Basic Techniques 3, Photochemistry (II), Chapter 8, Measurement of fluorescence and phosphorescence" (published by Maruzen Co., Ltd.).

Example 59

Emission of Compound (3-67) of the Present Invention

The compound (3-67) of the present invention was dissolved in THF, the resultant solution was purged with argon gas, and thus the emission spectrum of the compound (excitation wavelength: 400 nm) was determined at room temperature, by using RF-5300PC, manufactured by Shimadzu Corp. The compound showed strong red emission (maximum emission wavelength: 696 nm). The emission quantum yield was determined to be 0.37 (as a standard, using the quantum yield 0.546 of quinine sulfate salt in 0.5M sulfuric acid solution), according to the method described in "New Experimental Chemistry Lectures 4, Basic Techniques 3, Photochemistry (II), Chapter 8, Measurement of fluorescence and phosphorescence" (published by Maruzen Co., Ltd.).

Example 60

Emission of Compound (2-476) of the Present Invention

The compound (2-476) of the present invention was dissolved in THF, the resultant solution was purged with argon gas, and thus the emission spectrum of the compound (excitation wavelength: 340 nm) was determined at room temperature, by using RF-5300PC, manufactured by Shimadzu Corp. The compound showed strong red emission (maximum emission wavelength: 654 nm). The emission quantum yield was determined to be 0.47 (as a standard, using the quantum yield 0.546 of quinine sulfate salt in 0.5M sulfuric acid solution), according to the method described in "New Experimental Chemistry Lectures 4, Basic Techniques 3, Photochemistry (II), Chapter 8, Measurement of fluorescence and phosphorescence" (published by Maruzen Co., Ltd.).

Example 61

Emission of Compound (2-477) of the Present Invention

The compound (2-477) of the present invention was dissolved in THF, the resultant solution was purged with argon gas, and thus the emission spectrum of the compound (excitation wavelength: 340 nm) was determined at room temperature, by using RF-5300PC, manufactured by Shimadzu Corp. The compound showed strong red emission (maximum emission wavelength: 696 nm). The emission quantum yield was determined to be 0.16 (as a standard, using the quantum yield 0.546 of quinine sulfate salt in 0.5M sulfuric acid solution), according to the method described in "New Experimental Chemistry Lectures 4, Basic Techniques 3, Photochemistry (II), Chapter 8, Measurement of fluorescence and phosphorescence" (published by Maruzen Co., Ltd.).

Example 62

Emission of Compound (2-43) of the Present Invention

The compound (2-43) of the present invention was dissolved in THF, the resultant solution was purged with argon gas, and thus the emission spectrum of the compound (excitation wavelength: 350 nm) was determined at room temperature, by using Absolute PL Quantum Yield Analyzer (C9920-02), manufactured by Hamamatsu Photonics K.K. The compound showed strong red emission (maximum emission wavelength: 707 nm). The emission quantum yield was 0.14.

Example 63

Emission of Compound (2-357) of the Present Invention

The compound (2-357) of the present invention was dissolved in THF, the resultant solution was purged with argon gas, and thus the emission spectrum of the compound (excitation wavelength: 350 nm) was determined at room temperature, by using Absolute PL Quantum Yield Analyzer (09920-02), manufactured by Hamamatsu Photonics K.K. The compound showed strong red emission (maximum emission wavelength: 664 nm). The emission quantum yield was 0.26.

Example 64

Emission of Compound (2-496) of the Present Invention

The compound (2-496) of the present invention was dissolved in THF, the resultant solution was purged with argon gas, and thus the emission spectrum of the compound (excitation wavelength: 350 nm) was determined at room temperature, by using Absolute PL Quantum Yield Analyzer (C9920-02), manufactured by Hamamatsu Photonics K.K. The compound showed strong red emission (maximum emission wavelength: 635 nm). The emission quantum yield was 0.54.

Comparative Example 1

Tris(2-phenylpyridine) iridium complex described in the above Patent Document 1, showed green emission (maximum emission wavelength: 513 nm) in THF.

From the examples above, it is made apparent that the metal coordination compounds of the present invention represented by formula (1), (2) or (11) exhibit excellent emission characteristics in the visible light region (red region). Further, it is made apparent that it is possible to adjust the emission wavelength, by introducing various substituents into the ligands of the metal coordination compounds of the present invention, or by changing the ligands L. Thus, the metal coordination compounds of the present invention can be used in various applications such as, organic electroluminescent device materials, electrochemiluminescence (ECL) device materials, emission sensors, photosensitizers, displays, photographic materials, laser dyes, color filter dyes, optical communications, color conversion filters, backlights, illuminations, photosensitizing dyes, and various light sources.

The invention claimed is:

1. A metal coordination compound, of the structure represented by formula (1):

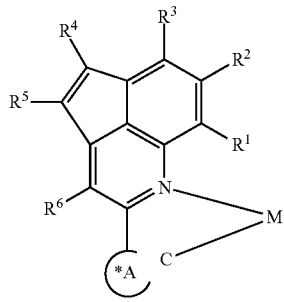

Formula (1)

*A means Ring A wherein, in formula (1), M represents a platinum group element; N represents a nitrogen atom; C represents a carbon atom; $R^1$ to $R^3$ and $R^6$ represent a hydrogen atom or an alkyl group having 1 to 30 carbon atoms which is unsubstituted or substituted; $R^4$ and $R^5$ represent a hydrogen atom, an alkyl group having 1 to 30 carbon atoms which is unsubstituted or substituted; or are bonded to each other, to form an unsubstituted phenyl ring structure; and the ring A represents an aromatic hydrocarbon ring or an aromatic hetero ring, each of which ring may have a substituent selected from the group consisting of a trifluoromethyl group, a halogen atom, an alkyl group having 1 to 30 carbon atoms, and an aryl group having 6 to 30 carbon atoms, each of which is unsubstituted or substituted.

2. The metal coordination compound according to claim 1, wherein the ring A is a benzene ring, a substituted benzene ring, a naphthalene ring, a substituted naphthalene ring, a thiophene ring, a substituted thiophene ring, a furan ring, a substituted furan ring, a fluorene ring, or a substituted fluorene ring.

3. The metal coordination compound according to claim 1, wherein M is iridium.

4. A light-emitting material, comprising the metal coordination compound according to claim 1.

5. A light-emitting device, comprising the light-emitting material according to claim 4.

6. A metal coordination compound, represented by formula (2):

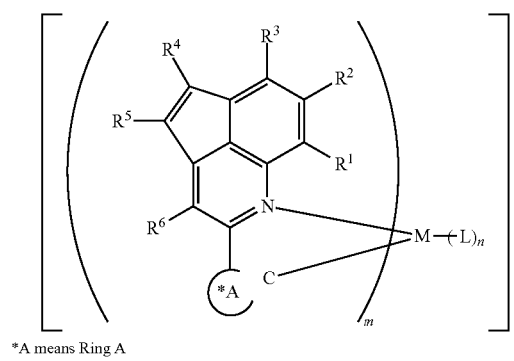

Formula (2)

*A means Ring A wherein, in formula (2), M represents a platinum group element; N represents a nitrogen atom; C represents a carbon atom; m is an integer of 1 to 3; n is an integer of 0 to 2; m+n is 2 or 3; $R^1$ to $R^3$ and $R^6$ represent a hydrogen atom or an alkyl group having 1 to 30 carbon atoms which is unsubstituted or substituted; $R^4$ and $R^5$ represent a hydrogen atom, an alkyl group having 1 to 30 carbon atoms which is unsubstituted or substituted, or are bonded to each other, to form an unsubstituted phenyl ring structure; the ring A represents an aromatic hydrocarbon ring or an aromatic hetero ring, each of which ring may have a substituent selected from the group consisting of a trifluoromethyl group, a halogen atom, an alkyl group having 1 to 30 carbon atoms, and an aryl group having 6 to 30 carbon atoms, each of which is unsubstituted or substituted; L represents a bidentate ligand; Q represents a counter anion; and k is an integer of 0 to 2.

7. The metal coordination compound according to claim 6, wherein L is an anionic bidentate ligand.

8. The metal coordination compound according to claim 6, wherein L is a bidentate ligand forming M-nitrogen and M-carbon bonds, a bidentate ligand forming M-nitrogen and M-oxygen bonds, a bidentate ligand forming two M-oxygen bonds, a bidentate ligand forming two M-nitrogen bonds, a bidentate ligand forming two M-sulfur bonds, a bidentate ligand forming two M-phosphorus bonds, or a bidentate ligand forming two M-carbon bonds.

9. The metal coordination compound according to claim 6, wherein L is represented by any one of formulae (3) to (10):

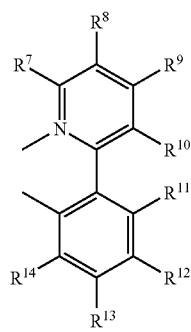

(3)

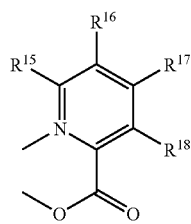

(4)

345
-continued (5)

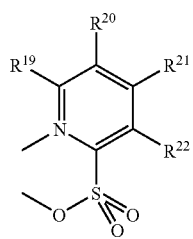

(6)

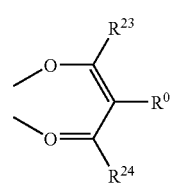

(7)

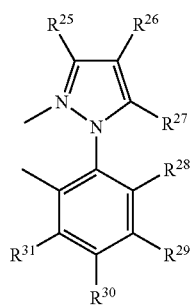

(8)

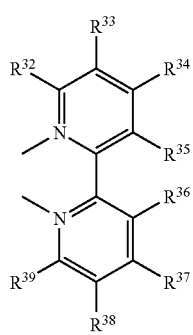

346
-continued (9)

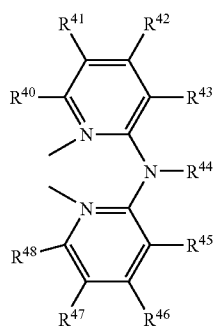

(10)

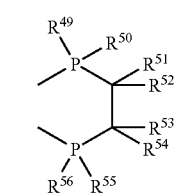

wherein, in formulae (3) to (10), $R^7$ to $R^{56}$, and $R^0$ each independently represent a hydrogen atom or a substituent, and the adjacent substituents may bond to each other, to form a ring structure.

10. The metal coordination compound according to claim 9, wherein L is represented by any one of formulae (3) to (6).

11. The metal coordination compound according to claim 6, wherein the ring A is a benzene ring, a substituted benzene ring, a naphthalene ring, a substituted naphthalene ring, a thiophene ring, a substituted thiophene ring, a furan ring, a substituted furan ring, a fluorene ring, or a substituted fluorene ring.

12. The metal coordination compound according to claim 6, wherein m=3 and n=0.

13. The metal coordination compound according to claim 6, Wherein m=2 and n=1.

14. The metal coordination compound according to claim 6, wherein M is iridium.

15. A light-emitting material, comprising the metal coordination compound according to claim 6.

16. A light-emitting device, comprising the light-emitting material according to claim 15.

17. A metal coordination compound, represented by formula (11):

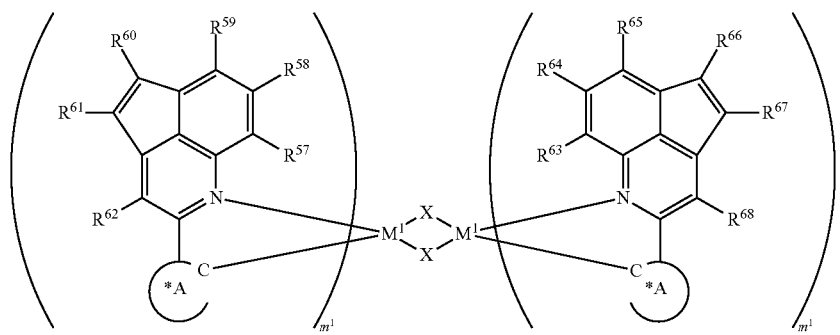

Formula (11)

*A means Ring A wherein, in formula (11), $M^1$ represents iridium, platinum, rhodium, or palladium; N represents a nitrogen atom; C represents a carbon atom; $m^1$ is an integer of 1 or 2; $R^{57}$ to $R^{59}$, $R^{62}$ to $R^{65}$, and $R^{68}$ each independently represent a hydrogen atom or an alkyl group having 1 to 30 carbon atoms which is unsubstituted or substituted; $R^{60}$ and $R^{61}$ represent a hydrogen atom, an alkyl group having 1 to 30 carbon atoms which is unsubstituted or substituted, or are bonded to each other to form an unsubstituted phenyl ring structure; $R^{66}$ and $R^{67}$ represent a hydrogen atom, an alkyl group having 1 to 30 carbon atoms which is unsubstituted or substituted, or are bonded to each other to form an unsubstituted phenyl ring, structure; the rings A each represent an aromatic hydrocarbon ring or an aromatic hetero ring, each of which ring may have a substituent selected from the group consisting of a trifluoromenthyl group, a halogen atom, an alkyl group having 1 to 30 carbon atoms, and an aryl group having 6 to 30 carbon atoms, each of which is unsubstituted or substituted; and the adjacent substituents may bond to each other, to form a ring structure; and X represents a halogen atom.

18. A light-emitting material, comprising the metal coordination compound according to claim 17.

19. A light-emitting device, comprising the light-emitting material according to claim 18.

20. An aromatic compound, represented by formula (12):

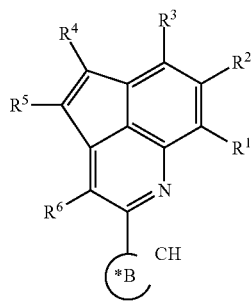

Formula (12)

*B means Ring B wherein, in formula (12), N represents a nitrogen atom; C represents a carbon atom; $R^1$ to $R^3$ and $R^6$ represent a hydrogen atom or an alkyl group having 1 to 30 carbon atoms which is unsubstituted or substituted; $R^4$ and $R^5$ represent a hydrogen atom, an alkyl group having 1 to 30 carbon atoms which is unsubstituted or substituted, or bond to each other, to form an unsubstituted phenyl ring structure, but $R^6$ and the ring B do not bond to each other, to form any ring structure; the ring B is a benzene ring, a substituted benzene ring, a naphthalene ring, a substituted naphthalene ring, a thiophene ring, a substituted thiophene ring, a furan ring, a substituted furan ring, a fluorene ring, or a substituted fluorene ring, each of which ring may have a substituent selected from the group consisting of a trifluoromenthyl group, a halogen atom, an alkyl group having 1 to 30 carbon atoms, and an aryl group having 6 to 30 carbon atoms, each of which is unsubstituted or substituted.

21. the metal coordination compound according to claim 1, wherein the substituent on the ring A is a substituted aryl group having 6 to 30 carbon atoms.

22. The metal coordination compound according to claim 1, wherein M is iridium or platinum.

23. The metal coordination compound according to claim 6, wherein M is iridium or platinum.

24. The metal coordination compound according to claim 1, wherein the ring A is a benzene ring; a substituted benzene ring which has a substituent selected from the group consisting of a trifluoromethyl group, a halogen atom, an alkyl group having 1 to 30 carbon atoms, and an aryl group having 6 to 30 carbon atoms; a naphthalene ring; a thiophene ring; a benzofuran ring; or a fluorene ring.

25. The metal coordination compound according to claim 6, wherein the ring A is a benzene ring; a substituted benzene ring which has a substituent selected from the group consisting of a trifluoromethyl group, a halogen atom, an alkyl group having 1 to 30 carbon atoms, and an aryl group having 6 to 30 carbon atoms; a naphthalene ring; a thiophene ring; a benzofuran ring; or a fluorene ring.

26. The metal coordination compound according to claim 17, wherein the ring A is a benzene ring; a substituted benzene ring which has a substituent selected from the group consisting of a trifluoromethyl group, a halogen atom, an alkyl group having 1 to 30 carbon atoms, and an aryl group having 6 to 30 carbon atoms; a naphthalene ring; a thiophene ring; a benzofuran ring; or a fluorene ring.

27. The metal coordination compound according to claim 6, wherein the counter anion Q is at least one selected from the group consisting of an alkali metal ion, an alkali-earth metal ion, a halogen ion, a perchlorate ion, a $PF_6$ ion, an ammonium ion, a $CF_3CF_2CF_2COO$ ion, a $SbF_6$ ion, a dicyan amide ion, a bis(trifluoromethanesulfonyl)amide ion, a borate ion, and a phosphonium ion.

28. The metal coordination compound according to claim 17, wherein the halogen atom X is a chlorine atom or a bromine atom.

29. The metal coordination compound according to claim 9, wherein the substituent represented by any one of $R^7$ to $R^{56}$ and $R^0$ is selected from the group consisting of a halogen atom, an alkyl group having 1 to 30 carbon atoms, an aryl group having 6 to 30 carbon atoms, an amino group having 0 to 30 carbon atoms, and an alkoxy group having 1 to 30 carbon atoms, each of which is unsubstituted or substituted.

* * * * *